US012297437B2

(12) United States Patent
Donnelly et al.

(10) Patent No.: US 12,297,437 B2
(45) Date of Patent: May 13, 2025

(54) OPTOGENETIC INDUCTION OF MEMBRANELESS ORGANELLES

(71) Applicant: UNIVERSITY OF PITTSBURGH—OF THE COMMONWEALTH SYSTEM OF HIGHER EDUCATION, Pittsburgh, PA (US)

(72) Inventors: Christopher James Donnelly, Pittsburgh, PA (US); Joseph Patrick Clarke, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1194 days.

(21) Appl. No.: 16/639,789

(22) PCT Filed: Aug. 17, 2018

(86) PCT No.: PCT/IB2018/056224
§ 371 (c)(1),
(2) Date: Feb. 18, 2020

(87) PCT Pub. No.: WO2019/035074
PCT Pub. Date: Feb. 21, 2019

(65) Prior Publication Data

US 2020/0224204 A1 Jul. 16, 2020

Related U.S. Application Data

(60) Provisional application No. 62/547,161, filed on Aug. 18, 2017.

(51) Int. Cl.

| | |
|---|---|
| ***C12N 15/00*** | (2006.01) |
| ***C07K 14/415*** | (2006.01) |
| ***C12N 15/63*** | (2006.01) |
| ***C12Q 1/02*** | (2006.01) |
| ***C12Q 1/6811*** | (2018.01) |
| *A61N 5/06* | (2006.01) |

(52) U.S. Cl.
CPC ............ *C12N 15/63* (2013.01); *C07K 14/415* (2013.01); *C12Q 1/025* (2013.01); *C12Q 1/6811* (2013.01); *A61N 5/062* (2013.01)

(58) Field of Classification Search
CPC .... C12Q 1/6806; C12Q 1/6811; C12N 15/63; C12N 15/62; C12N 15/85; C12N 15/90; C12N 15/907; C12N 2800/80
USPC .......................................................... 435/375
See application file for complete search history.

(56) References Cited

U.S. PATENT DOCUMENTS 9,097,703 B2 8/2015 Dolmetsch

FOREIGN PATENT DOCUMENTS

WO 2011/130540 10/2011

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Sfakianos et al. Biochem Soc, trancs. 2016, 44, pp. 1411-1416.*
Shin, Yongdae, et al. "Spatiotemporal control of intracellular phase transitions using light-activated optoDroplets." Cell 168.1-2 (2017): 159-171.
Kennedy, Matthew J., et al. "Rapid blue-light-mediated induction of protein interactions in living cells." Nature methods 7.12 (2010): 973.
Taslimi, Amir, et al. "An optimized optogenetic clustering tool for probing protein interaction and function." Nature communications 5.1 (2014): 1-9.
Wang, Xue, Xianjun Chen, and Yi Yang. "Spatiotemporal control of gene expression by a light-switchable transgene system." Nature methods 9.3 (2012): 266.
Zoltowski, Brian D., and Brian R. Crane. "Light activation of the LOV protein vivid generates a rapidly exchanging dimer." Biochemistry 47.27 (2008): 7012-7019.
Beaucage, S. L., and M. H. Caruthers. "Deoxynucleoside phosphoramidites—a new class of key intermediates for deoxypolynucleotide synthesis." Tetrahedron Letters 22.20 (1981): 1859-1862.
Matteucci, Mark Douglas, and M. Ho Caruthers. "Synthesis of deoxyoligonucleotides on a polymer support." Journal of the American Chemical Society 103.11 (1981): 3185-3191.
Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology 8.1 (1988): 466-472.
O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.
Altschul, Stephen F., et al. "Gapped BLAST and PSI-BLAST: a new generation of protein database search programs." Nucleic acids research 25.17 (1997): 3389-3402.
Altschul, Stephen F., et al. "Basic local alignment search tool." Journal of molecular biology 215.3 (1990): 403-410.
Henikoff, Steven, and Jorja G. Henikoff. "Amino acid substitution matrices from protein blocks." Proceedings of the National Academy of Sciences 89.22 (1992): 10915-10919.

(Continued)

*Primary Examiner* — Robert B Mondesi
*Assistant Examiner* — Mohammad Y Meah
(74) *Attorney, Agent, or Firm* — Meunier Carlin & Curfman LLC

(57) ABSTRACT

The present disclosure relates to compounds, compositions, and methods for the induction of membraneless organelles.

11 Claims, 29 Drawing Sheets

Specification includes a Sequence Listing.

(56) References Cited

OTHER PUBLICATIONS

Karlin, Samuel, and Stephen F. Altschul. "Applications and statistics for multiple high-scoring segments in molecular sequences." Proceedings of the National Academy of Sciences 90.12 (1993): 5873-5877.
International Preliminary Report on Patentability issued for Application No. Application No. PCT/IB2018/056224, dated Feb. 27, 2020.
International Search Report and Written Opinion dated Jan. 22, 2019, from International Application No. PCT/IB2018/056224, 14 pages.
Shin, Y. et al. "Spatiotemporal Control of Intracellular Phase Transitions Using Light-Activated optoDroplets", Cells, Jan. 12, 2017, vol. 168, No. 1-2, pp. 159-171.
ADDGENE "Addgene: pHR-SFFV-dCas9-BFP", Webpage, Feb. 22, 2017.
Riback, J.A. et al. "Stress-Triggered Phase Separation Is an Adaptive, Evolutionarily Tuned Response", Cell, Mar. 9, 2017, vol. 168, No. 6, pp. 1028-1040.
Zhang, P. et al. "OptoGranules reveal the evolution of stress granules to ALS-FTD pathology", BioRxiv, Jun. 15, 2018, 35 pages.

* cited by examiner

Fig. 11A-D

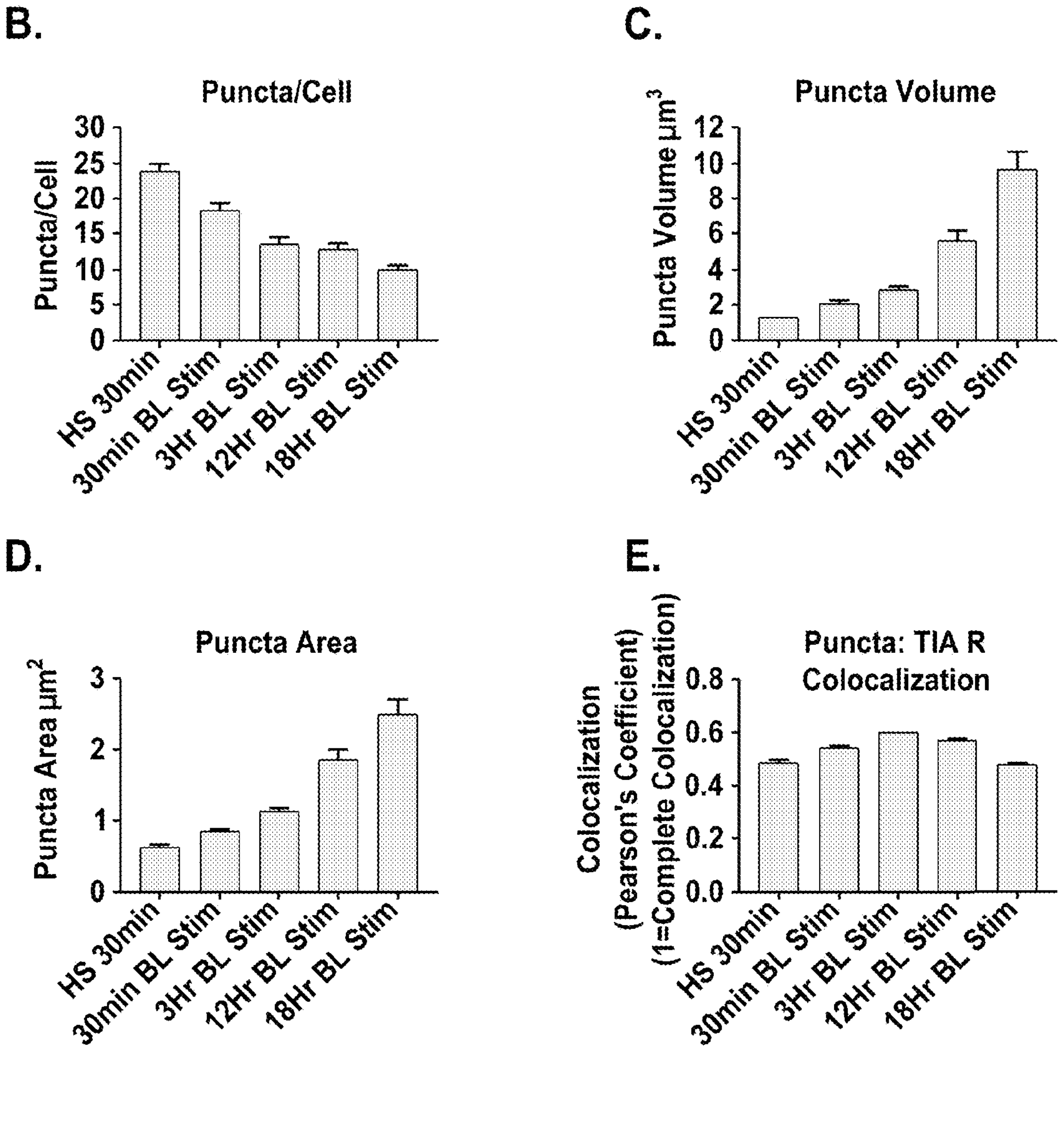
Fig. 18B-E

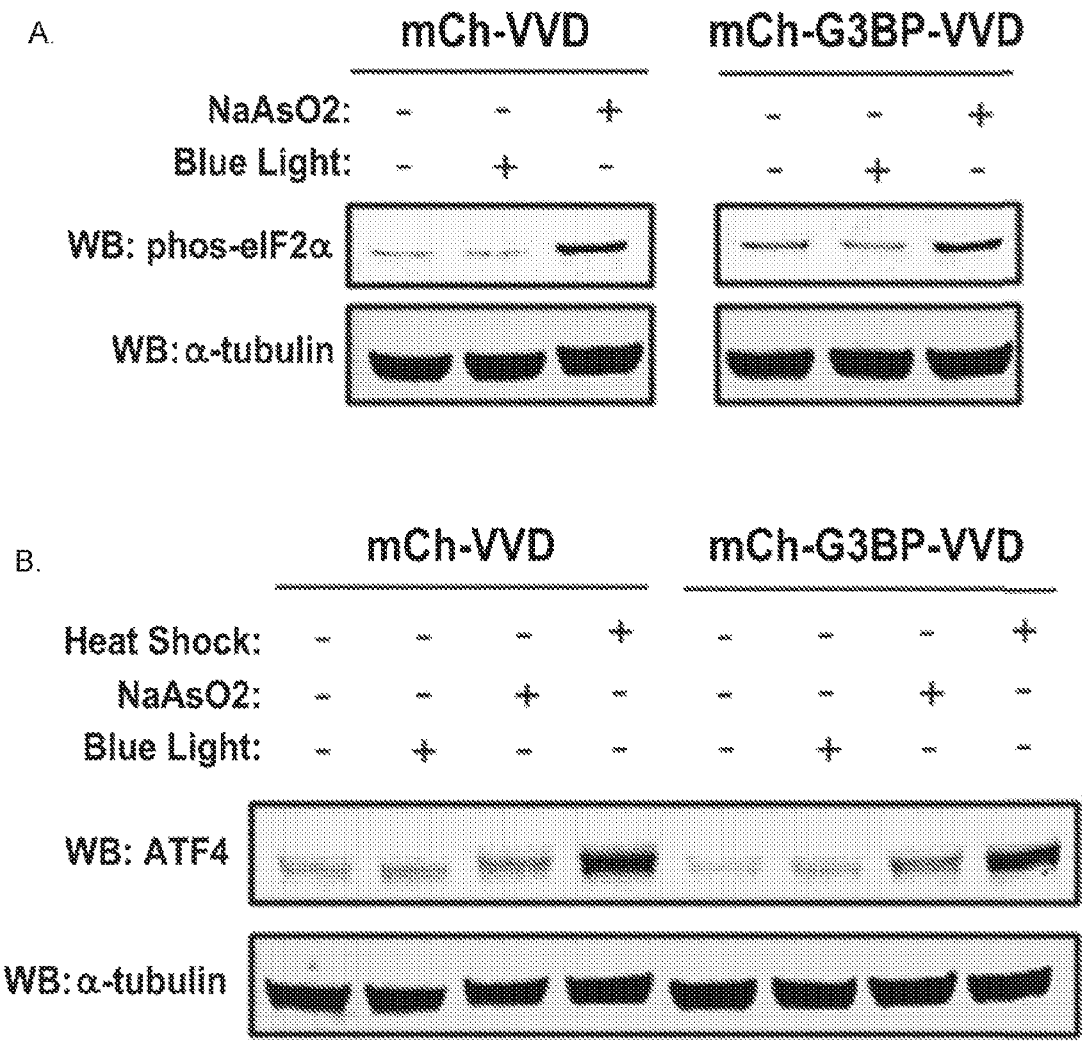
Fig. 21A-B
A.
| | mCh-VVD | | | mCh-G3BP-VVD | | |
|---|---|---|---|---|---|---|
| NaAsO2: | − | − | + | − | − | + |
| Blue Light: | − | + | − | − | + | − |
WB: phos-eIF2α
WB: α-tubulin
B.
| | mCh-VVD | | | | mCh-G3BP-VVD | | | |
|---|---|---|---|---|---|---|---|---|
| Heat Shock: | − | − | − | + | − | − | − | + |
| NaAsO2: | − | − | + | − | − | − | + | − |
| Blue Light: | − | + | − | − | − | + | − | − |
WB: ATF4
WB: α-tubulin
Fig. 21A-B

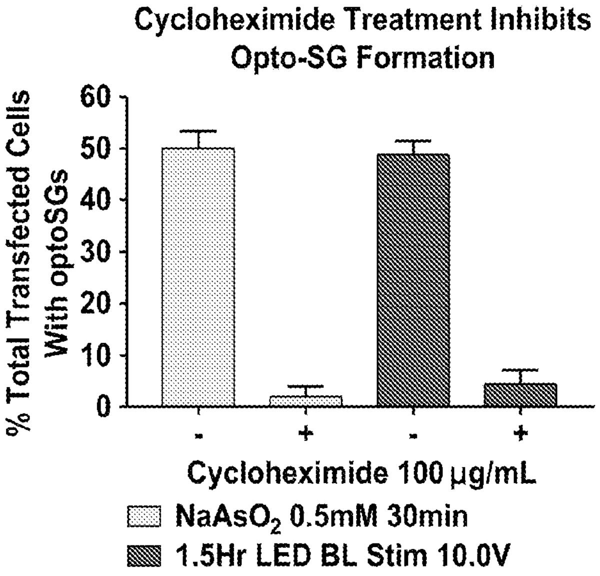
Fig. 23B
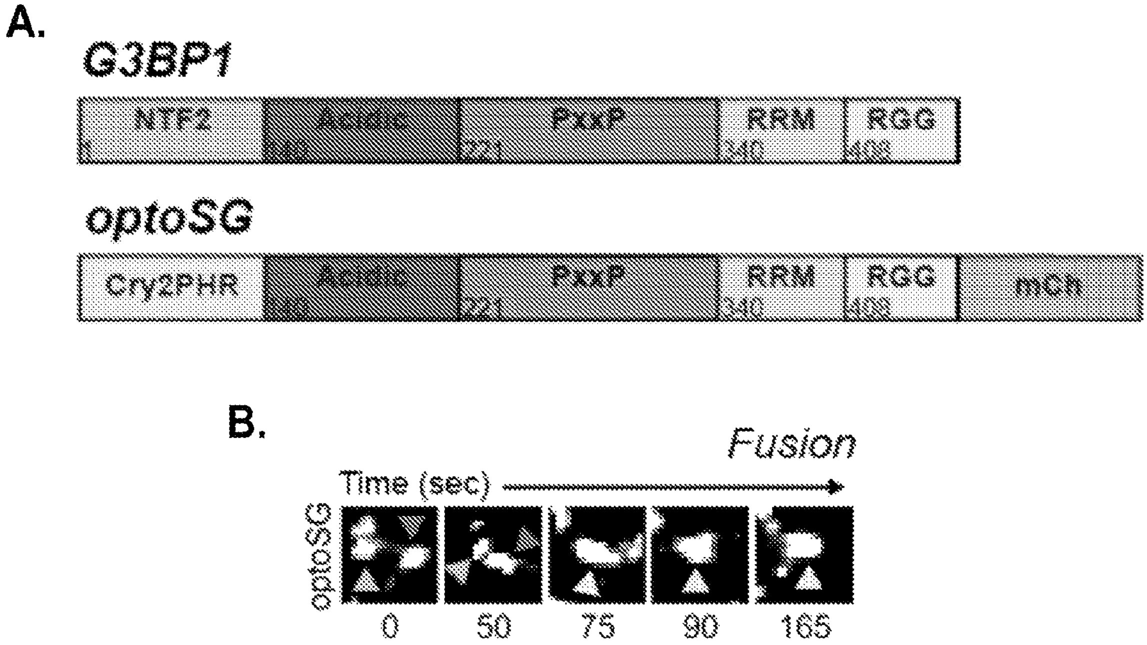
Fig. 24A-B

C.
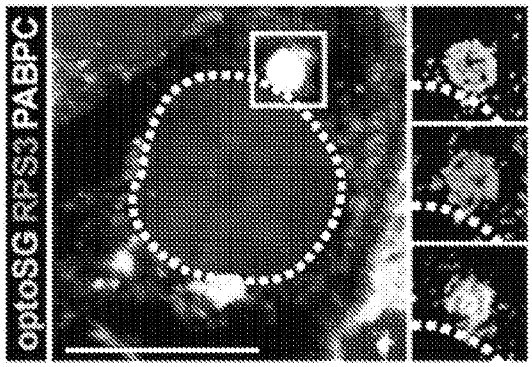
D.
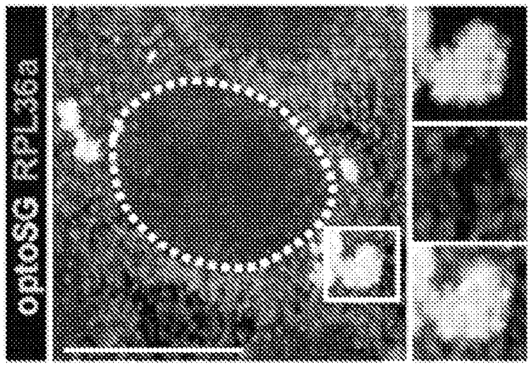
E.
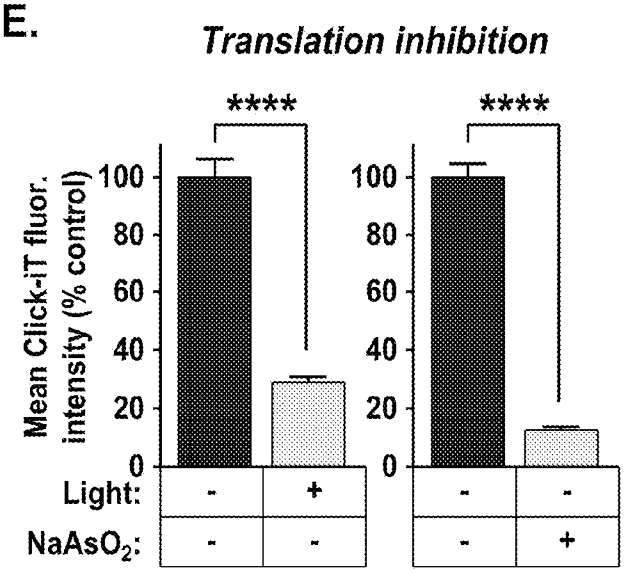
Fig. 24C-E Cont.

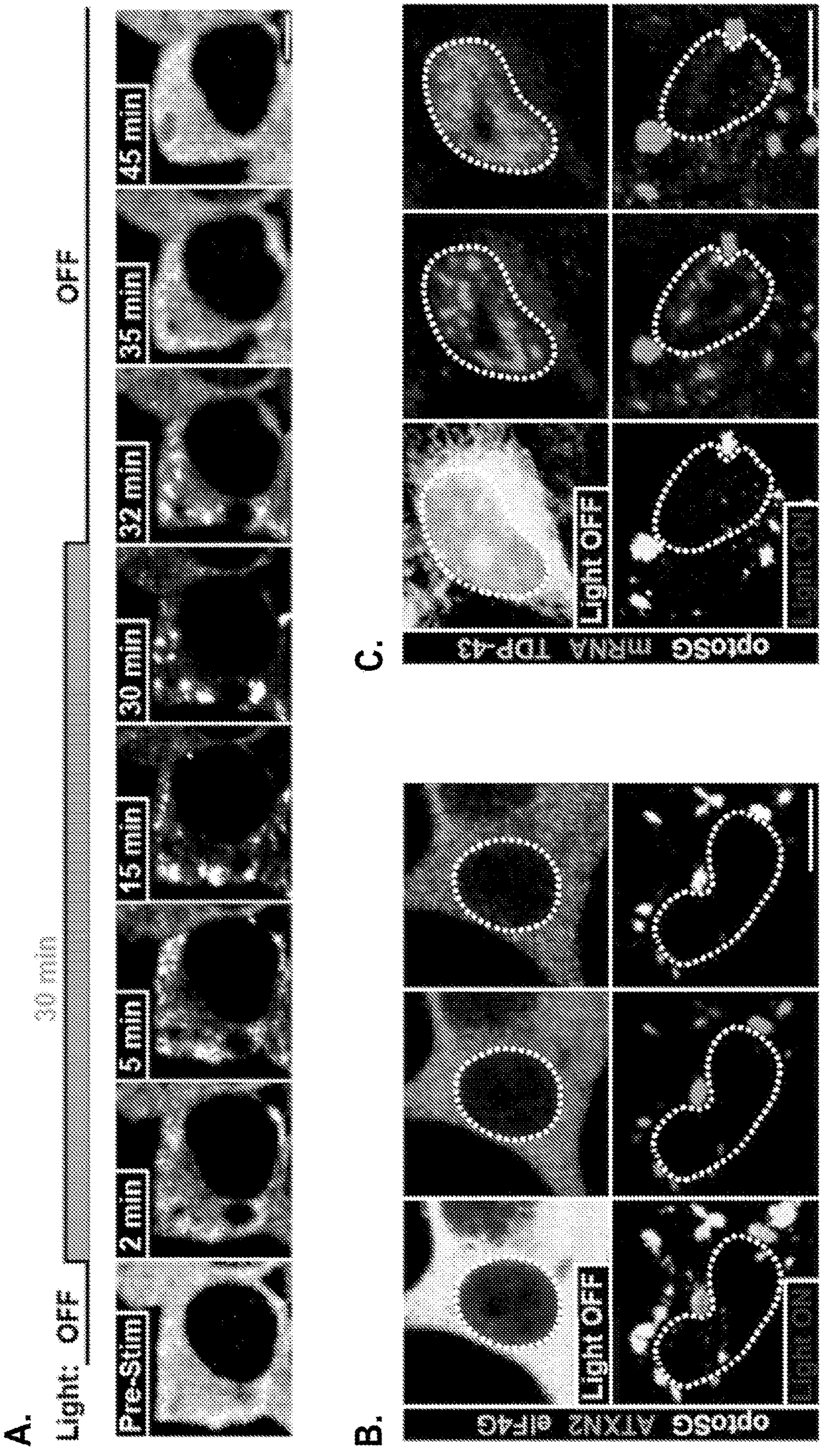
Fig. 25A-C

OPTOGENETIC INDUCTION OF MEMBRANELESS ORGANELLES

CROSS REFERENCE TO RELATED APPLICATIONS

This application is a 371 of PCT/IB2018/056224, filed Aug. 17, 2018, which claims the benefit of U.S. Provisional Patent Application Ser. No. 62/547,161 filed Aug. 18, 2017, the disclosure of which is expressly incorporated herein by reference.

FIELD

The present disclosure relates to compounds, compositions, and methods for the induction of membraneless organelles.

BACKGROUND

Organelles are cellular compartments that perform specific functions and are required for proper cellular homeostasis. Membraneless organelles are a class of organelles that do not contain a lipid membrane separating them from the cytoplasmic liquid. There are a number of cytoplasmic and nuclear membraneless organelles, each of which perform distinct cellular functions. The underlying biochemistry required for the formation of these organelles was long misunderstood since it was unclear how the membraneless organelles separated themselves from the cytoplasmic milieu.

Recent evidence suggests that the protein components of membraneless organelles contain low complexity domains (LCDs), or intrinsically disordered regions (IDRs). These LCDs and/or IDRs, when focally concentrated, undergo liquid-liquid phase separation (LLPS) due to self-interactions through weak multivalent attractive forces. These forces can be further stabilized by nucleic acids (RNA or DNA) and other molecules commonly found in each membraneless organelle.

There are a variety of cytoplasmic and nuclear membraneless organelles and their functions vary widely. Notably, a number of these membraneless organelles have been implicated in diseases. For example, abnormal stress granule and nucleoli dynamics are thought to contribute to the neuropathology of Amyotrophic Lateral Sclerosis, Alzheimer's Disease, Frontotemporal Dementia, and Parkinson's Disease. Mutations in components of stress granules are also found in certain cancers. Additionally, abnormal processing body (p-body) function has also been implicated in cancer pathobiology.

To date, no studies have been able to precisely control the spatial and temporal formation and/or dynamics of functional membraneless organelles, thus making their study in disease speculative. The ability to control these organelles would prove useful for manipulating specific cellular processes and would be invaluable for molecular and cellular biology. Current studies to manipulate membraneless organelle function rely on deleting key components of the structure, thus preventing their formation. This methodology, however, does not allow one to address the consequence of aberrant organelle formation, nor does it allow for researchers to control and interrogate their function. What is needed are new and improved methods for inducing membraneless organelles in mammalian cell lines and animal models.

The compounds, compositions, and methods disclosed herein address these and other needs.

SUMMARY

Disclosed herein are compounds, compositions, and methods for inducing membraneless organelles in a cell or animal model. The inventors have developed a novel method to induce the formation of membraneless organelles using blue light stimulation. The compounds, compositions, and methods herein allow for the temporal and spatial tunability of membraneless organelle formation. These new methods enable researchers, for the first time, to stimulate the formation of these structures. These methods disclosed herein are utilized, for example, to study disease and for drug screening.

In one aspect, disclosed herein is a nucleotide sequence encoding a chimeric polypeptide, comprising: a first nucleotide sequence encoding a light-induced oligomerization domain and a second nucleotide sequence encoding a low complexity domain from a membraneless organelle target protein.

In one aspect, disclosed herein is an expression vector encoding a chimeric polypeptide, comprising: a first nucleotide sequence encoding a light-induced oligomerization domain and a second nucleotide sequence encoding a low complexity domain from a membraneless organelle target protein, wherein the first nucleotide sequence is operably linked to a promoter.

In one aspect, disclosed herein is a nucleotide sequence encoding a chimeric polypeptide, comprising: a first nucleotide sequence encoding a low complexity domain from a membraneless organelle target protein and a second nucleotide sequence encoding a light-induced oligomerization domain.

In one aspect, disclosed herein is an expression vector encoding a chimeric polypeptide, comprising: a first nucleotide sequence encoding a low complexity domain from a membraneless organelle target protein and a second nucleotide sequence encoding a light-induced oligomerization domain, wherein the first nucleotide sequence is operably linked to a promoter.

In one aspect, disclosed herein is a cell comprising a nucleotide sequence encoding a chimeric polypeptide, comprising: a first nucleotide sequence encoding a light-induced oligomerization domain and a second nucleotide sequence encoding a membraneless organelle target protein.

In one aspect, disclosed herein is a cell comprising a nucleotide sequence encoding a chimeric polypeptide, comprising: a first nucleotide sequence encoding a membraneless organelle target protein and a second nucleotide sequence encoding a light-induced oligomerization domain.

In one aspect, disclosed herein is a chimeric polypeptide comprising: a light-induced oligomerization domain; and a low complexity domain from a membraneless organelle target protein.

In one aspect, disclosed herein is a chimeric polypeptide comprising: a low complexity domain from a membraneless organelle target protein; and a light-induced oligomerization domain.

In one aspect, disclosed herein is a method of inducing a membraneless organelle in a cell, comprising the steps: introducing into the cell an expression vector encoding a chimeric polypeptide, comprising:

- a first nucleotide sequence encoding a light-induced oligomerization domain and a second nucleotide sequence encoding a low complexity domain from a membraneless organelle target protein, wherein the first nucleotide sequence is operably linked to a promoter;

expressing the chimeric polypeptide; and inducing oligomerization of the chimeric polypeptide by stimulation with blue light.

In another aspect, disclosed herein is a method of screening for an agent that modulates formation of a membraneless organelle, comprising the steps:

introducing into a cell an expression vector encoding a chimeric polypeptide, comprising:

a first nucleotide sequence encoding a light-induced oligomerization domain and a second nucleotide sequence encoding a low complexity domain from a membraneless organelle target protein, wherein the first nucleotide sequence is operably linked to a promoter;

expressing the chimeric polypeptide;

introducing the agent into a culture media comprising the cell;

inducing oligomerization of the chimeric polypeptide by stimulation with blue light; and determining modulation of the formation of the membraneless organelle by the agent.

In one aspect, disclosed herein is a method of inducing a membraneless organelle in a cell, comprising the steps:

introducing into the cell an expression vector encoding a chimeric polypeptide, comprising:

a first nucleotide sequence encoding a low complexity domain from a membraneless organelle target protein and a second nucleotide sequence encoding a light-induced oligomerization domain, wherein the first nucleotide sequence is operably linked to a promoter;

expressing the chimeric polypeptide; and inducing oligomerization of the chimeric polypeptide by stimulation with blue light.

In another aspect, disclosed herein is a method of screening for an agent that modulates formation of a membraneless organelle, comprising the steps:

introducing into a cell an expression vector encoding a chimeric polypeptide, comprising:

a first nucleotide sequence encoding a low complexity domain from a membraneless organelle target protein and a second nucleotide sequence encoding a light-induced oligomerization domain, wherein the first nucleotide sequence is operably linked to a promoter;

expressing the chimeric polypeptide;

introducing the agent into a culture media comprising the cell;

inducing oligomerization of the chimeric polypeptide by stimulation with blue light; and determining modulation of the formation of the membraneless organelle by the agent.

In one embodiment, the light-induced oligomerization domain is selected from the group consisting of CRY2 PHR, CRY2OLIG, NcVVD, NcVVDY50W, NcVVDY50W/I74V/I85V/LINKERA, NcVVDY50W/I52C/I74V/I85V/LINKERA, NcVVDY50W/C71V/174V/185V/LINKERA, NcVVDY50W/I52C/C71V/I74V/I85V/LINKERA, NcVVDY50W/I74V/I85V/LINKERB, NcVVDY50W/152C/174V/185V/LINKERB, NcVVDY50W/C71V/174V/185V/LINKERB, NcVVDY50W/I52C/C71V/I74V/I85V/LINKERB, NcLOV, and VfAU1LOV. In one embodiment, the light-induced oligomerization domain is NcVVDY50W. In one embodiment, the light-induced oligomerization domain is NcVVDY50W/I74/I85/LINKERA. In one embodiment, the light-induced oligomerization domain is NcVVDY50W/I52C/I74/I85/LINKERA. In one embodiment, the light-induced oligomerization domain is NcVVDY50W/C71V/I74/I85/LINKERA. In one embodiment, the light-induced oligomerization domain is NcVVDY50W/I52C/C71V/I74/I85/LINKERA. In one embodiment, the light-induced oligomerization domain is NcVVDY50W/I74/I85/LINKERB. In one embodiment, the light-induced oligomerization domain is NcVVDY50W/I52C/I74/I85/LINKERB. In one embodiment, the light-induced oligomerization domain is NcVVDY50W/C71V/I74/I85/LINKERB. In one embodiment, the light-induced oligomerization domain is NcVVDY50W/I52C/C71V/I74/I85/LINKERB. In one embodiment, the light-induced oligomerization domain is CRY2OLIG. In one embodiment, the light-induced oligomerization domain is CRY2 PHR. In one embodiment, the light-induced oligomerization domain comprises a LOV domain. In one embodiment, the light-induced oligomerization domain comprises a LOV domain from the VVD protein. In one embodiment, the light-induced oligomerization domain comprises a LOV domain from the LOV protein. In one embodiment, the light-induced oligomerization domain comprises a PHR domain. In one embodiment, the light-induced oligomerization domain comprises a PHR domain, from the CRY2 protein.

In one embodiment, the low complexity domain is from a membraneless organelle target protein. In one embodiment, the low complexity domain from a membraneless organelle target protein is from a cytoplasmic membraneless organelle target protein.

In one embodiment, the low complexity domain from a membraneless organelle target protein is from a stress granule target protein. In one embodiment, the low complexity domain is from a stress granule target protein selected from the group consisting of PABC1, TIAR, G3BP1, G3BP2, DDX6, TDRD3, and ATXN2. In one embodiment, the low complexity domain from a membraneless organelle target protein is G3BP1. In one embodiment, the low complexity domain from a membraneless organelle target protein is an NTF2 domain truncated G3BP1. In one embodiment, the low complexity domain from a membraneless organelle target protein is an acidic domain truncated G3BP1. In one embodiment, the low complexity domain from a membraneless organelle target protein is a PxxP domain truncated G3BP1. In one embodiment, the low complexity domain from a membraneless organelle target protein is an RRM domain truncated G3BP1. In one embodiment, the low complexity domain from a membraneless organelle target protein is an RGG domain truncated G3BP1.

In one embodiment, the low complexity domain from a membraneless organelle target protein is from a P-body target protein. In one embodiment, the low complexity domain is from a P-body target protein selected from the group consisting of DCP1A, DCP2, LSM1, TNRC6A, MEX3A, EDC4, XRN1, and DDX3X.

In one embodiment, the low complexity domain from a membraneless organelle target protein is from a ribonuclear transport granule target protein. In one embodiment, the low complexity domain is from a ribonuclear transport granule target protein selected from the group consisting of IGFBP1, STAU1, PURA, FMR1, FXR1, and FXR2.

In one embodiment, the low complexity domain from a membraneless organelle target protein is from a nuclear membraneless organelle target protein.

In one embodiment, the low complexity domain from a membraneless organelle target protein is from a nucleolus target protein. In one embodiment, the low complexity domain is from a nucleolus target protein selected from the group consisting of NCL, NPM1, and FBL.

In one embodiment, the low complexity domain from a membraneless organelle target protein is from a nuclear speckle target protein. In one embodiment, the low complexity domain is from a nuclear speckle target protein selected from the group consisting of SRSF2, PNN, and SRSF1.

In one embodiment, the low complexity domain from a membraneless organelle target protein is from a nuclear stress body target protein. In one embodiment, the low complexity domain is from nuclear stress body target protein SAFB.

In one embodiment, the low complexity domain from a membraneless organelle target protein is from a nuclear paraspeckle target protein. In one embodiment, the low complexity domain is from a nuclear paraspeckle target protein selected from the group consisting of SFPQ, NONO, and PSPC1.

In one embodiment, the low complexity domain from a membraneless organelle target protein is from a cajal body target protein. In one embodiment, the low complexity domain is from cajal body target protein COIL.

In one embodiment, the low complexity domain from a membraneless organelle target protein is from a PML body target protein. In one embodiment, the low complexity domain is from PML body target protein PML.

In one embodiment, the low complexity domain from a membraneless organelle target protein is from a chromatoid body/germ granule target protein. In one embodiment, the low complexity domain is from chromatoid body/germ granule target protein DDX4.

In one embodiment, the cell is a mammalian cell. In one embodiment, the cell is a human cell.

In one embodiment, the blue light has a wavelength between 405 nm and 499 nm. In one embodiment, the blue light has a wavelength of about 465 nm.

BRIEF DESCRIPTION OF THE DRAWINGS

The accompanying figures, which are incorporated in and constitute a part of this specification, illustrate several aspects described below.

FIG. 2A) The stress granules exhibit a composition that matches the heat shock induced stress granules and contain the stress granule component, Ataxin-2 protein. FIG. 2B) The stress granules exhibit a composition that matches the heat shock induced stress granules and contain the stress granule component, TIAR protein. A DNA arrangement that generates the NcVVDY50W-G3BP1 was developed and expressed in HEK293 cells. Under normal conditions, the NcVVDY50W-G3BP1 remains diffuse in the cytoplasm. When endogenous stress granule formation is induced with heat shock, the NcVVDY50W-G3BP1 forms stress granules that stain positive for key markers including Ataxin-2 and TIAR. To test if blue light exposure can induce stress granule formation, a light treatment paradigm was developed and the resulting light-induced stress granules are similarly stained positive for Ataxin-2 and TIAR.

FIG. 16A shows a representative image of time lapsed image during blue light on/off treatment at different time points from FIG. 15. FIG. 16B shows quantification of puncta formation and dissociation rate over time from FIG. 15. Light induced stress granules are dynamic and can be repeatedly stimulated to control their function in the absence of toxic cellular stressors.

FIG. 17A) NcVVDY50W-G3BP1 was expressed in HEK293 cells. Stress granule formation can be temporally controlled with light stimulation at different voltages. FIG. 17B) NcVVDY50W-G3BP1 expressing HEK293 cells were longitudinally imaged every 30 seconds and exposed to different voltages (1.0V, or 5.0V, or 10.0V) of blue light in between each image for 30 minutes, over a time-course of 6 hours. The light was then removed and cells were imaged every 30 seconds without light in between each image to study the rate of formation of the light induced stress granules.

FIGS. 18A-18E. Optogenetically induced stress granules dynamics can be chronically formed for hours in the absence of cell stressors. NcVVDY50W-G3BP1 was expressed in HEK293 cells. FIG. 18A shows stress granules can be chronically formed for hours with light stimulation in the absence of toxic cell stressors. Light paradigms were developed to chronically form stress granules with light for up to 18 hours. The light induced stress granules are positive for both key markers such as PABPC1 and sequester mRNA throughout the time course, indicating they are functional. FIG. 18B shows the number of puncta per cell over time after stimulation with blue light. FIG. 18C shows the puncta volume over time after stimulation with blue light. FIG. 18D shows the puncta area over time after stimulation with blue light.

FIG. 18E shows the colocalization of puncta and TIAR over time after stimulation with blue light. The stress granules decrease in number and increase in size over the time course indicating their fluid nature, a characteristic of stress granules. No previous study has been able to induce stress granule formation for more than 2-3 hours as the cells die from the treatment to induce stress granules. Thus, these are the first studies to create chronic stress granules for over 2-3 hours.

FIGS. 21A-21B. Optogenetically induced stress granules are specifically formed by blue light and do not use a cell stress. Total cellular protein from blue light induced stress granules using G3BP1-NcVVDY50W protein arrangement was collected. Subsequent Western blotting of collected total protein, probing for phospho-eIF2α (FIG. 21A) and ATF4 (FIG. 21B), both of which are components of the integrated stress response (ISR) pathway, indicates that optogenetically induced stress granules do not induce a cell stress to form stress granules using the G3BP1-NcVVDY50W protein arrangement.

FIGS. 23A-23B. Translational inhibition with cycloheximide inhibits optogenetically induced stress granule formation. When endogenous stress granule formation is induced with $NaAsO_2$ (0.5 mM, 30 min treatment), the G3BP1-NcVVDY50W forms stress granules that stain positive for the key marker eIF4G. When cycloheximide, a translational inhibitor, is added 1 and a half hours before $NaAsO_2$ treatment, endogenous stress granule formation is attenuated (FIG. 23A). When cycloheximide is added 1 and a half hours before blue light stimulation, optogenetically induced stress granules fail to form (FIG. 23B). These results indicate that like endogenous stress granules, optogenetically induced stress granules require cellular translational machinery to form.

FIGS. 24A-24E. Replacing the G3BP1 NTF2 domain, which is required for G3BP1 self-oligomerization (optoSG), with oligomerizing photoreceptors, is sufficient to initiate the formation of optogenetic stress granules. FIG. 24A) Schematics of an additional approach to seed optoStress Granules (optoSGs) employing truncated G3BP1 protein and replacing the NTF2 oligomerizing domain with a photoreceptor with the capacity to oligomerize (in this instance Cry2-PHR, but also works with chronic stimulation of dimerizing photoreceptor). FIG. 24B) HEK cells expressing Cry2 PHR-ΔNTF-G3BP1 were exposed to blue light LED stimulation for 30 minutes to induce the formation of optoSGs. SGs were monitored for 165 seconds for fission and fusion and exhibit the liquid-like droplet properties of endogenously formed stress granules. FIG. 24C) Cry2 PHR-ΔNTF-G3BP1 optoSGs colocalize with endogenous stress granule markers including PABPC1 and the 40S ribosomal component RPS3, FIG. 24D) but not the 60S ribosomal component RPL36a. FIG. 24E) De novo protein synthesis was analyzed as described above using Click-iT biochemistry and show that light induced Cry2 PHR-ΔNTF-G3BP1 optoSGs inhibit cellular protein synthesis to a similar degree as sodium arsenite induced stress granules.

FIGS. 25A-25C. OptoStress Granules (optoSGs) (Cry2-delta NTF-G3BP1) display liquid-like properties of membraneless organelles and colocalize with translation initiation factors and mRNA. FIG. 25A) Longitudinal live imaging of HEKs expressing Cry2 PHR-ΔNTF-G3BP1 exposed to blue light LED stimulation show that optoSGs are form after 15 minutes and exhibit a residence time of approximately 2-3 minutes before dissipating. FIG. 25B) Cry2 PHR-ΔNTF-G3BP1 optoSGs colocalize with mature stress granule markers Ataxin2 and eIF4G translational factors as well as FIG. 25C) mRNA and TDP-43. Together these data indicate that optoSGs using the Cry2 PHR-ΔNTF-G3BP1 approach as well as the full length G3BP1 protein seed core of stress granule like structures that function as endogenous stress granules to inhibit protein synthesis in the absence of the intrinsic stress response.

DETAILED DESCRIPTION

Figure 1:
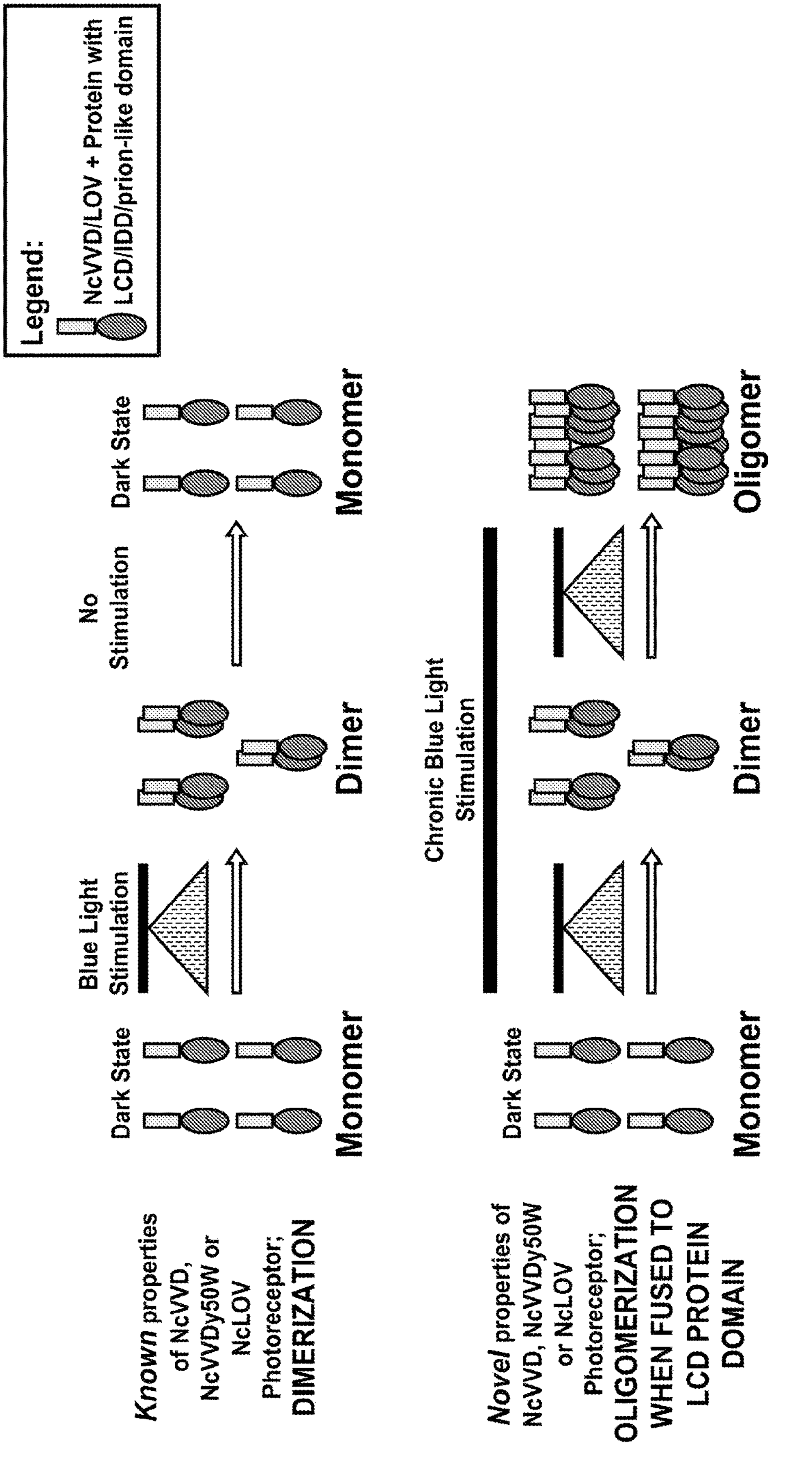
FIG. 1. Schematic of a dimerizing photoreceptor upon light stimulation. When fused to proteins that make up the core of membraneless organelles and often contain LCDs/IDRs, and employing a specific light stimulation paradigm, this photoreceptor is used for oligomerization. The oligomerization of core proteins of membraneless organelles initiate their formation. These novel light stimulation paradigms are used induce oligomerization of fusions proteins with LCDs.
Figure 2A:
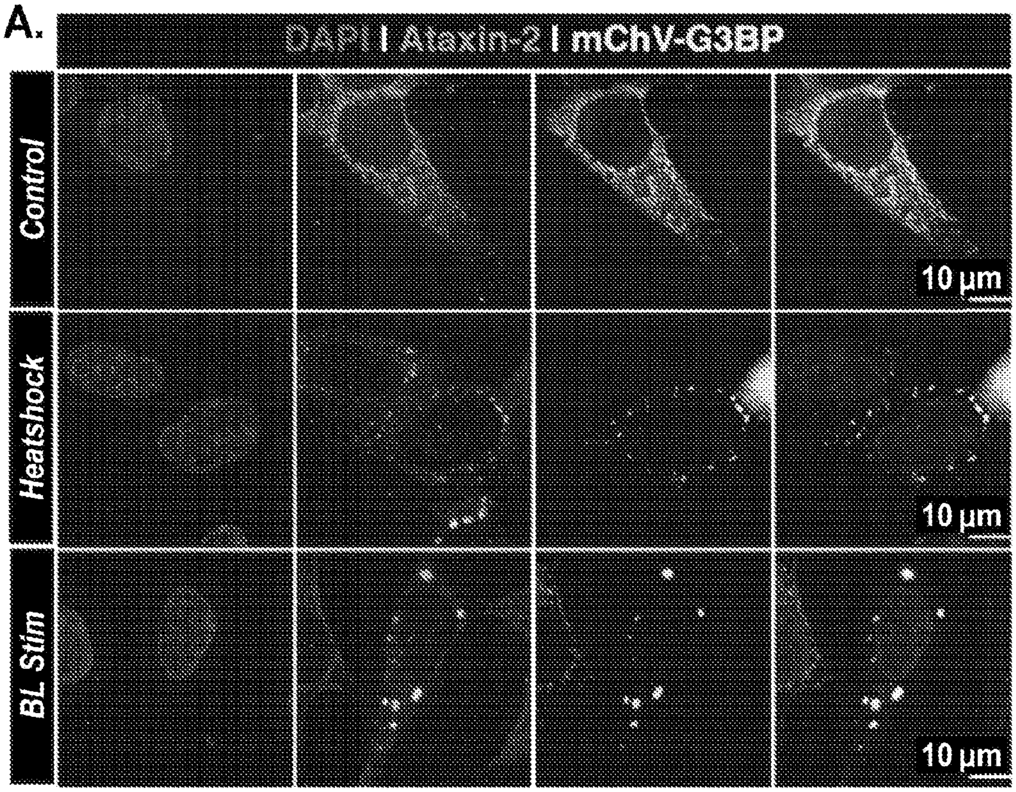
FIGS. 2A-2B. Blue light induced stress granules using a NcVVDY50W-G3BP1 protein arrangement.
Figure 2B:
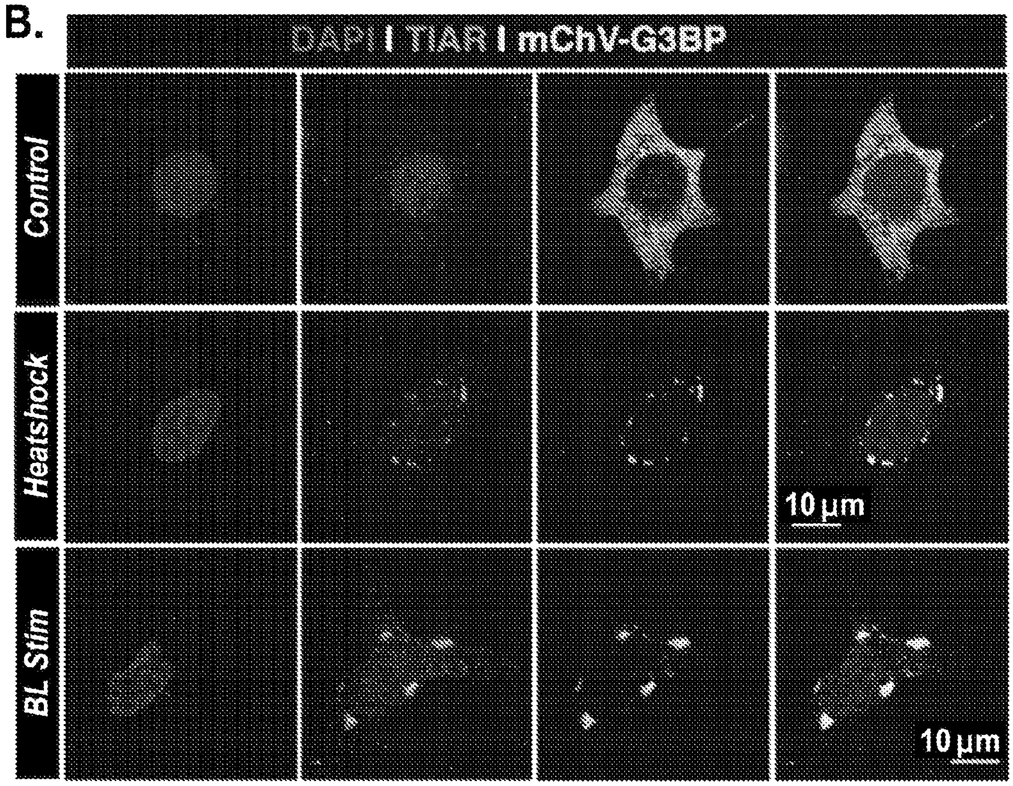
Figure 3:
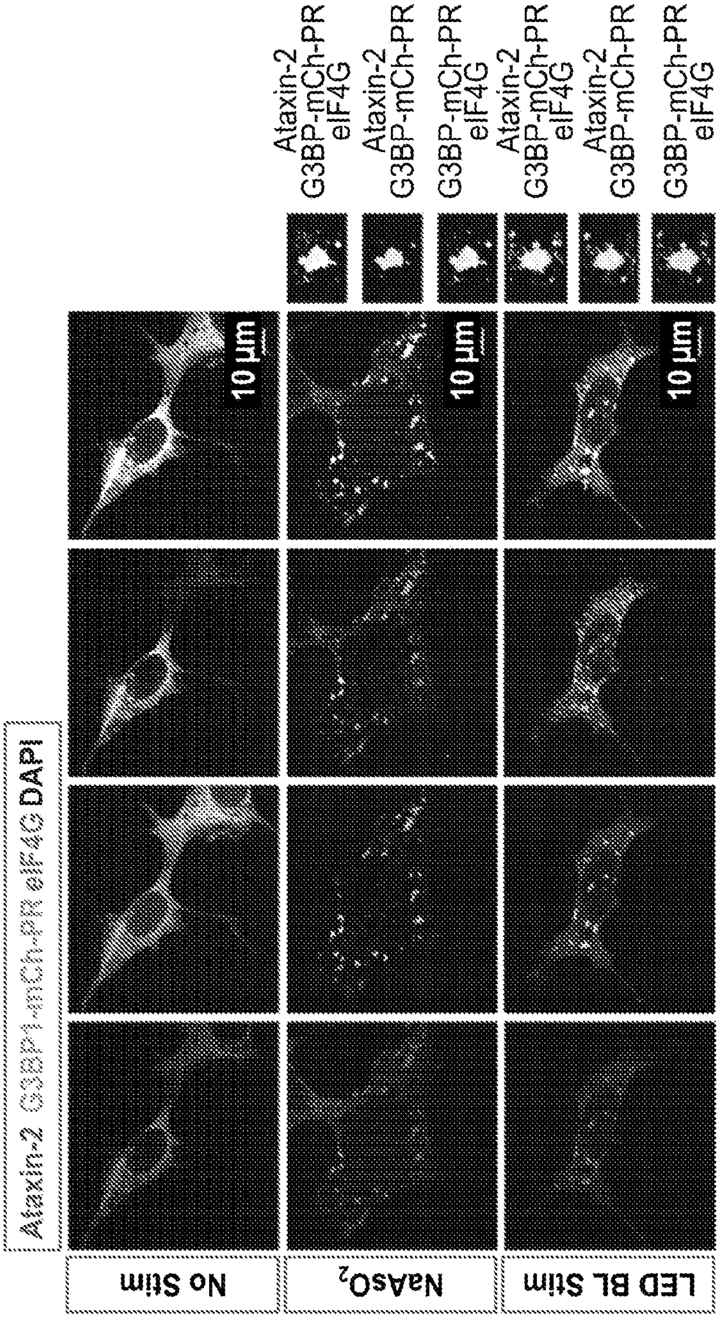
FIG. 3. Blue light induced stress granule using G3BP1-NcVVDY50W protein arrangement exhibit a composition that matches sodium arsenite ($NaAsO_2$) induced stress granules and contain the stress granule components, Ataxin-2 and eIF4G. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for the key translation factor eIF4G, and the stress granule marker Ataxin-2. Blue light induced stress granules were also found to colocalize with the key translation factor eIF4G, and the stress granule marker Ataxin-2.
Figure 4:
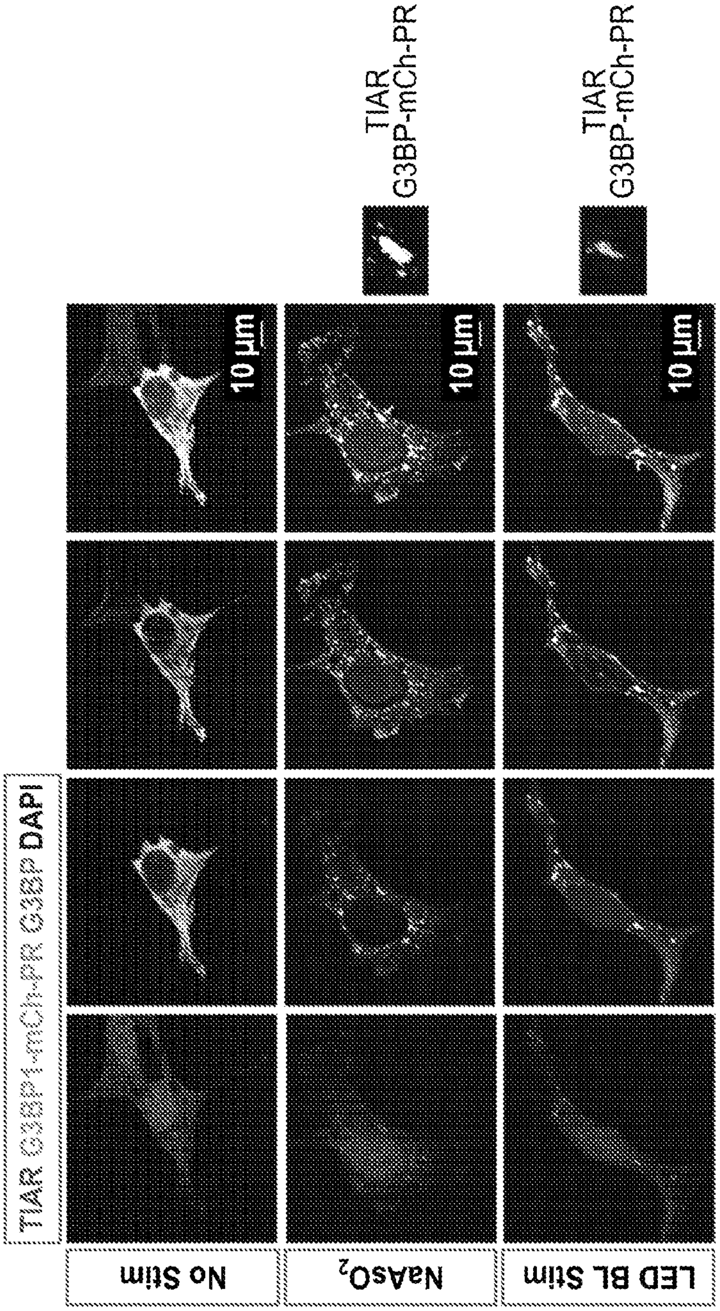
FIG. 4. Blue light induced stress granules using G3BP1-NcVVDY50W protein arrangement exhibit a composition that matches sodium arsenite ($NaAsO_2$) induced stress granules and contain the stress granule components, TIAR and G3BP. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for key markers TIAR and G3BP. Blue light induced stress granules were also found to colocalize with the key stress granule markers TIAR and G3BP. Under normal conditions, the G3BP1-NcVVDY50W remains diffuse in the cytoplasm. When endogenous stress granule formation were induced with sodium arsenite, the G3BP1-NcVVDY50W forms stress granules that probe positive for key markers, including TIAR and G3BP. To test if blue light exposure can induce stress granule formation, a light treatment paradigm was developed to produce light-induced stress granules that also probe positive for TIAR and G3BP. Inserts are 3D images of stress granules indicated by arrows.
Figure 5:
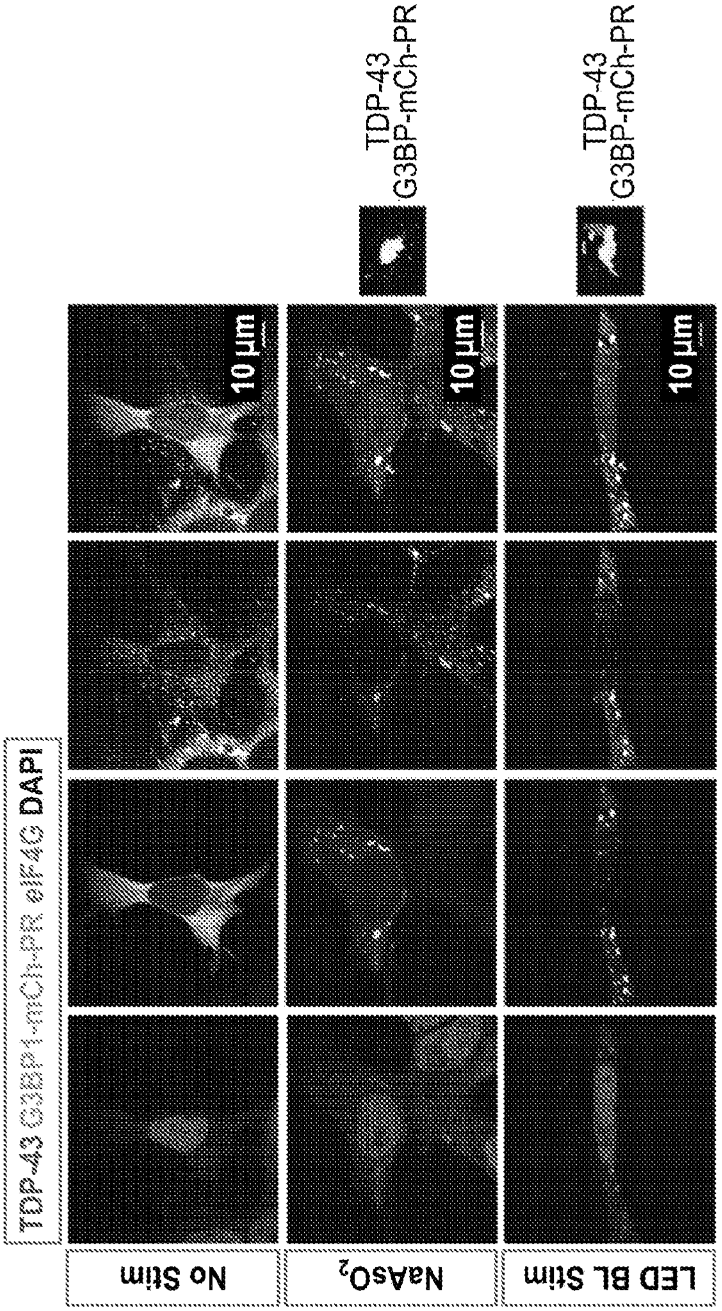
FIG. 5. Blue light induced stress granules using G3BP1-NcVVDY50W protein arrangement exhibit a composition that matches sodium arsenite induced ($NaAsO_2$) stress granules and contain the stress granule components, TDP-43 and eIF4G. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for key markers TDP-43 and eIF4G. Blue light induced stress granules were also found to colocalize with the key stress granule markers TIAR and G3BP. As an example of this technology, DNA arrangements were developed that generated G3BP1-NcVVDY50W, and expressed in HEK293 cells. Under normal conditions, the G3BP1-NcVVDY50W remains diffuse in the cytoplasm. When endogenous stress granule formation is induced with sodium arsenite, the G3BP1-NcVVDY50W forms stress granules that probe positive for key markers, including TDP-43 and eIF4G. To test if blue light exposure can induce stress granule formation, a light treatment paradigm was developed to produce light-induced stress granules that also probe positive for TDP-43 and eIF4G. Inserts are 3D images of stress granules indicated by arrows.
Figure 6A:
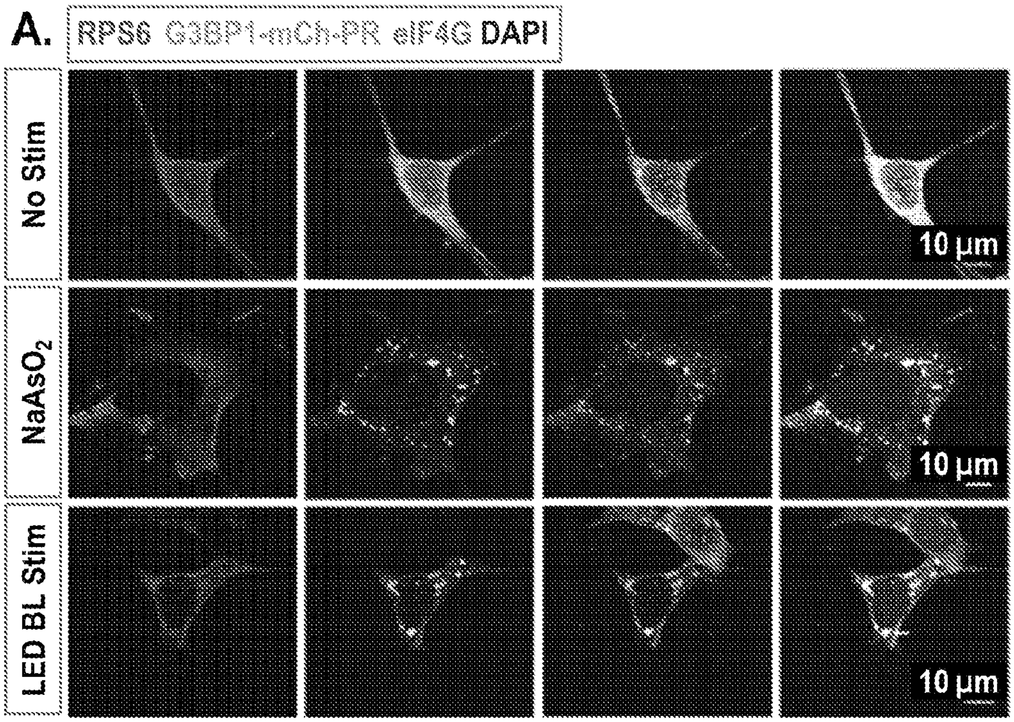
FIGS. 6A-6B. Blue light induced stress granules using G3BP1-NcVVDY50W protein arrangement exhibit a composition that matches sodium arsenite ($NaAsO_2$) induced stress granules and contain the stress granule components, RPS6 and eIF4G (FIG. 6A), as well as Ataxin-2 and RPS3 (FIG. 6B). Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for key markers RPS6 and eIF4G (FIG. 6A), as well as Ataxin-2 and RPS3 (FIG. 6B). Blue light induced stress granules were also found to colocalize with the key stress granule markers RPS6 and eIF4G (FIG. 6A), as well as Ataxin-2 and RPS3 (FIG. 6B).
Figure 6B:
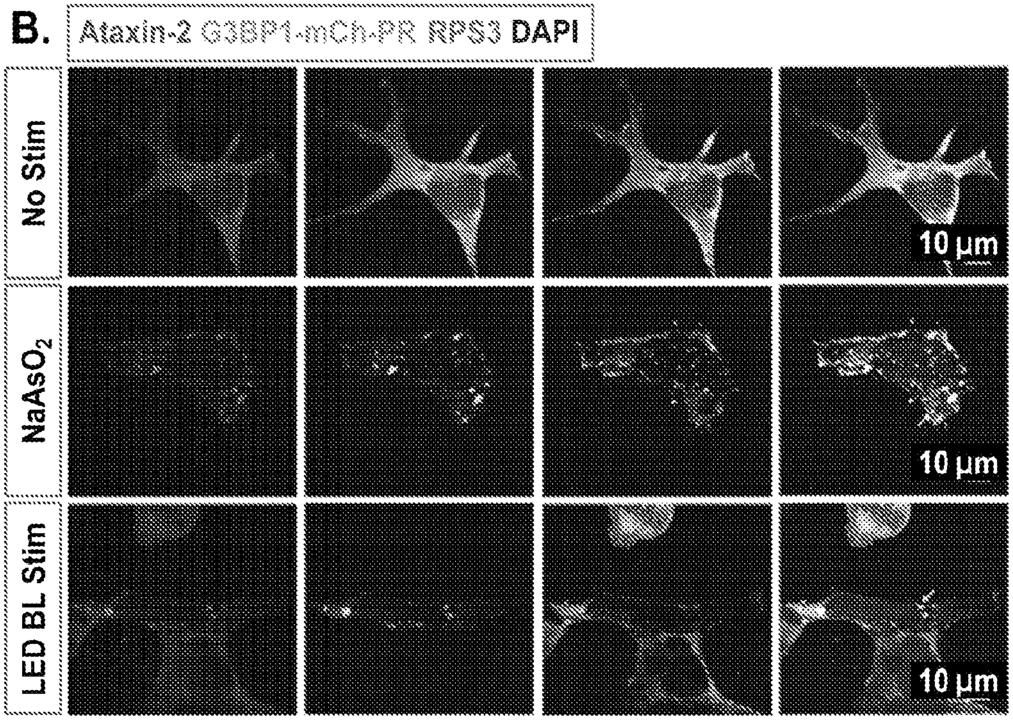
Figure 7A:
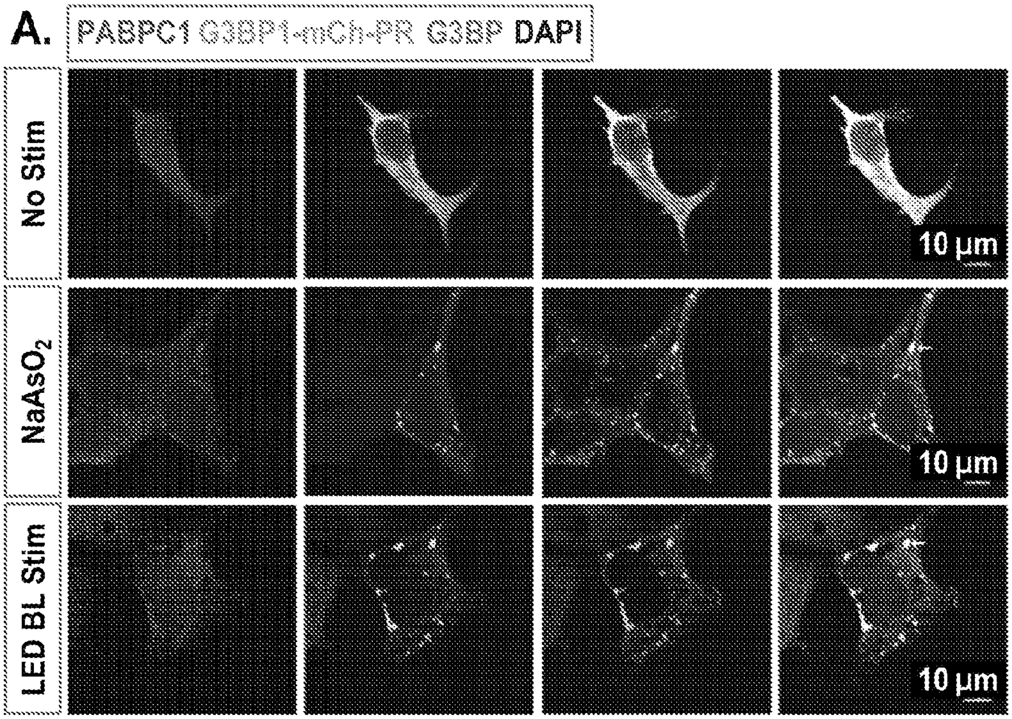
FIGS. 7A-7B. Blue light induced stress granules using G3BP1-NcVVDY50W protein arrangement exhibit a composition that matches sodium arsenite ($NaAsO_2$) induced stress granules and contain the stress granule components, PABPC1 and G3BP (FIG. 7A), as well as eIF3H and eIF4G (FIG. 7B). Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for key markers PABPC1 and G3BP (FIG. 7A), as well as eIF3H and eIF4G (FIG. 7B). Blue light induced stress granules were also found to colocalize with the key stress granule markers PABPC1 and G3BP (FIG. 7A), as well as eIF3H and eIF4G (FIG. 7B).
Figure 7B:
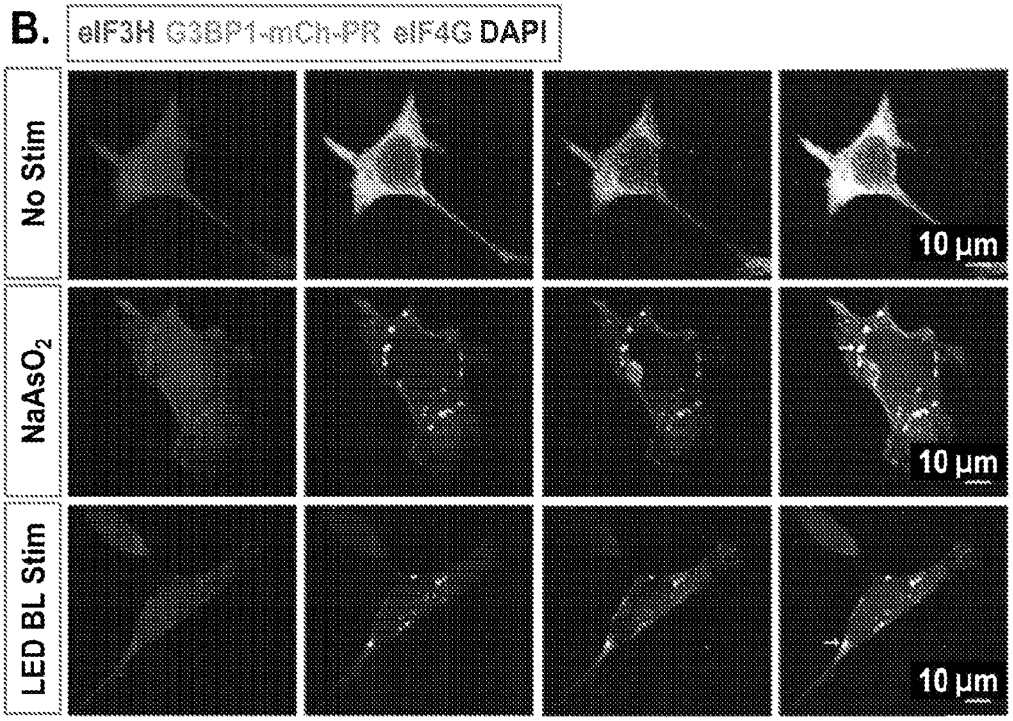
Figure 8:
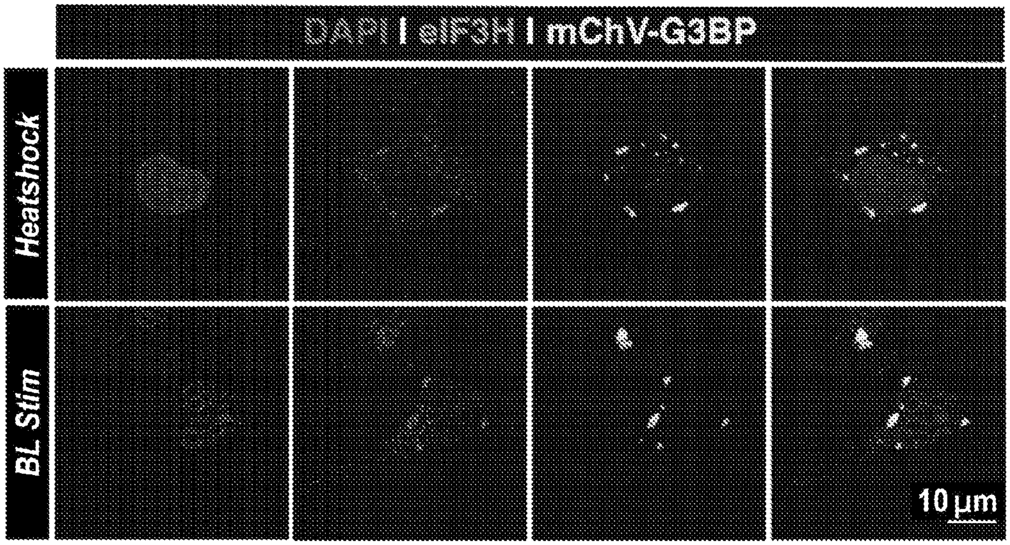
FIG. 8. Blue light induced stress granules using NcVVDY50W-G3BP1 protein arrangement exhibit a composition that matches heat shock induced stress granules and contain the stress granule component, eIF3H protein. Under normal conditions, NcVVDY50W-G3BP1 remains diffuse in the cytoplasm. When endogenous stress granule formation is induced with heat shock, the NcVVDY50W-G3BP1 forms stress granules that stain positive for the key translation factor eIF3H. Blue light induced stress granules were also found to colocalize with the key stress granule marker eIF3H.
Figure 9:
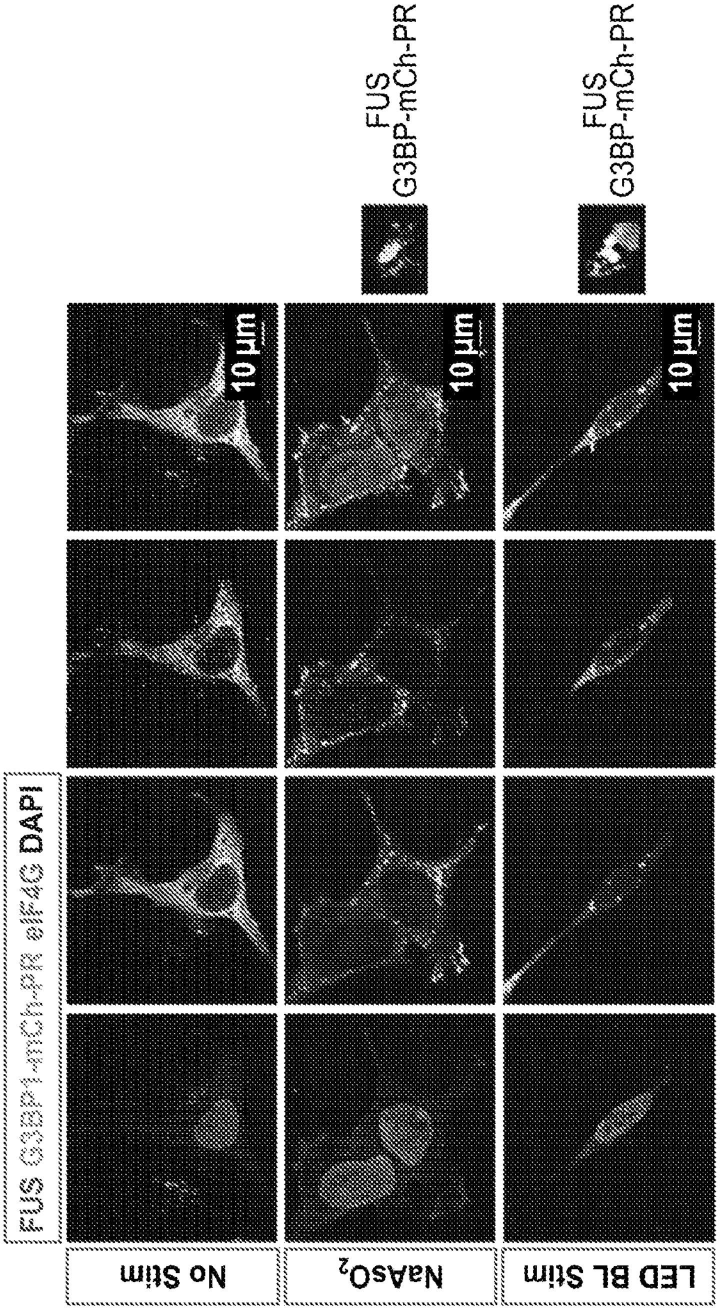
FIG. 9. Blue light induced stress granules using G3BP1-NcVVDY50W protein arrangement exhibit a composition that matches sodium arsenite induced ($NaAsO_2$) stress granules and contain the stress granule components, FUS and eIF4G. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for key markers FUS and eIF4G. Blue light induced stress granules were also found to colocalize with the key stress granule markers FUS and G3BP.
Figure 10:
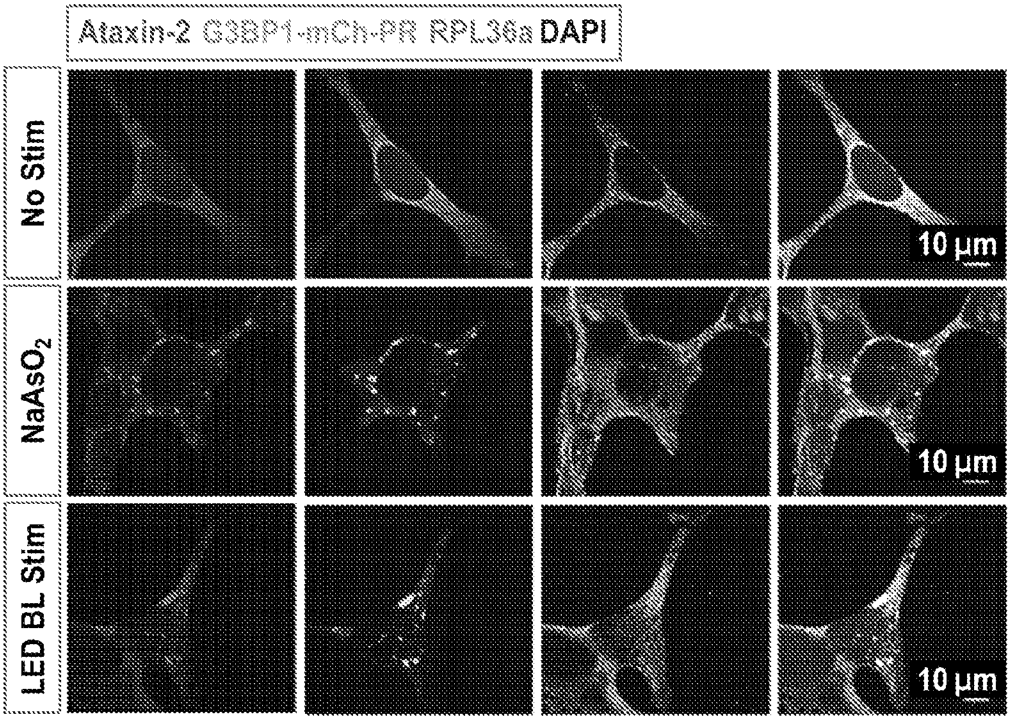
FIG. 10. Blue light induced stress granules using G3BP1-NcVVDY50W protein arrangement exhibit a composition that matches sodium arsenite induced ($NaAsO_2$) stress granules and contain the stress granule component Ataxin-2, but not RPL36a. RPL36a is a component of the 60S ribosome and is not recruited to endogenous stress granules. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for the key marker Ataxin-2, but not RPL36a. Blue light induced stress granules were also found to colocalize with the key stress granule marker Ataxin-2, but not RPL36a. This indicates that seeding light induced stress granule core through G3BP1 oligomerization forms granules that mimic endogenous stress granule structure.
Figure 11:
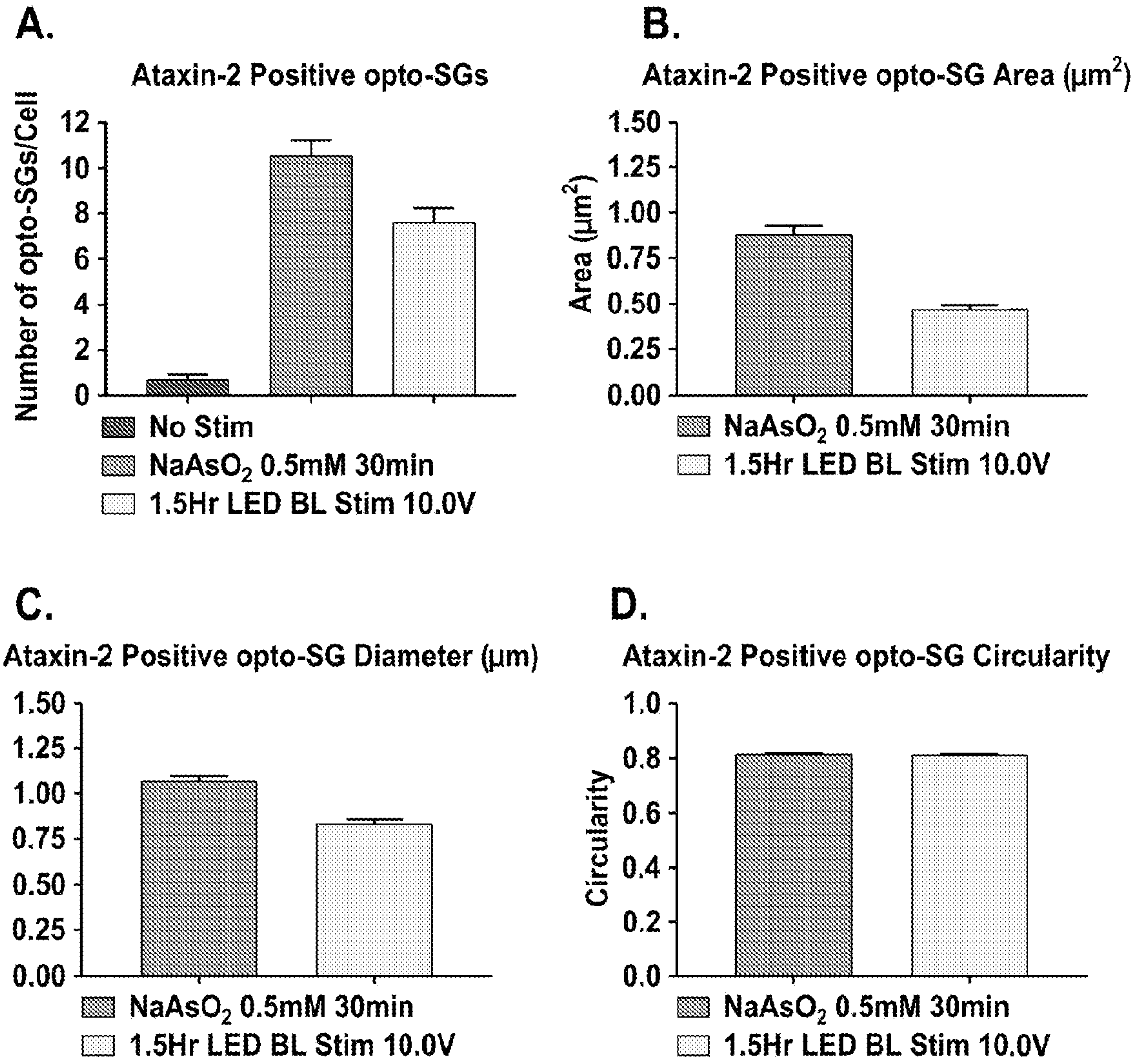
FIGS. 11A-11D. Blue light induced stress granules using G3BP1-NcVVDY50W protein arrangement exhibit a cellular occurrence and structural characteristics that matches sodium arsenite induced ($NaAsO_2$) stress granules and contain the stress granule component Ataxin-2. Under normal conditions, G3BP1-NcVVDY50W remains diffuse in the cytoplasm. When endogenous stress granule formation is induced with $NaAsO_2$ (0.5 mM, 30 min treatment), the G3BP1-NcVVDY50W forms stress granules that stain positive for the key marker Ataxin-2, and occur in the cell 11 times on average (FIG. 11A). They also have a defined shape that gives them a defined area (FIG. 11B), diameter (FIG. 11C) and circularity (FIG. 11D). Blue light induced stress granules were also found to colocalize with the key stress granule marker Ataxin-2, and also have similar characteristics as endogenously formed stress granules (FIG. 11A-11D).
Figure 12:
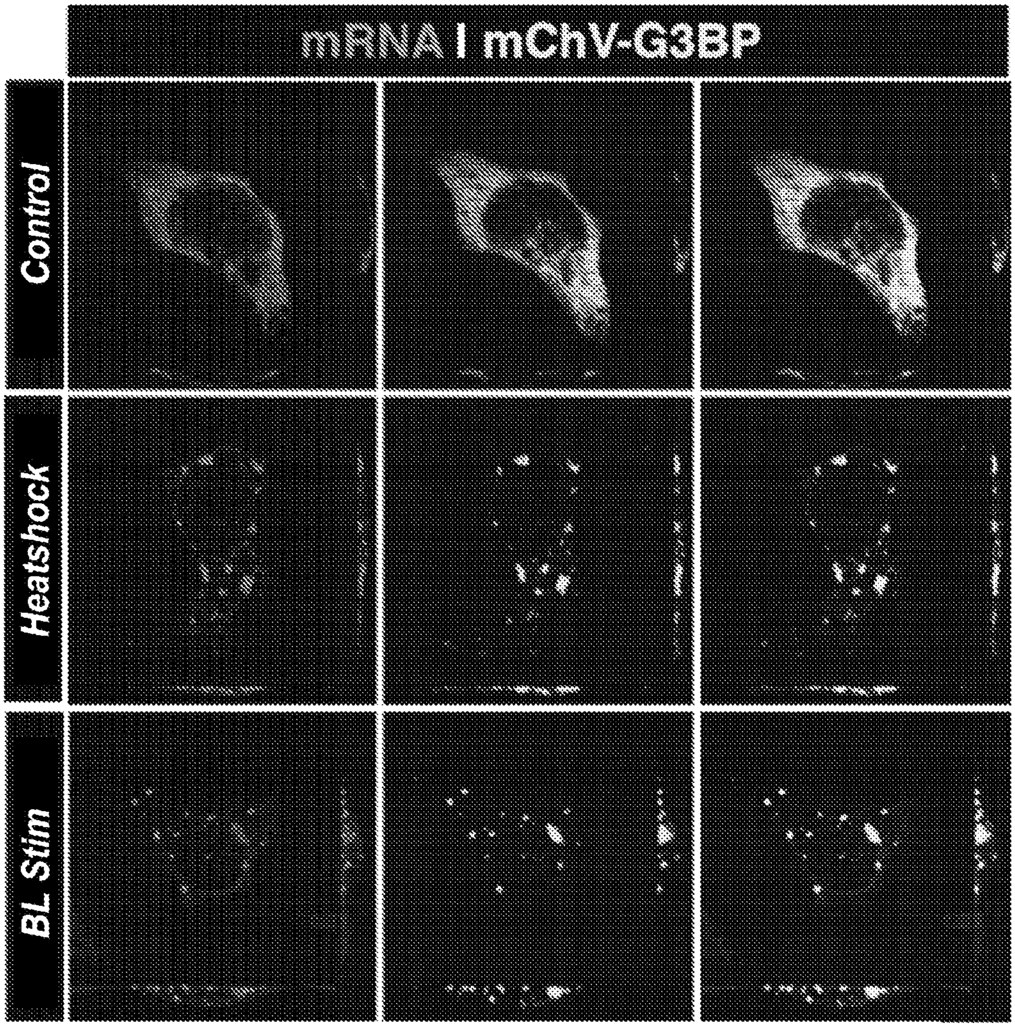
FIG. 12. Blue light induced stress granules using NcVVDY50W-G3BP1 protein arrangement sequester mRNA, indicating they are functional. Under normal conditions, NcVVDY50W-G3BP1 remains diffuse in the cytoplasm. When endogenous stress granule formation was induced with heat shock, the NcVVDY50W-G3BP1 formed stress granules that sequester mRNA, the primary function of stress granules. Blue light induced stress granules also sequester cytoplasmic mRNA indicating they are functional.
Figure 13:
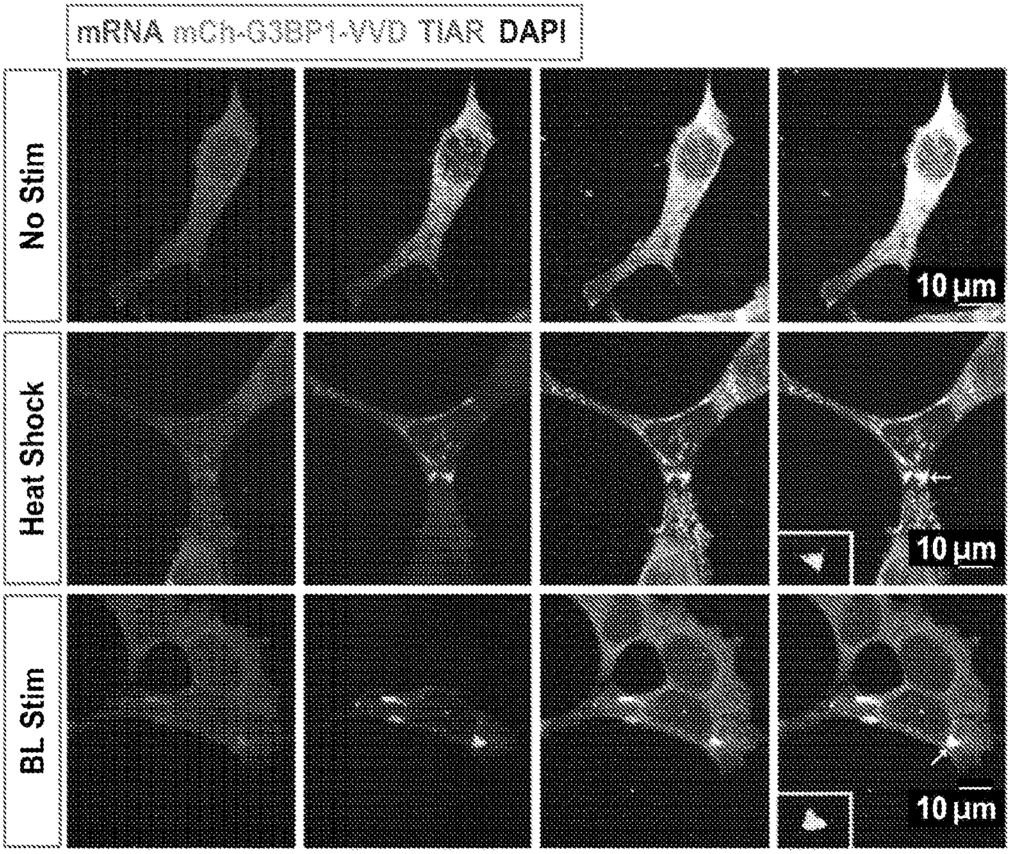
FIG. 13. Blue light induced stress granules using G3BP1-NcVVDY50W protein arrangement sequester mRNA, indicating they are functional. Under normal conditions, G3BP1-NcVVDY50W remains diffuse in the cytoplasm. When endogenous stress granule formation was induced with sodium arsenite ($NaAsO_2$), the G3BP1-NcVVDY50W formed stress granules that sequester mRNA, the primary function of stress granules, and colocalized with the key stress granule marker TIAR. Blue light induced stress granules also sequester cytoplasmic mRNA indicating they are functional, and colocalized with the key stress granule marker TIAR.
Figure 14A:
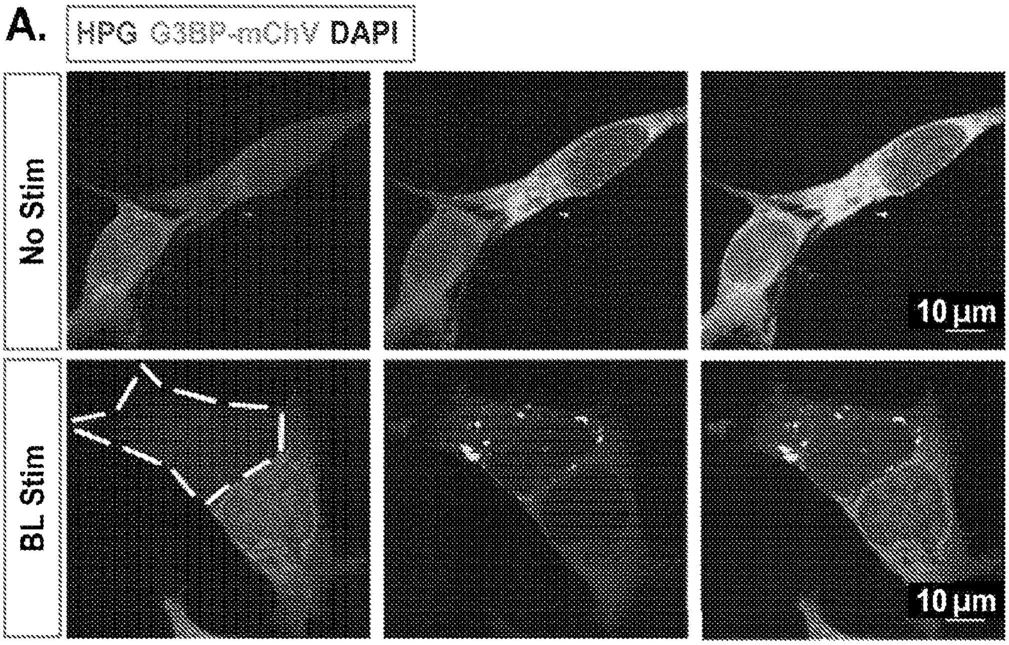
FIGS. 14A-14B. Optogenetically induced stress granules function as endogenous stress granules and stall protein synthesis. The major function of endogenous stress granules is to bind mRNAs and halt protein synthesis until the cellular stress is removed. To test this, cells expressing G3BP1-NcVVDY50W were either exposed to blue light stimulation or not for 30 minutes and protein translation was assessed. Prior to the translation assay, cells were treated with cyclohexamide for one hour to inhibit protein synthesis and then the cyclohexamide was removed and cells were provided L-Homopropargylglycine (HPG) for one hour. HPG acts as a methionine amino acid analog and is incorporated into newly synthesized proteins. Click-iT™ chemistry was then performed to detect HPG and cells were imaged. Green signal indicates newly synthesized proteins during the time at which HPG is present in the media. Cells with light-induced stress granules show little to no HPG signal indicating protein synthesis was stalled during the HPG incubation due to blue-light induced stress granules (FIG. 14A). Analysis indicates that there was a 40% reduction in protein synthesis with light-induced stress granules (FIG. 14B). These results indicate that the light-induced stress granules perform the same key function as endogenous stress granules and inhibit protein synthesis throughout the time of their formation.
Figure 14B:
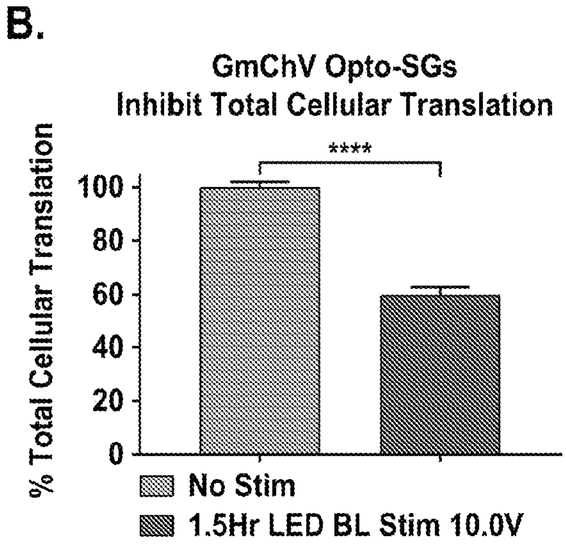

Disclosed herein are compounds, compositions, and methods for inducing membraneless organelles in a cell or animal. The inventors have developed a novel method to induce the formation of membraneless organelles using blue light stimulation. The compounds, compositions, and methods herein allow for the temporal and spatial tunability of membraneless organelle formation. These new methods enable researchers, for the first time, to stimulate the formation of these structures. These methods are used for disease studies and for drug screening.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

The term "polynucleotide", "nucleotide sequence", or "nucleic acid sequence" refers to a single or double stranded polymer composed of nucleotide monomers.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EFla promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" or "expression vector" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "membraneless organelle" as used herein refers to a class of organelles that do not contain a lipid membrane separating them from the nuclear or cytoplasmic liquid. Membraneless organelles contain proteins with low complexity domains or intrinsically disordered regions (LCDs, IDRs) which, when focally concentrated, undergo liquid-liquid phase separation (LLPS) due to attractive forces that force them to self-interact through weak multivalent attractive forces. These forces can be further stabilized by nucleic acids (RNA or DNA) and other molecules commonly found in each membraneless organelle. Nonlimiting examples of membraneless organelles include stress granules, P-bodies, transport RNP, nucleolus, nuclear speckles, nuclear stress bodies, PML bodies, Cajal bodies, and nuclear paraspeckles. The term "membraneless organelle target protein" as used herein refers to any protein containing: a low complexity domain or intrinsically disordered region (LCD, IDR) which, when focally concentrated, undergoes liquid-liquid phase separation (LLPS) due to attractive forces that force them to self-interact through weak multivalent attractive forces; and forming part of a membraneless organelle.

The term "variant" or "derivative" as used herein refers to an amino acid sequence derived from the amino acid sequence of the parent protein having one or more amino acid substitutions, insertions, and/or deletions.

Chimeric Constructs

In one aspect, disclosed herein is a nucleotide sequence encoding a chimeric polypeptide, comprising: a first nucleotide sequence encoding a light-induced oligomerization domain and a second nucleotide sequence encoding a low complexity domain from a membraneless organelle target protein.

In one aspect, disclosed herein is a nucleotide sequence encoding a chimeric polypeptide, comprising: a first nucleotide sequence encoding a low complexity domain from a membraneless organelle target protein and a second nucleotide sequence encoding a light-induced oligomerization domain.

In some embodiments, the low complexity domain from a membraneless organelle target protein has been previously shown to be required for the formation of a membraneless organelle. In some embodiments, the target LCD-containing protein has been shown to prevent specific organelle formation when removed from the cell.

In one aspect, disclosed herein is an expression vector encoding a chimeric polypeptide, comprising: a first nucleotide sequence encoding a light-induced oligomerization domain and a second nucleotide sequence encoding a low complexity domain from a membraneless organelle target protein, wherein the first nucleotide sequence is operably linked to a promoter.

In some embodiments, the expression vector encoding a chimeric polypeptide is comprised in a plasmid or in a virus or viral vector. A plasmid or a viral vector can be capable of extrachromosomal replication or, optionally, can integrate into the host genome. As used herein, the term "integrated" used in reference to an expression vector (e.g., a plasmid or viral vector) means the expression vector, or a portion thereof, is incorporated (physically inserted or ligated) into the chromosomal DNA of a host cell. As used herein, a "viral vector" refers to a virus-like particle containing genetic material which can be introduced into a eukaryotic cell without causing substantial pathogenic effects to the eukaryotic cell. A wide range of viruses or viral vectors can be used for transduction, but should be compatible with the cell type the virus or viral vector are transduced into (e.g., low toxicity, capability to enter cells). Suitable viruses and viral vectors include adenovirus, lentivirus, retrovirus, among others. In some embodiments, the expression vector encoding a chimeric polypeptide is a naked DNA or is comprised in a nanoparticle (e.g., liposomal vesicle, porous silicon nanoparticle, gold-DNA conjugate particle, polyethylenimine polymer particle, cationic peptides, etc.).

The fusion constructs disclosed herein can be fused with the light-induced oligomerization domain at either the 5' end or the 3' end of the nucleic acid sequence or protein sequence. Thus, for every chimeric construct disclosed herein, the fusion of the chimeric polypeptide with the light-induced oligomerization and the membraneless organelle target protein reversed (in a 5' to 3' direction) is also disclosed. In one aspect, disclosed herein is an expression vector encoding a chimeric polypeptide, comprising: a first nucleotide sequence encoding a low complexity domain from a membraneless organelle target protein and a second nucleotide sequence encoding a light-induced oligomerization domain, wherein the first nucleotide sequence is operably linked to a promoter.

In some embodiments, the first nucleotide sequence is positioned upstream of the second nucleotide sequence. In some embodiments, the first nucleotide sequence is positioned downstream of the second nucleotide sequence.

In some embodiments, the nucleotide sequence (nucleic acid sequence) is an isolated or purified nucleotide sequence (nucleic acid sequence). In some embodiments, the chimeric polypeptide is an isolated or purified chimeric polypeptide.

In some embodiments, where the sequences disclosed herein contain a methionine at the start of the protein, the protein without the methionine is also disclosed. In some embodiments, where the sequences disclosed herein do not contain a methionine at the start of the protein, the protein with the methionine at the start of the protein is also disclosed.

In one aspect, disclosed herein is a cell comprising a nucleotide sequence encoding a chimeric polypeptide, comprising: a first nucleotide sequence encoding a light-induced oligomerization domain and a second nucleotide sequence encoding a membraneless organelle target protein.

In one aspect, disclosed herein is a cell comprising a nucleotide sequence encoding a chimeric polypeptide, comprising: a first nucleotide sequence encoding a membraneless organelle target protein and a second nucleotide sequence encoding a light-induced oligomerization domain.

In one aspect, disclosed herein is a chimeric polypeptide comprising: a light-induced oligomerization domain; and a low complexity domain from a membraneless organelle target protein.

In one aspect, disclosed herein is a chimeric polypeptide comprising: a low complexity domain from a membraneless organelle target protein; and a light-induced oligomerization domain.

In one embodiment, the light-induced oligomerization domain is selected from the group consisting of CRY2 PHR, CRY2OLIG, NcVVD, NcVVDY50W, NcVVDY50W/I74V/I85V/LINKERA, NcVVDY50W/I52C/I74V/I85V/LINKERA, NcVVDY50W/C71V/174V/185V/LINKERA, NcVVDY50W/I52C/C71V/I74V/I85V/LINKERA, NcVVDY50W/I74V/I85V/LINKERB, NcVVDY50W/152C/174V/185V/LINKERB, NcVVDY50W/C71V/174V/185V/LINKERB, NcVVDY50W/I52C/C71V/I74V/I85V/LINKERB, NcLOV, and VfAU1LOV. In one embodiment, the light-induced oligomerization domain is selected from the group CRY2 PHR, CRY2OLIG, NcVVD, NcVVDY50W, NcVVDY50W/I74V/I85V/LINKERA, NcVVDY50W/I52C/I74V/I85V/LINKERA, NcVVDY50W/C71V/I74V/I85V/LINKERA, NcVVDY50W/I52C/C71V/I74V/I85V/LINKERA, NcVVDY50W/I74V/I85V/LINKERB, NcVVDY50W/152C/174V/185V/LINKERB, NcVVDY50W/C71V/174V/185V/LINKERB, NcVVDY50W/I52C/C71V/I74V/I85V/LINKERB, NcLOV, VfAU1LOV, YtvA, EL222, RsLOV, AsLOV2, a variant thereof, or a fragment thereof.

In one embodiment, the light-induced oligomerization domain is NcVVDY50W. In one embodiment, the light-induced oligomerization domain is NcVVDY50W/I74/I85/LINKERA. In one embodiment, the light-induced oligomerization domain is NcVVDY50W/I52C/I74/I85/LINKERA. In one embodiment, the light-induced oligomerization domain is NcVVDY50W/C71V/I74/I85/LINKERA. In one embodiment, the light-induced oligomerization domain is NcVVDY50W/I52C/C71V/I74/I85/LINKERA. In one embodiment, the light-induced oligomerization domain is NcVVDY50W/I74/I85/LINKERB. In one embodiment, the light-induced oligomerization domain is NcVVDY50W/I52C/I74/I85/LINKERB. In one embodiment, the light-induced oligomerization domain is NcVVDY50W/C71V/I74/I85/LINKERB. In one embodiment, the light-induced oligomerization domain is NcVVDY50W/I52C/C71V/I74/I85/LINKERB. In one embodiment, the light-induced oligomerization domain is CRY2OLIG. In one embodiment, the light-induced oligomerization domain is CRY2 PHR. In one embodiment, the light-induced oligomerization domain is VfAU1LOV. In one embodiment, the light-induced oligomerization domain is YtvA. In one embodiment, the light-induced oligomerization domain is EL222. In one embodiment, the light-induced oligomerization domain is RsLOV. In one embodiment, the light-induced oligomerization domain is AsLOV2.

In one embodiment, the light-induced oligomerization domain comprises a LOV domain. In one embodiment, the light-induced oligomerization domain comprises a LOV domain from the VVD protein. In one embodiment, the light-induced oligomerization domain comprises a LOV domain from the LOV protein. In one embodiment, the light-induced oligomerization domain comprises a PHR domain. In one embodiment, the light-induced oligomerization domain comprises a PHR domain, from the CRY2 protein.

In one embodiment, the light-induced oligomerization domain is at least 90% identical to CRY2 PHR. In one embodiment, the light-induced oligomerization domain is at least 90% identical to NcVVD. In one embodiment, the light-induced oligomerization domain is at least 90% identical to NcVVDY50W. In one embodiment, the light-induced oligomerization domain is at least 90% identical to NcLOV. In one embodiment, the light-induced oligomerization domain is CRY2OLIG. In one embodiment, the light-induced oligomerization domain is at least 90% identical to CRY2 PHR. In one embodiment, the light-induced oligomerization domain is at least 90% identical to VfAU1LOV. In one embodiment, the light-induced oligomerization domain is at least 60% (for example, at least 60%, at least 70%, at least 80%, at least 90%, at least 95%) identical to CRY2 PHR, CRY2OLIG, NcVVD, NcVVDY50W, NcLOV, and VfAU1LOV. In one embodiment, the light-induced oligomerization domain is at least 60% (for example, at least 60%, at least 70%, at least 80%, at least 90%, at least 95%) identical to the PHR or LOV domain from the following proteins: CRY2 PHR, CRY2OLIG, NcVVD, NcVVDY50W, NcLOV, and VfAU1LOV.

In one embodiment, the light-induced oligomerization domain is at least 60% (for example, at least 60%, at least 70%, at least 80%, at least 90%, at least 95%) identical to a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:107, SEQ ID NO:108, SEQ ID NO:109, and SEQ ID NO:110. In some embodiments, a protein fragment of SEQ ID NO:1, SEQ ID NO:2, SEQ ID NO:3, SEQ ID NO:4, SEQ ID NO:5, SEQ ID NO:6, SEQ ID NO:7, SEQ ID NO:107, SEQ ID NO:108, SEQ ID NO:109, or SEQ ID NO:110 is used as the light-induced oligomerization domain. In some embodiments, a protein fragment of SEQ ID NO:1, SEQ ID NO:2, SEQ ID NO:3, SEQ ID NO:4, SEQ ID NO:5, SEQ ID NO:6, SEQ ID NO:7, SEQ ID NO:107, SEQ ID NO:108, SEQ ID NO:109, or SEQ ID NO:110 is used as the light-induced oligomerization domain, wherein the fragment is sufficient for light-induced oligomerization.

In one embodiment, the light-induced oligomerization domain is a LOV domain. In one embodiment, the light-induced oligomerization domain is a PHR domain. In one embodiment, the light-induced oligomerization domain is a LOV domain selected from NcVVD, NcVVDY50W, and NcLOV. In one embodiment, the light-induced oligomerization domain is a PHR domain selected from CRY2 PHR and CRY2OLIG.

In one embodiment, the low complexity domain is from a membraneless organelle target protein. In one embodiment, the low complexity domain from a membraneless organelle target protein is from a cytoplasmic membraneless organelle target protein.

In one embodiment, the low complexity domain from a membraneless organelle target protein is from a stress granule target protein. In one embodiment, the low complexity domain is from a stress granule target protein selected from the group consisting of PABC1, TIAR, G3BP1, G3BP2, DDX6, TDRD3, ATXN2, variants thereof, and fragments thereof. In one embodiment, the low complexity domain is from a stress granule target protein selected from the group consisting of an amino acid sequence with at least 60% (for example, at least 60%, at least 70%, at least 80%, at least 90%, at least 95%) identity to PABC1, TIAR, G3BP1, G3BP2, DDX6, TDRD3, ATXN2, variants thereof, and fragments thereof.

In one embodiment, the low complexity domain from a membraneless organelle target protein is G3BP1. In one embodiment, the low complexity domain from a membraneless organelle target protein is the G3BP1 protein lacking an NTF2 domain. In one embodiment, the low complexity domain from a membraneless organelle target protein is the G3BP1 protein lacking an NTF2 domain and replaced with a oligomerizing or dimerizing photoreceptor. In one embodiment, the low complexity domain from a membraneless organelle target protein is an acidic domain truncated G3BP1. In one embodiment, the low complexity domain from a membraneless organelle target protein is a PxxP domain truncated G3BP1. In one embodiment, the low complexity domain from a membraneless organelle target protein is an RRM domain truncated G3BP1. In one embodiment, the low complexity domain from a membraneless organelle target protein is an RGG domain truncated G3BP1.

In one embodiment, the low complexity domain is from a stress granule target protein selected from the group consisting of PABC1, Gle1, TIA1, TIAR, G3BP1, mTOR, DYRK3, Staufen, eIF3H, eIF4A, eIF4E, eIF4G, TTP, HuR, FMRP, FXR1/2, ZBP1, RSK2, NXF1, Mcm2, Mcm4, DDX6 (Dhh1), DPYSL3, DCTN1, USP10, CAPRIN1, variants thereof, and fragments thereof. In one embodiment, the low complexity domain is from a stress granule target protein selected from the group consisting of an amino acid sequence with at least 60% (for example, at least 60%, at least 70%, at least 80%, at least 90%, at least 95%) identity to PABC1, Gle1, TIA1, TIAR, G3BP1, mTOR, DYRK3, Staufen, eIF3H, eIF4A, eIF4E, eIF4G, TTP, HuR, FMRP, FXR1/2, ZBP1, RSK2, NXF1, Mcm2, Mcm4, DDX6 (Dhh1), DPYSL3, DCTN1, USP10, CAPRIN1, variants thereof, and fragments thereof.

In one embodiment, the low complexity domain from a membraneless organelle target protein is from a P-body target protein. In one embodiment, the low complexity domain is from a P-body target protein selected from the group consisting of DCP1A, DCP2, LSM1, TNRC6A, MEX3A, EDC4, XRN1, DDX3X, variants thereof, and fragments thereof. In one embodiment, the low complexity domain is from a P-body target protein selected from the group consisting of Dcp1, Dcp2, Lsm1, Hedis, GW182, Pop2, Pan2, Mex3A, Pat1, Edc4, Xm1, DDX3, DDX6, variants thereof, and fragments thereof. In one embodiment, the low complexity domain is from a P-body target protein selected from the group consisting of an amino acid sequence with at least 60% (for example, at least 60%, at least 70%, at least 80%, at least 90%, at least 95%) identity to Dcp1, Dcp2, Lsm1, Hedis, GW182, Pop2, Pan2, Mex3A, Pat1, Edc4, Xrn1, DDX3, DDX6, variants thereof, and fragments thereof.

In one embodiment, the low complexity domain from a membraneless organelle target protein is from a ribonuclear transport granule target protein. In one embodiment, the low complexity domain is from a ribonuclear transport granule target protein selected from the group consisting of IGFBP1, STAU1, PURA, FMR1, FXR1, FXR2, variants thereof, and fragments thereof. In one embodiment, the low complexity domain is from a ribonuclear transport granule target protein selected from the group consisting of an amino acid sequence with at least 60% (for example, at least 60%, at least 70%, at least 80%, at least 90%, at least 95%) identity to IGFBP1, STAU1, PURA, FMR1, FXR1, FXR2, variants thereof, and fragments thereof.

In one embodiment, the low complexity domain from a membraneless organelle target protein is from a nuclear membraneless organelle target protein.

In one embodiment, the low complexity domain from a membraneless organelle target protein is from a nucleolus target protein. In one embodiment, the low complexity domain is from a nucleolus target protein selected from the group consisting of NCL, NPM1, 1-BL, variants thereof, and fragments thereof. In one embodiment, the low complexity domain is from a nucleolus target protein selected from the group consisting of NCL, NPM1, FBL, HNRNPA3, HspA8, RPS19, HMGB2, RCC2, KI-67, variants thereof, and fragments thereof. In one embodiment, the low complexity domain is from a nucleolus target protein selected from the group consisting of an amino acid sequence with at least 60% (for example, at least 60%, at least 70%, at least 80%, at least 90%, at least 95%) identity to NCL, NPM1, FBL, HNRNPA3, HspA8, RPS19, HMGB2, RCC2, KI-67, variants thereof, and fragments thereof.

In one embodiment, the low complexity domain from a membraneless organelle target protein is from a nuclear speckle target protein. In one embodiment, the low complexity domain is from a nuclear speckle target protein selected from the group consisting of SRSF2, PNN, SRSF1, variants thereof, and fragments thereof. In one embodiment, the low complexity domain is from a nuclear speckle target protein selected from the group consisting of eIF4E, eIF4AIII, SC35, Pinin, SRSF1, variants thereof, and fragments thereof. In one embodiment, the low complexity domain is from a nuclear speckle target protein selected from the group consisting of an amino acid sequence with at least 60% (for example, at least 60%, at least 70%, at least 80%, at least 90%, at least 95%) identity to eIF4E, eIF4AIII, SC35, Pinin, SRSF1, variants thereof, and fragments thereof.

In one embodiment, the low complexity domain from a membraneless organelle target protein is from a nuclear stress body target protein. In one embodiment, the low complexity domain is from a nuclear stress body target protein selected from the group consisting of SAFB, variants thereof, and fragments thereof. In one embodiment, the low complexity domain is from a nuclear stress body target protein selected from the group consisting of an amino acid sequence with at least 60% (for example, at least 60%, at least 70%, at least 80%, at least 90%, at least 95%) identity to SAFB, variants thereof, and fragments thereof.

In one embodiment, the low complexity domain from a membraneless organelle target protein is from a nuclear paraspeckle target protein. In one embodiment, the low complexity domain is from a nuclear paraspeckle target protein selected from the group consisting of SFPQ, NONO, PSPC1, variants thereof, and fragments thereof. In one embodiment, the low complexity domain is from a nuclear paraspeckle target protein selected from the group consisting of PSF/SFPQ, P54NRB/NONO, PSPC1, variants thereof, and fragments thereof. In one embodiment, the low complexity domain is from a nuclear paraspeckle target protein selected from the group consisting of an amino acid sequence with at least 60% (for example, at least 60%, at least 70%, at least 80%, at least 90%, at least 95%) identity to PSF/SFPQ, P54NRB/NONO, PSPC1, variants thereof, and fragments thereof.

In one embodiment, the low complexity domain from a membraneless organelle target protein is from a cajal body target protein. In one embodiment, the low complexity domain is from a cajal body target protein selected from the group consisting of COIL. In one embodiment, the low complexity domain is from a caj al body target protein selected from the group consisting of Coilin, SMN1, SMN2, FLASH (CASP8AP2), variants thereof, and fragments thereof. In one embodiment, the low complexity domain is from a cajal body target protein selected from the group consisting of an amino acid sequence with at least 60% (for example, at least 60%, at least 70%, at least 80%, at least 90%, at least 95%) identity to Coilin, SMN1, SMN2, FLASH (CASP8AP2), variants thereof, and fragments thereof.

In one embodiment, the low complexity domain from a membraneless organelle target protein is from a PML body target protein. In one embodiment, the low complexity domain is from a PML body target protein selected from the group consisting of PML, variants thereof, and fragments thereof. In one embodiment, the low complexity domain is from a PML body target protein selected from the group consisting of an amino acid sequence with at least 60% (for example, at least 60%, at least 70%, at least 80%, at least 90%, at least 95%) identity to PML, variants thereof, and fragments thereof.

In one embodiment, the low complexity domain from a membraneless organelle target protein is from a chromatoid body/germ granule target protein. In one embodiment, the low complexity domain is from a chromatoid body/germ granule target protein selected from the group consisting of DDX4, variants thereof, and fragments thereof. In one embodiment, the low complexity domain is from a chromatoid body/germ granule target protein selected from the group consisting of an amino acid sequence with at least 60% (for example, at least 60%, at least 70%, at least 80%, at least 90%, at least 95%) identity to DDX4, variants thereof, and fragments thereof.

In one embodiment, the cell is a mammalian cell. In one embodiment, the cell is a human cell. In one embodiment, the cell is an isolated cell.

In one embodiment, the blue light has a wavelength between 405 nm and 499 nm. In one embodiment, the blue light has a wavelength of about 465 nm.

In one embodiment, the low complexity domain from a membraneless organelle target protein is selected from Tables 2-10. In one embodiment, the low complexity domain is from any membraneless organelle target protein. In one embodiment, the low complexity domain is from any membraneless organelle target protein that, when focally concentrated, undergoes liquid-liquid phase separation (LLPS) due to attractive forces that force them to self-interact through weak multivalent attractive forces.

In one embodiment, the low complexity domain from a membraneless organelle target protein is selected from the group consisting of an amino acid sequence with at least 90% identity to a membraneless organelle target protein is selected from Tables 2-10. In one embodiment, the low complexity domain from a membraneless organelle target protein is selected from the group consisting of an amino acid sequence with at least 90% identity to a low complexity domain from a membraneless organelle target protein is selected from Table 2. In one embodiment, the low complexity domain from a membraneless organelle target protein is selected from the group consisting of an amino acid sequence with at least 90% identity to a low complexity domain from a membraneless organelle target protein is selected from Table 3. In one embodiment, the low complexity domain from a membraneless organelle target protein is selected from the group consisting of an amino acid sequence with at least 90% identity to a low complexity domain from a membraneless organelle target protein is selected from Table 4. In one embodiment, the low complexity domain from a membraneless organelle target protein is selected from the group consisting of an amino acid sequence with at least 90% identity to a low complexity domain from a membraneless organelle target protein is selected from Table 5. In one embodiment, the low complexity domain from a membraneless organelle target protein is selected from the group consisting of an amino acid sequence with at least 90% identity to a low complexity domain from a membraneless organelle target protein is selected from Table 6. In one embodiment, the low complexity domain from a membraneless organelle target protein is selected from the group consisting of an amino acid sequence with at least 90% identity to a low complexity domain from a membraneless organelle target protein is selected from Table 7. In one embodiment, the low complexity domain from a membraneless organelle target protein is selected from the group consisting of an amino acid sequence with at least 90% identity to a low complexity domain from a membraneless organelle target protein is selected from Table 8. In one embodiment, the low complexity domain from a membraneless organelle target protein is selected from the group consisting of an amino acid sequence with at least 90% identity to a low complexity domain from a membraneless organelle target protein is selected from Table 9. In one embodiment, the low complexity domain from a membraneless organelle target protein is selected from the group consisting of an amino acid sequence with at least 90% identity to a low complexity domain from a membraneless organelle target protein is selected from Table 10. In one embodiment, the low complexity domain from a membraneless organelle target protein is selected from an orthologue of the group consisting of a membraneless organelle target protein selected from Tables 2-10.

In one embodiment, the low complexity domain from a membraneless organelle target protein is selected from the group consisting of an amino acid sequence with at least 60% (for example, at least 60%, at least 70%, at least 80%, at least 90%, at least 95%) identity to a membraneless organelle target protein is selected from Tables 2-10. In one embodiment, the low complexity domain is a variant or a fragment of a membraneless organelle target protein, wherein the membraneless organelle target protein is selected from Tables 2-10.

In one embodiment, the low complexity domain from a membraneless organelle target protein is G3BP1. In one embodiment, the low complexity domain from a membraneless organelle target protein is selected from the group consisting of an amino acid sequence with at least 60% (for example, at least 60%, at least 70%, at least 80%, at least 90%, at least 95%) identity to G3BP1.

In one embodiment, a VVD light-induced oligomerization domain is fused to a low complexity domain of G3BP1. In one embodiment, a VVD light-induced oligomerization is fused to full length G3BP1 (comprising a low complexity domain). In one embodiment, a NcVVDY50W light-induced oligomerization domain is fused to a low complexity domain of G3BP1. In one embodiment, a NcVVDY50W light-induced oligomerization is fused to full length G3BP1 (comprising a low complexity domain).

In one embodiment, the nucleotide sequence encoding the chimeric polypeptide may further comprise a nucleotide sequence encoding a fluorescent protein (to allow visualization of the membraneless organelles by fluorescence). In one embodiment, the fluorescent protein is mCherry (mCh). In some embodiments, the fluorescent protein is GFP or YFP.

In some embodiments, the chimeric polypeptide comprises an amino acid sequence selected from SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, or SEQ ID NO:106.

In some embodiments, the chimeric polypeptide comprises an amino acid sequence that is at least 60% (for example, at least 60%, at least 70%, at least 80%, at least 90%, at least 95%) identical to a sequence selected from one of SEQ ID NO:9 to 106. In some embodiments, a protein fragment of one of SEQ ID NO:9 to 106 is used. In some embodiments, a protein fragment of one of SEQ ID NO:9 to 106 is used, wherein the fragment is sufficient for light-induced oligomerization.

Methods

In one aspect, disclosed herein is a method of inducing a membraneless organelle in a cell, comprising the steps:

introducing into the cell an expression vector encoding a chimeric polypeptide, comprising:

- a first nucleotide sequence encoding a light-induced oligomerization domain and a second nucleotide sequence encoding a low complexity domain from a membraneless organelle target protein, wherein the first nucleotide sequence is operably linked to a promoter;

expressing the chimeric polypeptide; and inducing oligomerization of the chimeric polypeptide by stimulation with blue light.

In another aspect, disclosed herein is a method of screening for an agent that modulates formation of a membraneless organelle, comprising the steps:

introducing into a cell an expression vector encoding a chimeric polypeptide, comprising:

- a first nucleotide sequence encoding a light-induced oligomerization domain and a second nucleotide sequence encoding a low complexity domain from a membraneless organelle target protein, wherein the first nucleotide sequence is operably linked to a promoter;

expressing the chimeric polypeptide;

introducing the agent into a culture media comprising the cell;

inducing oligomerization of the chimeric polypeptide by stimulation with blue light; and determining modulation of the formation of the membraneless organelle by the agent.

In one aspect, disclosed herein is a method of inducing a membraneless organelle in a cell, comprising the steps:

introducing into the cell an expression vector encoding a chimeric polypeptide, comprising:

- a first nucleotide sequence encoding a low complexity domain from a membraneless organelle target protein and a second nucleotide sequence encoding a light-induced oligomerization domain, wherein the first nucleotide sequence is operably linked to a promoter;

expressing the chimeric polypeptide; and inducing oligomerization of the chimeric polypeptide by stimulation with blue light.

In another aspect, disclosed herein is a method of screening for an agent that modulates formation of a membraneless organelle, comprising the steps:

introducing into a cell an expression vector encoding a chimeric polypeptide, comprising:

a first nucleotide sequence encoding a low complexity domain from a membraneless organelle target protein and a second nucleotide sequence encoding a light-induced oligomerization domain, wherein the first nucleotide sequence is operably linked to a promoter;

expressing the chimeric polypeptide;

introducing the agent into a culture media comprising the cell;

inducing oligomerization of the chimeric polypeptide by stimulation with blue light; and determining modulation of the formation of the membraneless organelle by the agent.

In some embodiments, the modulation includes the increase in formation of membraneless organelles. In some embodiments, the modulation includes the decrease in formation of membraneless organelles.

In one embodiment, the light-induced oligomerization domain is selected from the group consisting of CRY2 PHR, CRY2OLIG, NcVVD, NcVVDY50W, NcVVDY50W/I74V/I85V/LINKERA, NcVVDY50W/I52C/I74V/I85V/LINKERA, NcVVDY50W/C71V/174V/185V/LINKERA, NcVVDY50W/I52C/C71V/I74V/I85V/LINKERA, NcVVDY50W/I74V/I85V/LINKERB, NcVVDY50W/152C/174V/185V/LINKERB, NcVVDY50W/C71V/174V/185V/LINKERB, NcVVDY50W/I52C/C71V/I74V/I85V/LINKERB, NcLOV, and VfAU1LOV. In one embodiment, the light-induced oligomerization domain is selected from the group CRY2 PHR, CRY2OLIG, NcVVD, NcVVDY50W, NcVVDY50W/174V/185V/LINKERA, NcVVDY50W/152C/174V/185V/LINKERA, NcVVDY50W/C71V/I74V/I85V/LINKERA, NcVVDY50W/I52C/C71V/I74V/I85V/LINKERA, NcVVDY50W/I74V/I85V/LINKERB, NcVVDY50W/152C/174V/185V/LINKERB, NcVVDY50W/C71V/174V/185V/LINKERB, NcVVDY50W/I52C/C71V/I74V/I85V/LINKERB, NcLOV, VfAU1LOV, YtvA, EL222, RsLOV, AsLOV2, a variant thereof, or a fragment thereof. In one embodiment, the light-induced oligomerization domain is NcVVDY50W. In one embodiment, the light-induced oligomerization domain is CRY2OLIG. In one embodiment the light-induced oligomerization domain in CRY2 PHR.

In one embodiment, the low complexity domain from a membraneless organelle target protein is selected from the group consisting of an amino acid sequence of a membraneless organelle target protein listed in Tables 2-10. In one embodiment, the low complexity domain from a membraneless organelle target protein is selected from the group consisting of an amino acid sequence with at least 90% identity to a membraneless organelle target protein listed in Tables 2-10. In one embodiment, the low complexity domain from a membraneless organelle target protein is selected from the group consisting of an amino acid sequence with at least 60% (for example, at least 60%, at least 70%, at least 80%, at least 90%, at least 95%) identity to a membraneless organelle target protein is selected from Tables 2-10. In one embodiment, the low complexity domain from a membraneless organelle target protein is G3BP1. In one embodiment, the low complexity domain from a membraneless organelle target protein is an NTF2 domain truncated G3BP1. In one embodiment, the low complexity domain from a membraneless organelle target protein is an acidic domain truncated G3BP1. In one embodiment, the low complexity domain from a membraneless organelle target protein is a PxxP domain truncated G3BP1. In one embodiment, the low complexity domain from a membraneless organelle target protein is an RRM domain truncated G3BP1. In one embodiment, the low complexity domain from a membraneless organelle target protein is an RGG domain truncated G3BP1.

In one embodiment, the cell is a mammalian cell. In one embodiment, the cell is a human cell. In one embodiment, the cell is selected from the group consisting of yeast, insect, avian, fish, worm, amphibian, xenopus, bacteria, algae and mammalian cells. In one embodiment, disclosed herein is a non-human transgenic organism, wherein the organism is an insect, fish, bird, worm, amphibian, xenopus, or non-human mammal. In one embodiment, the cell can be a glial cell or a neuronal cell.

As used herein, the term "introducing," "introduce," and grammatical variations thereof, as it relates to introducing an expression vector into a cell, refers to any method suitable for transferring the expression vector into the cell. The term includes as examples, but is not limited to, conjugation, transformation/transfection (e.g., divalent cation exposure, heat shock, electroporation), nuclear microinjection, incubation with calcium phosphate polynucleotide precipitate, high velocity bombardment with polynucleotide-coated microprojectiles (e.g., via gene gun), lipofection, cationic polymer complexation (e.g., DEAE-dextran, polyethylenimine), dendrimer complexation, mechanical deformation of cell membranes (e.g., cell-squeezing), sonoporation, optical transfection, impalefection, hydrodynamic polynucleotide delivery, *Agrobacterium*-mediated transformation, transduction (e.g., transduction with a virus or viral vector), natural or artificial competence, protoplast fusion, magnetofection, nucleofection, or combinations thereof. An introduced expression vector, or a polynucleotide therefrom, can be genetically integrated or exist extrachromosomally.

A range of blue light wavelengths can be used in the disclosed methods. In one embodiment, the blue light has a wavelength from about 400 nm to about 500 nm. In one embodiment, the blue light has a wavelength from about 405 nm to about 499 nm. In one embodiment, the blue light has a wavelength from about 420 nm to about 490 nm. In one embodiment, the blue light has a wavelength from about 450 nm to about 490 nm. In one embodiment, the blue light has a wavelength from about 460 nm to about 495 nm. In one embodiment, the blue light has a wavelength of about 488 nm. In one embodiment, the blue light has a wavelength of about 475 nm. In one embodiment, the blue light has a wavelength of about 465 nm. In one embodiment, the blue light has a wavelength between 405 nm and 499 nm.

In one embodiment, the blue light has a wavelength of about 405 nm, about 410 nm, about 415 nm, about 420 nm, about 425 nm, about 430 nm, about 435 nm, about 440 nm, about 445 nm, about 450 nm, about 455 nm, about 460 nm, about 465 nm, about 470 nm, about 475 nm, about 480 nm, about 485 nm, about 490 nm, about 495 nm, or about 500 nm.

The methods can include various degrees of blue light stimulation. In some embodiments, the stimulation is acute or, optionally, chronic. Acute stimulation refers stimulation with pulses of blue light from about 0.2 to about 60 seconds, wherein the wavelength of the blue light can be any herein disclosed blue light wavelength. In some embodiments, the acute stimulation includes pulses of blue light from about 0.5 seconds to about 30 seconds, from about 1 second to about 20 seconds, or about 5 seconds. The blue light can be provided by a blue light source or a broad-spectrum light source filtered for the disclosed wavelengths.

In some embodiments, acute stimulation can result in temporary aggregation of a light-induced oligomerization domain (e.g., cytoplasmic prion-like domains/LCD/IDD protein fragments). Temporary aggregation, in some embodiments, includes protein aggregation observable by the herein disclosed methods for less than about twenty minutes or, optionally, less than about fifteen minutes, less than about ten minutes, or about five minutes or less. In some embodiments, acute stimulation does not result in aggregation of cytoplasmic prion-like domains/LCD/IDD protein fragments for twenty minutes or more.

Chronic stimulation is defined by exposure to blue light having a wavelength from about 400 nm to about 500 nm for a duration of about 1 minute or longer (for example, at least 1 minute, at least 5 minutes, at least 10 minutes, at least 30 minutes, at least 60 minutes, at least 2 hours, at least 4 hours, at least 8 hours, at least 12 hours, at least 24 hours, at least 36 hours, or more) from about 0.1 $mW/cm^2$ to 8 $mW/cm^2$ (within 400 nm-500 nm wavelength).

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Optogenetic Induction of Membraneless Organelles

A series of DNA arrangements have been developed consisting of the CRY2 (OLIG or PHR) or LOV photoreceptor domain which cluster or homodimerize in response to blue light exposure and require intracellular FAD (Table 1). These DNA arrangements comprise the DNA sequence of genes that encode for proteins that contain low complexity domains (LCDs) and comprise a membraneless organelle target protein (Tables 2-10).

Table 1 indicates the protein domains that exhibit photoreceptor activity in response to blue light stimulation. These domains are used to generate fusion proteins with the core proteins of membraneless organelles that seed these structures when exposed to specific light paradigms. Some of these photoreceptors self-oligomerize and some can dimerize. A novel method was employed using LEDs to chronically treat cells with light to force dimerizing proteins to oligomerize and seed organelle structures when fused to the core protein. Photoreceptor protein sequences were modified and the generated synthetic sequences were used to investigate the light-responsiveness of the LOV domain to enhance or mitigate dimerizing formation and dissociation time.

Tables 2-10 includes a list of core components of membraneless organelles (stress granules, P-bodies, transport RNP, nucleolus, nuclear speckles, nuclear stress bodies, PML bodies, Cajal bodies, nuclear paraspeckles) that also contain low complexity domains/intrinsically disordered regions (LCD/IDR). Arrangements of the photoreceptors listed in Table 1 are fused to the genes encoding the key components of membraneless organelles listed in Tables 2-10. When expressed in cells and exposed to specific light treatments, the photoreceptor enhances the focal concentration of the membraneless organelle core protein and this promotes LCD/IDR self-interaction which initiates the formation of membraneless organelles through the recruitment of adaptor proteins and other molecules. Together, this allows for the formation of light-induced membraneless organelles.

TABLE 1

List of photoreceptors/light-induced oligomerization domains to optogenetically induce membraneless organelles in cells with blue light exposure.

| Nomenclature | Protein Domain | Organism | Light Stimuli (nm) | Light Response | Features |
|---|---|---|---|---|---|
| CRYPHR | Photolyase homology region (PHR) | *Arabidopsis* | 405-499 | homo-oligomerization | Endogenous protein domain |
| CRY2OLIG | Photolyase homology region (PHR) with | *Arabidopsis* | 405-499 | homo-oligomerization | E490G Mutation to enhance clustering |
| NcVVD | Light-oxygen-voltage-sensing (LOV) domain | *Neurospora* | 405-499 | homo-dimerization | LOV domain of VVD gene |
| NcVVDY5OW | Light-oxygen-voltage-sensing (LOV) domain | *Neurospora* | 405-499 | homo-dimerization | VVD Y50G Mutation to enhance clustering |
| NcLOV | Light-oxygen-voltage-sensing (LOV) domain | *Neurospora* | 405-499 | homo-dimerization | Clustering LOV domain from NcVVD with no linker |
| Vfau1 | Light-oxygen-voltage-sensing (LOV) domain | *Vucheria frigida* | 405-499 | homo-dimerization | — |
| YtvA | Light-oxygen-voltage-sensing (LOV) domain | *Bacillus subtillis* | 405-499 | homo-dimerization | — |
| EL222 | Light-oxygen-voltage-sensing (LOV) domain | *Erythrobacter litoralis* | 405-499 | homo-dimerization | — |
| RsLOV | Light-oxygen-voltage-sensing (LOV) domain | *Rhodobacter sphaeroides* | 405-499 | homo-dimerization | — |

TABLE 1-continued

List of photoreceptors/light-induced oligomerization domains to optogenetically induce membraneless organelles in cells with blue light exposure.

| Nomenclature | Protein Domain | Organism | Light Stimuli (nm) | Light Response | Features |
|---|---|---|---|---|---|
| AsLOV2 | Light-oxygen-voltage-sensing (LOV) domain | *Avena sativa* | 405-499 | Intramolecular conformational change | — |
| | | | Modified Photoreceptors | | |
| NcVVDY50W, I52C, LINKER A | Light-oxygen-voltage-sensing (LOV) domain | *Neurospora* | 405-499 | homo-dimerization | LOV domain of VVD gene with altered light responsive properties and linker domains |
| NcVVDY50W, LINKER A | Light-oxygen-voltage-sensing (LOV) domain | *Neurospora* | 405-499 dimerization | homo- gene with altered | LOV domain of VVD light responsive properties and linker domains |
| NcVVDY50W, I52C, LINKER A | Light-oxygen-voltage-sensing (LOV) domain | *Neurospora* | 405-499 | homo-dimerization | LOV domain of VVD gene with altered light responsive properties and linker domains |
| NcVVDY50W, I52C, LINKER A | Light-oxygen-voltage-sensing (LOV) domain | *Neurospora* | 405-499 | homo-dimerization | LOV domain of VVD gene with altered light responsive properties and linker domains |
| NcVVDY50W, LINKER B | Light-oxygen-voltage-sensing (LOV) domain | *Neurospora* | 405-499 | homo-dimerization | LOV domain of VVD gene with altered light responsive properties and linker domains |
| NcVVDY50W, I52C, LINKER B | Light-oxygen-voltage-sensing (LOV) domain | *Neurospora* | 405-499 | homo-dimerization | LOV domain of VVD gene with altered light responsive properties and linker domains |
| NcVVDY50W, I52C, LINKER B | Light-oxygen-voltage-sensing (LOV) domain | *Neurospora* | 405-499 | homo-dimerization | LOV domain of VVD gene with altered light responsive properties and linker domains |
| NcVVDY50W, I52C, LINKER B | Light-oxygen-voltage-sensing (LOV) domain | *Neurospora* | 405-499 | homo-dimerization | LOV domain of VVD gene with altered light responsive properties and linker domains |

TABLE 2

Stress Granule Genes and Proteins
Stress Granules

| Gene Name | Human Gene | Human Protein |
|---|---|---|
| PABC1 | NC_000005.10 | XP_016864445.1, XP_005248287.1 |
| TIA1 | NG_029967.1 | NP_001338437.1, NP_001338438.1, NP_001338439.1, NP_001338440.1, NP_001338441.1, NP_001338442.1, NP_001338443.1, NP_001338444.1, NP_001338445.1, NP_001338446.1, NP_001338447.1, NP_001338448.1, NP_001338449.1, |

TABLE 2-continued

Stress Granule Genes and Proteins
Stress Granules

| Gene Name | Human Gene | Human Protein |
|---|---|---|
| | | NP_001338450.1, NP_001338451.1, NP_001338452.1, NP_001338453.1, NP_001338454.1 |
| TIAR | NC_027300.1 | XP_014053672.1 |
| G3BP1 | NC_000005.10 | XP_006714812.1, XP_006714813.1, XP_016864411.1, XP_016864412.1 |
| G3BP2 | NC_000004.12 | NP_036429.2 NP_987101.1, NP_987100.1 |
| DDX6 | NC_000011.10 | NP_001244120 |

TABLE 2-continued

| Stress Granule Genes and Proteins<br>Stress Granules | | |
|---|---|---|
| Gene Name | Human Gene | Human Protein |
| TDRD3 | NC_000013.11 | NP_001139542.1, NP_001139543.1 |
| ATXN2 | NC_027903.1 | XP_015008288.1, XP_015008298.1, XP_015008295.1, XP_015008297.1, XP_015008300.1, XP_002808037.2 |

TABLE 3

| P-Body Genes and Proteins<br>P-Bodies | | |
|---|---|---|
| Gene Name | Human Gene | Human Protein |
| DCP1A | NC_000003.12 | NP_001277133.1, NP_001277134.1, NP_001277135, NP_001277136.1, NP_060873.4 |
| DCP2 | NC_000005.10 | XP_016864652.1 |
| LSM1 | NC_000008.11 | NP_055277.1 |
| TNRC6A | NC_000016.10 | XP_005255314.1, XP_005255311.1, XP_016878643.1, XP_016878635.1, XP_016878640.1, XP_016878637.1, XP_016878638.1, XP_016878639.1, XP_016878641.1, XP_016878633.1, XP_016878632.1, XP_016878634.1, XP_016878636.1 |
| MEX3A | NC_000001.11 | NP_001087194.1 |
| EDC4 | NC_000016.10 | NP_055144.3 |
| XRN1 | NC_000003.12 | NP_001269786.1, NP_001269788.1, NP_061874.3 |
| DDX3X | NC_000023.11 | NP_001180345.1, NP_001180346.1, NP_001347.3 |

TABLE 4

| Ribonuclear Transport Granule Genes and Proteins<br>Ribonuclear Transport Granules | | |
|---|---|---|
| Gene Name | Human Gene | Human Protein |
| IGFBP1 | NC_000017.11 | NP_006537.3, NP_001153895.1 |
| STAU1 | NC_000020.11 | NP_001032405.1, NP_001306063.1, NP_001306064.1, NP_001309856.1, NP_001309857.1, NP_001309858.1, NP_001309859.1, NP_001309860.1, NP_001309861.1, |

TABLE 4-continued

| Ribonuclear Transport Granule Genes and Proteins<br>Ribonuclear Transport Granules | | |
|---|---|---|
| Gene Name | Human Gene | Human Protein |
| | | NP_004593.2, NP_059347.2, NP_059348.2 |
| PURA | NC_000005.10 | NP_005850.1 |
| FMR1 | NC_000023.11 | NP_001172004.1, NP_001172005.1, NP_001172010.1, NP_001172011.1, NP_002015.1 |
| FXR1 | NC_000003.12 | NP_001013456.1, NP_001013457.1, NP_005078.2 |
| FXR2 | NC_000017.11 | NP_004851.2 |

TABLE 5

| Nucleolus Genes and Proteins<br>Nucleolus | | |
|---|---|---|
| Gene Name | Human Gene | Human Protein |
| NCL | NC_000002.12 | NP_005372.2 |
| NPM1 | NC_000005.10 | NP_954654.1, NP_002511.1, NP_001032827.1 |
| FBL | NC_000019.10 | XP_005258708.1, XP_011524925.1 |

TABLE 6

| Nuclear Speckles—Genes and Proteins<br>Nuclear Speckles | | |
|---|---|---|
| Gene Name | Human Gene | Human Protein |
| SRSF2 | NC_000017.11 | NP_003007.2, NP_001182356.1 |
| PNN | NC_000014.9 | NP_002678.2 |
| SRSF1 | NC_000017.11 | NP-001071634.1, NP_008855.1 |

TABLE 7

| Nuclear Stress Bodies—Genes and Proteins<br>Nuclear Stress Bodies | | |
|---|---|---|
| Gene Name | Human Gene | Human Protein |
| SAFB | NC_000019.10 | NP_002958.2, NP_001307501.1, NP_001307500.1, NP_001188269.1, NP_001188268.1, NP_001188267.1 |

TABLE 8

| PML Bodies—Genes and Proteins<br>PML Bodies | | |
|---|---|---|
| Gene Name | Human Gene | Human Protein |
| PML | NC_000015.10 | NP_002666.1, NP_150241.2, NP_150242.1, NP_150243.2, NP_150247.2, NP_150249.1, NP_150250.2, NP_150252.1, NP_150253.2 |

TABLE 9

| Cajal Bodies—Genes and Proteins<br>Cajal Bodies | | |
|---|---|---|
| Gene Name | Human Gene | Human Protein |
| COIL | NC_000017.11 | NP_004636.1 |

TABLE 10

| Nuclear Paraspeckles—Genes and Proteins<br>Nuclear Paraspeckles | | |
|---|---|---|
| Gene Name | Human Gene | Human Protein |
| SFPQ | NC_000001.11 | NP_005057.1 |
| NONO (PNN) | NC_000023.11 | NP_031389.3, NP_001138882.1, NP_001138881.1, NP_001138880.1 |
| PSPC1 | NC_000013.11 | NP_001035879.1 |

When these unique DNA arrangements are expressed in cells, they generate fusion proteins. Light exposure forces the fusion protein into close proximity and by employing acute, chronic, or repeated light stimulation, intracellular phase separation of the core proteins that comprise the membraneless organelle is driven by the LCD/IDR domain of the respective proteins. This seeding of the core structure allows for the recruitment of additional proteins and factors for the maturation of the organelle (FIGS. 3-25). This temporal and spatial control of organelle formation is novel and is used in both basic biological studies regarding the role of these organelles in cell function and in diseases, including for example, neurodegeneration and cancer.

In this example, cytoplasmic stress granules are formed using the methods disclosed herein. Cytoplasmic stress granules are membraneless organelles that form in the presence of extracellular stressors such as oxidative stress, osmotic stress, and heat shock. Their primary function is to inhibit the translation or mRNAs until the stressor is removed. Stress granules have been implicated in the initiation of many neurodegenerative disease pathologies, such as Amyotrophic Lateral Sclerosis, Alzheimer's Disease, Frontotemporal Dementia, and Parkinson's Disease, since the key proteins of these are found in stress granules. Stress granule dysfunction is also implicated in some cancers since certain cancer-causing mutations (e.g. DDX3X) are key components of these organelles.

While stress granule dynamics are shown to be altered in these diseases, the true contributions of stress granules to disease pathobiology is unknown since the only current method to form these organelles is to introduce an extracellular stressor (e.g. heat stress at 43° C., exposure to sodium arsenite) which is toxic to cells and ultimately kills the cells being studied. The longest studies of stress granules to date are only on the order of a few hours and so, the importance of these organelles in the initiation of neurodegeneration or cancer cannot be assessed. Therefore, a method to control stress granule formation was developed using light, without the need for any extracellular stressors. To achieve this, the DNA encoding specific photoreceptor protein domains that self-bind with blue light exposure were linked to the DNA of a key protein required for the formation of stress granules, G3BP1 or TIA1. These arrangements were then expressed in HEK293 cells and were tested for their ability to form functional stress granules with various blue light treatment paradigms. It was shown that the LOV photoreceptor domain, from the Vivid protein of *N. crassa*, which is known to dimerize with blue light exposure, when fused to G3BP1 and exposed to 15-1080 min of 465 nm light at 0.1-1.0 mW/cm2 initiates the formation of a core stress granule structure consisting of the photoreceptors fused to G3BP1 that recruits additional G3BP1 and accessory proteins that comprise stress granules and allow for their maturation. This likely involved the liquid-liquid phase separation (LLPS) and dimerization and oligomerization of G3BP1 (concept represented in FIG. 1).

Figure 15:
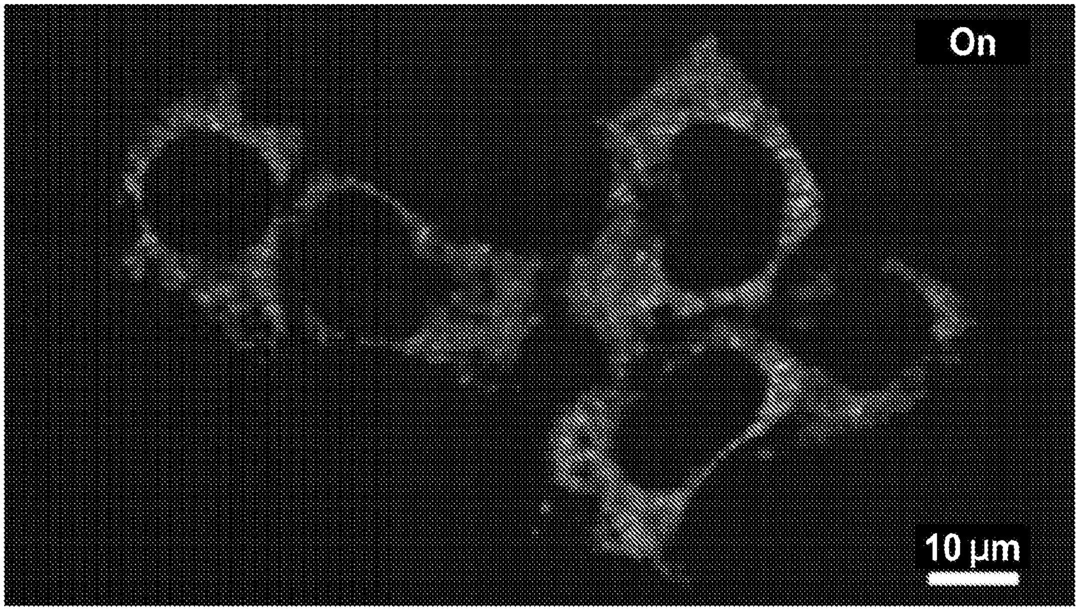
FIG. 15. Optogenetically induced stress granules are tunable. NcVVDY50W-G3BP1 was expressed in HEK293 cells. Stress granules can be controlled with light stimulation and repeatedly formed. NcVVDY50W-G3BP1 expressing HEK293 cells were longitudinally imaged every 30 seconds and exposed to blue light in between each image for 30 minutes. The light was then removed and cells were imaged every 30 seconds without light in between each image to study the rate of formation and dissociation of the light induced stress granules.
Figure 16A:
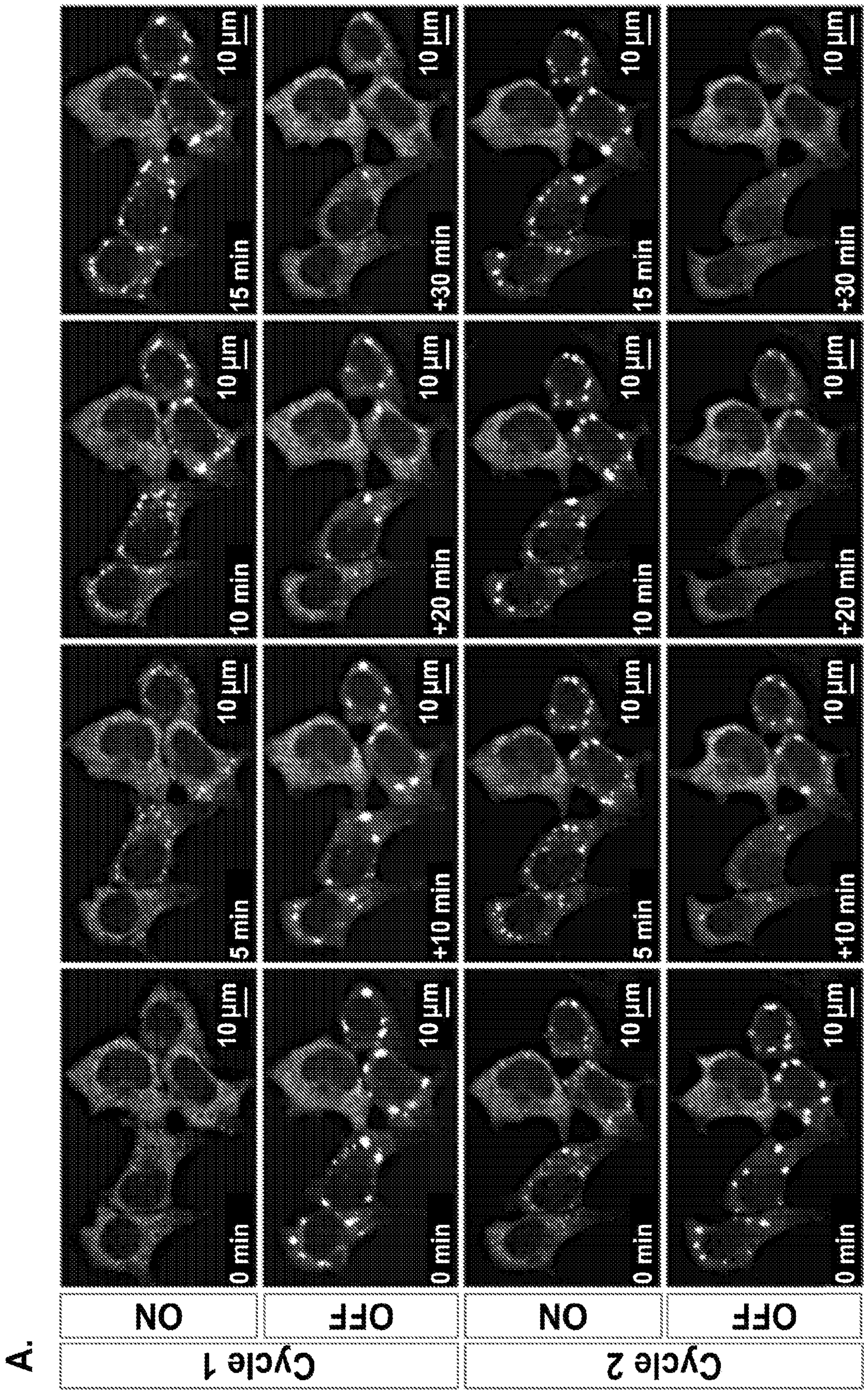
FIGS. 16A-16B. Quantification of optogenetically induced stress granules dynamics
Figure 16B:
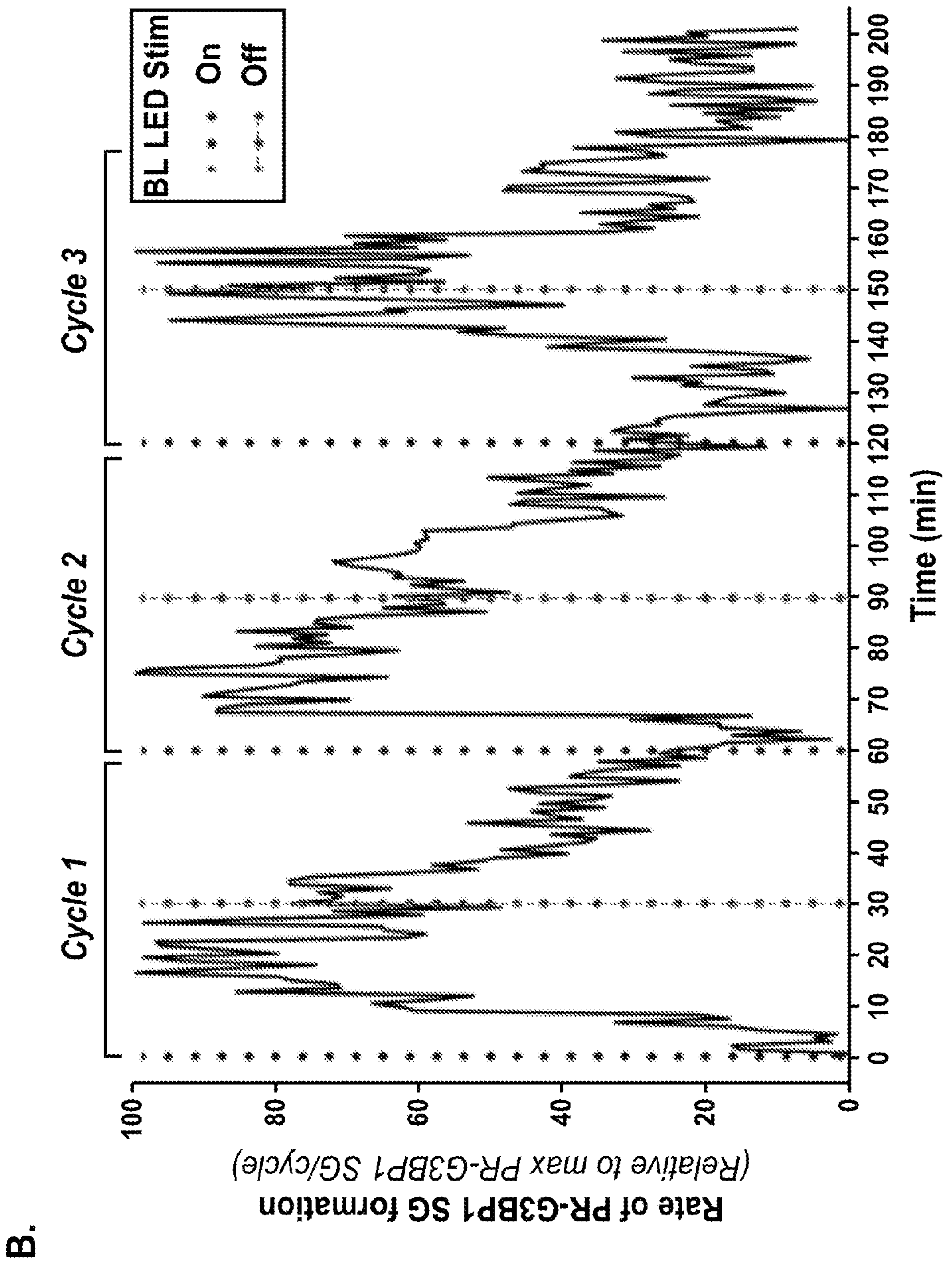
Figure 17A:
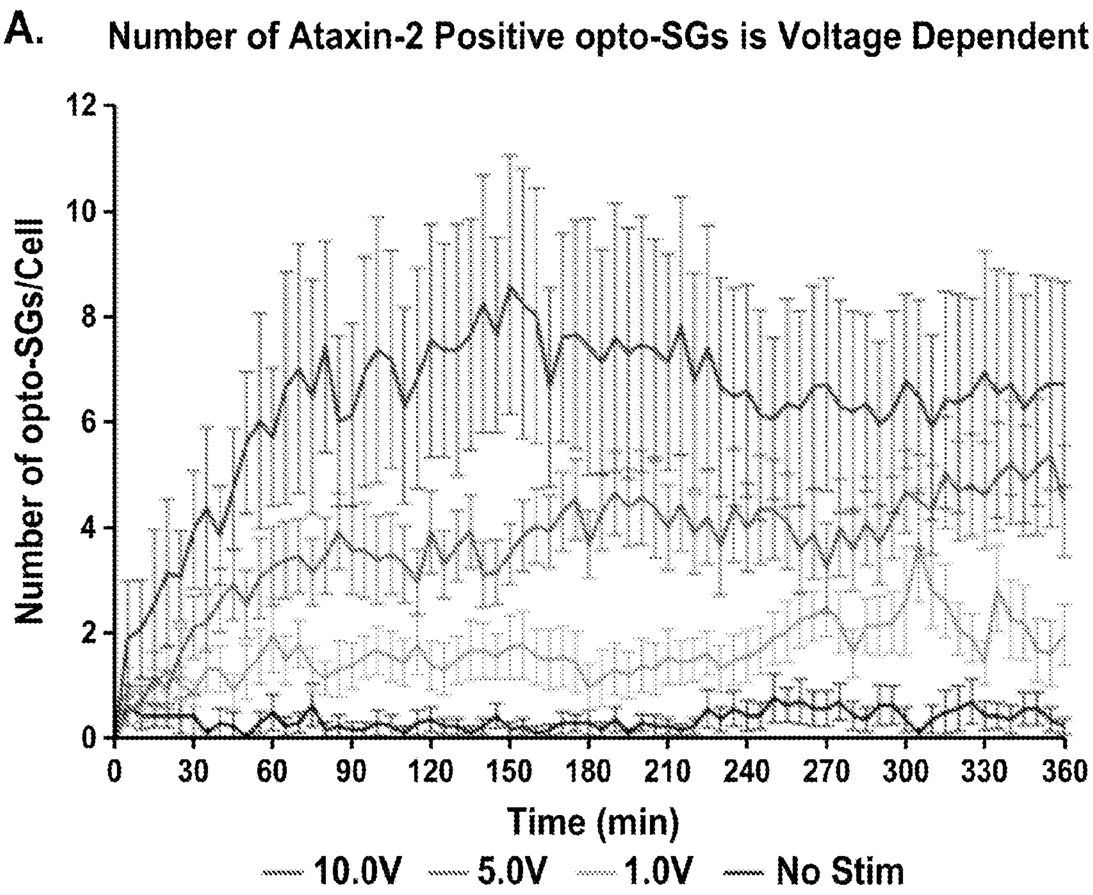
FIGS. 17A-17B. Optogenetically induced stress granules are tunable with different voltages of blue light stimulation.
Figure 17B:
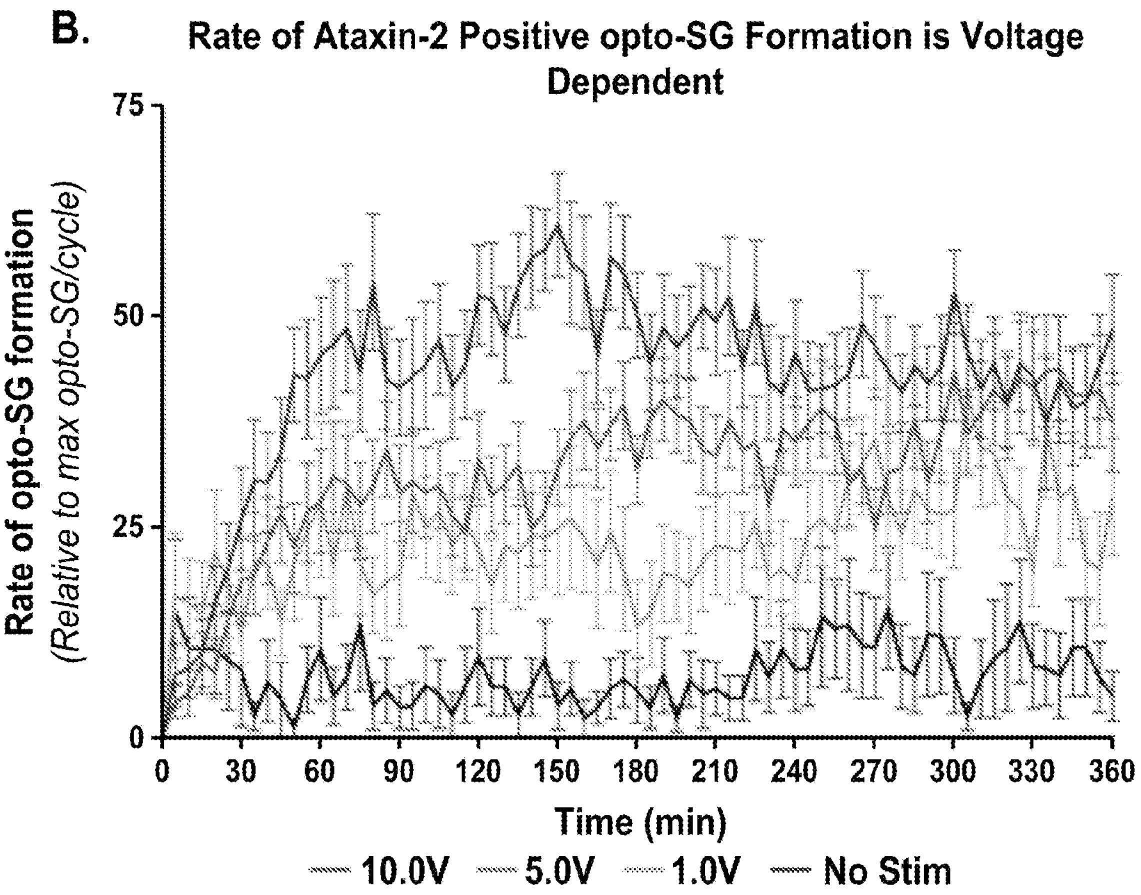
Figure 18A:
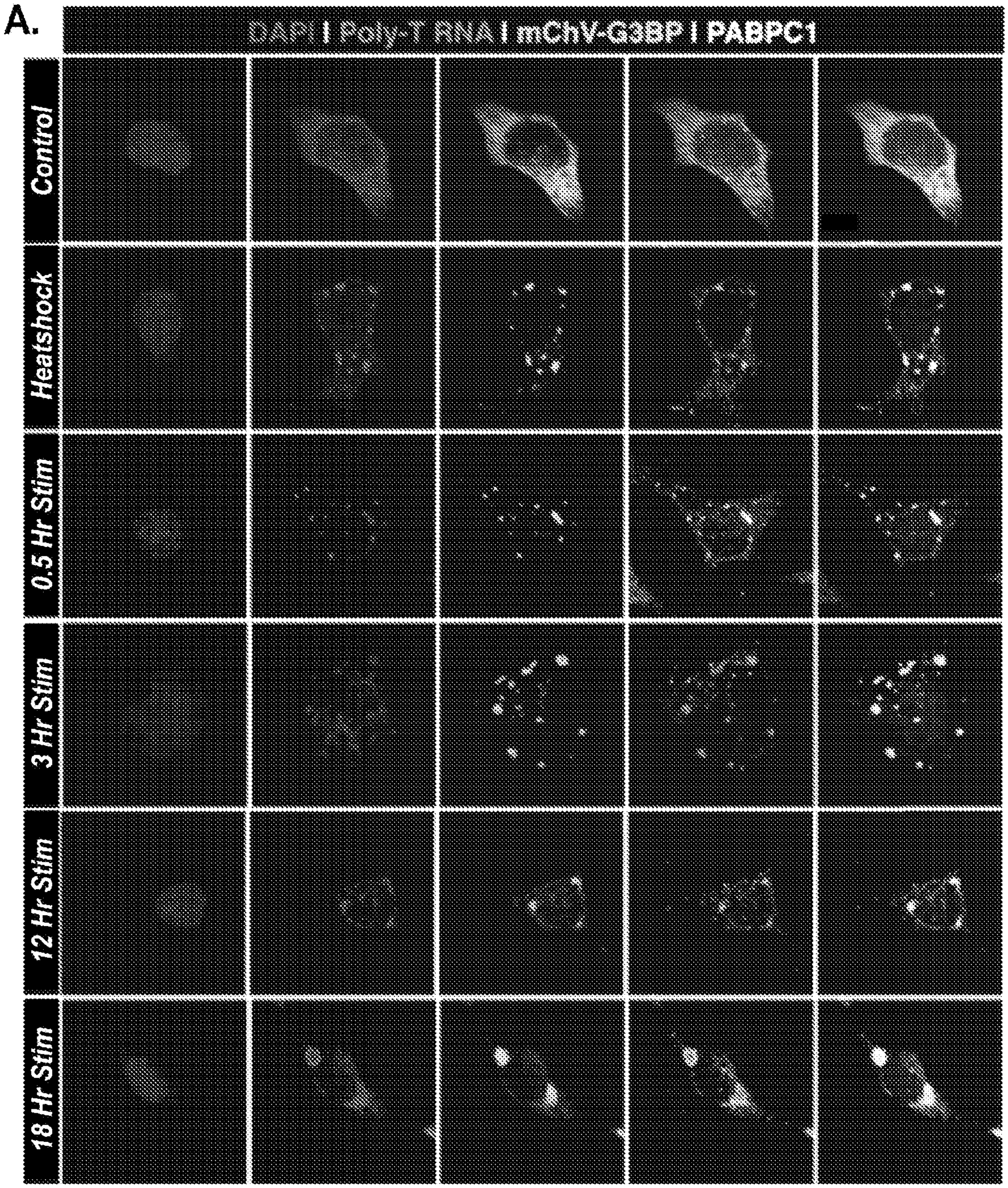
Figure 19:
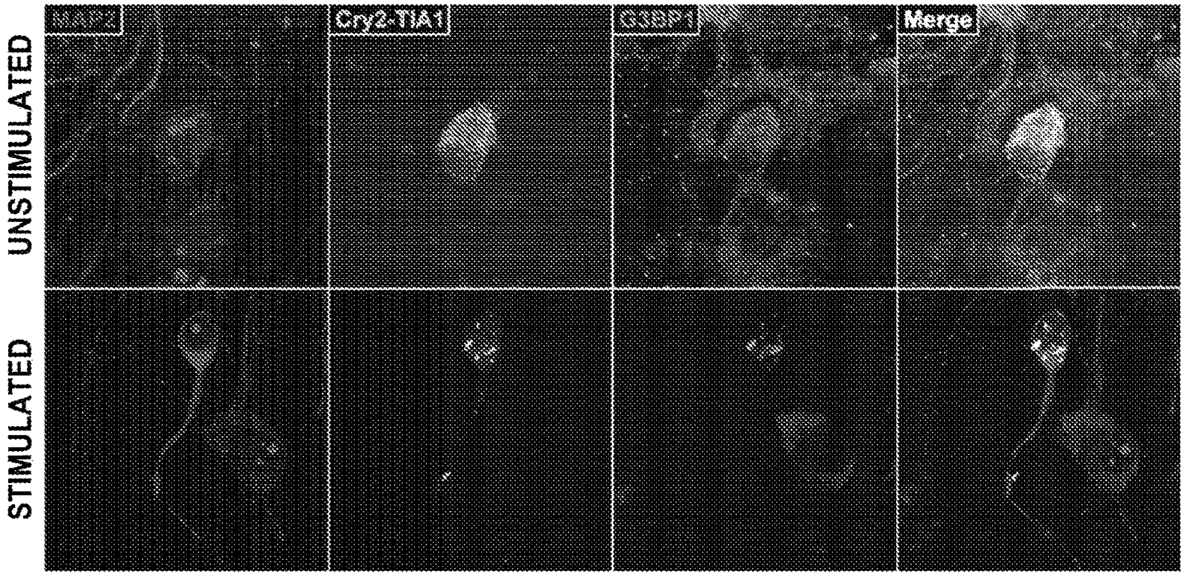
FIG. 19. Optogenetically induced stress granules can be formed with a Cry2Olig-TIA1 protein arrangement and blue light stimulation in rodent cortical neurons. In addition to G3BP, TIA1 is another core component of stress granules and required for their formation in cells. To show that optogenetic induction of membraneless organelles can be performed with a variety of core protein components that 1) contain low complexity domains and 2) the organelle cannot form under endogenous conditions when that specific core component is removed, a Cry2Olig-TIA1 DNA construct was generated and expressed it in rat cortical neuron cultures. The cells were then exposed to 30 minutes of blue light stimulation, or not, and counterstained for markers of stress granules. It was observed that TIA1 clusters form with blue light stimulation (bottom) and these colocalize with G3BP, a marker of stress granules. This data shows that the methodology is valid for a variety of membraneless organelles using their core LCD-containing protein components and photoreceptor arrangement along with defined blue light stimulation paradigms.
Figure 20:
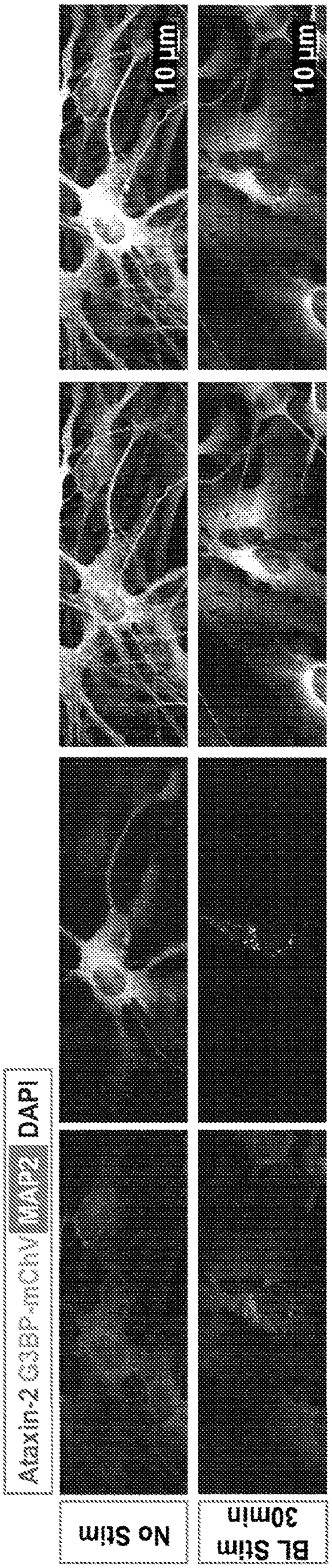
FIG. 20. Blue light induced stress granules using a G3BP1-NcVVDY50W protein arrangement in ReNCell differentiated cortical neuron-like cells. A DNA arrangement that generates the G3BP1-NcVVDY50W was developed and expressed in ReNCell differentiated cortical neuron-like cells. To confirm differentiation of ReN cells to cortical neuron-like cells, cultures were probed for MAP2, a protein that is only expressed in neurons. Under normal conditions, the NcVVDY50W-G3BP1 remains diffuse in the cytoplasm. Blue light induced stress granules were found to colocalize with the key stress granule marker Ataxin-2.
Figure 22A:
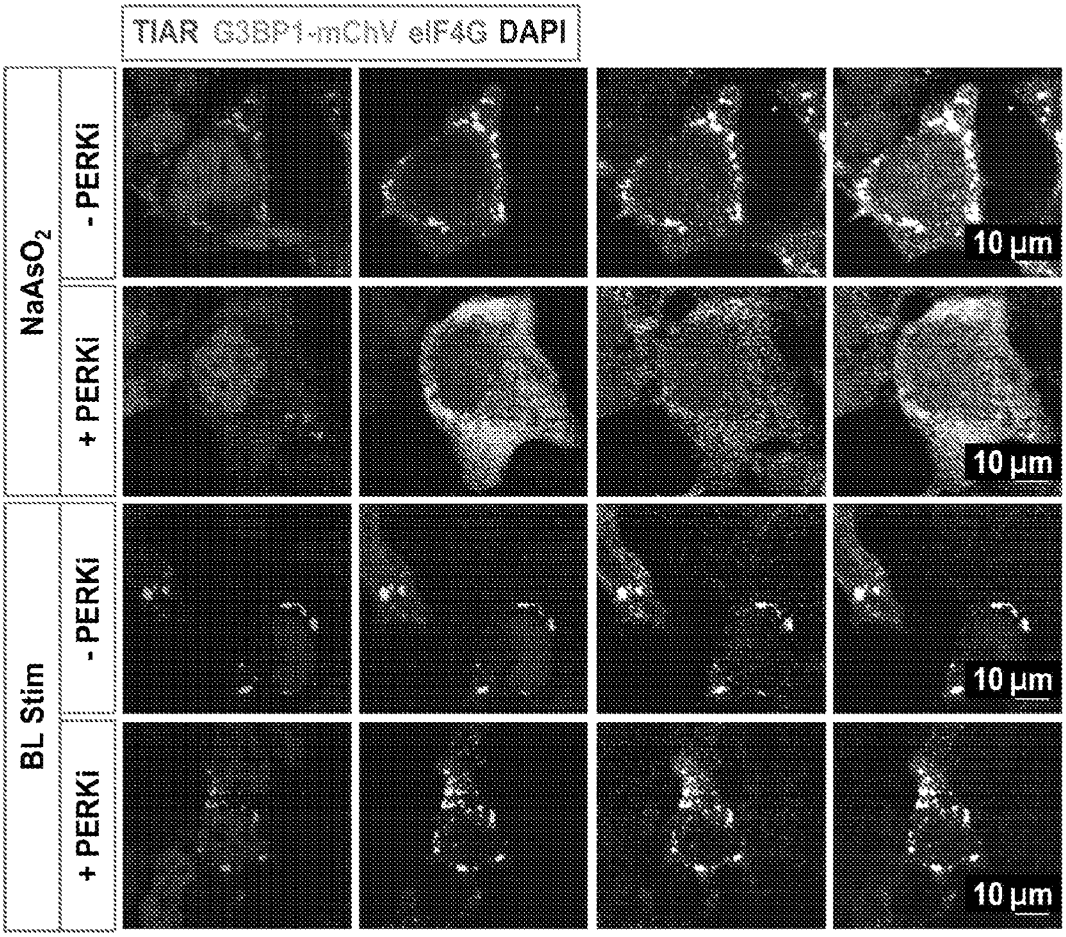
FIGS. 22A-22B. Optogenetically induced stress granule formation is not affected by cell stress pathway inhibitor GSK2606414 (PERK inhibitor; PERKi). When endogenous stress granule formation is induced with $NaAsO_2$ (0.5 mM, 30 min treatment), the G3BP1-NcVVDY50W forms stress granules that stain positive for key markers TIAR and eIF4G. When GSK2606414, a PERK kinase inhibitor, is added 1 hour before $NaAsO_2$ treatment, endogenous stress granule formation is attenuated (FIG. 22A). When GSK2606414 is added 1 hour before blue light stimulation, there is no change in stress granule formation (FIG. 22B). These results further indicate that optogenetically induced stress granules do not use a cell stress to form.
Figure 22B:
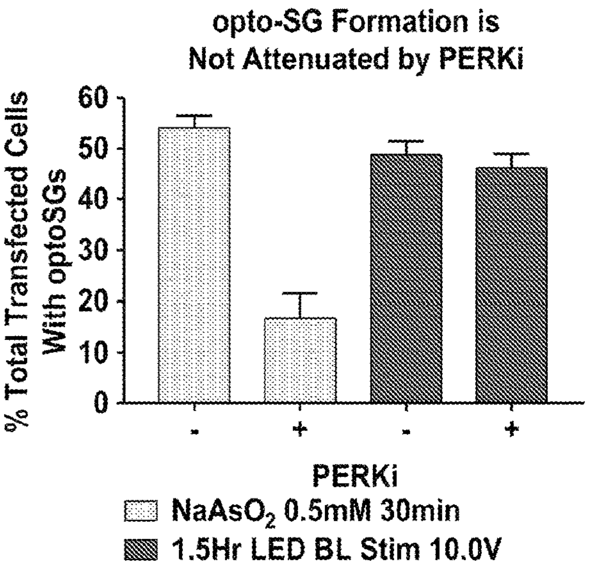
Figure 23A:
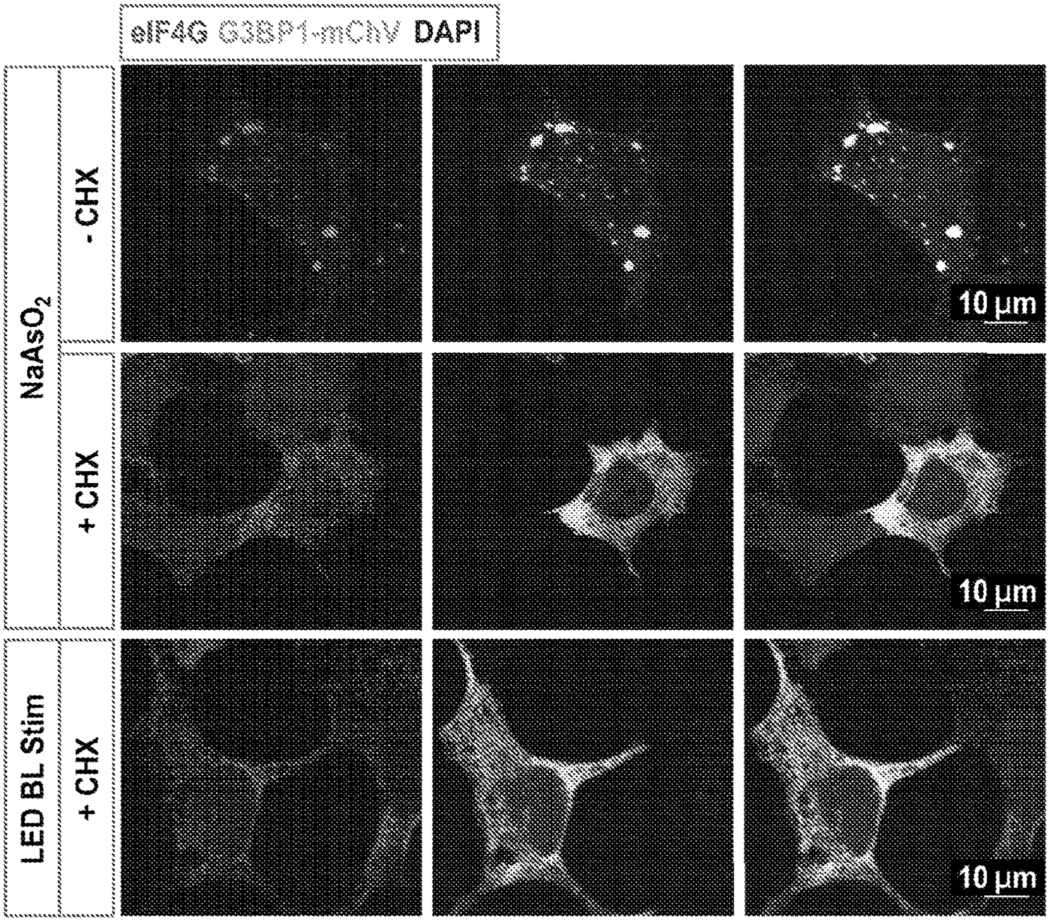

These light induced stress granules colocalize with key stress granule components, including Ataxin-2, TIAR, G3BP, eIF4G, eIF3H, RPS3, RPS6, TDP-43, FUS mRNA, and PABPC1 (FIGS. 2-9, 12, 13, 18, 20, 22, 23, 24, 25). Furthermore, the colocalization with mRNA (FIGS. 12 and 13) indicates the light induced stress granules are likely inhibiting mRNA translation. Note that the light induced stress granules appear identical to naturally occurring stress granules induced by heat shock treatment for 30 minutes at 42° C. (FIG. 2, 8, 12, 13, 18), or 0.5 mM sodium arsenite treatment for 30 minutes (FIGS. 3-7, 9, 10, 20-25). The light induced stress granules are tunable and can be initiated over multiple rounds with light as shown in FIG. 16 (and represented at different time points in FIG. 16), enabling an unprecedented level of control over the light induced stress granule that has not been previously achieved. Finally, light induced stress granules can be generated for multiple hours with chronic light treatment (FIG. 18) and colocalize with key stress granule markers throughout the entire time course. The stress granules are dynamic as they increase in size and decrease in number over time with chronic stimulation, suggesting fusion events (FIGS. 15 and 16). This is a hallmark characteristic of membraneless organelles. Light induced optoStress Granules (optoSGs) exhibit similar physiological properties as endogenously induced stress granules but in the absence of extracellular cell stress. Namely, western blot analysis shows that light induced stress granules do not activate the intrinsic stress response (FIG. 21). Consistent with this, optoSGs are not inhibited by PERK inhibitors (FIG. 22) which prevent eIF2α phosphorylation. However, they are inhibited in response to the translational inhibitor, cycloheximide (FIG. 23), suggesting that while the stress response is not necessary for their formation, the recruitment of ribosomal subunits is required. Together, these data show that the light induced stress granules mimic stress granules formed using extracellular stressors but in the absence of the intrinsic stress response (ISR).

The data shown here focuses on the formation of light-induced stress granules. In addition, this technology is also applied to other cytoplasmic or nuclear organelles. These methods only require that the photoreceptor has access to the FAD cofactor, which is present in both the cytoplasm and nucleus, and that the target membraneless organelle core protein contains a LCDs/IDRs to initiate liquid-liquid phase separation (LLPS). In some embodiments, the arrangement of any combination of DNA/protein fusion sequences listed in Tables 1 and 2-10 are included within the scope of the present disclosure. In some embodiments, the light treatments can consist of acute (<1 min) or chronic stimulation (>1 min) paradigms of blue light (405-495 nm) at 0.1-10 mW/cm2.

The DNA arrangement disclosed herein can encode for the CRY2 (PHR domain) or VVD/LOV (LOV domain) photoreceptor proteins (or for example, proteins within 90% similarity) (Table 1) fused to core proteins that contain low complexity domains (LCDs) and are required for the formation of membraneless organelles listed in Table 2 and the methodology of employing blue light exposure treatment paradigms times to induce the formation of functional membraneless organelles.

Finally, the compounds and compositions disclosed herein can be used in this methodology, and the resulting protein aggregates and cell viability are determined as a readout for drug screening that targets alterations in the function of these organelles.

The methods herein are used for the generation of novel model systems in concert with light treatment. These photoreceptor sequences are inserted into the genome of various in vitro and in vivo systems which act as a new model to study these organelles and to study the relationship of these organelles in disease. Nonlimiting examples include: a) In vitro: human and rodent cell lines, induced pluripotent stem cells (iPSCs), yeast, and/or b) In vivo invertebrates: *Drosophila melanogaster* (fruit fly), *Caenorhabditis elegans* (round worm), *Danio rerio* (zebrafish), and/or c) In vivo vertebrates: mouse, rat, non-human primate The described models, (such as iPSC) with edited genomes are used in basic science studies and for high throughput drug screening systems. To achieve this, the formation, or disruption, of these organelles is initiated under temporal and spatial control by stimulating cells with light. Cell viability is then monitored and the formation and residence time of the membraneless organelle or other relevant pathologies are measured in the presence of a compound (or compound libraries). Additional assays include employing survival and neuropathology of in vivo models following induction with light.

To date, no one has successfully created functional membraneless organelles. In this example, novel DNA/protein arrangements are disclosed comprising fusions of 1) photoreceptors and 2) target proteins that are core components of membraneless organelles along with specific light treatment paradigms to create these functional structures. The photoreceptor protein domains have previously been identified and known to dimerize (self-bind) with blue light as it is their natural function in their host organism. The core components of the various membraneless organelles are identified from a number of studies over the past three decades. A common feature of these core proteins is that they contain intrinsically disordered regions/low complexity domains that, when in a high concentration in a liquid solution such as the cytosol in the cell, undergo liquid-liquid phase separation (LLPS) due to weak, attractive multivalent forces conferred by the intrinsically disordered regions/low complexity domains. Disclosed herein are arrangements of photoreceptors that self-bind and the core components of membraneless organelles that contain intrinsically disordered regions/low complexity domains to initiate LLPS and subsequently generate a functional membraneless organelle. For these results, the example of a cytoplasmic stress granule was analyzed. The methods disclosed herein are also applied to any other cytoplasmic or nuclear membraneless organelles. Also disclosed herein are novel photoreceptor and membraneless organelle DNA/protein arrangements that initiate LLPS and recruit additional factors necessary to create a functional membraneless organelle in the cell cytoplasm or the nucleus. Light stimulation paradigms to treat the arrangements are also disclosed herein. The combinations in Tables 1 and 2-10 can be used in cell or animal models to create functional membraneless organelles.

Disclosed herein are DNA/protein arrangements using the Cry2—target protein arrangement. Also disclosed are studies that employ the LOV domain of the Vivid protein from *N. crassa*. This photoreceptor is smaller than Cry2. However, the LOV domain has not been shown to oligomerize, and has only been published to dimerize. Herein, protein arrangements of the Vivid LOV domain and the stress granule core protein, G3BP1 (as well as other core proteins of membraneless organelles) have been developed, along with specific blue light treatments to force this dimerizing protein to cluster, and thus creating functional G3BP1 stress granule cores which then recruit other stress granule factors to generate a light-induced membraneless organelle. These findings are further unexpected since the Vivid LOV domain has not previously been shown to oligomerize with light. With the treatments and DNA arrangement disclosed herein, the Vivid LOV domain is used to force the oligomerization of proteins that contain low complexity domains/intrinsically disordered regions.

These tools and methods disclosed herein are used in the field of neurodegeneration since stress granules, nucleoli, p-bodies and other membraneless organelles have been linked to a number of diseases including Alzheimer's Disease, Frontotemporal Dementia, Parkinson's Disease, Lewy body Dementia, and Traumatic Brain Injury to name a few. Beyond neurodegeneration, aberrant function of many listed membraneless organelles such as stress granules (Table 2), are observed in cancers. This technology allows development of these structures in a tunable manner, thus providing a platform to investigate their relevance in a variety of disorders and can be used to screen for drugs or therapeutics as modifiers of the induced organelles.

In addition to use in drug discovery using the DNA/protein arrangements, cell and animal models for each membraneless organelle are of great interest to the scientific research community. This technology allows researchers, for the first time, to control the initiation of these functional organelles to study their role in basic biological processes that span a variety of fields including neuroscience, molecular and cellular biology, chemistry and biochemistry, cancer biology, pharmacology, and bioengineering.

SEQUENCES

Sequences of Photoreceptor Tools:

| Amino Acid Sequences of the Photolyase-Homologous Region (PHR) domain of the *Arabidopsis* Cryptochrome 2 protein: |
|---|
| Cryptochrome 2 PHR Domain; Cry2PHR:<br>MKMDKKTIVWFRRDLRIEDNPALAAAAHEGSVFPVFIWCPEEEGQFYPGRASRWWMKQSLAHLSQSLKALGSDL<br>TLIKTHNTISAILDCIRVTGATKVVFNHLYDPVSLVRDHTVKEKLVERGISVQSYNGDLLYEPWEIYCEKGKPFTSFNSY<br>WKKCLDMSIESVMLPPPWRLMPITAAAEAIWACSIEELGLENEAEKPSNALLTRAWSPGWSNADKLLNEFIEKQLI<br>DYAKNSKKVVGNSTSLLSPYLHFGEISVRHVFQCARMKQIIWARDKNSEGEESADLFLRGIGLREYSRYICFNFPFTH<br>EQSLLSHLRFFPWDADVDKFKAWRQGRTGYPLVDAGMRELWATGWMHNRIRVIVSSFAVKFLLLPWKWGMKY<br>FWDTLLDADLECDILGWQYISGSIPDGHELDRLDNPALQGAKYDPEGEYIRQWLPELARLPTEWIHHPWDAPLTVL<br>KASGVELGTNYAKPIVDIDTARELLAKAISRTREAQIMIGAA (SEQ ID NO: 1) |
| Cryptochrome 2 PHR Domain with E490G substitution; Cry2Olig:<br>MKMDKKTIVWFRRDLRIEDNPALAAAAHEGSVFPVFIWCPEEEGQFYPGRASRWWMKQSLAHLSQSLKALGSDL<br>TLIKTHNTISAILDCIRVTGATKVVFNHLYDPVSLVRDHTVKEKLVERGISVQSYNGDLLYEPWEIYCEKGKPFTSFNSY<br>WKKCLDMSIESVMLPPPWRLMPITAAAEAIWACSIEELGLENEAEKPSNALLTRAWSPGWSNADKLLNEFIEKQLI<br>DYAKNSKKVVGNSTSLLSPYLHFGEISVRHVFQCARMKQIIWARDKNSEGEESADLFLRGIGLREYSRYICFNFPFTH<br>EQSLLSHLRFFPWDADVDKFKAWRQGRTGYPLVDAGMRELWATGWMHNRIRVIVSSFAVKFLLLPWKWGMKY<br>FWDTLLDADLECDILGWQYISGSIPDGHELDRLDNPALQGAKYDPEGEYIRQWLPELARLPTEWIHHPWDAPLTVL<br>KASGVELGTNYAKPIVDIDTARELLAKAISRTRGAQIMIGAA (SEQ ID NO: 2) |
| Amino Acid Sequences containing the Light-Oxygen-Voltage-Sensing Domain (LOV) from *Neurospora crassa* Vivid protein:<br>VVD LOV Domain only:<br>MTSCALILCDLKQKDTPIVYASEAFLYMTGYSNAEVLGRNCRFLQSPDGMVKPKSTRKYVDSNTINTMRKAIDRNA<br>EVQVEVVNFKKNGQRFVNFLTMIPVRDETGEYRYSMGFQCETE (SEQ ID NO: 3) |
| NcVivid (NcVVD):<br>MHTLYAPGGYDIMGYLIQIMNRPNPQVELGPVDTSCALILCDLKQKDTPIVYASEAFLYMTGYSNAEVLGRNCRFL<br>QSPDGMVKPKSTRKYVDSNTINTMRKAIDRNAEVQVEVVNFKKNGQRFVNFLTMIPVRDETGEYRYSMGFQCET<br>E (SEQ ID NO: 4) |
| NcVivid Y50W substitution; NcVVDY50W:<br>MHTLYAPGGYDIMGWLIQIMNRPNPQVELGPVDTSCALILCDLKQKDTPIVYASEAFLYMTGYSNAEVLGRNCRFL<br>QSPDGMVKPKSTRKYVDSNTINTMRKAIDRNAEVQVEVVNFKKNGQRFVNFLTMIPVRDETGEYRYSMGFQCET<br>E (SEQ ID NO: 5) |
| Amino Acid Sequences of the *Vaucheria frigida* (Yellow-green alga) (*Conferva frigida*) Aureochrome1 protein (Gene is AUREO1):<br>VfAU1 (A8QW55):<br>MNGLTPPLMFCSRSDDPSSTSNINLDDVFADVFFNSNGELLDIDEIDDFGDNTCPKSSMSVDDDASSQVFQGHLF<br>GNALSSIALSDSDGDLSTGIYESQGNASRGKSLRTKSSGSISSELTEAQKVERRERNREHAKRSRVRKKFLLESLQQSVN<br>ELNHENNCLKESIREHLGPRGDSLIAQCSPEADTLLTDNPSKANRILEDPDYSLVKALQMAQQNFVITDASLPDNPIV<br>YASRGFLTLTGYSLDQILGRNCRFLQGPETDPRAVDKIRNAITKGVDTSVCLLNYRQDGTTFWNLFFVAGLRDSKGN<br>IVNYVGVQSKVSEDYAKLLVNEQNIEYKGVRTSNMLRRK (SEQ ID NO: 6) |
| VfAU1-LOV domain:<br>PDYSLVKALQMAQQNFVITDASLPDNPIVYASRGFLTLTGYSLDQILGRNCRFLQGPETDPRAVDKIRNAITKGVDT<br>SVCLLNYRQDGTTFWNLFFVAGLRDSKGNIVNYVGVQSKVSEDYAKLLVNEQNIEYKGVRTSNMLRRK (SEQ ID<br>NO: 7) |
| VfAU-DNA sequence-VfAU1-LOV domain (No Start codon):<br>Cctgactacagtctcgtgaaggctctgcaaatggcacaacagaatttttgtcattacagacgcctccctcccagacaaccctatcgtctacgccagt<br>agagggtttctgacactgacaggctattctctcgaccagatcctgggcaggaactgcaggtttctgcaagggccagaaacagacccaagagctg<br>tggataagatcaggaatgccatcaccaaaggcgttgataccagtgtctgtctgctgaattatagacaggatggcacaaccttctggaatctcttct<br>tcgtggctggactcagagattctaagggcaatattgtcaactacgtcggagtgcagtcaaaggtgagcgaagattatgccaagctgctggtcaa<br>cgagcagaacattgagtacaaaggtgtgcgcaccagtaacatgctgcgcagaaag (SEQ ID NO: 8) |
| NcVivid Y50W with G3BP1 Full Length Protein; NcVVDY50W-G3BP1<br>MHTLYAPGGYDIMGWLIQIMNRPNPQVELGPVDTSCALILCDLKQKDTPIVYASEAFLYMTGYSNAEVLGRNCRFL<br>QSPDGMVKPKSTRKYVDSNTINTMRKAIDRNAEVQVEVVNFKKNGQRFVNFLTMIPVRDETGEYRYSMGFQCET<br>EMVMEKPSPLLVGREFVRQYYTLLNQAPDMLHRFYGKNSSYVHGGLDSNGKPADAVYGQKEIHRKVMSQNFTN<br>CHTKIRHVDAHATLNDGVVVQVMGLLSNNNQALRRFMQTFVLAPEGSVANKFYVHNDIFRYQDEVFGGFVTEP<br>QEESEEEVEEPEERQQTPEVVPDDSGTFYDQAVVSNDMEEHLEEPVAEPEPDPEPEPEQEPVSEIQEEKPEPVLEET<br>APEDAQKSSSPAPADIAQTVQEDLRTFSWASVTSKNLPPSGAVPVTGIPPHVVKVPASQPRPESKPESQIPPQRPQ<br>RDQRVREQRINIPPQRGPRPIREAGEQGDIEPRRMVRHPDSHQLFIGNLPHEVDKSELKDFFQSYGNVVELRINSG<br>GKLPNFGFVVFDDSEPVQKVLSNRPIMFRGEVRLNVEEKKTRAAREGDRRDNRLRGPGGPRGGLGGGMRGPPR<br>GGMVQKPGFGVGRGLAPRQKLIPMARRAWLEHGHSCFLCEIVIRSQFHTTYEPEA (SEQ ID NO: 9) |
| NcVivid Y50W with G3BP1 NTF2 Domain Deletion Mutation; NcVVDY50W-G3BP1dNTF2<br>MHTLYAPGGYDIMGWLIQIMNRPNPQVELGPVDTSCALILCDLKQKDTPIVYASEAFLYMTGYSNAEVLGRNCRFL<br>QSPDGMVKPKSTRKYVDSNTINTMRKAIDRNAEVQVEVVNFKKNGQRFVNFLTMIPVRDETGEYRYSMGFQCET<br>EMGFVTEPQEESEEEVEEPEERQQTPEVVPDDSGTFYDQAVVSNDMEEHLEEPVAEPEPDPEPEPEQEPVSEIQEE<br>KPEPVLEETAPEDAQKSSSPAPADIAQTVQEDLRTFSWASVTSKNLPPSGAVPVTGIPPHVVKVPASQPRPESKPES<br>QIPPQRPQRDQRVREQRINIPPQRGPRPIREAGEQGDIEPRRMVRHPDSHQLFIGNLPHEVDKSELKDFFQSYGNV |

-continued

Amino Acid Sequences of the Photolyase-Homologous Region (PHR) domain of the *Arabidopsis* Cryptochrome 2 protein:

VELRINSGGKLPNFGFVVFDDSEPVQKVLSNRPIMFRGEVRLNVEEKKTRAAREGDRRDNRLRGPGGPRGGLGGG
MRGPPRGGMVQKPGFGVGRGLAPRQKLIPMARRAWLEHGHSCFLCEIVIRSQFHTTYEPEA (SEQ ID NO: 10)

NcVivid Y50W with G3BP1 Acidic Domain Deletion Mutation; NcVVDY50W-G3BP1dAcidic
MHTLYAPGGYDIMGWLIQIMNRPNPQVELGPVDTSCALILCDLKQKDTPIVYASEAFLYMTGYSNAEVLGRNCRFL
QSPDGMVKPKSTRKYVDSNTINTMRKAIDRNAEVQVEVVNFKKNGQRFVNFLTMIPVRDETGEYRYSMGFQCET
EMVMEKPSPLLVGREFVRQYYTLLNQAPDMLHRFYGKNSSYVHGGLDSNGKPADAVYGQKEIHRKVMSQNFTN
CHTKIRHVDAHATLNDGVVVQVMGLLSNNNQALRRFMQTFVLAPEGSVANKFYVHNDIFRYQDEVFGTAPEDA
QKSSSPAPADIAQTVQEDLRTFSWASVTSKNLPPSGAVPVTGIPPHVVKVPASQPRPESKPESQIPPQRPQRDQRV
REQRINIPPQRGPRPIREAGEQGDIEPRRMVRHPDSHQLFIGNLPHEVDKSELKDFFQSYGNVVELRINSGGKLPNF
GFVVFDDSEPVQKVLSNRPIMFRGEVRLNVEEKKTRAAREGDRRDNRLRGPGGPRGGLGGGMRGPPRGGMVQ
KPGFGVGRGLAPRQKLIPMARRAWLEHGHSCFLCEIVIRSQFHTTYEPEA (SEQ ID NO: 11)

NcVivid Y50W with G3BP1 PxxP Domain Deletion Mutation; NcVVDY50W-G3BP1dPxxP
MHTLYAPGGYDIMGWLIQIMNRPNPQVELGPVDTSCALILCDLKQKDTPIVYASEAFLYMTGYSNAEVLGRNCRFL
QSPDGMVKPKSTRKYVDSNTINTMRKAIDRNAEVQVEVVNFKKNGQRFVNFLTMIPVRDETGEYRYSMGFQCET
EMVMEKPSPLLVGREFVRQYYTLLNQAPDMLHRFYGKNSSYVHGGLDSNGKPADAVYGQKEIHRKVMSQNFTN
CHTKIRHVDAHATLNDGVVVQVMGLLSNNNQALRRFMQTFVLAPEGSVANKFYVHNDIFRYQDEVFGGFVTEP
QEESEEEVEEPEERQQTPEVVPDDSGTFYDQAVVSNDMEEHLEEPVAEPEPDPEPEPEQEPVSEIQEEKPEPVLEE
QLFIGNLPHEVDKSELKDFFQSYGNVVELRINSGGKLPNFGFVVFDDSEPVQKVLSNRPIMFRGEVRLNVEEKKTRA
AREGDRRDNRLRGPGGPRGGLGGGMRGPPRGGMVQKPGFGVGRGLAPRQKLIPMARRAWLEHGHSCFLCEIVI
RSQFHTTYEPEA (SEQ ID NO: 12)

NcVivid Y50W with G3BP1 RRM Domain Deletion Mutation; NcVVDY50W-G3BP1dRRM
MHTLYAPGGYDIMGWLIQIMNRPNPQVELGPVDTSCALILCDLKQKDTPIVYASEAFLYMTGYSNAEVLGRNCRFL
QSPDGMVKPKSTRKYVDSNTINTMRKAIDRNAEVQVEVVNFKKNGQRFVNFLTMIPVRDETGEYRYSMGFQCET
EMVMEKPSPLLVGREFVRQYYTLLNQAPDMLHRFYGKNSSYVHGGLDSNGKPADAVYGQKEIHRKVMSQNFTN
CHTKIRHVDAHATLNDGVVVQVMGLLSNNNQALRRFMQTFVLAPEGSVANKFYVHNDIFRYQDEVFGGFVTEP
QEESEEEVEEPEERQQTPEVVPDDSGTFYDQAVVSNDMEEHLEEPVAEPEPDPEPEPEQEPVSEIQEEKPEPVLEET
APEDAQKSSSPAPADIAQTVQEDLRTFSWASVTSKNLPPSGAVPVTGIPPHVVKVPASQPRPESKPESQIPPQRPQ
RDQRVREQRINIPPQRGPRPIREAGEQGDIEPRRMVRHPDSHEKKTRAAREGDRRDNRLRGPGGPRGGLGGGM
RGPPRGGMVQKPGFGVGRGLAPRQKLIPMARRAWLEHGHSCFLCEIVIRSQFHTTYEPEA (SEQ ID NO: 13)

NcVivid Y50W with G3BP1 RGG Domain Deletion Mutation; NcVVDY50W-G3BP1dRGG
MHTLYAPGGYDIMGWLIQIMNRPNPQVELGPVDTSCALILCDLKQKDTPIVYASEAFLYMTGYSNAEVLGRNCRFL
QSPDGMVKPKSTRKYVDSNTINTMRKAIDRNAEVQVEVVNFKKNGQRFVNFLTMIPVRDETGEYRYSMGFQCET
EMVMEKPSPLLVGREFVRQYYTLLNQAPDMLHRFYGKNSSYVHGGLDSNGKPADAVYGQKEIHRKVMSQNFTN
CHTKIRHVDAHATLNDGVVVQVMGLLSNNNQALRRFMQTFVLAPEGSVANKFYVHNDIFRYQDEVFGGFVTEP
QEESEEEVEEPEERQQTPEVVPDDSGTFYDQAVVSNDMEEHLEEPVAEPEPDPEPEPEQEPVSEIQEEKPEPVLEET
APEDAQKSSSPAPADIAQTVQEDLRTFSWASVTSKNLPPSGAVPVTGIPPHVVKVPASQPRPESKPESQIPPQRPQ
RDQRVREQRINIPPQRGPRPIREAGEQGDIEPRRMVRHPDSHQLFIGNLPHEVDKSELKDFFQSYGNVVELRINSG
GKLPNFGFVVFDDSEPVQKVLSNRPIMFRGEVRLNVE (SEQ ID NO: 14)

NcVivid Y50W with G3BP1 RRMRGG Domain Deletion Mutation; NcVVDY50W-G3BP1dRRMRGG
MHTLYAPGGYDIMGWLIQIMNRPNPQVELGPVDTSCALILCDLKQKDTPIVYASEAFLYMTGYSNAEVLGRNCRFL
QSPDGMVKPKSTRKYVDSNTINTMRKAIDRNAEVQVEVVNFKKNGQRFVNFLTMIPVRDETGEYRYSMGFQCET
EMVMEKPSPLLVGREFVRQYYTLLNQAPDMLHRFYGKNSSYVHGGLDSNGKPADAVYGQKEIHRKVMSQNFTN
CHTKIRHVDAHATLNDGVVVQVMGLLSNNNQALRRFMQTFVLAPEGSVANKFYVHNDIFRYQDEVFGGFVTEP
QEESEEEVEEPEERQQTPEVVPDDSGTFYDQAVVSNDMEEHLEEPVAEPEPDPEPEPEQEPVSEIQEEKPEPVLEET
APEDAQKSSSPAPADIAQTVQEDLRTFSWASVTSKNLPPSGAVPVTGIPPHVVKVPASQPRPESKPESQIPPQRPQ
RDQRVREQRINIPPQRGPRPIREAGEQGDIEPRRMVRHPDSH (SEQ ID NO: 15)

G3BP1 Full Length Protein with NcVivid Y50W; G3BP1-NcVVDY50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHQLFIGNLPHEVDKSELKDFFQSYGNVVELRINSGGKL
PNFGFVVFDDSEPVQKVLSNRPIMFRGEVRLNVEEKKTRAAREGDRRDNRLRGPGGPRGGLGGGMRGPPRGGM
VQKPGFGVGRGLAPRQKLIPMARRAWLEHGHSCFLCEIVIRSQFHTTYEPEAMHTLYAPGGYDIMGWLIQIMNRP
NPQVELGPVDTSCALILCDLKQKDTPIVYASEAFLYMTGYSNAEVLGRNCRFLQSPDGMVKPKSTRKYVDSNTINT
MRKAIDRNAEVQVEVVNFKKNGQRFVNFLTMIPVRDETGEYRYSMGFQCETE (SEQ ID NO: 16)

G3BP1 NTF2 Domain Deletion Mutation with NcVivid Y50W; G3BP1dNTF2-NcVivid Y50W
MGFVTEPQEESEEEVEEPEERQQTPEVVPDDSGTFYDQAVVSNDMEEHLEEPVAEPEPDPEPEPEQEPVSEIQEEK
PEPVLEETAPEDAQKSSSPAPADIAQTVQEDLRTFSWASVTSKNLPPSGAVPVTGIPPHVVKVPASQPRPESKPESQ
IPPQRPQRDQRVREQRINIPPQRGPRPIREAGEQGDIEPRRMVRHPDSHQLFIGNLPHEVDKSELKDFFQSYGNVV
ELRINSGGKLPNFGFVVFDDSEPVQKVLSNRPIMFRGEVRLNVEEKKTRAAREGDRRDNRLRGPGGPRGGLGGG
MRGPPRGGMVQKPGFGVGRGLAPRQKLIPMARRAWLEHGHSCFLCEIVIRSQFHTTYEPEAMHTLYAPGGYDIM
GWLIQIMNRPNPQVELGPVDTSCALILCDLKQKDTPIVYASEAFLYMTGYSNAEVLGRNCRFLQSPDGMVKPKSTR
KYVDSNTINTMRKAIDRNAEVQVEVVNFKKNGQRFVNFLTMIPVRDETGEYRYSMGFQCETE (SEQ ID NO: 17)

G3BP1 Acidic Domain Deletion Mutation with NcVivid Y50W; G3BP1dAcidic-NcVivid Y50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGTAPEDAQ
KSSSPAPADIAQTVQEDLRTFSWASVTSKNLPPSGAVPVTGIPPHVVKVPASQPRPESKPESQIPPQRPQRDQRVR -continued

| Amino Acid Sequences of the Photolyase-Homologous Region (PHR) domain of the *Arabidopsis* Cryptochrome 2 protein: |
| --- |

EQRINIPPQRGPRPIREAGEQGDIEPRRMVRHPDSHQLFIGNLPHEVDKSELKDFFQSYGNVVELRINSGGKLPNFG
FVVFDDSEPVQKVLSNRPIMFRGEVRLNVEEKKTRAAREGDRRDNRLRGPGGPRGGLGGGMRGPPRGGMVQKP
GFGVGRGLAPRQKLIPMARRAWLEHGHSCFLCEIVIRSQFHTTYEPEAMHTLYAPGGYDIMGWLIQIMNRPNPQ
VELGPVDTSCALILCDLKQKDTPIVYASEAFLYMTGYSNAEVLGRNCRFLQSPDGMVKPKSTRKYVDSNTINTMRK
AIDRNAEVQVEVVNFKKNGQRFVNFLTMIPVRDETGEYRYSMGFQCETE (SEQ ID NO: 18)

G3BP1 PxxP Domain Deletion Mutation with NcVivid Y50W; G3BP1dPxxP-NcVivid Y50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEEQLFI
GNLPHEVDKSELKDFFQSYGNVVELRINSGGKLPNFGFVVFDDSEPVQKVLSNRPIMFRGEVRLNVEEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEAMHTLYAPGGYDIMGWLIQIMNRPNPQVELGPVDTSCALILCDLKQKDTPIVYASEAFLYMTGYSN
AEVLGRNCRFLQSPDGMVKPKSTRKYVDSNTINTMRKAIDRNAEVQVEVVNFKKNGQRFVNFLTMIPVRDETGEY
RYSMGFQCETE (SEQ ID NO: 19)

G3BP1 RRM Domain Deletion Mutation with NcVivid Y50W; G3BP1dRRM-NcVivid Y50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHEKKTRAAREGDRRDNRLRGPGGPRGGLGGGMRG
PPRGGMVQKPGFGVGRGLAPRQKLIPMARRAWLEHGHSCFLCEIVIRSQFHTTYEPEAMHTLYAPGGYDIMGWL
IQIMNRPNPQVELGPVDTSCALILCDLKQKDTPIVYASEAFLYMTGYSNAEVLGRNCRFLQSPDGMVKPKSTRKYV
DSNTINTMRKAIDRNAEVQVEVVNFKKNGQRFVNFLTMIPVRDETGEYRYSMGFQCETE (SEQ ID NO: 20)

G3BP1 RGG Domain Deletion Mutation with NcVivid Y50W; G3BP1dRGG-NcVivid Y50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHQLFIGNLPHEVDKSELKDFFQSYGNVVELRINSGGKL
PNFGFVVFDDSEPVQKVLSNRPIMFRGEVRLNVEMHTLYAPGGYDIMGWLIQIMNRPNPQVELGPVDTSCALILC
DLKQKDTPIVYASEAFLYMTGYSNAEVLGRNCRFLQSPDGMVKPKSTRKYVDSNTINTMRKAIDRNAEVQVEVVN
FKKNGQRFVNFLTMIPVRDETGEYRYSMGFQCETE (SEQ ID NO: 21)

G3BP1 RRMRGG Domain Deletion Mutation with NcVivid Y50W; G3BP1dRRMRGG-NcVivid Y50W
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQWQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHMHTLYAPGGYDIMGWLIQIMNRPNPQVELGPVDT
SCALILCDLKQKDTPIVYASEAFLYMTGYSNAEVLGRNCRFLQSPDGMVKPKSTRKYVDSNTINTMRKAIDRNAEV
QVEVVNFKKNGQRFVNFLTMIPVRDETGEYRYSMGFQCETE (SEQ ID NO: 22)

NcVivid Y50W, I74V and I85V substitutions with a short 3' GSG repeat linker sequence, and G3BP1 Full Length Protein; NcVVDY50W/I74V/I85V-LINKERA-G3BP1:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGSGSGSGSGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVEEKKTRAAREGDRRDNRLRGPGGPR
GGLGGGMRGPPRGGMVQKPGFGVGRGLAPRQKLIPMARRAWLEHGHSCFLCEIVIRSQFHTTYEPEA (SEQ ID NO: 23)

NcVivid Y50W, I74V and I85V substitutions with a short 3' GSG repeat linker sequence, and G3BP1 NTF2 Domain Deletion Mutation; NcVVDY50W/I74V/I85V-LINKERA-G3BP1dNTF2:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGSGSGSGSGSGMGFVTEPQEESEEEVEEPEERQQTPEVVPDDSGTFYDQAVVSNDMEEHLEEPVAEPEPD
PEPEPEQEPVSEIQEEKPEPVLEETAPEDAQKSSSPAPADIAQTVQEDLRTFSWASVTSKNLPPSGAVPVTGIPPHVV
KVPASQPRPESKPESQIPPQRPQRDQRVREQRINIPPQRGPRPIREAGEQGDIEPRRMVRHPDSHQLFIGNLPHEV
DKSELKDFFQSYGNVVELRINSGGKLPNFGFVVFDDSEPVQKVLSNRPIMFRGEVRLNVEEKKTRAAREGDRRDNR
LRGPGGPRGGLGGGMRGPPRGGMVQKPGFGVGRGLAPRQKLIPMARRAWLEHGHSCFLCEIVIRSQFHTTYEPE
A (SEQ ID NO: 24)

NcVivid Y50W, I74V and I85V substitutions with a short 3' GSG repeat linker sequence, and G3BP1 Acidic Domain Deletion Mutation; NcVVDY50W/I74V/I85V-LINKERA-G3BP1dAcidic:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGSGSGSGSGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGTAPEDAQKSSSPAPADIAQTVQEDLRTFSWASVTSKNLPPSGAVPVTGIPPHVVKVPASQPRPESKPE -continued Amino Acid Sequences of the Photolyase-Homologous Region (PHR) domain of the *Arabidopsis* Cryptochrome 2 protein:

SQIPPQRPQRDQRVREQRINIPPQRGPRPIREAGEQGDIEPRRMVRHPDSHQLFIGNLPHEVDKSELKDFFQSYGN
VVELRINSGGKLPNFGFVVFDDSEPVQKVLSNRPIMFRGEVRLNVEEKKTRAAREGDRRDNRLRGPGGPRGGLGG
GMRGPPRGGMVQKPGFGVGRGLAPRQKLIPMARRAWLEHGHSCFLCEIVIRSQFHTTYEPEA (SEQ ID NO: 25)

NcVivid Y50W, I74V and I85V substitutions with a short 3' GSG repeat linker sequence, and G3BP1 PxxP Domain Deletion Mutation; NcVVDY50W/I74V/I85V-LINKERA-G3BP1dPxxP:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEEQLFIGNLPHEVDKSELKDFFQSYGNVVELRINSGGKLPNFGFVVFDDSEPVQKVLSNRPIMFR
GEVRLNVEEKKTRAAREGDRRDNRLRGPGGPRGGLGGGMRGPPRGGMVQKPGFGVGRGLAPRQKLIPMARRA
WLEHGHSCFLCEIVIRSQFHTTYEPEA (SEQ ID NO: 26)

NcVivid Y50W, I74V and I85V substitutions with a short 3' GSG repeat linker sequence, and G3BP1 RRM Domain Deletion Mutation; NcVVDY50W/I74V/I85V-LINKERA-G3BP1dRRM:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHEKKTRAAREGDRRDNRLR
GPGGPRGGLGGGMRGPPRGGMVQKPGFGVGRGLAPRQKLIPMARRAWLEHGHSCFLCEIVIRSQFHTTYEPEA
(SEQ ID NO: 27)

NcVivid Y50W, I74V and I85V substitutions with a short 3' GSG repeat linker sequence, and G3BP1 RGG Domain Deletion Mutation; NcVVDY50W/I74V/I85V-LINKERA-G3BP1dRGG:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVE (SEQ ID NO: 28)

NcVivid Y50W, I74V and I85V substitutions with a short 3' GSG repeat linker sequence, and G3BP1 RRMRGG Domain Deletion Mutation; NcVVDY50W/I74V/I85V-LINKERA-G3BP1dRRMRGG:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSH (SEQ ID NO: 29)

NcVivid Y50W, I52C, I74V and I85V substitutions with a short 3' GSG repeat linker sequence, and G3BP1 Full Length Protein; NcVVDY50W/I74V/I85V-LINKERA-G3BP1:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVEEKKTRAAREGDRRDNRLRGPGGPR
GGLGGGMRGPPRGGMVQKPGFGVGRGLAPRQKLIPMARRAWLEHGHSCFLCEIVIRSQFHTTYEPEA (SEQ ID NO: 30)

NcVivid Y50W, I52C, I74V and I85V substitutions with a short 3' GSG repeat linker sequence, and G3BP1 NTF2 Domain Deletion Mutation; NcVVDY50W/I74V/I85V-LINKERA-G3BP1dNTF2:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD
NRLRGPGGPRGGLGGGMRGPPRGGMVQKPGFGVGRGLAPRQKLIPMARRAWLEHGHSCFLCEIVIRSQFHTTY
EPEA (SEQ ID NO: 31)

NcVivid Y50W, I52C, I74V and I85V substitutions with a short 3' GSG repeat linker sequence, and G3BP1 Acidic Domain Deletion Mutation; NcVVDY50W/I74V/I85V-LINKERA-G3BP1dAcidic:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ -continued

| Amino Acid Sequences of the Photolyase-Homologous Region (PHR) domain of the *Arabidopsis* Cryptochrome 2 protein: |
|---|
| CETE**GSGGSGGSGGSG**MVMEKPSPLLVGREFVRQYYTLLNQAPDMLHRFYGKNSSYVHGGLDSNGKPADAVYG<br>QKEIHRKVMSQNFTNCHTKIRHVDAHATLNDGVVVQVMGLLSNNNQALRRFMQTFVLAPEGSVANKFYVHNDI<br>FRYQDEVFGTAPEDAQKSSSPAPADIAQTVQEDLRTFSWASVTSKNLPPSGAVPVTGIPPHVVKVPASQPRPESKP<br>ESQIPPQRPQRDQRVREQRINIPPQRGPRPIREAGEQGDIEPRRMVRHPDSHQLFIGNLPHEVDKSELKDFFQSYG<br>NVVELRINSGGKLPNFGFVVFDDSEPVQKVLSNRPIMFRGEVRLNVEEKKTRAAREGDRRDNRLRGPGGPRGGLG<br>GGMRGPPRGGMVQKPGFGVGRGLAPRQKLIPMARRAWLEHGHSCFLCEIVIRSQFHTTYEPEA (SEQ ID<br>NO: 32) |
| NcVivid Y50W, I52C, I74V and I85V substitutions with a short 3' GSG repeat linker sequence, and G3BP1 PxxP Domain Deletion Mutation; NcVVDY50W/I74V/I85V-LINKERA-G3BP1dPxxP:<br>MHTLYAPGGYDIMG**WLC**QIMNRPNPQVELGPVDTSCAL**V**LCDLKQKDTP**V**VYASEAFLYMTGYSNAEVLGRNC<br>RFLQSPDGMVKPKSTRKYVDSNTINTMRKAIDRNAEVQVEVVNFKKNGQRFVNFLTMIPVRDETGEYRYSMGFQ<br>CETE**GSGGSGGSGGSG**MVMEKPSPLLVGREFVRQYYTLLNQAPDMLHRFYGKNSSYVHGGLDSNGKPADAVYG<br>QKEIHRKVMSQNFTNCHTKIRHVDAHATLNDGVVVQVMGLLSNNNQALRRFMQTFVLAPEGSVANKFYVHNDI<br>FRYQDEVFGGFVTEPQEESEEEVEEPEERQQTPEVVPDDSGTFYDQAVVSNDMEEHLEEPVAEPEPDPEPEPEQEP<br>VSEIQEEKPEPVLEEQLFIGNLPHEVDKSELKDFFQSYGNVVELRINSGGKLPNFGFVVFDDSEPVQKVLSNRPIMFR<br>GEVRLNVEEKKTRAAREGDRRDNRLRGPGGPRGGLGGGMRGPPRGGMVQKPGFGVGRGLAPRQKLIPMARRA<br>WLEHGHSCFLCEIVIRSQFHTTYEPEA (SEQ ID NO: 33) |
| NcVivid Y50W, I52C, I74V and I85V substitutions with a short 3' GSG repeat linker sequence, and G3BP1 RRM Domain Deletion Mutation; NcVVDY50W/I74V/I85V-LINKERA-G3BP1dRRM:<br>MHTLYAPGGYDIMG**WLC**QIMNRPNPQVELGPVDTSCAL**V**LCDLKQKDTP**V**VYASEAFLYMTGYSNAEVLGRNC<br>RFLQSPDGMVKPKSTRKYVDSNTINTMRKAIDRNAEVQVEVVNFKKNGQRFVNFLTMIPVRDETGEYRYSMGFQ<br>CETE**GSGGSGGSGGSG**MVMEKPSPLLVGREFVRQYYTLLNQAPDMLHRFYGKNSSYVHGGLDSNGKPADAVYG<br>QKEIHRKVMSQNFTNCHTKIRHVDAHATLNDGVVVQVMGLLSNNNQALRRFMQTFVLAPEGSVANKFYVHNDI<br>FRYQDEVFGGFVTEPQEESEEEVEEPEERQQTPEVVPDDSGTFYDQAVVSNDMEEHLEEPVAEPEPDPEPEPEQEP<br>VSEIQEEKPEPVLEETAPEDAQKSSSPAPADIAQTVQEDLRTFSWASVTSKNLPPSGAVPVTGIPPHVVKVPASQPR<br>PESKPESQIPPQRPQRDQRVREQRINIPPQRGPRPIREAGEQGDIEPRRMVRHPDSHEKKTRAAREGDRRDNRLR<br>GPGGPRGGLGGGMRGPPRGGMVQKPGFGVGRGLAPRQKLIPMARRAWLEHGHSCFLCEIVIRSQFHTTYEPEA<br>(SEQ ID NO: 34) |
| NcVivid Y50W, I52C, I74V and I85V substitutions with a short 3' GSG repeat linker sequence, and G3BP1 RGG Domain Deletion Mutation; NcVVDY50W/I74V/I85V-LINKERA-G3BP1dRGG:<br>MHTLYAPGGYDIMG**WLC**QIMNRPNPQVELGPVDTSCAL**V**LCDLKQKDTP**V**VYASEAFLYMTGYSNAEVLGRNC<br>RFLQSPDGMVKPKSTRKYVDSNTINTMRKAIDRNAEVQVEVVNFKKNGQRFVNFLTMIPVRDETGEYRYSMGFQ<br>CETE**GSGGSGGSGGSG**MVMEKPSPLLVGREFVRQYYTLLNQAPDMLHRFYGKNSSYVHGGLDSNGKPADAVYG<br>QKEIHRKVMSQNFTNCHTKIRHVDAHATLNDGVVVQVMGLLSNNNQALRRFMQTFVLAPEGSVANKFYVHNDI<br>FRYQDEVFGGFVTEPQEESEEEVEEPEERQQTPEVVPDDSGTFYDQAVVSNDMEEHLEEPVAEPEPDPEPEPEQEP<br>VSEIQEEKPEPVLEETAPEDAQKSSSPAPADIAQTVQEDLRTFSWASVTSKNLPPSGAVPVTGIPPHVVKVPASQPR<br>PESKPESQIPPQRPQRDQRVREQRINIPPQRGPRPIREAGEQGDIEPRRMVRHPDSHQLFIGNLPHEVDKSELKDFF<br>QSYGNVVELRINSGGKLPNFGFVVFDDSEPVQKVLSNRPIMFRGEVRLNVE (SEQ ID NO: 35) |
| NcVivid Y50W, I52C, I74V and I85V substitutions with a short 3' GSG repeat linker sequence, and G3BP1 RRMRGG Domain Deletion Mutation; NcVVDY50W/I74V/I85V-LINKERA-G3BP1dRRMRGG:<br>MHTLYAPGGYDIMG**WLC**QIMNRPNPQVELGPVDTSCAL**V**LCDLKQKDTP**V**VYASEAFLYMTGYSNAEVLGRNC<br>RFLQSPDGMVKPKSTRKYVDSNTINTMRKAIDRNAEVQVEVVNFKKNGQRFVNFLTMIPVRDETGEYRYSMGFQ<br>CETE**GSGGSGGSGGSG**MVMEKPSPLLVGREFVRQYYTLLNQAPDMLHRFYGKNSSYVHGGLDSNGKPADAVYG<br>QKEIHRKVMSQNFTNCHTKIRHVDAHATLNDGVVVQVMGLLSNNNQALRRFMQTFVLAPEGSVANKFYVHNDI<br>FRYQDEVFGGFVTEPQEESEEEVEEPEERQQTPEVVPDDSGTFYDQAVVSNDMEEHLEEPVAEPEPDPEPEPEQEP<br>VSEIQEEKPEPVLEETAPEDAQKSSSPAPADIAQTVQEDLRTFSWASVTSKNLPPSGAVPVTGIPPHVVKVPASQPR<br>PESKPESQIPPQRPQRDQRVREQRINIPPQRGPRPIREAGEQGDIEPRRMVRHPDSH (SEQ ID NO: 36) |
| NcVivid Y50W, C71V, I74V and I85V substitutions with a short 3' GSG repeat linker sequence, and G3BP1 Full Length Protein; NcVVDY50W/I74V/I85V-LINKERA-G3BP1:<br>MHTLYAPGGYDIMG**WL**IQIMNRPNPQVELGPVDTS**V**AL**V**LCDLKQKDTP**V**VYASEAFLYMTGYSNAEVLGRNCR<br>FLQSPDGMVKPKSTRKYVDSNTINTMRKAIDRNAEVQVEVVNFKKNGQRFVNFLTMIPVRDETGEYRYSMGFQC<br>ETE**GSGGSGGSGGSG**MVMEKPSPLLVGREFVRQYYTLLNQAPDMLHRFYGKNSSYVHGGLDSNGKPADAVYGQ<br>KEIHRKVMSQNFTNCHTKIRHVDAHATLNDGVVVQVMGLLSNNNQALRRFMQTFVLAPEGSVANKFYVHNDIF<br>RYQDEVFGGFVTEPQEESEEEVEEPEERQQTPEVVPDDSGTFYDQAVVSNDMEEHLEEPVAEPEPDPEPEPEQEP<br>VSEIQEEKPEPVLEETAPEDAQKSSSPAPADIAQTVQEDLRTFSWASVTSKNLPPSGAVPVTGIPPHVVKVPASQPR<br>PESKPESQIPPQRPQRDQRVREQRINIPPQRGPRPIREAGEQGDIEPRRMVRHPDSHQLFIGNLPHEVDKSELKDFF<br>QSYGNVVELRINSGGKLPNFGFVVFDDSEPVQKVLSNRPIMFRGEVRLNVEEKKTRAAREGDRRDNRLRGPGGPR<br>GGLGGGMRGPPRGGMVQKPGFGVGRGLAPRQKLIPMARRAWLEHGHSCFLCEIVIRSQFHTTYEPEA (SEQ ID<br>NO: 37) |
| NcVivid Y50W, C71V, I74V and I85V substitutions with a short 3' GSG repeat linker sequence, and G3BP1 NTF2 Domain Deletion Mutation; NcVVDY50W/I74V/I85V-LINKERA-G3BP1dNTF2:<br>MHTLYAPGGYDIMG**WL**IQIMNRPNPQVELGPVDTS**V**AL**V**LCDLKQKDTP**V**VYASEAFLYMTGYSNAEVLGRNCR<br>FLQSPDGMVKPKSTRKYVDSNTINTMRKAIDRNAEVQVEVVNFKKNGQRFVNFLTMIPVRDETGEYRYSMGFQC<br>ETEG**SGGSGGSGGSG**MGFVTEPQEESEEEVEEPEERQQTPEVVPDDSGTFYDQAVVSNDMEEHLEEPVAEPEPD<br>PEPEPEQEPVSEIQEEKPEPVLEETAPEDAQKSSSPAPADIAQTVQEDLRTFSWASVTSKNLPPSGAVPVTGIPPHVV<br>KVPASQPRPESKPESQIPPQRPQRDQRVREQRINIPPQRGPRPIREAGEQGDIEPRRMVRHPDSHQLFIGNLPHEV<br>DKSELKDFFQSYGNVVELRINSGGKLPNFGFVVFDDSEPVQKVLSNRPIMFRGEVRLNVEEKKTRAAREGDRRDNR<br>LRGPGGPRGGLGGGMRGPPRGGMVQKPGFGVGRGLAPRQKLIPMARRAWLEHGHSCFLCEIVIRSQFHTTYEPE<br>A (SEQ ID NO: 38) |

-continued

| Amino Acid Sequences of the Photolyase-Homologous Region (PHR) domain of the *Arabidopsis* Cryptochrome 2 protein: |
|---|

NcVivid Y50W, C71V, I74V and I85V substitutions with a short 3' GSG repeat linker sequence, and G3BP1 Acidic Domain Deletion Mutation; NcVVDY50W/I74V/I85V-LINKERA-G3BP1dAcidic:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGTAPEDAQKSSSPAPADIAQTVQEDLRTFSWASVTSKNLPPSGAVPVTGIPPHVVKVPASQPRPESKPE
SQIPPQRPQRDQRVREQRINIPPQRGPRPIREAGEQGDIEPRRMVRHPDSHQLFIGNLPHEVDKSELKDFFQSYGN
VVELRINSGGKLPNFGFVVFDDSEPVQKVLSNRPIMFRGEVRLNVEEKKTRAAREGDRRDNRLRGPGGPRGGLGG
GMRGPPRGGMVQKPGFGVGRGLAPRQKLIPMARRAWLEHGHSCFLCEIVIRSQFHTTYEPEA (SEQ ID NO: 39)

NcVivid Y50W, C71V, I74V and I85V substitutions with a short 3' GSG repeat linker sequence, and G3BP1 PxxP Domain Deletion Mutation; NcVVDY50W/I74V/I85V-LINKERA-G3BP1dPxxP:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEEQLFIGNLPHEVDKSELKDFFQSYGNVVELRINSGGKLPNFGFVVFDDSEPVQKVLSNRPIMFR
GEVRLNVEEKKTRAAREGDRRDNRLRGPGGPRGGLGGGMRGPPRGGMVQKPGFGVGRGLAPRQKLIPMARRA
WLEHGHSCFLCEIVIRSQFHTTYEPEA (SEQ ID NO: 40)

NcVivid Y50W, C71V, I74V and I85V substitutions with a short 3' GSG repeat linker sequence, and G3BP1 RRM Domain Deletion Mutation; NcVVDY50W/I74V/I85V-LINKERA-G3BP1dRRM:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHEKKTRAAREGDRRDNRLR
GPGGPRGGLGGGMRGPPRGGMVQKPGFGVGRGLAPRQKLIPMARRAWLEHGHSCFLCEIVIRSQFHTTYEPEA
(SEQ ID NO: 41)

NcVivid Y50W, C71V, I74V and I85V substitutions with a short 3' GSG repeat linker sequence, and G3BP1 RGG Domain Deletion Mutation; NcVVDY50W/I74V/I85V-LINKERA-G3BP1dRGG:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVE (SEQ ID NO: 42)

NcVivid Y50W, C71V, I74V and I85V substitutions with a short 3' GSG repeat linker sequence, and G3BP1 RRMRGG Domain Deletion Mutation; NcVVDY50W/I74V/I85V-LINKERA-G3BP1dRRMRGG:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGMVMEKPSPLLVGREFVRQYYTLLNQAPDMLHRFYGKNSSYVHGGLDSNGKPADAVYGQ
KEIHRKVMSQNFTNCHTKIRHVDAHATLNDGVVVQVMGLLSNNNQALRRFMQTFVLAPEGSVANKFYVHNDIF
RYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSH (SEQ ID NO: 43)

NcVivid Y50W, I52C, C71V, I74V and I85V substitutions with a short 3' GSG repeat linker sequence, and G3BP1 Full Length Protein; NcVVDY50W/I74V/I85V-LINKERA-G3BP1:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVEEKKTRAAREGDRRDNRLRGPGGPR
GGLGGGMRGPPRGGMVQKPGFGVGRGLAPRQKLIPMARRAWLEHGHSCFLCEIVIRSQFHTTYEPEA (SEQ ID NO: 44)

NcVivid Y50W, I52C, C71V, I74V and I85V substitutions with a short 3' GSG repeat linker sequence, and G3BP1 NTF2 Domain Deletion Mutation; NcVVDY50W/I74V/I85V-LINKERA-G3BP1dNTF2:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD -continued Amino Acid Sequences of the Photolyase-Homologous Region (PHR) domain of the *Arabidopsis* Cryptochrome 2 protein:

NRLRGPGGPRGGLGGGMRGPPRGGMVQKPGFGVGRGLAPRQKLIPMARRAWLEHGHSCFLCEIVIRSQFHTTY
EPEA (SEQ ID NO: 45)

NcVivid Y50W, I52C, C71V, I74V and I85V substitutions with a short 3' GSG repeat linker sequence, and G3BP1 Acidic Domain Deletion Mutation; NcVVDY50W/I74V/I85V-LINKERA-G3BP1dAcidic:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGTAPEDAQKSSSPAPADIAQTVQEDLRTFSWASVTSKNLPPSGAVPVTGIPPHVVKVPASQPRPESKP
ESQIPPQRPQRDQRVREQRINIPPQRGPRPIREAGEQGDIEPRRMVRHPDSHQLFIGNLPHEVDKSELKDFFQSYG
NVVELRINSGGKLPNFGFVVFDDSEPVQKVLSNRPIMFRGEVRLNVEEKKTRAAREGDRRDNRLRGPGGPRGGLG
GGMRGPPRGGMVQKPGFGVGRGLAPRQKLIPMARRAWLEHGHSCFLCEIVIRSQFHTTYEPEA (SEQ ID
NO: 46)

NcVivid Y50W, I52C, C71V, I74V and I85V substitutions with a short 3' GSG repeat linker sequence, and G3BP1 PxxP Domain Deletion Mutation; NcVVDY50W/I74V/I85V-LINKERA-G3BP1dPxxP:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEEQLFIGNLPHEVDKSELKDFFQSYGNVVELRINSGGKLPNFGFVVFDDSEPVQKVLSNRPIMFR
GEVRLNVEEKKTRAAREGDRRDNRLRGPGGPRGGLGGGMRGPPRGGMVQKPGFGVGRGLAPRQKLIPMARRA
WLEHGHSCFLCEIVIRSQFHTTYEPEA (SEQ ID NO: 47)

NcVivid Y50W, I52C, C71V, I74V and I85V substitutions with a short 3' GSG repeat linker sequence, and G3BP1 RRM Domain Deletion Mutation; NcVVDY50W/I74V/I85V-LINKERA-G3BP1dRRM:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHEKKTRAAREGDRRDNRLR
GPGGPRGGLGGGMRGPPRGGMVQKPGFGVGRGLAPRQKLIPMARRAWLEHGHSCFLCEIVIRSQFHTTYEPEA
(SEQ ID NO: 48)

NcVivid Y50W, I52C, C71V, I74V and I85V substitutions with a short 3' GSG repeat linker sequence, and G3BP1 RGG Domain Deletion Mutation; NcVVDY50W/I74V/I85V-LINKERA-G3BP1dRGG:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSHQLFIGNLPHEVDKSELKDFF
QSYGNVVELRINSGGKLPNFGFVVFDDSEPVQKVLSNRPIMFRGEVRLNVE (SEQ ID NO: 49)

NcVivid Y50W, I52C, C71V, I74V and I85V substitutions with a short 3' GSG repeat linker sequence, and G3BP1 RRMRGG Domain Deletion Mutation; NcVVDY50W/I74V/I85V-LINKERA-G3BP1dRRMRGG:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGMVMEKPSPLLVGREFVRQYYTLLNQAPDMLHRFYGKNSSYVHGGLDSNGKPADAVYG
QKEIHRKVMSQNFTNCHTKIRHVDAHATLNDGVVVQVMGLLSNNNQALRRFMQTFVLAPEGSVANKFYVHNDI
FRYQDEVFGGFVTEPQEESEEEVEEPEERQQTPEVVPDDSGTFYDQAVVSNDMEEHLEEPVAEPEPDPEPEPEQEP
VSEIQEEKPEPVLEETAPEDAQKSSSPAPADIAQTVQEDLRTFSWASVTSKNLPPSGAVPVTGIPPHVVKVPASQPR
PESKPESQIPPQRPQRDQRVREQRINIPPQRGPRPIREAGEQGDIEPRRMVRHPDSH (SEQ ID NO: 50)

NcVivid Y50W, I74V and I85V substitutions with a long 3' GSG repeat linker sequence, and G3BP1 Full Length Protein; NcVVDY50W/I74V/I85V-LINKERB-G3BP1:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD
NRLRGPGGPRGGLGGGMRGPPRGGMVQKPGFGVGRGLAPRQKLIPMARRAWLEHGHSCFLCEIVIRSQFHTTY
EPEA (SEQ ID NO: 51)

NcVivid Y50W, I74V and I85V substitutions with a long 3' GSG repeat linker sequence, and G3BP1 NTF2 Domain Deletion Mutation; NcVVDY50W/I74V/I85V-LINKERB-G3BP1dNTF2:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC -continued

| Amino Acid Sequences of the Photolyase-Homologous Region (PHR) domain of the *Arabidopsis* Cryptochrome 2 protein: |
|---|
| ETE**GSGGSGGSGGSGGTGGSGGSG**MGFVTEPQEESEEEVEEPEERQQTPEVVPDDSGTFYDQAVVSNDMEEHL<br>EEPVAEPEPDPEPEPEQEPVSEIQEEKPEPVLEETAPEDAQKSSSPAPADIAQTVQEDLRTFSWASVTSKNLPPSGAV<br>PVTGIPPHVVKVPASQPRPESKPESQIPPQRPQRDQRVREQRINIPPQRGPRPIREAGEQGDIEPRRMVRHPDSHQ<br>LFIGNLPHEVDKSELKDFFQSYGNVVELRINSGGKLPNFGFVVFDDSEPVQKVLSNRPIMFRGEVRLNVEEKKTRAA<br>REGDRRDNRLRGPGGPRGGLGGGMRGPPRGGMVQKPGFGVGRGLAPRQKLIPMARRAWLEHGHSCFLCEIVIR<br>SQFHTTYEPEA (SEQ ID NO: 52) |

NcVivid Y50W, I74V and I85V substitutions with a long 3' GSG repeat linker sequence, and G3BP1 Acidic Domain Deletion Mutation; NcVVDY50W/I74V/I85V-LINKERB-G3BP1dAcidic:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGTAPEDAQKSSSPAPADIAQTVQEDLRTFSWASVTSKNLPPSGAVPVTGIPPHVVKVPA
SQPRPESKPESQIPPQRPQRDQRVREQRINIPPQRGPRPIREAGEQGDIEPRRMVRHPDSHQLFIGNLPHEVDKSE
LKDFFQSYGNVVELRINSGGKLPNFGFVVFDDSEPVQKVLSNRPIMFRGEVRLNVEEKKTRAAREGDRRDNRLRGP
GGPRGGLGGGMRGPPRGGMVQKPGFGVGRGLAPRQKLIPMARRAWLEHGHSCFLCEIVIRSQFHTTYEPEA
(SEQ ID NO: 53)

NcVivid Y50W, I74V and I85V substitutions with a long 3' GSG repeat linker sequence, and G3BP1 PxxP Domain Deletion Mutation; NcVVDY50W/I74V/I85V-LINKERB-G3BP1dPxxP:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEEQLFIGNLPHEVDKSELKDFFQSYGNVVELRINSGGKLPNFGFVVFDDSEPVQK
VLSNRPIMFRGEVRLNVEEKKTRAAREGDRRDNRLRGPGGPRGGLGGGMRGPPRGGMVQKPGFGVGRGLAPR
QKLIPMARRAWLEHGHSCFLCEIVIRSQFHTTYEPEA (SEQ ID NO: 54)

NcVivid Y50W, I74V and I85V substitutions with a long 3' GSG repeat linker sequence, and G3BP1 RRM Domain Deletion Mutation; NcVVDY50W/I74V/I85V-LINKERB-G3BP1dRRM:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEA (SEQ ID NO: 55)

NcVivid Y50W, I74V and I85V substitutions with a long 3' GSG repeat linker sequence, and G3BP1 RGG Domain Deletion Mutation; NcVVDY50W/I74V/I85V-LINKERB-G3BP1dRGG:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVE (SEQ ID NO: 56)

NcVivid Y50W, I74V and I85V substitutions with a long 3' GSG repeat linker sequence, and G3BP1 RRMRGG Domain Deletion Mutation; NcVVDY50W/I74V/I85V-LINKERB-G3BP1dRRMRGG:
MHTLYAPGGYDIMGWLIQIMNRPNPQVELGPVDTSCALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSH (SEQ ID NO: 57)

NcVivid Y50W, I52C, I74V and I85V substitutions with a long 3' GSG repeat linker sequence, and G3BP1 Full Length Protein; NcVVDY50W/I74V/I85V-LINKERB-G3BP1:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD
NRLRGPGGPRGGLGGGMRGPPRGGMVQKPGFGVGRGLAPRQKLIPMARRAWLEHGHSCFLCEIVIRSQFHTTY
EPEA (SEQ ID NO: 58)

-continued

Amino Acid Sequences of the Photolyase-Homologous Region (PHR) domain of the *Arabidopsis* Cryptochrome 2 protein:

NcVivid Y50W, I52C, I74V and I85V substitutions with a long 3' GSG repeat linker sequence, and G3BP1 NTF2 Domain Deletion Mutation; NcVVDY50W/I74V/I85V-LINKERB-G3BP1dNTF2:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMGFVTEPQEESEEEVEEPEERQQTPEVVPDDSGTFYDQAVVSNDMEEH
LEEPVAEPEPDPEPEPEQEPVSEIQEEKPEPVLEETAPEDAQKSSSPAPADIAQTVQEDLRTFSWASVTSKNLPPSGA
VPVTGIPPHVVKVPASQPRPESKPESQIPPQRPQRDQRVREQRINIPPQRGPRPIREAGEQGDIEPRRMVRHPDSH
QLFIGNLPHEVDKSELKDFFQSYGNVVELRINSGGKLPNFGFVVFDDSEPVQKVLSNRPIMFRGEVRLNVEEKKTRA
AREGDRRDNRLRGPGGPRGGLGGGMRGPPRGGMVQKPGFGVGRGLAPRQKLIPMARRAWLEHGHSCFLCEIVI
RSQFHTTYEPEA (SEQ ID NO: 59)

NcVivid Y50W, I52C, I74V and I85V substitutions with a long 3' GSG repeat linker sequence, and G3BP1 Acidic Domain Deletion Mutation; NcVVDY50W/I74V/I85V-LINKERB-G3BP1dAcidic:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGTAPEDAQKSSSPAPADIAQTVQEDLRTFSWASVISKNLPPSGAVPVTGIPPHVVKVP
ASQPRPESKPESQIPPQRPQRDQRVREQRINIPPQRGPRPIREAGEQGDIEPRRMVRHPDSHQLFIGNLPHEVDKS
ELKDFFQSYGNVVELRINSGGKLPNFGFVVFDDSEPVQKVLSNRPIMFRGEVRLNVEEKKTRAAREGDRRDNRLRG
PGGPRGGLGGGMRGPPRGGMVQKPGFGVGRGLAPRQKLIPMARRAWLEHGHSCFLCEIVIRSQFHTTYEPEA
(SEQ ID NO: 60)

NcVivid Y50W, I52C, I74V and I85V substitutions with a long 3' GSG repeat linker sequence, and G3BP1 PxxP Domain Deletion Mutation; NcVVDY50W/I74V/I85V-LINKERB-G3BP1dPxxP:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEEQLFIGNLPHEVDKSELKDFFQSYGNVVELRINSGGKLPNFGFVVFDDSEPVQ
KVLSNRPIMFRGEVRLNVEEKKTRAAREGDRRDNRLRGPGGPRGGLGGGMRGPPRGGMVQKPGFGVGRGLAP
RQKLIPMARRAWLEHGHSCFLCEIVIRSQFHTTYEPEA (SEQ ID NO: 61)

NcVivid Y50W, I52C, I74V and I85V substitutions with a long 3' GSG repeat linker sequence, and G3BP1 RRM Domain Deletion Mutation; NcVVDY50W/I74V/I85V-LINKERB-G3BP1dRRM:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEA (SEQ ID NO: 62)

NcVivid Y50W, I52C, I74V and I85V substitutions with a long 3' GSG repeat linker sequence, and G3BP1 RGG Domain Deletion Mutation; NcVVDY50W/I74V/I85V-LINKERB-G3BP1dRGG:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVE (SEQ ID NO: 63)

NcVivid Y50W, I52C, I74V and I85V substitutions with a long 3' GSG repeat linker sequence, and G3BP1 RRMRGG Domain Deletion Mutation; NcVVDY50W/I74V/I85V-LINKERB-G3BP1dRRMRGG:
MHTLYAPGGYDIMGWLCQIMNRPNPQVELGPVDTSCALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSH (SEQ ID
NO: 64)

NcVivid Y50W, C71V, I74V and I85V substitutions with a long 3' GSG repeat linker sequence, and G3BP1 Full Length Protein; NcVVDY50W/I74V/I85V-LINKERB-G3BP1:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP -continued

| Amino Acid Sequences of the Photolyase-Homologous Region (PHR) domain of the *Arabidopsis* Cryptochrome 2 protein: |
|---|

DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD
NRLRGPGGPRGGLGGGMRGPPRGGMVQKPGFGVGRGLAPRQKLIPMARRAWLEHGHSCFLCEIVIRSQFHTTY
EPEA (SEQ ID NO: 65)

NcVivid Y50W, C71V, I74V and I85V substitutions with a long 3' GSG repeat linker sequence, and G3BP1 NTF2 Domain Deletion Mutation; NcVVDY50W/I74V/I85V-LINKERB-G3BP1dNTF2:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMGFVTEPQEESEEEVEEPEERQQTPEVVPDDSGTFYDQAVVSNDMEEHL
EEPVAEPEPDPEPEPEQEPVSEIQEEKPEPVLEETAPEDAQKSSSPAPADIAQTVQEDLRTFSWASVTSKNLPPSGAV
PVTGIPPHVVKVPASQPRPESKPESQIPPQRPQRDQRVREQRINIPPQRGPRPIREAGEQGDIEPRRMVRHPDSHQ
LFIGNLPHEVDKSELKDFFQSYGNVVELRINSGGKLPNFGFVVFDDSEPVQKVLSNRPIMFRGEVRLNVEEKKTRAA
REGDRRDNRLRGPGGPRGGLGGGMRGPPRGGMVQKPGFGVGRGLAPRQKLIPMARRAWLEHGHSCFLCEIVIR
SQFHTTYEPEA (SEQ ID NO: 66)

NcVivid Y50W, C71V, I74V and I85V substitutions with a long 3' GSG repeat linker sequence, and G3BP1 Acidic Domain Deletion Mutation; NcVVDY50W/I74V/I85V-LINKERB-G3BP1dAcidic:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGTAPEDAQKSSSPAPADIAQTVQEDLRTFSWASVTSKNLPPSGAVPVTGIPPHVVKVPA
SQPRPESKPESQIPPQRPQRDQRVREQRINIPPQRGPRPIREAGEQGDIEPRRMVRHPDSHQLFIGNLPHEVDKSE
LKDFFQSYGNVVELRINSGGKLPNFGFVVFDDSEPVQKVLSNRPIMFRGEVRLNVEEKKTRAAREGDRRDNRLRGP
GGPRGGLGGGMRGPPRGGMVQKPGFGVGRGLAPRQKLIPMARRAWLEHGHSCFLCEIVIRSQFHTTYEPEA
(SEQ ID NO: 67)

NcVivid Y50W, C71V, I74V and I85V substitutions with a long 3' GSG repeat linker sequence, and G3BP1 PxxP Domain Deletion Mutation; NcVVDY50W/I74V/I85V-LINKERB-G3BP1dPxxP:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEEQLFIGNLPHEVDKSELKDFFQSYGNVVELRINSGGKLPNFGFVVFDDSEPVQK
VLSNRPIMFRGEVRLNVEEKKTRAAREGDRRDNRLRGPGGPRGGLGGGMRGPPRGGMVQKPGFGVGRGLAPR
QKLIPMARRAWLEHGHSCFLCEIVIRSQFHTTYEPEA (SEQ ID NO: 68)

NcVivid Y50W, C71V, I74V and I85V substitutions with a long 3' GSG repeat linker sequence, and G3BP1 RRM Domain Deletion Mutation; NcVVDY50W/I74V/I85V-LINKERB-G3BP1dRRM:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHND1FRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEA (SEQ ID NO: 69)

NcVivid Y50W, C71V, I74V and I85V substitutions with a long 3' GSG repeat linker sequence, and G3BP1 RGG Domain Deletion Mutation; NcVVDY50W/I74V/I85V-LINKERB-G3BP1dRGG:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVE (SEQ ID NO: 70)

NcVivid Y50W, C71V, I74V and I85V substitutions with a long 3' GSG repeat linker sequence, and G3BP1 RRMRGG Domain Deletion Mutation; NcVVDY50W/I74V/I85V-LINKERB-G3BP1dRRMRGG:
MHTLYAPGGYDIMGWLIQIMNRPNPQVELGPVDTSVALVLCDLKQKDTPVVYASEAFLYMTGYSNAEVLGRNCR
FLQSPDGMVKPKSTRKYVDSNTINTMRKAIDRNAEVQVEVVNFKKNGQRFVNFLTMIPVRDETGEYRYSMGFQC
ETEGSGGSGGSGGSGGTGGSGGSGMVMEKPSPLLVGREFVRQYYTLLNQAPDMLHRFYGKNSSYVHGGLDSNG
KPADAVYGQKEIHRKVMSQNFTNCHTKIRHVDAHATLNDGVVVQVMGLLSNNNQALRRFMQTFVLAPEGSVA
NKFYVHNDIFRYQDEVFGGFVTEPQEESEEEVEEPEERQQTPEVVPDDSGTFYDQAVVSNDMEEHLEEPVAEPEP
DPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSH (SEQ ID NO: 71)

-continued

Amino Acid Sequences of the Photolyase-Homologous Region (PHR) domain of the *Arabidopsis* Cryptochrome 2 protein:

NcVivid Y50W, I52C, C71V, I74V and I85V substitutions with a long 3' GSG repeat linker sequence, and G3BP1 Full Length Protein; NcVVDY50W/I74V/I85V-LINKERB-G3BP1:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVEEKKTRAAREGDRRD
NRLRGPGGPRGGLGGGMRGPPRGGMVQKPGFGVGRGLAPRQKLIPMARRAWLEHGHSCFLCEIVIRSQFHTTY
EPEA (SEQ ID NO: 72)

NcVivid Y50W, I52C, C71V, I74V and I85V substitutions with a long 3' GSG repeat linker sequence, and G3BP1 NTF2 Domain Deletion Mutation; NcVVDY50W/I74V/I85V-LINKERB-G3BP1dNTF2:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMGFVTEPQEESEEEVEEPEERQQTPEVVPDDSGTFYDQAVVSNDMEEH
LEEPVAEPEPDPEPEPEQEPVSEIQEEKPEPVLEETAPEDAQKSSSPAPADIAQTVQEDLRTFSWASVTSKNLPPSGA
VPVTGIPPHVVKVPASQPRPESKPESQIPPQRPQRDQRVREQRINIPPQRGPRPIREAGEQGDIEPRRMVRHPDSH
QLFIGNLPHEVDKSELKDFFQSYGNVVELRINSGGKLPNFGFVVFDDSEPVQKVLSNRPIMFRGEVRLNVEEKKTRA
AREGDRRDNRLRGPGGPRGGLGGGMRGPPRGGMVQKPGFGVGRGLAPRQKLIPMARRAWLEHGHSCFLCEIVI
RSQFHTTYEPEA (SEQ ID NO: 73)

NcVivid Y50W, I52C, C71V, I74V and I85V substitutions with a long 3' GSG repeat linker sequence, and G3BP1 Acidic Domain Deletion Mutation; NcVVDY50W/I74V/I85V-LINKERB-G3BP1dAcidic:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGTAPEDAQKSSSPAPADIAQTVQEDLRTFSWASVISKNLPPSGAVPVTGIPPHVVKVP
ASQPRPESKPESQIPPQRPQRDQRVREQRINIPPQRGPRPIREAGEQGDIEPRRMVRHPDSHQLFIGNLPHEVDKS
ELKDFFQSYGNVVELRINSGGKLPNFGFVVFDDSEPVQKVLSNRPIMFRGEVRLNVEEKKTRAAREGDRRDNRLRG
PGGPRGGLGGGMRGPPRGGMVQKPGFGVGRGLAPRQKLIPMARRAWLEHGHSCFLCEIVIRSQFHTTYEPEA
(SEQ ID NO: 74)

NcVivid Y50W, I52C, C71V, I74V and I85V substitutions with a long 3' GSG repeat linker sequence, and G3BP1 PxxP Domain Deletion Mutation; NcVVDY50W/I74V/I85V-LINKERB-G3BP1dPxxP:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEEQLFIGNLPHEVDKSELKDFFQSYGNVVELRINSGGKLPNFGFVVFDDSEPVQ
KVLSNRPIMFRGEVRLNVEEKKTRAAREGDRRDNRLRGPGGPRGGLGGGMRGPPRGGMVQKPGFGVGRGLAP
RQKLIPMARRAWLEHGHSCFLCEIVIRSQFHTTYEPEA (SEQ ID NO: 75)

NcVivid Y50W, I52C, C71V, I74V and I85V substitutions with a long 3' GSG repeat linker sequence, and G3BP1 RRM Domain Deletion Mutation; NcVVDY50W/I74V/I85V-LINKERB-G3BP1dRRM:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEA (SEQ ID NO: 76)

NcVivid Y50W, I52C, C71V, I74V and I85V substitutions with a long 3' GSG repeat linker sequence, and G3BP1 RGG Domain Deletion Mutation; NcVVDY50W/I74V/I85V-LINKERB-G3BP1dRGG:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN
GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSHQLFIGNLPH
EVDKSELKDFFQSYGNVVELRINSGGKLPNFGFVVFDDSEPVQKVLSNRPIMFRGEVRLNVE (SEQ ID NO: 77)

NcVivid Y50W, I52C, C71V, I74V and I85V substitutions with a long 3' GSG repeat linker sequence, and G3BP1 RRMRGG Domain Deletion Mutation; NcVVDY50W/I74V/I85V-LINKERB-G3BP1dRRMRGG:
MHTLYAPGGYDIMGWLCQIMNRPNPQVELGPVDTSVALVLCDLKQKDTPVVYASEAFLYMTGYSNAEVLGRNC
RFLQSPDGMVKPKSTRKYVDSNTINTMRKAIDRNAEVQVEVVNFKKNGQRFVNFLTMIPVRDETGEYRYSMGFQ
CETEGSGGSGGSGGSGGTGGSGGSGMVMEKPSPLLVGREFVRQYYTLLNQAPDMLHRFYGKNSSYVHGGLDSN -continued

| Amino Acid Sequences of the Photolyase-Homologous Region (PHR) domain of the *Arabidopsis* Cryptochrome 2 protein: |
|---|

GKPADAVYGQKEIHRKVMSQNFTNCHTKIRHVDAHATLNDGVVVQVMGLLSNNNQALRRFMQTFVLAPEGSV
ANKFYVHNDIFRYQDEVFGGFVTEPQEESEEEVEEPEERQQTPEVVPDDSGTFYDQAVVSNDMEEHLEEPVAEPE
PDPEPEPEQEPVSEIQEEKPEPVLEETAPEDAQKSSSPAPADIAQTVQEDLRTFSWASVTSKNLPPSGAVPVTGIPPH
VVKVPASQPRPESKPESQIPPQRPQRDQRVREQRINIPPQRGPRPIREAGEQGDIEPRRMVRHPDSH (SEQ ID NO: 78)

Cry2Olig with G3BP1 Full Length Protein; Cry2Olig-G3BP1
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSHQLFIGNLPHEVDKSELKDFFQSYGNVVELRINSGGKLPNFGFVVFDDSEPVQKVLSNRPIMFRGEVRLNV
EEKKTRAAREGDRRDNRLRGPGGPRGGLGGGMRGPPRGGMVQKPGFGVGRGLAPRQKLIPMARRAWLEHGH
SCFLCEIVIRSQFHTTYEPEA (SEQ ID NO: 79)

Cry2Olig with G3BP1 NTF2 Domain Deletion Mutation; Cry2Olig-G3BP1dNTF2
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMGFVTEPQEESEEEVEEPEERQQTPEVVPDDSGTF
YDQAVVSNDMEEHLEEPVAEPEPDPEPEPEQEPVSEIQEEKPEPVLEETAPEDAQKSSSPAPADIAQTVQEDLRTFS
WASVTSKNLPPSGAVPVTGIPPHVVKVPASQPRPESKPESQIPPQRPQRDQRVREQRINIPPQRGPRPIREAGEQG
DIEPRRMVRHPDSHQLFIGNLPHEVDKSELKDFFQSYGNVVELRINSGGKLPNFGFVVFDDSEPVQKVLSNRPIMF
RGEVRLNVEEKKTRAAREGDRRDNRLRGPGGPRGGLGGGMRGPPRGGMVQKPGFGVGRGLAPRQKLIPMARR
AWLEHGHSCFLCEIVIRSQFHTTYEPEA (SEQ ID NO: 80)

Cry2Olig with G3BP1 Acidic Domain Deletion Mutation; Cry2Olig-G3BP1dAcidic
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGTAPEDAQKSSSPAPADIAQTVQEDLRTFSWASVTSKNLPPSG
AVPVTGIPPHVVKVPASQPRPESKPESQIPPQRPQRDQRVREQRINIPPQRGPRPIREAGEQGDIEPRRMVRHPDS
HQLFIGNLPHEVDKSELKDFFQSYGNVVELRINSGGKLPNFGFVVFDDSEPVQKVLSNRPIMFRGEVRLNVEEKKTR
AAREGDRRDNRLRGPGGPRGGLGGGMRGPPRGGMVQKPGFGVGRGLAPRQKLIPMARRAWLEHGHSCFLCEI
VIRSQFHTTYEPEA (SEQ ID NO: 81)

Cry2Olig with G3BP1 PxxP Domain Deletion Mutation; Cry2Olig-G3BP1dPxxP
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEEQLFIGNLPHEVDKSELKDFFQSYGNVVELRINSGGKLP
NFGFVVFDDSEPVQKVLSNRPIMFRGEVRLNVEEKKTRAAREGDRRDNRLRGPGGPRGGLGGGMRGPPRGGM
VQKPGFGVGRGLAPRQKLIPMARRAWLEHGHSCFLCEIVIRSQFHTTYEPEA (SEQ ID NO: 82)

Cry2Olig with G3BP1 RRM Domain Deletion Mutation; Cry2Olig-G3BP1dRRM
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN -continued

| Amino Acid Sequences of the Photolyase-Homologous Region (PHR) domain of the *Arabidopsis* Cryptochrome 2 protein: |
|---|

LPPSGAVPVTGIPPHVVKVPASQPRPESKPESQIPPQRPQRDQRVREQRINIPPQRGPRPIREAGEQGDIEPRRMV
RHPDSHEKKTRAAREGDRRDNRLRGPGGPRGGLGGGMRGPPRGGMVQKPGFGVGRGLAPRQKLIPMARRAW
LEHGHSCFLCEIVIRSQFHTTYEPEA (SEQ ID NO: 83)

Cry2Olig with G3BP1 RGG Domain Deletion Mutation; Cry2Olig-G3BP1dRGG
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSHQLFIGNLPHEVDKSELKDFFQSYGNVVELRINSGGKLPNFGFVVFDDSEPVQKVLSNRPIMFRGEVRLNV
E (SEQ ID NO: 84)

Cry2Olig with G3BP1 RRMRGG Domain Deletion Mutation; Cry2Olig-G3BP1dRRMRGG
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTRGAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSH (SEQ ID NO: 85)

G3BP1 Full Length Protein with Cry2Olig; G3BP1-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHQLFIGNLPHEVDKSELKDFFQSYGNVVELRINSGGKL
PNFGFVVFDDSEPVQKVLSNRPIMFRGEVRLNVEEKKTRAAREGDRRDNRLRGPGGPRGGLGGGMRGPPRGGM
VQKPGFGVGRGLAPRQKLIPMARRAWLEHGHSCFLCEIVIRSQFHTTYEPEAMKMDKKTIVWFRRDLRIEDNPAL
AAAAHEGSVFPVFIWCPEEEGQFYPGRASRWWMKQSLAHLSQSLKALGSDLTLIKTHNTISAILDCIRVTGATKVVF
NHLYDPVSLVRDHTVKEKLVERGISVQSYNGDLLYEPWEIYCEKGKPFTSFNSYWKKCLDMSIESVMLPPPWRLMP
ITAAAEAIWACSIEELGLENEAEKPSNALLTRAWSPGWSNADKLLNEFIEKQLIDYAKNSKKVVGNSTSLLSPYLHFG
EISVRHVFQCARMKQIIWARDKNSEGEESADLFLRGIGLREYSRYICFNFPFTHEQSLLSHLRFFPWDADVDKFKAW
RQGRTGYPLVDAGMRELWATGWMHNRIRVIVSSFAVKFLLLPWKWGMKYFWDTLLDADLECDILGWQYISGSI
PDGHELDRLDNPALQGAKYDPEGEYIRQWLPELARLPTEWIHHPWDAPLTVLKASGVELGTNYAKPIVDIDTAREL
LAKAISRTRGAQIMIGAA (SEQ ID NO: 86)

G3BP1 NTF2 Domain Deletion Mutation with Cry2Olig; G3BP1dNTF2-Cry2Olig
MGFVTEPQEESEEEVEEPEERQQTPEVVPDDSGTFYDQAVVSNDMEEHLEEPVAEPEPDPEPEPEQEPVSEIQEEK
PEPVLEETAPEDAQKSSSPAPADIAQTVQEDLRTFSWASVTSKNLPPSGAVPVTGIPPHVVKVPASQPRPESKPESQ
IPPQRPQRDQRVREQRINIPPQRGPRPIREAGEQGDIEPRRMVRHPDSHQLFIGNLPHEVDKSELKDFFQSYGNVV
ELRINSGGKLPNFGFVVFDDSEPVQKVLSNRPIMFRGEVRLNVEEKKTRAAREGDRRDNRLRGPGGPRGGLGGG
MRGPPRGGMVQKPGFGVGRGLAPRQKLIPMARRAWLEHGHSCFLCEIVIRSQFHTTYEPEAMKMDKKTIVWFR
RDLRIEDNPALAAAAHEGSVFPVFIWCPEEEGQFYPGRASRWWMKQSLAHLSQSLKALGSDLTLIKTHNTISAILDC
IRVTGATKVVFNHLYDPVSLVRDHTVKEKLVERGISVQSYNGDLLYEPWEIYCEKGKPFTSFNSYWKKCLDMSIESV
MLPPPWRLMPITAAAEAIWACSIEELGLENEAEKPSNALLTRAWSPGWSNADKLLNEFIEKQLIDYAKNSKKVVGN
STSLLSPYLHFGEISVRHVFQCARMKQIIWARDKNSEGEESADLFLRGIGLREYSRYICFNFPFTHEQSLLSHLRFFPW
DADVDKFKAWRQGRTGYPLVDAGMRELWATGWMHNRIRVIVSSFAVKFLLLPWKWGMKYFWDTLLDADLEC
DILGWQYISGSIPDGHELDRLDNPALQGAKYDPEGEYIRQWLPELARLPTEWIHHPWDAPLTVLKASGVELGTNYA
KPIVDIDTARELLAKAISRTRGAQIMIGAA (SEQ ID NO: 87)

G3BP1 Acidic Domain Deletion Mutation with Cry2Olig; G3BP1dAcidic-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGTAPEDAQ
KSSSPAPADIAQTVQEDLRTFSWASVTSKNLPPSGAVPVTGIPPHVVKVPASQPRPESKPESQIPPQRPQRDQRVR
EQRINIPPQRGPRPIREAGEQGDIEPRRMVRHPDSHQLFIGNLPHEVDKSELKDFFQSYGNVVELRINSGGKLPNFG
FVVFDDSEPVQKVLSNRPIMFRGEVRLNVEEKKTRAAREGDRRDNRLRGPGGPRGGLGGGMRGPPRGGMVQKP
GFGVGRGLAPRQKLIPMARRAWLEHGHSCFLCEIVIRSQFHTTYEPEAMKMDKKTIVWFRRDLRIEDNPALAAAA
HEGSVFPVFIWCPEEEGQFYPGRASRWWMKQSLAHLSQSLKALGSDLTLIKTHNTISAILDCIRVTGATKVVFNHLY
DPVSLVRDHTVKEKLVERGISVQSYNGDLLYEPWEIYCEKGKPFTSFNSYWKKCLDMSIESVMLPPPWRLMPITAA
AEAIWACSIEELGLENEAEKPSNALLTRAWSPGWSNADKLLNEFIEKQLIDYAKNSKKVVGNSTSLLSPYLHFGEISV
RHVFQCARMKQIIWARDKNSEGEESADLFLRGIGLREYSRYICFNFPFTHEQSLLSHLRFFPWDADVDKFKAWRQG
RTGYPLVDAGMRELWATGWMHNRIRVIVSSFAVKFLLLPWKWGMKYFWDTLLDADLECDILGWQYISGSIPDG
HELDRLDNPALQGAKYDPEGEYIRQWLPELARLPTEWIHHPWDAPLTVLKASGVELGTNYAKPIVDIDTARELLAK -continued

| Amino Acid Sequences of the Photolyase-Homologous Region (PHR) domain of the *Arabidopsis* Cryptochrome 2 protein: |
|---|

AISRTRGAQIMIGAA (SEQ ID NO: 88)

G3BP1 PxxP Domain Deletion Mutation with Cry2Olig; G3BP1dPxxP-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEEQLFI
GNLPHEVDKSELKDFFQSYGNVVELRINSGGKLPNFGFVVFDDSEPVQKVLSNRPIMFRGEVRLNVEEKKTRAARE
GDRRDNRLRGPGGPRGGLGGGMRGPPRGGMVQKPGFGVGRGLAPRQKLIPMARRAWLEHGHSCFLCEIVIRS
QFHTTYEPEAMKMDKKTIVWFRRDLRIEDNPALAAAAHEGSVFPVFIWCPEEEGQFYPGRASRWWMKQSLAHL
SQSLKALGSDLTLIKTHNTISAILDCIRVTGATKVVFNHLYDPVSLVRDHTVKEKLVERGISVQSYNGDLLYEPWEIYCE
KGKPFTSFNSYWKKCLDMSIESVMLPPPWRLMPITAAAEAIWACSIEELGLENEAEKPSNALLTRAWSPGWSNAD
KLLNEFIEKQLIDYAKNSKKVVGNSTSLLSPYLHFGEISVRHVFQCARMKQIIWARDKNSEGEESADLFLRGIGLREYS
RYICFNFPFTHEQSLLSHLRFFPWDADVDKFKAWRQGRTGYPLVDAGMRELWATGWMHNRIRVIVSSFAVKFLLL
PWKWGMKYFWDTLLDADLECDILGWQYISGSIPDGHELDRLDNPALQGAKYDPEGEYIRQWLPELARLPTEWIH
HPWDAPLTVLKASGVELGTNYAKPIVDIDTARELLAKAISRTRGAQIMIGAA (SEQ ID NO: 89)

G3BP1 RRM Domain Deletion Mutation with Cry2Olig; G3BP1dRRM-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHEKKTRAAREGDRRDNRLRGPGGPRGGLGGGMRG
PPRGGMVQKPGFGVGRGLAPRQKLIPMARRAWLEHGHSCFLCEIVIRSQFHTTYEPEAMKMDKKTIVWFRRDLRI
EDNPALAAAAHEGSVFPVFIWCPEEEGQFYPGRASRWWMKQSLAHLSQSLKALGSDLTLIKTHNTISAILDCIRVT
GATKVVFNHLYDPVSLVRDHTVKEKLVERGISVQSYNGDLLYEPWEIYCEKGKPFTSFNSYWKKCLDMSIESVMLPP
PWRLMPITAAAEAIWACSIEELGLENEAEKPSNALLTRAWSPGWSNADKLLNEFIEKQLIDYAKNSKKVVGNSTSLL
SPYLHFGEISVRHVFQCARMKQIIWARDKNSEGEESADLFLRGIGLREYSRYICFNFPFTHEQSLLSHLRFFPWDADV
DKFKAWRQGRTGYPLVDAGMRELWATGWMHNRIRVIVSSFAVKFLLLPWKWGMKYFWDTLLDADLECDILGW
QYISGSIPDGHELDRLDNPALQGAKYDPEGEYIRQWLPELARLPTEWIHHPWDAPLTVLKASGVELGTNYAKPIVDI
DTARELLAKAISRTRGAQIMIGAA (SEQ ID NO: 90)

G3BP1 RGG Domain Deletion Mutation with Cry2Olig; G3BP1dRGG-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHQLFIGNLPHEVDKSELKDFFQSYGNVVELRINSGGKL
PNFGFVVFDDSEPVQKVLSNRPIMFRGEVRLNVEMKMDKKTIVWFRRDLRIEDNPALAAAAHEGSVFPVFIWCPE
EEGQFYPGRASRWWMKQSLAHLSQSLKALGSDLTLIKTHNTISAILDCIRVTGATKVVFNHLYDPVSLVRDHTVKEK
LVERGISVQSYNGDLLYEPWEIYCEKGKPFTSFNSYWKKCLDMSIESVMLPPPWRLMPITAAAEAIWACSIEELGLE
NEAEKPSNALLTRAWSPGWSNADKLLNEFIEKQLIDYAKNSKKVVGNSTSLLSPYLHFGEISVRHVFQCARMKQIIW
ARDKNSEGEESADLFLRGIGLREYSRYICFNFPFTHEQSLLSHLRFFPWDADVDKFKAWRQGRTGYPLVDAGMREL
WATGWMHNRIRVIVSSFAVKFLLLPWKWGMKYFWDTLLDADLECDILGWQYISGSIPDGHELDRLDNPALQGAK
YDPEGEYIRQWLPELARLPTEWIHHPWDAPLTVLKASGVELGTNYAKPIVDIDTARELLAKAISRTRGAQIMIGAA
(SEQ ID NO: 91)

G3BP1 RRMRGG Domain Deletion Mutation with Cry2Olig; G3BP1dRRMRGG-Cry2Olig
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHMKMDKKTIVWFRRDLRIEDNPALAAAAHEGSVFP
VFIWCPEEEGQFYPGRASRWWMKQSLAHLSQSLKALGSDLTLIKTHNTISAILDCIRVTGATKVVFNHLYDPVSLVR
DHTVKEKLVERGISVQSYNGDLLYEPWEIYCEKGKPFTSFNSYWKKCLDMSIESVMLPPPWRLMPITAAAEAIWAC
SIEELGLENEAEKPSNALLTRAWSPGWSNADKLLNEFIEKQLIDYAKNSKKVVGNSTSLLSPYLHFGEISVRHVFQCA
RMKQIIWARDKNSEGEESADLFLRGIGLREYSRYICFNFPFTHEQSLLSHLRFFPWDADVDKFKAWRQGRTGYPLV
DAGMRELWATGWMHNRIRVIVSSFAVKFLLLPWKWGMKYFWDTLLDADLECDILGWQYISGSIPDGHELDRLD
NPALQGAKYDPEGEYIRQWLPELARLPTEWIHHPWDAPLIVLKASGVELGTNYAKPIVDIDTARELLAKAISRTRGA
QIMIGAA (SEQ ID NO: 92)

Cry2PHR with G3BP1 Full Length Protein; Cry2PHR-G3BP1
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSHQLFIGNLPHEVDKSELKDFFQSYGNVVELRINSGGKLPNFGFVVFDDSEPVQKVLSNRPIMFRGEVRLNV
EEKKTRAAREGDRRDNRLRGPGGPRGGLGGGMRGPPRGGMVQKPGFGVGRGLAPRQKLIPMARRAWLEHGH
SCFLCEIVIRSQFHTTYEPEA (SEQ ID NO: 93)

-continued

| Amino Acid Sequences of the Photolyase-Homologous Region (PHR) domain of the *Arabidopsis* Cryptochrome 2 protein: |
|---|

Cry2PHR with G3BP1 NTF2 Domain Deletion Mutation; Cry2PHR-G3BP1dNTF2
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMGFVTEPQEESEEEVEEPEERQQTPEVVPDDSGTFY
DQAVVSNDMEEHLEEPVAEPEPDPEPEPEQEPVSEIQEEKPEPVLEETAPEDAQKSSSPAPADIAQTVQEDLRTFS
WASVTSKNLPPSGAVPVTGIPPHVVKVPASQPRPESKPESQIPPQRPQRDQRVREQRINIPPQRGPRPIREAGEQG
DIEPRRMVRHPDSHQLFIGNLPHEVDKSELKDFFQSYGNVVELRINSGGKLPNFGFVVFDDSEPVQKVLSNRPIMF
RGEVRLNVEEKKTRAAREGDRRDNRLRGPGGPRGGLGGGMRGPPRGGMVQKPGFGVGRGLAPRQKLIPMARR
AWLEHGHSCFLCEIVIRSQFHTTYEPEA (SEQ ID NO: 94)

Cry2PHR with G3BP1 Acidic Domain Deletion Mutation; Cry2PHR-G3BP1dAcidic
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGTAPEDAQKSSSPAPADIAQTVQEDLRTFSWASVTSKNLPPSG
AVPVTGIPPHVVKVPASQPRPESKPESQIPPQRPQRDQRVREQRINIPPQRGPRPIREAGEQGDIEPRRMVRHPDS
HQLFIGNLPHEVDKSELKDFFQSYGNVVELRINSGGKLPNFGFVVFDDSEPVQKVLSNRPIMFRGEVRLNVEEKKTR
AAREGDRRDNRLRGPGGPRGGLGGGMRGPPRGGMVQKPGFGVGRGLAPRQKLIPMARRAWLEHGHSCFLCEI
VIRSQFHTTYEPEA (SEQ ID NO: 95)

Cry2PHR with G3BP1 PxxP Domain Deletion Mutation; Cry2PHR-G3BP1dPxxP
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEEQLFIGNLPHEVDKSELKDFFQSYGNVVELRINSGGKLP
NFGFVVFDDSEPVQKVLSNRPIMFRGEVRLNVEEKKTRAAREGDRRDNRLRGPGGPRGGLGGGMRGPPRGGM
VQKPGFGVGRGLAPRQKLIPMARRAWLEHGHSCFLCEIVIRSQFHTTYEPEA (SEQ ID NO: 96)

Cry2PHR with G3BP1 RRM Domain Deletion Mutation; Cry2PHR-G3BP1dRRM
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSHEKKTRAAREGDRRDNRLRGPGGPRGGLGGGMRGPPRGGMVQKPGFGVGRGLAPRQKLIPMARRAW
LEHGHSCFLCEIVIRSQFHTTYEPEA (SEQ ID NO: 97)

Cry2PHR with G3BP1 RGG Domain Deletion Mutation; Cry2PHR-G3BP1dRGG
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY
WKKCLDMSIESVMLPPPWRLMPITAAAEAIWACSIEELGLENEAEKPSNALLTRAWSPGWSNADKLLNEFIEKQLI
DYAKNSKKVVGNSTSLLSPYLHFGEISVRHVFQCARMKQIIWARDKNSEGEESADLFLRGIGLREYSRYICFNFPFTH
EQSLLSHLRFFPWDADVDKFKAWRQGRTGYPLVDAGMRELWATGWMHNRIRVIVSSFAVKFLLLPWKWGMKY
FWDTLLDADLECDILGWQYISGSIPDGHELDRLDNPALQGAKYDPEGEYIRQWLPELARLPTEWIHHPWDAPLTVL
KASGVELGTNYAKPIVDIDTARELLAKAISRTREAQIMIGAAMVMEKPSPLLVGREFVRQYYTLLNQAPDMLHRFY
GKNSSYVHGGLDSNGKPADAVYGQKEIHRKVMSQNFTNCHTKIRHVDAHATLNDGVVVQVMGLLSNNNQALR
RFMQTFVLAPEGSVANKFYVHNDIFRYQDEVFGGFVTEPQEESEEEVEEPEERQQTPEVVPDDSGTFYDQAVVSN
DMEEHLEEPVAEPEPDPEPEPEQEPVSEIQEEKPEPVLEETAPEDAQKSSSPAPADIAQTVQEDLRTFSWASVTSKN
LPPSGAVPVTGIPPHVVKVPASQPRPESKPESQIPPQRPQRDQRVREQRINIPPQRGPRPIREAGEQGDIEPRRMV
RHPDSHQLFIGNLPHEVDKSELKDFFQSYGNVVELRINSGGKLPNFGFVVFDDSEPVQKVLSNRPIMFRGEVRLNV
E (SEQ ID NO: 98)

Cry2PHR with G3BP1 RRMRGG Domain Deletion Mutation; Cry2PHR-G3BP1dRRMRGG
MKMDKKTIVWFRRDLRIEDNPALAAAAHEGSVFPVFIWCPEEEGQFYPGRASRWWMKQSLAHLSQSLKALGSDL
TLIKTHNTISAILDCIRVTGATKVVFNHLYDPVSLVRDHTVKEKLVERGISVQSYNGDLLYEPWEIYCEKGKPFTSFNSY -continued

| Amino Acid Sequences of the Photolyase-Homologous Region (PHR) domain of the *Arabidopsis* Cryptochrome 2 protein: |
|---|
| WKKCLDMSIESVMLPPPWRLMPITAAAEAIWACSIEELGLENEAEKPSNALLTRAWSPGWSNADKLLNEFIEKQLI<br>DYAKNSKKVVGNSTSLLSPYLHFGEISVRHVFQCARMKQIIWARDKNSEGEESADLFLRGIGLREYSRYICFNFPFTH<br>EQSLLSHLRFFPWDADVDKFKAWRQGRTGYPLVDAGMRELWATGWMHNRIRVIVSSFAVKFLLLPWKWGMKY<br>FWDTLLDADLECDILGWQYISGSIPDGHELDRLDNPALQGAKYDPEGEYIRQWLPELARLPTEWIHHPWDAPLTVL<br>KASGVELGTNYAKPIVDIDTARELLAKAISRTREAQIMIGAAMVMEKPSPLLVGREFVRQYYTLLNQAPDMLHRFY<br>GKNSSYVHGGLDSNGKPADAVYGQKEIHRKVMSQNFTNCHTKIRHVDAHATLNDGVVVQVMGLLSNNNQALR<br>RFMQTFVLAPEGSVANKFYVHNDIFRYQDEVFGGFVTEPQEESEEEVEEPEERQQTPEVVPDDSGTFYDQAVVSN<br>DMEEHLEEPVAEPEPDPEPEPEQEPVSEIQEEKPEPVLEETAPEDAQKSSSPAPADIAQTVQEDLRTFSWASVTSKN<br>LPPSGAVPVTGIPPHVVKVPASQPRPESKPESQIPPQRPQRDQRVREQRINIPPQRGPRPIREAGEQGDIEPRRMV<br>RHPDSH (SEQ ID NO: 99) |
| G3BP1 Full Length Protein with Cry2PHR; G3BP1-Cry2PHR<br>MVMEKPSPLLVGREFVRQYYTLLNQAPDMLHRFYGKNSSYVHGGLDSNGKPADAVYGQKEIHRKVMSQNFTNC<br>HTKIRHVDAHATLNDGVVVQVMGLLSNNNQALRRFMQTFVLAPEGSVANKFYVHNDIFRYQDEVFGGFVTEPQE<br>ESEEEVEEPEERQQTPEVVPDDSGTFYDQAVVSNDMEEHLEEPVAEPEPDPEPEPEQEPVSEIQEEKPEPVLEETAP<br>EDAQKSSSPAPADIAQTVQEDLRTFSWASVTSKNLPPSGAVPVTGIPPHVVKVPASQPRPESKPESQIPPQRPQRD<br>QRVREQRINIPPQRGPRPIREAGEQGDIEPRRMVRHPDSHQLFIGNLPHEVDKSELKDFFQSYGNVVELRINSGGKL<br>PNFGFVVFDDSEPVQKVLSNRPIMFRGEVRLNVEEKKTRAAREGDRRDNRLRGPGGPRGGLGGGMRGPPRGGM<br>VQKPGFGVGRGLAPRQKLIPMARRAWLEHGHSCFLCEIVIRSQFHTTYEPEAMKMDKKTIVWFRRDLRIEDNPAL<br>AAAAHEGSVFPVFIWCPEEEGQFYPGRASRWWMKQSLAHLSQSLKALGSDLTLIKTHNTISAILDCIRVTGATKVVF<br>NHLYDPVSLVRDHTVKEKLVERGISVQSYNGDLLYEPWEIYCEKGKPFTSFNSYWKKCLDMSIESVMLPPPWRLMP<br>ITAAAEAIWACSIEELGLENEAEKPSNALLTRAWSPGWSNADKLLNEFIEKQLIDYAKNSKKVVGNSTSLLSPYLHFG<br>EISVRHVFQCARMKQIIWARDKNSEGEESADLFLRGIGLREYSRYICFNFPFTHEQSLLSHLRFFPWDADVDKFKAW<br>RQGRTGYPLVDAGMRELWATGWMHNRIRVIVSSFAVKFLLLPWKWGMKYFWDTLLDADLECDILGWQYISGSI<br>PDGHELDRLDNPALQGAKYDPEGEYIRQWLPELARLPTEWIHHPWDAPLTVLKASGVELGTNYAKPIVDIDTAREL<br>LAKAISRTREAQIMIGAA (SEQ ID NO: 100) |
| G3BP1 NTF2 Domain Deletion Mutation with Cry2PHR; G3BP1dNTF2-Cry2PHR<br>MGFVTEPQEESEEEVEEPEERQQTPEVVPDDSGTFYDQAVVSNDMEEHLEEPVAEPEPDPEPEPEQEPVSEIQEEK<br>PEPVLEETAPEDAQKSSSPAPADIAQTVQEDLRTFSWASVTSKNLPPSGAVPVTGIPPHVVKVPASQPRPESKPESQ<br>IPPQRPQRDQRVREQRINIPPQRGPRPIREAGEQGDIEPRRMVRHPDSHQLFIGNLPHEVDKSELKDFFQSYGNVV<br>ELRINSGGKLPNFGFVVFDDSEPVQKVLSNRPIMFRGEVRLNVEEKKTRAAREGDRRDNRLRGPGGPRGGLGGG<br>MRGPPRGGMVQKPGFGVGRGLAPRQKLIPMARRAWLEHGHSCFLCEIVIRSQFHTTYEPEAMKMDKKTIVWFR<br>RDLRIEDNPALAAAAHEGSVFPVFIWCPEEEGQFYPGRASRWWMKQSLAHLSQSLKALGSDLTLIKTHNTISAILDC<br>IRVTGATKVVFNHLYDPVSLVRDHTVKEKLVERGISVQSYNGDLLYEPWEIYCEKGKPFTSFNSYWKKCLDMSIESV<br>MLPPPWRLMPITAAAEAIWACSIEELGLENEAEKPSNALLTRAWSPGWSNADKLLNEFIEKQLIDYAKNSKKVVGN<br>STSLLSPYLHFGEISVRHVFQCARMKQIIWARDKNSEGEESADLFLRGIGLREYSRYICFNFPFTHEQSLLSHLRFFPW<br>DADVDKFKAWRQGRTGYPLVDAGMRELWATGWMHNRIRVIVSSFAVKFLLLPWKWGMKYFWDTLLDADLEC<br>DILGWQYISGSIPDGHELDRLDNPALQGAKYDPEGEYIRQWLPELARLPTEWIHHPWDAPLTVLKASGVELGTNYA<br>KPIVDIDTARELLAKAISRTREAQIMIGAA (SEQ ID NO: 101) |
| G3BP1 Acidic Domain Deletion Mutation with Cry2PHR; G3BP1dAcidic-Cry2PHR<br>MVMEKPSPLLVGREFVRQYYTLLNQAPDMLHRFYGKNSSYVHGGLDSNGKPADAVYGQKEIHRKVMSQNFTNC<br>HTKIRHVDAHATLNDGVVVQVMGLLSNNNQALRRFMQTFVLAPEGSVANKFYVHNDIFRYQDEVFGTAPEDAQ<br>KSSSPAPADIAQTVQEDLRTFSWASVTSKNLPPSGAVPVTGIPPHVVKVPASQPRPESKPESQIPPQRPQRDQRVR<br>EQRINIPPQRGPRPIREAGEQGDIEPRRMVRHPDSHQLFIGNLPHEVDKSELKDFFQSYGNVVELRINSGGKLPNFG<br>FVVFDDSEPVQKVLSNRPIMFRGEVRLNVEEKKTRAAREGDRRDNRLRGPGGPRGGLGGGMRGPPRGGMVQKP<br>GFGVGRGLAPRQKLIPMARRAWLEHGHSCFLCEIVIRSQFHTTYEPEAMKMDKKTIVWFRRDLRIEDNPALAAAA<br>HEGSVFPVFIWCPEEEGQFYPGRASRWWMKQSLAHLSQSLKALGSDLTLIKTHNTISAILDCIRVTGATKVVFNHLY<br>DPVSLVRDHTVKEKLVERGISVQSYNGDLLYEPWEIYCEKGKPFTSFNSYWKKCLDMSIESVMLPPPWRLMPITAA<br>AEAIWACSIEELGLENEAEKPSNALLTRAWSPGWSNADKLLNEFIEKQLIDYAKNSKKVVGNSTSLLSPYLHFGEISV<br>RHVFQCARMKQIIWARDKNSEGEESADLFLRGIGLREYSRYICFNFPFTHEQSLLSHLRFFPWDADVDKFKAWRQG<br>RTGYPLVDAGMRELWATGWMHNRIRVIVSSFAVKFLLLPWKWGMKYFWDTLLDADLECDILGWQYISGSIPDG<br>HELDRLDNPALQGAKYDPEGEYIRQWLPELARLPTEWIHHPWDAPLTVLKASGVELGTNYAKPIVDIDTARELLAK<br>AISRTREAQIMIGAA (SEQ ID NO: 102) |
| G3BP1 PxxP Domain Deletion Mutation with Cry2PHR; G3BP1dPxxP- Cry2PHR<br>MVMEKPSPLLVGREFVRQYYTLLNQAPDMLHRFYGKNSSYVHGGLDSNGKPADAVYGQKEIHRKVMSQNFTNC<br>HTKIRHVDAHATLNDGVVVQVMGLLSNNNQALRRFMQTFVLAPEGSVANKFYVHNDIFRYQDEVFGGFVTEPQE<br>ESEEEVEEPEERQQTPEVVPDDSGTFYDQAVVSNDMEEHLEEPVAEPEPDPEPEPEQEPVSEIQEEKPEPVLEEQLFI<br>GNLPHEVDKSELKDFFQSYGNVVELRINSGGKLPNFGFVVFDDSEPVQKVLSNRPIMFRGEVRLNVEEKKTRAARE<br>GDRRDNRLRGPGGPRGGLGGGMRGPPRGGMVQKPGFGVGRGLAPRQKLIPMARRAWLEHGHSCFLCEIVIRS<br>QFHTTYEPEAMKMDKKTIVWFRRDLRIEDNPALAAAAHEGSVFPVFIWCPEEEGQFYPGRASRWWMKQSLAHL<br>SQSLKALGSDLTLIKTHNTISAILDCIRVTGATKVVFNHLYDPVSLVRDHTVKEKLVERGISVQSYNGDLLYEPWEIYCE<br>KGKPFTSFNSYWKKCLDMSIESVMLPPPWRLMPITAAAEAIWACSIEELGLENEAEKPSNALLTRAWSPGWSNAD<br>KLLNEFIEKQLIDYAKNSKKVVGNSTSLLSPYLHFGEISVRHVFQCARMKQIIWARDKNSEGEESADLFLRGIGLREYS<br>RYICFNFPFTHEQSLLSHLRFFPWDADVDKFKAWRQGRTGYPLVDAGMRELWATGWMHNRIRVIVSSFAVKFLLL<br>PWKWGMKYFWDTLLDADLECDILGWQYISGSIPDGHELDRLDNPALQGAKYDPEGEYIRQWLPELARLPTEWIH<br>HPWDAPLTVLKASGVELGTNYAKPIVDIDTARELLAKAISRTREAQIMIGAA (SEQ ID NO: 103) |

-continued

Amino Acid Sequences of the Photolyase-Homologous Region (PHR) domain of the *Arabidopsis* Cryptochrome 2 protein:

G3BP1 RRM Domain Deletion Mutation with Cry2PHR; G3BP1dRRM- Cry2PHR
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHEKKTRAAREGDRRDNRLRGPGGPRGGLGGGMRG
PPRGGMVQKPGFGVGRGLAPRQKLIPMARRAWLEHGHSCFLCEIVIRSQFHTTYEPEAMKMDKKTIVWFRRDLRI
EDNPALAAAAHEGSVFPVFIWCPEEEGQFYPGRASRWWMKQSLAHLSQSLKALGSDLTLIKTHNTISAILDCIRVT
GATKVVFNHLYDPVSLVRDHTVKEKLVERGISVQSYNGDLLYEPWEIYCEKGKPFTSFNSYWKKCLDMSIESVMLPP
PWRLMPITAAAEAIWACSIEELGLENEAEKPSNALLTRAWSPGWSNADKLLNEFIEKQLIDYAKNSKKVVGNSTSLL
SPYLHFGEISVRHVFQCARMKQIIWARDKNSEGEESADLFLRGIGLREYSRYICFNFPFTHEQSLLSHLRFFPWDADV
DKFKAWRQGRTGYPLVDAGMRELWATGWMHNRIRVIVSSFAVKFLLLPWKWGMKYFWDTLLDADLECDILGW
QYISGSIPDGHELDRLDNPALQGAKYDPEGEYIRQWLPELARLPTEWIHHPWDAPLTVLKASGVELGTNYAKPIVDI
DTARELLAKAISRTREAQIMIGAA (SEQ ID NO: 104)

G3BP1 RGG Domain Deletion Mutation with Cry2PHR; G3BP1dRGG-Cry2PHR
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHQLFIGNLPHEVDKSELKDFFQSYGNVVELRINSGGKL
PNFGFVVFDDSEPVQKVLSNRPIMFRGEVRLNVEMKMDKKTIVWFRRDLRIEDNPALAAAAHEGSVFPVFIWCPE
EEGQFYPGRASRWWMKQSLAHLSQSLKALGSDLTLIKTHNTISAILDCIRVTGATKVVFNHLYDPVSLVRDHTVKEK
LVERGISVQSYNGDLLYEPWEIYCEKGKPFTSFNSYWKKCLDMSIESVMLPPPWRLMPITAAAEAIWACSIEELGLE
NEAEKPSNALLTRAWSPGWSNADKLLNEFIEKQLIDYAKNSKKVVGNSTSLLSPYLHFGEISVRHVFQCARMKQIIW
ARDKNSEGEESADLFLRGIGLREYSRYICFNFPFTHEQSLLSHLRFFPWDADVDKFKAWRQGRTGYPLVDAGMREL
WATGWMHNRIRVIVSSFAVKFLLLPWKWGMKYFWDTLLDADLECDILGWQYISGSIPDGHELDRLDNPALQGAK
YDPEGEYIRQWLPELARLPTEWIHHPWDAPLTVLKASGVELGTNYAKPIVDIDTARELLAKAISRTREAQIMIGAA
(SEQ ID NO: 105)

G3BP1 RRMRGG Domain Deletion Mutation with Cry2PHR; G3BP1dRRMRGG- Cry2PHR
MVMEKPSPLLVGREFVRQYYTLLNQAPDMLHRFYGKNSSYVHGGLDSNGKPADAVYGQKEIHRKVMSQNFTNC
HTKIRHVDAHATLNDGVVVQVMGLLSNNNQALRRFMQTFVLAPEGSVANKFYVHNDIFRYQDEVFGGFVTEPQE
ESEEEVEEPEERQQTPEVVPDDSGTFYDQAVVSNDMEEHLEEPVAEPEPDPEPEPEQEPVSEIQEEKPEPVLEETAP
EDAQKSSSPAPADIAQTVQEDLRTFSWASVTSKNLPPSGAVPVTGIPPHVVKVPASQPRPESKPESQIPPQRPQRD
QRVREQRINIPPQRGPRPIREAGEQGDIEPRRMVRHPDSHMKMDKKTIVWFRRDLRIEDNPALAAAAHEGSVFP
VFIWCPEEEGQFYPGRASRWWMKQSLAHLSQSLKALGSDLTLIKTHNTISAILDCIRVTGATKVVFNHLYDPVSLVR
DHTVKEKLVERGISVQSYNGDLLYEPWEIYCEKGKPFTSFNSYWKKCLDMSIESVMLPPPWRLMPITAAAEAIWAC
SIEELGLENEAEKPSNALLTRAWSPGWSNADKLLNEFIEKQLIDYAKNSKKVVGNSTSLLSPYLHFGEISVRHVFQCA
RMKQIIWARDKNSEGEESADLFLRGIGLREYSRYICFNFPFTHEQSLLSHLRFFPWDADVDKFKAWRQGRTGYPLV
DAGMRELWATGWMHNRIRVIVSSFAVKFLLLPWKWGMKYFWDTLLDADLECDILGWQYISGSIPDGHELDRLD
NPALQGAKYDPEGEYIRQWLPELARLPTEWIHHPWDAPLIVLKASGVELGTNYAKPIVDIDTARELLAKAISRTREA
QIMIGAA (SEQ ID NO: 106)

AsLOV2
GEFLATTLERIEKNFVITDP RLPDNPIIFASDSFLQLTEY SREEILGRNCRFLQGPETDR
ATVRKIRDAIDNQTEVTVQL INYTKSGKKFWNLFHLQPMR DQKGDVQYFIGVQLDGTEHV
RDAAEREGVMLIKKTAENID EAAKELPDANLRPEDLWANH G (SEQ ID NO: 107)

EL222
MLDMGQDRPI DGSGAPGADD TRVEVQPPAQ WVLDLIEASP IASVVSDPRL ADNPLIAINQ AFTDLTGYSE
EECVGRNCRF LAGSGTEPWL TDKIRQGVRE HKPVLVEILN YKKDGTPFRN AVLVAPIYDD DDELLYFLGS
QVEVDDDQPN MGMARRERAA EMLKTLSPRQ LEVTTLVASG LRNKEVAARL GLSEKTVKMH RGLVMEKLNL
KTSADLVRIA VEAGI (SEQ ID NO: 108)

Ytva
MASFQSFGIP GQLEVIKKAL DHVRVGVVIT DPALEDNPIV YVNQGFVQMT GYETEEILGK NCRFLQGKHT
DPAEVDNIRT ALQNKEPVTV QIQNYKKDGT MFWNELNIDP MEIEDKTYFV GIQNDITKQK
EYEKLLEDSL TEITALSTPI VPIRNGISAL PLVGNLTEER FNSIVCTLTN ILSTSKDDYL IIDLSGLAQV NEQTADQIFK
LSHLLKLTGT ELIITGIKPE LAMKMNKLDA NFSSLKTYSN VKDAVKVLPI M (SEQ ID NO: 109)

RsLOV
MDQKQFEKIRAVFDRSGVALTLVDMSLPEQPVVLANPPFLRMTGYTEGQILGFNCRFLQRGDENAQARAD
IRDALKLGRELQVVLRNYRANDEPFDNLLFLHPVGGRPDAPDYFLGSQFELGRSGNSEEAAAAGHAGALT
GELARIGTVAARLEMDSRRHLAQAAAALVRAWERRG (SEQ ID NO: 110)

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method of screening for an agent that modulates formation of a membraneless organelle, comprising the steps:

introducing into a cell a plasmid or viral vector comprising a nucleotide sequence encoding a chimeric polypeptide comprising at least 90% sequence identity to SEQ ID NO: 9-78, SEQ ID NO: 79-92, or SEQ ID NO: 93-106;

expressing the chimeric polypeptide;

introducing the agent into a culture media comprising the cell;

inducing oligomerization of the chimeric polypeptide by stimulation with blue light; and determining modulation of the formation of the membraneless organelle by the agent.

2. The method of claim 1, wherein the cell is a mammalian cell.

3. The method of claim 1, wherein the cell is a human cell.

4. The method of claim 1, wherein the blue light has a wavelength between 405 nm and 499 nm.

5. The method of claim 1, wherein the chimeric polypeptide comprises a light-induced oligomerization domain comprising at least 90% sequence identity to SEQ ID NO: 1, SEQ ID NO: 2.

6. The method of claim 1, wherein the chimeric polypeptide comprises a light-induced oligomerization domain comprising at least 90% sequence identity to SEQ ID NO: 3, SEQ ID NO: 107, SEQ ID NO: 110.

7. The method of claim 1, wherein the chimeric polypeptide comprises a light-induced oligomerization domain comprising at least 90% sequence identity to SEQ ID NO: 4, SEQ ID NO: 5.

8. The method of claim 1, wherein the chimeric polypeptide comprises a light-induced oligomerization domain comprising at least 90% sequence identity to SEQ ID NO: 6, SEQ ID NO: 7.

9. The method of claim 1, wherein the chimeric polypeptide comprises a light-induced oligomerization domain comprising at least 90% sequence identity to SEQ ID NO: 108.

10. The method of claim 1, wherein the chimeric polypeptide comprises a light-induced oligomerization domain comprising at least 90% sequence identity to SEQ ID NO: 109.

11. The method of claim 1, wherein the plasmid or viral vector comprises a first nucleotide sequence encoding the light-induced oligomerization domain, and a second nucleotide sequence encoding the low complexity domain from a membraneless organelle target protein, wherein the first nucleotide sequence is operably linked to a promoter.

* * * * *

SEQUENCE LISTING

<160> NUMBER OF SEQ ID NOS: 110

<210> SEQ ID NO 1
<211> LENGTH: 498
<212> TYPE: PRT
<213> ORGANISM: Arabidopsis

<400> SEQUENCE: 1

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

-continued

Phe Leu Leu Leu Pro Trp Lys Trp Gly Met Lys Tyr Phe Trp Asp Thr
370 375 380

Leu Leu Asp Ala Asp Leu Glu Cys Asp Ile Leu Gly Trp Gln Tyr Ile
385 390 395 400

Ser Gly Ser Ile Pro Asp Gly His Glu Leu Asp Arg Leu Asp Asn Pro
405 410 415

Ala Leu Gln Gly Ala Lys Tyr Asp Pro Glu Gly Glu Tyr Ile Arg Gln
420 425 430

Trp Leu Pro Glu Leu Ala Arg Leu Pro Thr Glu Trp Ile His His Pro
435 440 445

Trp Asp Ala Pro Leu Thr Val Leu Lys Ala Ser Gly Val Glu Leu Gly
450 455 460

Thr Asn Tyr Ala Lys Pro Ile Val Asp Ile Asp Thr Ala Arg Glu Leu
465 470 475 480

Leu Ala Lys Ala Ile Ser Arg Thr Arg Glu Ala Gln Ile Met Ile Gly
485 490 495

Ala Ala

<210> SEQ ID NO 2
<211> LENGTH: 498
<212> TYPE: PRT
<213> ORGANISM: Arabidopsis

<400> SEQUENCE: 2

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

-continued

```
Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala
```

<210> SEQ ID NO 3
<211> LENGTH: 119
<212> TYPE: PRT
<213> ORGANISM: Neurospora crassa

<400> SEQUENCE: 3

```
Met Thr Ser Cys Ala Leu Ile Leu Cys Asp Leu Lys Gln Lys Asp Thr
1               5                   10                  15

Pro Ile Val Tyr Ala Ser Glu Ala Phe Leu Tyr Met Thr Gly Tyr Ser
            20                  25                  30

Asn Ala Glu Val Leu Gly Arg Asn Cys Arg Phe Leu Gln Ser Pro Asp
        35                  40                  45

Gly Met Val Lys Pro Lys Ser Thr Arg Lys Tyr Val Asp Ser Asn Thr
    50                  55                  60

Ile Asn Thr Met Arg Lys Ala Ile Asp Arg Asn Ala Glu Val Gln Val
65                  70                  75                  80

Glu Val Val Asn Phe Lys Lys Asn Gly Gln Arg Phe Val Asn Phe Leu
                85                  90                  95

Thr Met Ile Pro Val Arg Asp Glu Thr Gly Glu Tyr Arg Tyr Ser Met
            100                 105                 110
```

```
Gly Phe Gln Cys Glu Thr Glu
        115


<210> SEQ ID NO 4
<211> LENGTH: 151
<212> TYPE: PRT
<213> ORGANISM: Neurospora crassa

<400> SEQUENCE: 4

Met His Thr Leu Tyr Ala Pro Gly Gly Tyr Asp Ile Met Gly Tyr Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu
145                 150


<210> SEQ ID NO 5
<211> LENGTH: 151
<212> TYPE: PRT
<213> ORGANISM: Neurospora crassa

<400> SEQUENCE: 5

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu
145                 150
```

<210> SEQ ID NO 6
<211> LENGTH: 348
<212> TYPE: PRT
<213> ORGANISM: Vaucheria frigida

<400> SEQUENCE: 6

```
Met Asn Gly Leu Thr Pro Pro Leu Met Phe Cys Ser Arg Ser Asp Asp
1               5                   10                  15

Pro Ser Ser Thr Ser Asn Ile Asn Leu Asp Asp Val Phe Ala Asp Val
            20                  25                  30

Phe Phe Asn Ser Asn Gly Glu Leu Leu Asp Ile Asp Glu Ile Asp Asp
        35                  40                  45

Phe Gly Asp Asn Thr Cys Pro Lys Ser Ser Met Ser Val Asp Asp Asp
    50                  55                  60

Ala Ser Ser Gln Val Phe Gln Gly His Leu Phe Gly Asn Ala Leu Ser
65                  70                  75                  80

Ser Ile Ala Leu Ser Asp Ser Gly Asp Leu Ser Thr Gly Ile Tyr Glu
                85                  90                  95

Ser Gln Gly Asn Ala Ser Arg Gly Lys Ser Leu Arg Thr Lys Ser Ser
            100                 105                 110

Gly Ser Ile Ser Ser Glu Leu Thr Glu Ala Gln Lys Val Glu Arg Arg
        115                 120                 125

Glu Arg Asn Arg Glu His Ala Lys Arg Ser Arg Val Arg Lys Lys Phe
    130                 135                 140

Leu Leu Glu Ser Leu Gln Gln Ser Val Asn Glu Leu Asn His Glu Asn
145                 150                 155                 160

Asn Cys Leu Lys Glu Ser Ile Arg Glu His Leu Gly Pro Arg Gly Asp
                165                 170                 175

Ser Leu Ile Ala Gln Cys Ser Pro Glu Ala Asp Thr Leu Leu Thr Asp
            180                 185                 190

Asn Pro Ser Lys Ala Asn Arg Ile Leu Glu Asp Pro Asp Tyr Ser Leu
        195                 200                 205

Val Lys Ala Leu Gln Met Ala Gln Gln Asn Phe Val Ile Thr Asp Ala
    210                 215                 220

Ser Leu Pro Asp Asn Pro Ile Val Tyr Ala Ser Arg Gly Phe Leu Thr
225                 230                 235                 240

Leu Thr Gly Tyr Ser Leu Asp Gln Ile Leu Gly Arg Asn Cys Arg Phe
                245                 250                 255

Leu Gln Gly Pro Glu Thr Asp Pro Arg Ala Val Asp Lys Ile Arg Asn
            260                 265                 270

Ala Ile Thr Lys Gly Val Asp Thr Ser Val Cys Leu Leu Asn Tyr Arg
        275                 280                 285

Gln Asp Gly Thr Thr Phe Trp Asn Leu Phe Phe Val Ala Gly Leu Arg
    290                 295                 300

Asp Ser Lys Gly Asn Ile Val Asn Tyr Val Gly Val Gln Ser Lys Val
305                 310                 315                 320

Ser Glu Asp Tyr Ala Lys Leu Leu Val Asn Glu Gln Asn Ile Glu Tyr
                325                 330                 335

Lys Gly Val Arg Thr Ser Asn Met Leu Arg Arg Lys
            340                 345
```

<210> SEQ ID NO 7
<211> LENGTH: 145
<212> TYPE: PRT
<213> ORGANISM: Vaucheria frigida -continued

<400> SEQUENCE: 7

```
Pro Asp Tyr Ser Leu Val Lys Ala Leu Gln Met Ala Gln Gln Asn Phe
1               5                   10                  15

Val Ile Thr Asp Ala Ser Leu Pro Asp Asn Pro Ile Val Tyr Ala Ser
            20                  25                  30

Arg Gly Phe Leu Thr Leu Thr Gly Tyr Ser Leu Asp Gln Ile Leu Gly
        35                  40                  45

Arg Asn Cys Arg Phe Leu Gln Gly Pro Glu Thr Asp Pro Arg Ala Val
    50                  55                  60

Asp Lys Ile Arg Asn Ala Ile Thr Lys Gly Val Asp Thr Ser Val Cys
65                  70                  75                  80

Leu Leu Asn Tyr Arg Gln Asp Gly Thr Thr Phe Trp Asn Leu Phe Phe
                85                  90                  95

Val Ala Gly Leu Arg Asp Ser Lys Gly Asn Ile Val Asn Tyr Val Gly
            100                 105                 110

Val Gln Ser Lys Val Ser Glu Asp Tyr Ala Lys Leu Leu Val Asn Glu
        115                 120                 125

Gln Asn Ile Glu Tyr Lys Gly Val Arg Thr Ser Asn Met Leu Arg Arg
    130                 135                 140

Lys
145
```

<210> SEQ ID NO 8
<211> LENGTH: 435
<212> TYPE: DNA
<213> ORGANISM: Vaucheria frigida

<400> SEQUENCE: 8

```
cctgactaca gtctcgtgaa ggctctgcaa atggcacaac agaattttgt cattacagac      60

gcctccctcc cagacaaccc tatcgtctac gccagtagag ggtttctgac actgacaggc     120

tattctctcg accagatcct gggcaggaac tgcaggtttc tgcaagggcc agaaacagac     180

ccaagagctg tggataagat caggaatgcc atcaccaaag gcgttgatac cagtgtctgt     240

ctgctgaatt atagacagga tggcacaacc ttctggaatc tcttcttcgt ggctggactc     300

agagattcta agggcaatat tgtcaactac gtcggagtgc agtcaaaggt gagcgaagat     360

tatgccaagc tgctggtcaa cgagcagaac attgagtaca aaggtgtgcg caccagtaac     420

atgctgcgca gaaag                                                      435
```

<210> SEQ ID NO 9
<211> LENGTH: 653
<212> TYPE: PRT
<213> ORGANISM: Artificial Sequence
<220> FEATURE:
<223> OTHER INFORMATION: Synthetic construct

<400> SEQUENCE: 9

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60
```

-continued

```
Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

Val Val Val Gln Val Met Gly Leu Leu Ser Asn Asn Asn Gln Ala Leu
                245                 250                 255

Arg Arg Phe Met Gln Thr Phe Val Leu Ala Pro Glu Gly Ser Val Ala
            260                 265                 270

Asn Lys Phe Tyr Val His Asn Asp Ile Phe Arg Tyr Gln Asp Glu Val
        275                 280                 285

Phe Gly Gly Phe Val Thr Glu Pro Gln Glu Glu Ser Glu Glu Glu Val
    290                 295                 300

Glu Glu Pro Glu Glu Arg Gln Gln Thr Pro Glu Val Val Pro Asp Asp
305                 310                 315                 320

Ser Gly Thr Phe Tyr Asp Gln Ala Val Val Ser Asn Asp Met Glu Glu
                325                 330                 335

His Leu Glu Glu Pro Val Ala Glu Pro Glu Pro Asp Pro Glu Pro Glu
            340                 345                 350

Pro Glu Gln Glu Pro Val Ser Glu Ile Gln Glu Glu Lys Pro Glu Pro
        355                 360                 365

Val Leu Glu Glu Thr Ala Pro Glu Asp Ala Gln Lys Ser Ser Ser Pro
    370                 375                 380

Ala Pro Ala Asp Ile Ala Gln Thr Val Gln Glu Asp Leu Arg Thr Phe
385                 390                 395                 400

Ser Trp Ala Ser Val Thr Ser Lys Asn Leu Pro Pro Ser Gly Ala Val
                405                 410                 415

Pro Val Thr Gly Ile Pro Pro His Val Val Lys Val Pro Ala Ser Gln
            420                 425                 430

Pro Arg Pro Glu Ser Lys Pro Glu Ser Gln Ile Pro Pro Gln Arg Pro
        435                 440                 445

Gln Arg Asp Gln Arg Val Arg Glu Gln Arg Ile Asn Ile Pro Pro Gln
    450                 455                 460

Arg Gly Pro Arg Pro Ile Arg Glu Ala Gly Glu Gln Gly Asp Ile Glu
465                 470                 475                 480
```

```
Pro Arg Arg Met Val Arg His Pro Asp Ser His Gln Leu Phe Ile Gly
                485                 490                 495

Asn Leu Pro His Glu Val Asp Lys Ser Glu Leu Lys Asp Phe Phe Gln
            500                 505                 510

Ser Tyr Gly Asn Val Val Glu Leu Arg Ile Asn Ser Gly Gly Lys Leu
        515                 520                 525

Pro Asn Phe Gly Phe Val Val Phe Asp Asp Ser Glu Pro Val Gln Lys
    530                 535                 540

Val Leu Ser Asn Arg Pro Ile Met Phe Arg Gly Glu Val Arg Leu Asn
545                 550                 555                 560

Val Glu Glu Lys Lys Thr Arg Ala Ala Arg Glu Gly Asp Arg Arg Asp
                565                 570                 575

Asn Arg Leu Arg Gly Pro Gly Gly Pro Arg Gly Gly Leu Gly Gly Gly
            580                 585                 590

Met Arg Gly Pro Pro Arg Gly Gly Met Val Gln Lys Pro Gly Phe Gly
        595                 600                 605

Val Gly Arg Gly Leu Ala Pro Arg Gln Lys Leu Ile Pro Met Ala Arg
    610                 615                 620

Arg Ala Trp Leu Glu His Gly His Ser Cys Phe Leu Cys Glu Ile Val
625                 630                 635                 640

Ile Arg Ser Gln Phe His Thr Thr Tyr Glu Pro Glu Ala
                645                 650


<210> SEQ ID NO 10
<211> LENGTH: 515
<212> TYPE: PRT
<213> ORGANISM: Artificial Sequence
<220> FEATURE:
<223> OTHER INFORMATION: Synthetic construct

<400> SEQUENCE: 10

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Gly Phe Val Thr Glu Pro Gln Glu
145                 150                 155                 160

Glu Ser Glu Glu Glu Val Glu Glu Pro Glu Glu Arg Gln Gln Thr Pro
                165                 170                 175

Glu Val Val Pro Asp Asp Ser Gly Thr Phe Tyr Asp Gln Ala Val Val
            180                 185                 190
```

Ser Asn Asp Met Glu Glu His Leu Glu Glu Pro Val Ala Glu Pro Glu
        195                 200                 205

Pro Asp Pro Glu Pro Glu Pro Glu Gln Glu Pro Val Ser Glu Ile Gln
    210                 215                 220

Glu Glu Lys Pro Glu Pro Val Leu Glu Glu Thr Ala Pro Glu Asp Ala
225                 230                 235                 240

Gln Lys Ser Ser Ser Pro Ala Pro Ala Asp Ile Ala Gln Thr Val Gln
                245                 250                 255

Glu Asp Leu Arg Thr Phe Ser Trp Ala Ser Val Thr Ser Lys Asn Leu
            260                 265                 270

Pro Pro Ser Gly Ala Val Pro Val Thr Gly Ile Pro Pro His Val Val
        275                 280                 285

Lys Val Pro Ala Ser Gln Pro Arg Pro Glu Ser Lys Pro Glu Ser Gln
    290                 295                 300

Ile Pro Pro Gln Arg Pro Gln Arg Asp Gln Arg Val Arg Glu Gln Arg
305                 310                 315                 320

Ile Asn Ile Pro Pro Gln Arg Gly Pro Arg Pro Ile Arg Glu Ala Gly
                325                 330                 335

Glu Gln Gly Asp Ile Glu Pro Arg Arg Met Val Arg His Pro Asp Ser
            340                 345                 350

His Gln Leu Phe Ile Gly Asn Leu Pro His Glu Val Asp Lys Ser Glu
        355                 360                 365

Leu Lys Asp Phe Phe Gln Ser Tyr Gly Asn Val Val Glu Leu Arg Ile
    370                 375                 380

Asn Ser Gly Gly Lys Leu Pro Asn Phe Gly Phe Val Val Phe Asp Asp
385                 390                 395                 400

Ser Glu Pro Val Gln Lys Val Leu Ser Asn Arg Pro Ile Met Phe Arg
                405                 410                 415

Gly Glu Val Arg Leu Asn Val Glu Glu Lys Lys Thr Arg Ala Ala Arg
            420                 425                 430

Glu Gly Asp Arg Arg Asp Asn Arg Leu Arg Gly Pro Gly Gly Pro Arg
        435                 440                 445

Gly Gly Leu Gly Gly Gly Met Arg Gly Pro Pro Arg Gly Gly Met Val
    450                 455                 460

Gln Lys Pro Gly Phe Gly Val Gly Arg Gly Leu Ala Pro Arg Gln Lys
465                 470                 475                 480

Leu Ile Pro Met Ala Arg Arg Ala Trp Leu Glu His Gly His Ser Cys
                485                 490                 495

Phe Leu Cys Glu Ile Val Ile Arg Ser Gln Phe His Thr Thr Tyr Glu
            500                 505                 510

Pro Glu Ala
        515

<210> SEQ ID NO 11
<211> LENGTH: 571
<212> TYPE: PRT
<213> ORGANISM: Artificial Sequence
<220> FEATURE:
<223> OTHER INFORMATION: Synthetic construct

<400> SEQUENCE: 11

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

-continued

```
Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

Val Val Val Gln Val Met Gly Leu Leu Ser Asn Asn Asn Gln Ala Leu
                245                 250                 255

Arg Arg Phe Met Gln Thr Phe Val Leu Ala Pro Glu Gly Ser Val Ala
            260                 265                 270

Asn Lys Phe Tyr Val His Asn Asp Ile Phe Arg Tyr Gln Asp Glu Val
        275                 280                 285

Phe Gly Thr Ala Pro Glu Asp Ala Gln Lys Ser Ser Ser Pro Ala Pro
    290                 295                 300

Ala Asp Ile Ala Gln Thr Val Gln Glu Asp Leu Arg Thr Phe Ser Trp
305                 310                 315                 320

Ala Ser Val Thr Ser Lys Asn Leu Pro Pro Ser Gly Ala Val Pro Val
                325                 330                 335

Thr Gly Ile Pro Pro His Val Val Lys Val Pro Ala Ser Gln Pro Arg
            340                 345                 350

Pro Glu Ser Lys Pro Glu Ser Gln Ile Pro Pro Gln Arg Pro Gln Arg
        355                 360                 365

Asp Gln Arg Val Arg Glu Gln Arg Ile Asn Ile Pro Pro Gln Arg Gly
    370                 375                 380

Pro Arg Pro Ile Arg Glu Ala Gly Glu Gln Gly Asp Ile Glu Pro Arg
385                 390                 395                 400

Arg Met Val Arg His Pro Asp Ser His Gln Leu Phe Ile Gly Asn Leu
                405                 410                 415

Pro His Glu Val Asp Lys Ser Glu Leu Lys Asp Phe Phe Gln Ser Tyr
            420                 425                 430

Gly Asn Val Val Glu Leu Arg Ile Asn Ser Gly Gly Lys Leu Pro Asn
        435                 440                 445
```

Phe Gly Phe Val Val Phe Asp Asp Ser Glu Pro Val Gln Lys Val Leu
    450                 455                 460

Ser Asn Arg Pro Ile Met Phe Arg Gly Glu Val Arg Leu Asn Val Glu
465                 470                 475                 480

Glu Lys Lys Thr Arg Ala Ala Arg Glu Gly Asp Arg Arg Asp Asn Arg
                485                 490                 495

Leu Arg Gly Pro Gly Gly Pro Arg Gly Gly Leu Gly Gly Gly Met Arg
            500                 505                 510

Gly Pro Pro Arg Gly Gly Met Val Gln Lys Pro Gly Phe Gly Val Gly
        515                 520                 525

Arg Gly Leu Ala Pro Arg Gln Lys Leu Ile Pro Met Ala Arg Arg Ala
    530                 535                 540

Trp Leu Glu His Gly His Ser Cys Phe Leu Cys Glu Ile Val Ile Arg
545                 550                 555                 560

Ser Gln Phe His Thr Thr Tyr Glu Pro Glu Ala
                565                 570

<210> SEQ ID NO 12
<211> LENGTH: 534
<212> TYPE: PRT
<213> ORGANISM: Artificial Sequence
<220> FEATURE:
<223> OTHER INFORMATION: Synthetic construct

<400> SEQUENCE: 12

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

-continued

```
Val Val Val Gln Val Met Gly Leu Leu Ser Asn Asn Asn Gln Ala Leu
                245                 250                 255

Arg Arg Phe Met Gln Thr Phe Val Leu Ala Pro Glu Gly Ser Val Ala
            260                 265                 270

Asn Lys Phe Tyr Val His Asn Asp Ile Phe Arg Tyr Gln Asp Glu Val
        275                 280                 285

Phe Gly Gly Phe Val Thr Glu Pro Gln Glu Glu Ser Glu Glu Glu Val
    290                 295                 300

Glu Glu Pro Glu Glu Arg Gln Gln Thr Pro Glu Val Val Pro Asp Asp
305                 310                 315                 320

Ser Gly Thr Phe Tyr Asp Gln Ala Val Val Ser Asn Asp Met Glu Glu
                325                 330                 335

His Leu Glu Glu Pro Val Ala Glu Pro Glu Pro Asp Pro Glu Pro Glu
            340                 345                 350

Pro Glu Gln Glu Pro Val Ser Glu Ile Gln Glu Glu Lys Pro Glu Pro
        355                 360                 365

Val Leu Glu Glu Gln Leu Phe Ile Gly Asn Leu Pro His Glu Val Asp
    370                 375                 380

Lys Ser Glu Leu Lys Asp Phe Phe Gln Ser Tyr Gly Asn Val Val Glu
385                 390                 395                 400

Leu Arg Ile Asn Ser Gly Gly Lys Leu Pro Asn Phe Gly Phe Val Val
                405                 410                 415

Phe Asp Asp Ser Glu Pro Val Gln Lys Val Leu Ser Asn Arg Pro Ile
            420                 425                 430

Met Phe Arg Gly Glu Val Arg Leu Asn Val Glu Glu Lys Lys Thr Arg
        435                 440                 445

Ala Ala Arg Glu Gly Asp Arg Arg Asp Asn Arg Leu Arg Gly Pro Gly
    450                 455                 460

Gly Pro Arg Gly Gly Leu Gly Gly Gly Met Arg Gly Pro Pro Arg Gly
465                 470                 475                 480

Gly Met Val Gln Lys Pro Gly Phe Gly Val Gly Arg Gly Leu Ala Pro
                485                 490                 495

Arg Gln Lys Leu Ile Pro Met Ala Arg Arg Ala Trp Leu Glu His Gly
            500                 505                 510

His Ser Cys Phe Leu Cys Glu Ile Val Ile Arg Ser Gln Phe His Thr
        515                 520                 525

Thr Tyr Glu Pro Glu Ala
    530
```

<210> SEQ ID NO 13
<211> LENGTH: 582
<212> TYPE: PRT
<213> ORGANISM: Artificial Sequence
<220> FEATURE:
<223> OTHER INFORMATION: Synthetic construct

<400> SEQUENCE: 13

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60
```

-continued

```
Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

Val Val Val Gln Val Met Gly Leu Leu Ser Asn Asn Asn Gln Ala Leu
                245                 250                 255

Arg Arg Phe Met Gln Thr Phe Val Leu Ala Pro Glu Gly Ser Val Ala
            260                 265                 270

Asn Lys Phe Tyr Val His Asn Asp Ile Phe Arg Tyr Gln Asp Glu Val
        275                 280                 285

Phe Gly Gly Phe Val Thr Glu Pro Gln Glu Glu Ser Glu Glu Glu Val
    290                 295                 300

Glu Glu Pro Glu Glu Arg Gln Gln Thr Pro Glu Val Val Pro Asp Asp
305                 310                 315                 320

Ser Gly Thr Phe Tyr Asp Gln Ala Val Val Ser Asn Asp Met Glu Glu
                325                 330                 335

His Leu Glu Glu Pro Val Ala Glu Pro Glu Pro Asp Pro Glu Pro Glu
            340                 345                 350

Pro Glu Gln Glu Pro Val Ser Glu Ile Gln Glu Glu Lys Pro Glu Pro
        355                 360                 365

Val Leu Glu Glu Thr Ala Pro Glu Asp Ala Gln Lys Ser Ser Ser Pro
    370                 375                 380

Ala Pro Ala Asp Ile Ala Gln Thr Val Gln Glu Asp Leu Arg Thr Phe
385                 390                 395                 400

Ser Trp Ala Ser Val Thr Ser Lys Asn Leu Pro Pro Ser Gly Ala Val
                405                 410                 415

Pro Val Thr Gly Ile Pro Pro His Val Val Lys Val Pro Ala Ser Gln
            420                 425                 430

Pro Arg Pro Glu Ser Lys Pro Glu Ser Gln Ile Pro Pro Gln Arg Pro
        435                 440                 445

Gln Arg Asp Gln Arg Val Arg Glu Gln Arg Ile Asn Ile Pro Pro Gln
    450                 455                 460

Arg Gly Pro Arg Pro Ile Arg Glu Ala Gly Glu Gln Gly Asp Ile Glu
465                 470                 475                 480
```

```
Pro Arg Arg Met Val Arg His Pro Asp Ser His Glu Lys Lys Thr Arg
                485                 490                 495

Ala Ala Arg Glu Gly Asp Arg Arg Asp Asn Arg Leu Arg Gly Pro Gly
            500                 505                 510

Gly Pro Arg Gly Gly Leu Gly Gly Gly Met Arg Gly Pro Pro Arg Gly
        515                 520                 525

Gly Met Val Gln Lys Pro Gly Phe Gly Val Gly Arg Gly Leu Ala Pro
    530                 535                 540

Arg Gln Lys Leu Ile Pro Met Ala Arg Arg Ala Trp Leu Glu His Gly
545                 550                 555                 560

His Ser Cys Phe Leu Cys Glu Ile Val Ile Arg Ser Gln Phe His Thr
                565                 570                 575

Thr Tyr Glu Pro Glu Ala
            580


<210> SEQ ID NO 14
<211> LENGTH: 562
<212> TYPE: PRT
<213> ORGANISM: Artificial Sequence
<220> FEATURE:
<223> OTHER INFORMATION: Synthetic construct

<400> SEQUENCE: 14

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

Val Val Val Gln Val Met Gly Leu Leu Ser Asn Asn Asn Gln Ala Leu
                245                 250                 255
```

Arg Arg Phe Met Gln Thr Phe Val Leu Ala Pro Glu Gly Ser Val Ala
260 265 270

Asn Lys Phe Tyr Val His Asn Asp Ile Phe Arg Tyr Gln Asp Glu Val
275 280 285

Phe Gly Gly Phe Val Thr Glu Pro Gln Glu Glu Ser Glu Glu Glu Val
290 295 300

Glu Glu Pro Glu Glu Arg Gln Gln Thr Pro Glu Val Val Pro Asp Asp
305 310 315 320

Ser Gly Thr Phe Tyr Asp Gln Ala Val Val Ser Asn Asp Met Glu Glu
325 330 335

His Leu Glu Glu Pro Val Ala Glu Pro Glu Pro Asp Pro Glu Pro Glu
340 345 350

Pro Glu Gln Glu Pro Val Ser Glu Ile Gln Glu Glu Lys Pro Glu Pro
355 360 365

Val Leu Glu Glu Thr Ala Pro Glu Asp Ala Gln Lys Ser Ser Ser Pro
370 375 380

Ala Pro Ala Asp Ile Ala Gln Thr Val Gln Glu Asp Leu Arg Thr Phe
385 390 395 400

Ser Trp Ala Ser Val Thr Ser Lys Asn Leu Pro Pro Ser Gly Ala Val
405 410 415

Pro Val Thr Gly Ile Pro Pro His Val Val Lys Val Pro Ala Ser Gln
420 425 430

Pro Arg Pro Glu Ser Lys Pro Glu Ser Gln Ile Pro Pro Gln Arg Pro
435 440 445

Gln Arg Asp Gln Arg Val Arg Glu Gln Arg Ile Asn Ile Pro Pro Gln
450 455 460

Arg Gly Pro Arg Pro Ile Arg Glu Ala Gly Glu Gln Gly Asp Ile Glu
465 470 475 480

Pro Arg Arg Met Val Arg His Pro Asp Ser His Gln Leu Phe Ile Gly
485 490 495

Asn Leu Pro His Glu Val Asp Lys Ser Glu Leu Lys Asp Phe Phe Gln
500 505 510

Ser Tyr Gly Asn Val Val Glu Leu Arg Ile Asn Ser Gly Gly Lys Leu
515 520 525

Pro Asn Phe Gly Phe Val Val Phe Asp Asp Ser Glu Pro Val Gln Lys
530 535 540

Val Leu Ser Asn Arg Pro Ile Met Phe Arg Gly Glu Val Arg Leu Asn
545 550 555 560

Val Glu

<210> SEQ ID NO 15
<211> LENGTH: 491
<212> TYPE: PRT
<213> ORGANISM: Artificial Sequence
<220> FEATURE:
<223> OTHER INFORMATION: Synthetic construct

<400> SEQUENCE: 15

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Cys Ala Leu Ile Leu Cys Asp Leu Lys Gln Lys Asp Thr
35 40 45

-continued

```
Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Met Val Met Glu Lys Pro Ser Pro Leu
145                 150                 155                 160

Leu Val Gly Arg Glu Phe Val Arg Gln Tyr Tyr Thr Leu Leu Asn Gln
                165                 170                 175

Ala Pro Asp Met Leu His Arg Phe Tyr Gly Lys Asn Ser Ser Tyr Val
            180                 185                 190

His Gly Gly Leu Asp Ser Asn Gly Lys Pro Ala Asp Ala Val Tyr Gly
        195                 200                 205

Gln Lys Glu Ile His Arg Lys Val Met Ser Gln Asn Phe Thr Asn Cys
    210                 215                 220

His Thr Lys Ile Arg His Val Asp Ala His Ala Thr Leu Asn Asp Gly
225                 230                 235                 240

Val Val Val Gln Val Met Gly Leu Leu Ser Asn Asn Asn Gln Ala Leu
                245                 250                 255

Arg Arg Phe Met Gln Thr Phe Val Leu Ala Pro Glu Gly Ser Val Ala
            260                 265                 270

Asn Lys Phe Tyr Val His Asn Asp Ile Phe Arg Tyr Gln Asp Glu Val
        275                 280                 285

Phe Gly Gly Phe Val Thr Glu Pro Gln Glu Glu Ser Glu Glu Glu Val
    290                 295                 300

Glu Glu Pro Glu Glu Arg Gln Gln Thr Pro Glu Val Val Pro Asp Asp
305                 310                 315                 320

Ser Gly Thr Phe Tyr Asp Gln Ala Val Val Ser Asn Asp Met Glu Glu
                325                 330                 335

His Leu Glu Glu Pro Val Ala Glu Pro Glu Pro Asp Pro Glu Pro Glu
            340                 345                 350

Pro Glu Gln Glu Pro Val Ser Glu Ile Gln Glu Glu Lys Pro Glu Pro
        355                 360                 365

Val Leu Glu Glu Thr Ala Pro Glu Asp Ala Gln Lys Ser Ser Ser Pro
    370                 375                 380

Ala Pro Ala Asp Ile Ala Gln Thr Val Gln Glu Asp Leu Arg Thr Phe
385                 390                 395                 400

Ser Trp Ala Ser Val Thr Ser Lys Asn Leu Pro Pro Ser Gly Ala Val
                405                 410                 415

Pro Val Thr Gly Ile Pro Pro His Val Val Lys Val Pro Ala Ser Gln
            420                 425                 430

Pro Arg Pro Glu Ser Lys Pro Glu Ser Gln Ile Pro Pro Gln Arg Pro
        435                 440                 445

Gln Arg Asp Gln Arg Val Arg Glu Gln Arg Ile Asn Ile Pro Pro Gln
    450                 455                 460
```

Arg Gly Pro Arg Pro Ile Arg Glu Ala Gly Glu Gln Gly Asp Ile Glu
465 470 475 480

Pro Arg Arg Met Val Arg His Pro Asp Ser His
485 490

<210> SEQ ID NO 16
<211> LENGTH: 653
<212> TYPE: PRT
<213> ORGANISM: Artificial Sequence
<220> FEATURE:
<223> OTHER INFORMATION: Synthetic construct

<400> SEQUENCE: 16

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Thr Ala Pro
210 215 220

Glu Asp Ala Gln Lys Ser Ser Ser Pro Ala Pro Ala Asp Ile Ala Gln
225 230 235 240

Thr Val Gln Glu Asp Leu Arg Thr Phe Ser Trp Ala Ser Val Thr Ser
245 250 255

Lys Asn Leu Pro Pro Ser Gly Ala Val Pro Val Thr Gly Ile Pro Pro
260 265 270

His Val Val Lys Val Pro Ala Ser Gln Pro Arg Pro Glu Ser Lys Pro
275 280 285

Glu Ser Gln Ile Pro Pro Gln Arg Pro Gln Arg Asp Gln Arg Val Arg
290 295 300

Glu Gln Arg Ile Asn Ile Pro Pro Gln Arg Gly Pro Arg Pro Ile Arg
305 310 315 320

Glu Ala Gly Glu Gln Gly Asp Ile Glu Pro Arg Arg Met Val Arg His
325 330 335

-continued

```
Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Arg Asp Asn Arg Leu Arg Gly Pro Gly
            420                 425                 430

Gly Pro Arg Gly Gly Leu Gly Gly Gly Met Arg Gly Pro Pro Arg Gly
        435                 440                 445

Gly Met Val Gln Lys Pro Gly Phe Gly Val Gly Arg Gly Leu Ala Pro
    450                 455                 460

Arg Gln Lys Leu Ile Pro Met Ala Arg Arg Ala Trp Leu Glu His Gly
465                 470                 475                 480

His Ser Cys Phe Leu Cys Glu Ile Val Ile Arg Ser Gln Phe His Thr
                485                 490                 495

Thr Tyr Glu Pro Glu Ala Met His Thr Leu Tyr Ala Pro Gly Gly Tyr
            500                 505                 510

Asp Ile Met Gly Trp Leu Ile Gln Ile Met Asn Arg Pro Asn Pro Gln
        515                 520                 525

Val Glu Leu Gly Pro Val Asp Thr Ser Cys Ala Leu Ile Leu Cys Asp
    530                 535                 540

Leu Lys Gln Lys Asp Thr Pro Ile Val Tyr Ala Ser Glu Ala Phe Leu
545                 550                 555                 560

Tyr Met Thr Gly Tyr Ser Asn Ala Glu Val Leu Gly Arg Asn Cys Arg
                565                 570                 575

Phe Leu Gln Ser Pro Asp Gly Met Val Lys Pro Lys Ser Thr Arg Lys
            580                 585                 590

Tyr Val Asp Ser Asn Thr Ile Asn Thr Met Arg Lys Ala Ile Asp Arg
        595                 600                 605

Asn Ala Glu Val Gln Val Glu Val Val Asn Phe Lys Lys Asn Gly Gln
    610                 615                 620

Arg Phe Val Asn Phe Leu Thr Met Ile Pro Val Arg Asp Glu Thr Gly
625                 630                 635                 640

Glu Tyr Arg Tyr Ser Met Gly Phe Gln Cys Glu Thr Glu
                645                 650


<210> SEQ ID NO 17
<211> LENGTH: 515
<212> TYPE: PRT
<213> ORGANISM: Artificial Sequence
<220> FEATURE:
<223> OTHER INFORMATION: Synthetic construct

<400> SEQUENCE: 17

Met Gly Phe Val Thr Glu Pro Gln Glu Glu Ser Glu Glu Glu Val Glu
1               5                   10                  15

Glu Pro Glu Glu Arg Gln Gln Thr Pro Glu Val Val Pro Asp Asp Ser
            20                  25                  30

Gly Thr Phe Tyr Asp Gln Ala Val Val Ser Asn Asp Met Glu Glu His
        35                  40                  45
```

-continued

```
Leu Glu Glu Pro Val Ala Glu Pro Glu Pro Asp Pro Glu Pro Glu Pro
    50                  55                  60

Glu Gln Glu Pro Val Ser Glu Ile Gln Glu Glu Lys Pro Glu Pro Val
65                  70                  75                  80

Leu Glu Glu Thr Ala Pro Glu Asp Ala Gln Lys Ser Ser Ser Pro Ala
                85                  90                  95

Pro Ala Asp Ile Ala Gln Thr Val Gln Glu Asp Leu Arg Thr Phe Ser
            100                 105                 110

Trp Ala Ser Val Thr Ser Lys Asn Leu Pro Pro Ser Gly Ala Val Pro
        115                 120                 125

Val Thr Gly Ile Pro Pro His Val Val Lys Val Pro Ala Ser Gln Pro
    130                 135                 140

Arg Pro Glu Ser Lys Pro Glu Ser Gln Ile Pro Pro Gln Arg Pro Gln
145                 150                 155                 160

Arg Asp Gln Arg Val Arg Glu Gln Arg Ile Asn Ile Pro Pro Gln Arg
                165                 170                 175

Gly Pro Arg Pro Ile Arg Glu Ala Gly Glu Gln Gly Asp Ile Glu Pro
            180                 185                 190

Arg Arg Met Val Arg His Pro Asp Ser His Gln Leu Phe Ile Gly Asn
        195                 200                 205

Leu Pro His Glu Val Asp Lys Ser Glu Leu Lys Asp Phe Phe Gln Ser
    210                 215                 220

Tyr Gly Asn Val Val Glu Leu Arg Ile Asn Ser Gly Gly Lys Leu Pro
225                 230                 235                 240

Asn Phe Gly Phe Val Val Phe Asp Asp Ser Glu Pro Val Gln Lys Val
                245                 250                 255

Leu Ser Asn Arg Pro Ile Met Phe Arg Gly Glu Val Arg Leu Asn Val
            260                 265                 270

Glu Glu Lys Lys Thr Arg Ala Ala Arg Glu Gly Asp Arg Arg Asp Asn
        275                 280                 285

Arg Leu Arg Gly Pro Gly Gly Pro Arg Gly Gly Leu Gly Gly Gly Met
    290                 295                 300

Arg Gly Pro Pro Arg Gly Gly Met Val Gln Lys Pro Gly Phe Gly Val
305                 310                 315                 320

Gly Arg Gly Leu Ala Pro Arg Gln Lys Leu Ile Pro Met Ala Arg Arg
                325                 330                 335

Ala Trp Leu Glu His Gly His Ser Cys Phe Leu Cys Glu Ile Val Ile
            340                 345                 350

Arg Ser Gln Phe His Thr Thr Tyr Glu Pro Glu Ala Met His Thr Leu
        355                 360                 365

Tyr Ala Pro Gly Gly Tyr Asp Ile Met Gly Trp Leu Ile Gln Ile Met
    370                 375                 380

Asn Arg Pro Asn Pro Gln Val Glu Leu Gly Pro Val Asp Thr Ser Cys
385                 390                 395                 400

Ala Leu Ile Leu Cys Asp Leu Lys Gln Lys Asp Thr Pro Ile Val Tyr
                405                 410                 415

Ala Ser Glu Ala Phe Leu Tyr Met Thr Gly Tyr Ser Asn Ala Glu Val
            420                 425                 430

Leu Gly Arg Asn Cys Arg Phe Leu Gln Ser Pro Asp Gly Met Val Lys
        435                 440                 445

Pro Lys Ser Thr Arg Lys Tyr Val Asp Ser Asn Thr Ile Asn Thr Met
    450                 455                 460
```

-continued

```
Arg Lys Ala Ile Asp Arg Asn Ala Glu Val Gln Val Glu Val Val Asn
465                 470                 475                 480

Phe Lys Lys Asn Gly Gln Arg Phe Val Asn Phe Leu Thr Met Ile Pro
                485                 490                 495

Val Arg Asp Glu Thr Gly Glu Tyr Arg Tyr Ser Met Gly Phe Gln Cys
            500                 505                 510

Glu Thr Glu
        515
```

<210> SEQ ID NO 18
<211> LENGTH: 571
<212> TYPE: PRT
<213> ORGANISM: Artificial Sequence
<220> FEATURE:
<223> OTHER INFORMATION: Synthetic construct

<400> SEQUENCE: 18

```
Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Thr Ala Pro Glu Asp
    130                 135                 140

Ala Gln Lys Ser Ser Ser Pro Ala Pro Ala Asp Ile Ala Gln Thr Val
145                 150                 155                 160

Gln Glu Asp Leu Arg Thr Phe Ser Trp Ala Ser Val Thr Ser Lys Asn
                165                 170                 175

Leu Pro Pro Ser Gly Ala Val Pro Val Thr Gly Ile Pro Pro His Val
            180                 185                 190

Val Lys Val Pro Ala Ser Gln Pro Arg Pro Glu Ser Lys Pro Glu Ser
        195                 200                 205

Gln Ile Pro Pro Gln Arg Pro Gln Arg Asp Gln Arg Val Arg Glu Gln
    210                 215                 220

Arg Ile Asn Ile Pro Pro Gln Arg Gly Pro Arg Pro Ile Arg Glu Ala
225                 230                 235                 240

Gly Glu Gln Gly Asp Ile Glu Pro Arg Arg Met Val Arg His Pro Asp
                245                 250                 255

Ser His Gln Leu Phe Ile Gly Asn Leu Pro His Glu Val Asp Lys Ser
            260                 265                 270

Glu Leu Lys Asp Phe Phe Gln Ser Tyr Gly Asn Val Val Glu Leu Arg
        275                 280                 285

Ile Asn Ser Gly Gly Lys Leu Pro Asn Phe Gly Phe Val Val Phe Asp
    290                 295                 300
```

Asp Ser Glu Pro Val Gln Lys Val Leu Ser Asn Arg Pro Ile Met Phe
305 310 315 320

Arg Gly Glu Val Arg Leu Asn Val Glu Glu Lys Lys Thr Arg Ala Ala
325 330 335

Arg Glu Gly Asp Arg Arg Asp Asn Arg Leu Arg Gly Pro Gly Gly Pro
340 345 350

Arg Gly Gly Leu Gly Gly Gly Met Arg Gly Pro Pro Arg Gly Gly Met
355 360 365

Val Gln Lys Pro Gly Phe Gly Val Gly Arg Gly Leu Ala Pro Arg Gln
370 375 380

Lys Leu Ile Pro Met Ala Arg Arg Ala Trp Leu Glu His Gly His Ser
385 390 395 400

Cys Phe Leu Cys Glu Ile Val Ile Arg Ser Gln Phe His Thr Thr Tyr
405 410 415

Glu Pro Glu Ala Met His Thr Leu Tyr Ala Pro Gly Gly Tyr Asp Ile
420 425 430

Met Gly Trp Leu Ile Gln Ile Met Asn Arg Pro Asn Pro Gln Val Glu
435 440 445

Leu Gly Pro Val Asp Thr Ser Cys Ala Leu Ile Leu Cys Asp Leu Lys
450 455 460

Gln Lys Asp Thr Pro Ile Val Tyr Ala Ser Glu Ala Phe Leu Tyr Met
465 470 475 480

Thr Gly Tyr Ser Asn Ala Glu Val Leu Gly Arg Asn Cys Arg Phe Leu
485 490 495

Gln Ser Pro Asp Gly Met Val Lys Pro Lys Ser Thr Arg Lys Tyr Val
500 505 510

Asp Ser Asn Thr Ile Asn Thr Met Arg Lys Ala Ile Asp Arg Asn Ala
515 520 525

Glu Val Gln Val Glu Val Val Asn Phe Lys Lys Asn Gly Gln Arg Phe
530 535 540

Val Asn Phe Leu Thr Met Ile Pro Val Arg Asp Glu Thr Gly Glu Tyr
545 550 555 560

Arg Tyr Ser Met Gly Phe Gln Cys Glu Thr Glu
565 570

<210> SEQ ID NO 19
<211> LENGTH: 534
<212> TYPE: PRT
<213> ORGANISM: Artificial Sequence
<220> FEATURE:
<223> OTHER INFORMATION: Synthetic construct

<400> SEQUENCE: 19

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

-continued

```
Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Gln Leu Phe
    210                 215                 220

Ile Gly Asn Leu Pro His Glu Val Asp Lys Ser Glu Leu Lys Asp Phe
225                 230                 235                 240

Phe Gln Ser Tyr Gly Asn Val Val Glu Leu Arg Ile Asn Ser Gly Gly
                245                 250                 255

Lys Leu Pro Asn Phe Gly Phe Val Val Phe Asp Asp Ser Glu Pro Val
            260                 265                 270

Gln Lys Val Leu Ser Asn Arg Pro Ile Met Phe Arg Gly Glu Val Arg
        275                 280                 285

Leu Asn Val Glu Glu Lys Lys Thr Arg Ala Ala Arg Glu Gly Asp Arg
    290                 295                 300

Arg Asp Asn Arg Leu Arg Gly Pro Gly Gly Pro Arg Gly Gly Leu Gly
305                 310                 315                 320

Gly Gly Met Arg Gly Pro Pro Arg Gly Gly Met Val Gln Lys Pro Gly
                325                 330                 335

Phe Gly Val Gly Arg Gly Leu Ala Pro Arg Gln Lys Leu Ile Pro Met
            340                 345                 350

Ala Arg Arg Ala Trp Leu Glu His Gly His Ser Cys Phe Leu Cys Glu
        355                 360                 365

Ile Val Ile Arg Ser Gln Phe His Thr Thr Tyr Glu Pro Glu Ala Met
    370                 375                 380

His Thr Leu Tyr Ala Pro Gly Gly Tyr Asp Ile Met Gly Trp Leu Ile
385                 390                 395                 400

Gln Ile Met Asn Arg Pro Asn Pro Gln Val Glu Leu Gly Pro Val Asp
                405                 410                 415

Thr Ser Cys Ala Leu Ile Leu Cys Asp Leu Lys Gln Lys Asp Thr Pro
            420                 425                 430

Ile Val Tyr Ala Ser Glu Ala Phe Leu Tyr Met Thr Gly Tyr Ser Asn
        435                 440                 445

Ala Glu Val Leu Gly Arg Asn Cys Arg Phe Leu Gln Ser Pro Asp Gly
    450                 455                 460

Met Val Lys Pro Lys Ser Thr Arg Lys Tyr Val Asp Ser Asn Thr Ile
465                 470                 475                 480

Asn Thr Met Arg Lys Ala Ile Asp Arg Asn Ala Glu Val Gln Val Glu
                485                 490                 495

Val Val Asn Phe Lys Lys Asn Gly Gln Arg Phe Val Asn Phe Leu Thr
            500                 505                 510
```

Met Ile Pro Val Arg Asp Glu Thr Gly Glu Tyr Arg Tyr Ser Met Gly
515 520 525

Phe Gln Cys Glu Thr Glu
530

<210> SEQ ID NO 20
<211> LENGTH: 582
<212> TYPE: PRT
<213> ORGANISM: Artificial Sequence
<220> FEATURE:
<223> OTHER INFORMATION: Synthetic construct

<400> SEQUENCE: 20

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Thr Ala Pro
210 215 220

Glu Asp Ala Gln Lys Ser Ser Ser Pro Ala Pro Ala Asp Ile Ala Gln
225 230 235 240

Thr Val Gln Glu Asp Leu Arg Thr Phe Ser Trp Ala Ser Val Thr Ser
245 250 255

Lys Asn Leu Pro Pro Ser Gly Ala Val Pro Val Thr Gly Ile Pro Pro
260 265 270

His Val Val Lys Val Pro Ala Ser Gln Pro Arg Pro Glu Ser Lys Pro
275 280 285

Glu Ser Gln Ile Pro Pro Gln Arg Pro Gln Arg Asp Gln Arg Val Arg
290 295 300

Glu Gln Arg Ile Asn Ile Pro Pro Gln Arg Gly Pro Arg Pro Ile Arg
305 310 315 320

Glu Ala Gly Glu Gln Gly Asp Ile Glu Pro Arg Arg Met Val Arg His
325 330 335

-continued

Pro Asp Ser His Glu Lys Lys Thr Arg Ala Ala Arg Glu Gly Asp Arg
340 345 350

Arg Asp Asn Arg Leu Arg Gly Pro Gly Gly Pro Arg Gly Gly Leu Gly
355 360 365

Gly Gly Met Arg Gly Pro Pro Arg Gly Gly Met Val Gln Lys Pro Gly
370 375 380

Phe Gly Val Gly Arg Gly Leu Ala Pro Arg Gln Lys Leu Ile Pro Met
385 390 395 400

Ala Arg Arg Ala Trp Leu Glu His Gly His Ser Cys Phe Leu Cys Glu
405 410 415

Ile Val Ile Arg Ser Gln Phe His Thr Thr Tyr Glu Pro Glu Ala Met
420 425 430

His Thr Leu Tyr Ala Pro Gly Gly Tyr Asp Ile Met Gly Trp Leu Ile
435 440 445

Gln Ile Met Asn Arg Pro Asn Pro Gln Val Glu Leu Gly Pro Val Asp
450 455 460

Thr Ser Cys Ala Leu Ile Leu Cys Asp Leu Lys Gln Lys Asp Thr Pro
465 470 475 480

Ile Val Tyr Ala Ser Glu Ala Phe Leu Tyr Met Thr Gly Tyr Ser Asn
485 490 495

Ala Glu Val Leu Gly Arg Asn Cys Arg Phe Leu Gln Ser Pro Asp Gly
500 505 510

Met Val Lys Pro Lys Ser Thr Arg Lys Tyr Val Asp Ser Asn Thr Ile
515 520 525

Asn Thr Met Arg Lys Ala Ile Asp Arg Asn Ala Glu Val Gln Val Glu
530 535 540

Val Val Asn Phe Lys Lys Asn Gly Gln Arg Phe Val Asn Phe Leu Thr
545 550 555 560

Met Ile Pro Val Arg Asp Glu Thr Gly Glu Tyr Arg Tyr Ser Met Gly
565 570 575

Phe Gln Cys Glu Thr Glu
580

<210> SEQ ID NO 21
<211> LENGTH: 562
<212> TYPE: PRT
<213> ORGANISM: Artificial Sequence
<220> FEATURE:
<223> OTHER INFORMATION: Synthetic construct

<400> SEQUENCE: 21

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

-continued

```
Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Met His Thr Leu Tyr
                405                 410                 415

Ala Pro Gly Gly Tyr Asp Ile Met Gly Trp Leu Ile Gln Ile Met Asn
            420                 425                 430

Arg Pro Asn Pro Gln Val Glu Leu Gly Pro Val Asp Thr Ser Cys Ala
        435                 440                 445

Leu Ile Leu Cys Asp Leu Lys Gln Lys Asp Thr Pro Ile Val Tyr Ala
    450                 455                 460

Ser Glu Ala Phe Leu Tyr Met Thr Gly Tyr Ser Asn Ala Glu Val Leu
465                 470                 475                 480

Gly Arg Asn Cys Arg Phe Leu Gln Ser Pro Asp Gly Met Val Lys Pro
                485                 490                 495

Lys Ser Thr Arg Lys Tyr Val Asp Ser Asn Thr Ile Asn Thr Met Arg
            500                 505                 510

Lys Ala Ile Asp Arg Asn Ala Glu Val Gln Val Glu Val Val Asn Phe
        515                 520                 525
```

Lys Lys Asn Gly Gln Arg Phe Val Asn Phe Leu Thr Met Ile Pro Val
    530                 535                 540

Arg Asp Glu Thr Gly Glu Tyr Arg Tyr Ser Met Gly Phe Gln Cys Glu
545                 550                 555                 560

Thr Glu

<210> SEQ ID NO 22
<211> LENGTH: 491
<212> TYPE: PRT
<213> ORGANISM: Artificial Sequence
<220> FEATURE:
<223> OTHER INFORMATION: Synthetic construct

<400> SEQUENCE: 22

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

```
Glu Ala Gly Glu Gln Gly Asp Ile Glu Pro Arg Arg Met Val Arg His
                325                 330                 335

Pro Asp Ser His Met His Thr Leu Tyr Ala Pro Gly Gly Tyr Asp Ile
            340                 345                 350

Met Gly Trp Leu Ile Gln Ile Met Asn Arg Pro Asn Pro Gln Val Glu
        355                 360                 365

Leu Gly Pro Val Asp Thr Ser Cys Ala Leu Ile Leu Cys Asp Leu Lys
    370                 375                 380

Gln Lys Asp Thr Pro Ile Val Tyr Ala Ser Glu Ala Phe Leu Tyr Met
385                 390                 395                 400

Thr Gly Tyr Ser Asn Ala Glu Val Leu Gly Arg Asn Cys Arg Phe Leu
                405                 410                 415

Gln Ser Pro Asp Gly Met Val Lys Pro Lys Ser Thr Arg Lys Tyr Val
            420                 425                 430

Asp Ser Asn Thr Ile Asn Thr Met Arg Lys Ala Ile Asp Arg Asn Ala
        435                 440                 445

Glu Val Gln Val Glu Val Val Asn Phe Lys Lys Asn Gly Gln Arg Phe
    450                 455                 460

Val Asn Phe Leu Thr Met Ile Pro Val Arg Asp Glu Thr Gly Glu Tyr
465                 470                 475                 480

Arg Tyr Ser Met Gly Phe Gln Cys Glu Thr Glu
                485                 490
```

<210> SEQ ID NO 23
<211> LENGTH: 665
<212> TYPE: PRT
<213> ORGANISM: Artificial Sequence
<220> FEATURE:
<223> OTHER INFORMATION: Synthetic construct

<400> SEQUENCE: 23

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190
```

-continued

```
Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Gln Leu Phe Ile Gly Asn Leu Pro His
            500                 505                 510

Glu Val Asp Lys Ser Glu Leu Lys Asp Phe Phe Gln Ser Tyr Gly Asn
        515                 520                 525

Val Val Glu Leu Arg Ile Asn Ser Gly Gly Lys Leu Pro Asn Phe Gly
    530                 535                 540

Phe Val Val Phe Asp Asp Ser Glu Pro Val Gln Lys Val Leu Ser Asn
545                 550                 555                 560

Arg Pro Ile Met Phe Arg Gly Glu Val Arg Leu Asn Val Glu Glu Lys
                565                 570                 575

Lys Thr Arg Ala Ala Arg Glu Gly Asp Arg Arg Asp Asn Arg Leu Arg
            580                 585                 590

Gly Pro Gly Gly Pro Arg Gly Gly Leu Gly Gly Gly Met Arg Gly Pro
        595                 600                 605
```

-continued

Pro Arg Gly Gly Met Val Gln Lys Pro Gly Phe Gly Val Gly Arg Gly
    610                 615                 620

Leu Ala Pro Arg Gln Lys Leu Ile Pro Met Ala Arg Arg Ala Trp Leu
625                 630                 635                 640

Glu His Gly His Ser Cys Phe Leu Cys Glu Ile Val Ile Arg Ser Gln
                645                 650                 655

Phe His Thr Thr Tyr Glu Pro Glu Ala
            660                 665

<210> SEQ ID NO 24
<211> LENGTH: 527
<212> TYPE: PRT
<213> ORGANISM: Artificial Sequence
<220> FEATURE:
<223> OTHER INFORMATION: Synthetic construct

<400> SEQUENCE: 24

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Gly Phe Val Thr Glu Pro Gln Glu Glu Ser Glu Glu
                165                 170                 175

Glu Val Glu Glu Pro Glu Glu Arg Gln Gln Thr Pro Glu Val Val Pro
            180                 185                 190

Asp Asp Ser Gly Thr Phe Tyr Asp Gln Ala Val Val Ser Asn Asp Met
        195                 200                 205

Glu Glu His Leu Glu Glu Pro Val Ala Glu Pro Glu Pro Asp Pro Glu
    210                 215                 220

Pro Glu Pro Glu Gln Glu Pro Val Ser Glu Ile Gln Glu Glu Lys Pro
225                 230                 235                 240

Glu Pro Val Leu Glu Glu Thr Ala Pro Glu Asp Ala Gln Lys Ser Ser
                245                 250                 255

Ser Pro Ala Pro Ala Asp Ile Ala Gln Thr Val Gln Glu Asp Leu Arg
            260                 265                 270

Thr Phe Ser Trp Ala Ser Val Thr Ser Lys Asn Leu Pro Pro Ser Gly
        275                 280                 285

Ala Val Pro Val Thr Gly Ile Pro Pro His Val Val Lys Val Pro Ala
    290                 295                 300

Ser Gln Pro Arg Pro Glu Ser Lys Pro Glu Ser Gln Ile Pro Pro Gln
305 310 315 320

Arg Pro Gln Arg Asp Gln Arg Val Arg Glu Gln Arg Ile Asn Ile Pro
325 330 335

Pro Gln Arg Gly Pro Arg Pro Ile Arg Glu Ala Gly Glu Gln Gly Asp
340 345 350

Ile Glu Pro Arg Arg Met Val Arg His Pro Asp Ser His Gln Leu Phe
355 360 365

Ile Gly Asn Leu Pro His Glu Val Asp Lys Ser Glu Leu Lys Asp Phe
370 375 380

Phe Gln Ser Tyr Gly Asn Val Val Glu Leu Arg Ile Asn Ser Gly Gly
385 390 395 400

Lys Leu Pro Asn Phe Gly Phe Val Val Phe Asp Asp Ser Glu Pro Val
405 410 415

Gln Lys Val Leu Ser Asn Arg Pro Ile Met Phe Arg Gly Glu Val Arg
420 425 430

Leu Asn Val Glu Glu Lys Lys Thr Arg Ala Ala Arg Glu Gly Asp Arg
435 440 445

Arg Asp Asn Arg Leu Arg Gly Pro Gly Gly Pro Arg Gly Gly Leu Gly
450 455 460

Gly Gly Met Arg Gly Pro Pro Arg Gly Gly Met Val Gln Lys Pro Gly
465 470 475 480

Phe Gly Val Gly Arg Gly Leu Ala Pro Arg Gln Lys Leu Ile Pro Met
485 490 495

Ala Arg Arg Ala Trp Leu Glu His Gly His Ser Cys Phe Leu Cys Glu
500 505 510

Ile Val Ile Arg Ser Gln Phe His Thr Thr Tyr Glu Pro Glu Ala
515 520 525

<210> SEQ ID NO 25
<211> LENGTH: 583
<212> TYPE: PRT
<213> ORGANISM: Artificial Sequence
<220> FEATURE:
<223> OTHER INFORMATION: Synthetic construct

<400> SEQUENCE: 25

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

-continued

```
Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Thr Ala
    290                 295                 300

Pro Glu Asp Ala Gln Lys Ser Ser Ser Pro Ala Pro Ala Asp Ile Ala
305                 310                 315                 320

Gln Thr Val Gln Glu Asp Leu Arg Thr Phe Ser Trp Ala Ser Val Thr
                325                 330                 335

Ser Lys Asn Leu Pro Pro Ser Gly Ala Val Pro Val Thr Gly Ile Pro
            340                 345                 350

Pro His Val Val Lys Val Pro Ala Ser Gln Pro Arg Pro Glu Ser Lys
        355                 360                 365

Pro Glu Ser Gln Ile Pro Pro Gln Arg Pro Gln Arg Asp Gln Arg Val
    370                 375                 380

Arg Glu Gln Arg Ile Asn Ile Pro Pro Gln Arg Gly Pro Arg Pro Ile
385                 390                 395                 400

Arg Glu Ala Gly Glu Gln Gly Asp Ile Glu Pro Arg Arg Met Val Arg
                405                 410                 415

His Pro Asp Ser His Gln Leu Phe Ile Gly Asn Leu Pro His Glu Val
            420                 425                 430

Asp Lys Ser Glu Leu Lys Asp Phe Phe Gln Ser Tyr Gly Asn Val Val
        435                 440                 445

Glu Leu Arg Ile Asn Ser Gly Gly Lys Leu Pro Asn Phe Gly Phe Val
    450                 455                 460

Val Phe Asp Asp Ser Glu Pro Val Gln Lys Val Leu Ser Asn Arg Pro
465                 470                 475                 480

Ile Met Phe Arg Gly Glu Val Arg Leu Asn Val Glu Glu Lys Lys Thr
                485                 490                 495

Arg Ala Ala Arg Glu Gly Asp Arg Arg Asp Asn Arg Leu Arg Gly Pro
            500                 505                 510

Gly Gly Pro Arg Gly Gly Leu Gly Gly Gly Met Arg Gly Pro Pro Arg
        515                 520                 525

Gly Gly Met Val Gln Lys Pro Gly Phe Gly Val Gly Arg Gly Leu Ala
    530                 535                 540

Pro Arg Gln Lys Leu Ile Pro Met Ala Arg Arg Ala Trp Leu Glu His
545                 550                 555                 560
```

```
Gly His Ser Cys Phe Leu Cys Glu Ile Val Ile Arg Ser Gln Phe His
                565                 570                 575

Thr Thr Tyr Glu Pro Glu Ala
            580


<210> SEQ ID NO 26
<211> LENGTH: 546
<212> TYPE: PRT
<213> ORGANISM: Artificial Sequence
<220> FEATURE:
<223> OTHER INFORMATION: Synthetic construct

<400> SEQUENCE: 26

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335
```

```
Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Gln Leu Phe Ile Gly Asn Leu Pro His Glu Val Asp Lys Ser Glu Leu
385                 390                 395                 400

Lys Asp Phe Phe Gln Ser Tyr Gly Asn Val Val Glu Leu Arg Ile Asn
                405                 410                 415

Ser Gly Gly Lys Leu Pro Asn Phe Gly Phe Val Val Phe Asp Asp Ser
            420                 425                 430

Glu Pro Val Gln Lys Val Leu Ser Asn Arg Pro Ile Met Phe Arg Gly
        435                 440                 445

Glu Val Arg Leu Asn Val Glu Glu Lys Lys Thr Arg Ala Ala Arg Glu
    450                 455                 460

Gly Asp Arg Arg Asp Asn Arg Leu Arg Gly Pro Gly Gly Pro Arg Gly
465                 470                 475                 480

Gly Leu Gly Gly Gly Met Arg Gly Pro Pro Arg Gly Gly Met Val Gln
                485                 490                 495

Lys Pro Gly Phe Gly Val Gly Arg Gly Leu Ala Pro Arg Gln Lys Leu
            500                 505                 510

Ile Pro Met Ala Arg Arg Ala Trp Leu Glu His Gly His Ser Cys Phe
        515                 520                 525

Leu Cys Glu Ile Val Ile Arg Ser Gln Phe His Thr Thr Tyr Glu Pro
    530                 535                 540

Glu Ala
545


<210> SEQ ID NO 27
<211> LENGTH: 594
<212> TYPE: PRT
<213> ORGANISM: Artificial Sequence
<220> FEATURE:
<223> OTHER INFORMATION: Synthetic construct

<400> SEQUENCE: 27

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140
```

```
Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Glu Lys Lys Thr Arg Ala Ala Arg Glu
            500                 505                 510

Gly Asp Arg Arg Asp Asn Arg Leu Arg Gly Pro Gly Gly Pro Arg Gly
        515                 520                 525

Gly Leu Gly Gly Gly Met Arg Gly Pro Pro Arg Gly Gly Met Val Gln
    530                 535                 540

Lys Pro Gly Phe Gly Val Gly Arg Gly Leu Ala Pro Arg Gln Lys Leu
545                 550                 555                 560
```

-continued

```
Ile Pro Met Ala Arg Arg Ala Trp Leu Glu His Gly His Ser Cys Phe
                565                 570                 575

Leu Cys Glu Ile Val Ile Arg Ser Gln Phe His Thr Thr Tyr Glu Pro
            580                 585                 590

Glu Ala
```

<210> SEQ ID NO 28
<211> LENGTH: 574
<212> TYPE: PRT
<213> ORGANISM: Artificial Sequence
<220> FEATURE:
<223> OTHER INFORMATION: Synthetic construct

<400> SEQUENCE: 28

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320
```

Glu Arg Gln Gln Thr Pro Glu Val Val Pro Asp Asp Ser Gly Thr Phe
325 330 335

Tyr Asp Gln Ala Val Val Ser Asn Asp Met Glu Glu His Leu Glu Glu
340 345 350

Pro Val Ala Glu Pro Glu Pro Asp Pro Glu Pro Glu Pro Glu Gln Glu
355 360 365

Pro Val Ser Glu Ile Gln Glu Glu Lys Pro Glu Pro Val Leu Glu Glu
370 375 380

Thr Ala Pro Glu Asp Ala Gln Lys Ser Ser Ser Pro Ala Pro Ala Asp
385 390 395 400

Ile Ala Gln Thr Val Gln Glu Asp Leu Arg Thr Phe Ser Trp Ala Ser
405 410 415

Val Thr Ser Lys Asn Leu Pro Pro Ser Gly Ala Val Pro Val Thr Gly
420 425 430

Ile Pro Pro His Val Val Lys Val Pro Ala Ser Gln Pro Arg Pro Glu
435 440 445

Ser Lys Pro Glu Ser Gln Ile Pro Pro Gln Arg Pro Gln Arg Asp Gln
450 455 460

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His Gln Leu Phe Ile Gly Asn Leu Pro His
500 505 510

Glu Val Asp Lys Ser Glu Leu Lys Asp Phe Phe Gln Ser Tyr Gly Asn
515 520 525

Val Val Glu Leu Arg Ile Asn Ser Gly Gly Lys Leu Pro Asn Phe Gly
530 535 540

Phe Val Val Phe Asp Asp Ser Glu Pro Val Gln Lys Val Leu Ser Asn
545 550 555 560

Arg Pro Ile Met Phe Arg Gly Glu Val Arg Leu Asn Val Glu
565 570

<210> SEQ ID NO 29
<211> LENGTH: 503
<212> TYPE: PRT
<213> ORGANISM: Artificial Sequence
<220> FEATURE:
<223> OTHER INFORMATION: Synthetic construct

<400> SEQUENCE: 29

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

-continued

```
Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His
            500
```

<210> SEQ ID NO 30
<211> LENGTH: 665

<212> TYPE: PRT
<213> ORGANISM: Artificial Sequence
<220> FEATURE:
<223> OTHER INFORMATION: Synthetic construct

<400> SEQUENCE: 30

```
Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380
```

-continued

Thr Ala Pro Glu Asp Ala Gln Lys Ser Ser Ser Pro Ala Pro Ala Asp
385 390 395 400

Ile Ala Gln Thr Val Gln Glu Asp Leu Arg Thr Phe Ser Trp Ala Ser
405 410 415

Val Thr Ser Lys Asn Leu Pro Pro Ser Gly Ala Val Pro Val Thr Gly
420 425 430

Ile Pro Pro His Val Val Lys Val Pro Ala Ser Gln Pro Arg Pro Glu
435 440 445

Ser Lys Pro Glu Ser Gln Ile Pro Pro Gln Arg Pro Gln Arg Asp Gln
450 455 460

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His Gln Leu Phe Ile Gly Asn Leu Pro His
500 505 510

Glu Val Asp Lys Ser Glu Leu Lys Asp Phe Phe Gln Ser Tyr Gly Asn
515 520 525

Val Val Glu Leu Arg Ile Asn Ser Gly Gly Lys Leu Pro Asn Phe Gly
530 535 540

Phe Val Val Phe Asp Asp Ser Glu Pro Val Gln Lys Val Leu Ser Asn
545 550 555 560

Arg Pro Ile Met Phe Arg Gly Glu Val Arg Leu Asn Val Glu Glu Lys
565 570 575

Lys Thr Arg Ala Ala Arg Glu Gly Asp Arg Arg Asp Asn Arg Leu Arg
580 585 590

Gly Pro Gly Gly Pro Arg Gly Gly Leu Gly Gly Gly Met Arg Gly Pro
595 600 605

Pro Arg Gly Gly Met Val Gln Lys Pro Gly Phe Gly Val Gly Arg Gly
610 615 620

Leu Ala Pro Arg Gln Lys Leu Ile Pro Met Ala Arg Arg Ala Trp Leu
625 630 635 640

Glu His Gly His Ser Cys Phe Leu Cys Glu Ile Val Ile Arg Ser Gln
645 650 655

Phe His Thr Thr Tyr Glu Pro Glu Ala
660 665

<210> SEQ ID NO 31
<211> LENGTH: 527
<212> TYPE: PRT
<213> ORGANISM: Artificial Sequence
<220> FEATURE:
<223> OTHER INFORMATION: Synthetic construct

<400> SEQUENCE: 31

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

-continued

```
Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Gly Phe Val Thr Glu Pro Gln Glu Glu Ser Glu Glu
                165                 170                 175

Glu Val Glu Glu Pro Glu Glu Arg Gln Gln Thr Pro Glu Val Val Pro
            180                 185                 190

Asp Asp Ser Gly Thr Phe Tyr Asp Gln Ala Val Val Ser Asn Asp Met
        195                 200                 205

Glu Glu His Leu Glu Glu Pro Val Ala Glu Pro Glu Pro Asp Pro Glu
    210                 215                 220

Pro Glu Pro Glu Gln Glu Pro Val Ser Glu Ile Gln Glu Glu Lys Pro
225                 230                 235                 240

Glu Pro Val Leu Glu Glu Thr Ala Pro Glu Asp Ala Gln Lys Ser Ser
                245                 250                 255

Ser Pro Ala Pro Ala Asp Ile Ala Gln Thr Val Gln Glu Asp Leu Arg
            260                 265                 270

Thr Phe Ser Trp Ala Ser Val Thr Ser Lys Asn Leu Pro Pro Ser Gly
        275                 280                 285

Ala Val Pro Val Thr Gly Ile Pro Pro His Val Val Lys Val Pro Ala
    290                 295                 300

Ser Gln Pro Arg Pro Glu Ser Lys Pro Glu Ser Gln Ile Pro Pro Gln
305                 310                 315                 320

Arg Pro Gln Arg Asp Gln Arg Val Arg Glu Gln Arg Ile Asn Ile Pro
                325                 330                 335

Pro Gln Arg Gly Pro Arg Pro Ile Arg Glu Ala Gly Glu Gln Gly Asp
            340                 345                 350

Ile Glu Pro Arg Arg Met Val Arg His Pro Asp Ser His Gln Leu Phe
        355                 360                 365

Ile Gly Asn Leu Pro His Glu Val Asp Lys Ser Glu Leu Lys Asp Phe
    370                 375                 380

Phe Gln Ser Tyr Gly Asn Val Val Glu Leu Arg Ile Asn Ser Gly Gly
385                 390                 395                 400

Lys Leu Pro Asn Phe Gly Phe Val Val Phe Asp Asp Ser Glu Pro Val
                405                 410                 415

Gln Lys Val Leu Ser Asn Arg Pro Ile Met Phe Arg Gly Glu Val Arg
            420                 425                 430

Leu Asn Val Glu Glu Lys Lys Thr Arg Ala Ala Arg Glu Gly Asp Arg
        435                 440                 445

Arg Asp Asn Arg Leu Arg Gly Pro Gly Gly Pro Arg Gly Gly Leu Gly
    450                 455                 460

Gly Gly Met Arg Gly Pro Pro Arg Gly Gly Met Val Gln Lys Pro Gly
465                 470                 475                 480

Phe Gly Val Gly Arg Gly Leu Ala Pro Arg Gln Lys Leu Ile Pro Met
                485                 490                 495
```

```
Ala Arg Arg Ala Trp Leu Glu His Gly His Ser Cys Phe Leu Cys Glu
            500                 505                 510

Ile Val Ile Arg Ser Gln Phe His Thr Thr Tyr Glu Pro Glu Ala
        515                 520                 525


<210> SEQ ID NO 32
<211> LENGTH: 583
<212> TYPE: PRT
<213> ORGANISM: Artificial Sequence
<220> FEATURE:
<223> OTHER INFORMATION: Synthetic construct

<400> SEQUENCE: 32

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Thr Ala
    290                 295                 300

Pro Glu Asp Ala Gln Lys Ser Ser Ser Pro Ala Pro Ala Asp Ile Ala
305                 310                 315                 320

Gln Thr Val Gln Glu Asp Leu Arg Thr Phe Ser Trp Ala Ser Val Thr
                325                 330                 335
```

-continued

Ser Lys Asn Leu Pro Pro Ser Gly Ala Val Pro Val Thr Gly Ile Pro
340 345 350

Pro His Val Val Lys Val Pro Ala Ser Gln Pro Arg Pro Glu Ser Lys
355 360 365

Pro Glu Ser Gln Ile Pro Pro Gln Arg Pro Gln Arg Asp Gln Arg Val
370 375 380

Arg Glu Gln Arg Ile Asn Ile Pro Pro Gln Arg Gly Pro Arg Pro Ile
385 390 395 400

Arg Glu Ala Gly Glu Gln Gly Asp Ile Glu Pro Arg Arg Met Val Arg
405 410 415

His Pro Asp Ser His Gln Leu Phe Ile Gly Asn Leu Pro His Glu Val
420 425 430

Asp Lys Ser Glu Leu Lys Asp Phe Phe Gln Ser Tyr Gly Asn Val Val
435 440 445

Glu Leu Arg Ile Asn Ser Gly Gly Lys Leu Pro Asn Phe Gly Phe Val
450 455 460

Val Phe Asp Asp Ser Glu Pro Val Gln Lys Val Leu Ser Asn Arg Pro
465 470 475 480

Ile Met Phe Arg Gly Glu Val Arg Leu Asn Val Glu Glu Lys Lys Thr
485 490 495

Arg Ala Ala Arg Glu Gly Asp Arg Arg Asp Asn Arg Leu Arg Gly Pro
500 505 510

Gly Gly Pro Arg Gly Gly Leu Gly Gly Gly Met Arg Gly Pro Pro Arg
515 520 525

Gly Gly Met Val Gln Lys Pro Gly Phe Gly Val Gly Arg Gly Leu Ala
530 535 540

Pro Arg Gln Lys Leu Ile Pro Met Ala Arg Arg Ala Trp Leu Glu His
545 550 555 560

Gly His Ser Cys Phe Leu Cys Glu Ile Val Ile Arg Ser Gln Phe His
565 570 575

Thr Thr Tyr Glu Pro Glu Ala
580

<210> SEQ ID NO 33
<211> LENGTH: 546
<212> TYPE: PRT
<213> ORGANISM: Artificial Sequence
<220> FEATURE:
<223> OTHER INFORMATION: Synthetic construct

<400> SEQUENCE: 33

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

-continued

```
Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Gln Leu Phe Ile Gly Asn Leu Pro His Glu Val Asp Lys Ser Glu Leu
385                 390                 395                 400

Lys Asp Phe Phe Gln Ser Tyr Gly Asn Val Val Glu Leu Arg Ile Asn
                405                 410                 415

Ser Gly Gly Lys Leu Pro Asn Phe Gly Phe Val Val Phe Asp Asp Ser
            420                 425                 430

Glu Pro Val Gln Lys Val Leu Ser Asn Arg Pro Ile Met Phe Arg Gly
        435                 440                 445

Glu Val Arg Leu Asn Val Glu Glu Lys Lys Thr Arg Ala Ala Arg Glu
    450                 455                 460

Gly Asp Arg Arg Asp Asn Arg Leu Arg Gly Pro Gly Gly Pro Arg Gly
465                 470                 475                 480

Gly Leu Gly Gly Gly Met Arg Gly Pro Pro Arg Gly Gly Met Val Gln
                485                 490                 495

Lys Pro Gly Phe Gly Val Gly Arg Gly Leu Ala Pro Arg Gln Lys Leu
            500                 505                 510

Ile Pro Met Ala Arg Arg Ala Trp Leu Glu His Gly His Ser Cys Phe
        515                 520                 525
```

```
Leu Cys Glu Ile Val Ile Arg Ser Gln Phe His Thr Thr Tyr Glu Pro
    530                 535                 540

Glu Ala
545


<210> SEQ ID NO 34
<211> LENGTH: 594
<212> TYPE: PRT
<213> ORGANISM: Artificial Sequence
<220> FEATURE:
<223> OTHER INFORMATION: Synthetic construct

<400> SEQUENCE: 34

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335
```

Tyr Asp Gln Ala Val Val Ser Asn Asp Met Glu Glu His Leu Glu Glu
340 345 350

Pro Val Ala Glu Pro Glu Pro Asp Pro Glu Pro Glu Pro Glu Gln Glu
355 360 365

Pro Val Ser Glu Ile Gln Glu Glu Lys Pro Glu Pro Val Leu Glu Glu
370 375 380

Thr Ala Pro Glu Asp Ala Gln Lys Ser Ser Ser Pro Ala Pro Ala Asp
385 390 395 400

Ile Ala Gln Thr Val Gln Glu Asp Leu Arg Thr Phe Ser Trp Ala Ser
405 410 415

Val Thr Ser Lys Asn Leu Pro Pro Ser Gly Ala Val Pro Val Thr Gly
420 425 430

Ile Pro Pro His Val Val Lys Val Pro Ala Ser Gln Pro Arg Pro Glu
435 440 445

Ser Lys Pro Glu Ser Gln Ile Pro Pro Gln Arg Pro Gln Arg Asp Gln
450 455 460

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His Glu Lys Lys Thr Arg Ala Ala Arg Glu
500 505 510

Gly Asp Arg Arg Asp Asn Arg Leu Arg Gly Pro Gly Gly Pro Arg Gly
515 520 525

Gly Leu Gly Gly Gly Met Arg Gly Pro Pro Arg Gly Gly Met Val Gln
530 535 540

Lys Pro Gly Phe Gly Val Gly Arg Gly Leu Ala Pro Arg Gln Lys Leu
545 550 555 560

Ile Pro Met Ala Arg Arg Ala Trp Leu Glu His Gly His Ser Cys Phe
565 570 575

Leu Cys Glu Ile Val Ile Arg Ser Gln Phe His Thr Thr Tyr Glu Pro
580 585 590

Glu Ala

<210> SEQ ID NO 35
<211> LENGTH: 574
<212> TYPE: PRT
<213> ORGANISM: Artificial Sequence
<220> FEATURE:
<223> OTHER INFORMATION: Synthetic construct

<400> SEQUENCE: 35

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

-continued

```
Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Gln Leu Phe Ile Gly Asn Leu Pro His
            500                 505                 510
```

```
Glu Val Asp Lys Ser Glu Leu Lys Asp Phe Phe Gln Ser Tyr Gly Asn
        515                 520                 525

Val Val Glu Leu Arg Ile Asn Ser Gly Gly Lys Leu Pro Asn Phe Gly
    530                 535                 540

Phe Val Val Phe Asp Asp Ser Glu Pro Val Gln Lys Val Leu Ser Asn
545                 550                 555                 560

Arg Pro Ile Met Phe Arg Gly Glu Val Arg Leu Asn Val Glu
                565                 570


<210> SEQ ID NO 36
<211> LENGTH: 503
<212> TYPE: PRT
<213> ORGANISM: Artificial Sequence
<220> FEATURE:
<223> OTHER INFORMATION: Synthetic construct

<400> SEQUENCE: 36

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300
```

-continued

Val Thr Glu Pro Gln Glu Glu Ser Glu Glu Glu Val Glu Glu Pro Glu
305 310 315 320

Glu Arg Gln Gln Thr Pro Glu Val Val Pro Asp Asp Ser Gly Thr Phe
325 330 335

Tyr Asp Gln Ala Val Val Ser Asn Asp Met Glu Glu His Leu Glu Glu
340 345 350

Pro Val Ala Glu Pro Glu Pro Asp Pro Glu Pro Glu Pro Glu Gln Glu
355 360 365

Pro Val Ser Glu Ile Gln Glu Glu Lys Pro Glu Pro Val Leu Glu Glu
370 375 380

Thr Ala Pro Glu Asp Ala Gln Lys Ser Ser Ser Pro Ala Pro Ala Asp
385 390 395 400

Ile Ala Gln Thr Val Gln Glu Asp Leu Arg Thr Phe Ser Trp Ala Ser
405 410 415

Val Thr Ser Lys Asn Leu Pro Pro Ser Gly Ala Val Pro Val Thr Gly
420 425 430

Ile Pro Pro His Val Val Lys Val Pro Ala Ser Gln Pro Arg Pro Glu
435 440 445

Ser Lys Pro Glu Ser Gln Ile Pro Pro Gln Arg Pro Gln Arg Asp Gln
450 455 460

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His
500

<210> SEQ ID NO 37
<211> LENGTH: 665
<212> TYPE: PRT
<213> ORGANISM: Artificial Sequence
<220> FEATURE:
<223> OTHER INFORMATION: Synthetic construct

<400> SEQUENCE: 37

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

-continued

Gly Ser Gly Met Val Met Glu Lys Pro Ser Pro Leu Leu Val Gly Arg
165 170 175

Glu Phe Val Arg Gln Tyr Tyr Thr Leu Leu Asn Gln Ala Pro Asp Met
180 185 190

Leu His Arg Phe Tyr Gly Lys Asn Ser Ser Tyr Val His Gly Gly Leu
195 200 205

Asp Ser Asn Gly Lys Pro Ala Asp Ala Val Tyr Gly Gln Lys Glu Ile
210 215 220

His Arg Lys Val Met Ser Gln Asn Phe Thr Asn Cys His Thr Lys Ile
225 230 235 240

Arg His Val Asp Ala His Ala Thr Leu Asn Asp Gly Val Val Val Gln
245 250 255

Val Met Gly Leu Leu Ser Asn Asn Asn Gln Ala Leu Arg Arg Phe Met
260 265 270

Gln Thr Phe Val Leu Ala Pro Glu Gly Ser Val Ala Asn Lys Phe Tyr
275 280 285

Val His Asn Asp Ile Phe Arg Tyr Gln Asp Glu Val Phe Gly Gly Phe
290 295 300

Val Thr Glu Pro Gln Glu Glu Ser Glu Glu Glu Val Glu Glu Pro Glu
305 310 315 320

Glu Arg Gln Gln Thr Pro Glu Val Val Pro Asp Asp Ser Gly Thr Phe
325 330 335

Tyr Asp Gln Ala Val Val Ser Asn Asp Met Glu Glu His Leu Glu Glu
340 345 350

Pro Val Ala Glu Pro Glu Pro Asp Pro Glu Pro Glu Pro Glu Gln Glu
355 360 365

Pro Val Ser Glu Ile Gln Glu Glu Lys Pro Glu Pro Val Leu Glu Glu
370 375 380

Thr Ala Pro Glu Asp Ala Gln Lys Ser Ser Ser Pro Ala Pro Ala Asp
385 390 395 400

Ile Ala Gln Thr Val Gln Glu Asp Leu Arg Thr Phe Ser Trp Ala Ser
405 410 415

Val Thr Ser Lys Asn Leu Pro Pro Ser Gly Ala Val Pro Val Thr Gly
420 425 430

Ile Pro Pro His Val Val Lys Val Pro Ala Ser Gln Pro Arg Pro Glu
435 440 445

Ser Lys Pro Glu Ser Gln Ile Pro Pro Gln Arg Pro Gln Arg Asp Gln
450 455 460

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His Gln Leu Phe Ile Gly Asn Leu Pro His
500 505 510

Glu Val Asp Lys Ser Glu Leu Lys Asp Phe Phe Gln Ser Tyr Gly Asn
515 520 525

Val Val Glu Leu Arg Ile Asn Ser Gly Gly Lys Leu Pro Asn Phe Gly
530 535 540

Phe Val Val Phe Asp Asp Ser Glu Pro Val Gln Lys Val Leu Ser Asn
545 550 555 560

Arg Pro Ile Met Phe Arg Gly Glu Val Arg Leu Asn Val Glu Glu Lys
565 570 575

```
Lys Thr Arg Ala Ala Arg Glu Gly Asp Arg Arg Asp Asn Arg Leu Arg
            580                 585                 590

Gly Pro Gly Gly Pro Arg Gly Gly Leu Gly Gly Gly Met Arg Gly Pro
        595                 600                 605

Pro Arg Gly Gly Met Val Gln Lys Pro Gly Phe Gly Val Gly Arg Gly
    610                 615                 620

Leu Ala Pro Arg Gln Lys Leu Ile Pro Met Ala Arg Arg Ala Trp Leu
625                 630                 635                 640

Glu His Gly His Ser Cys Phe Leu Cys Glu Ile Val Ile Arg Ser Gln
                645                 650                 655

Phe His Thr Thr Tyr Glu Pro Glu Ala
            660                 665


<210> SEQ ID NO 38
<211> LENGTH: 527
<212> TYPE: PRT
<213> ORGANISM: Artificial Sequence
<220> FEATURE:
<223> OTHER INFORMATION: Synthetic construct

<400> SEQUENCE: 38

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Gly Phe Val Thr Glu Pro Gln Glu Glu Ser Glu Glu
                165                 170                 175

Glu Val Glu Glu Pro Glu Glu Arg Gln Gln Thr Pro Glu Val Val Pro
            180                 185                 190

Asp Asp Ser Gly Thr Phe Tyr Asp Gln Ala Val Val Ser Asn Asp Met
        195                 200                 205

Glu Glu His Leu Glu Glu Pro Val Ala Glu Pro Glu Pro Asp Pro Glu
    210                 215                 220

Pro Glu Pro Glu Gln Glu Pro Val Ser Glu Ile Gln Glu Glu Lys Pro
225                 230                 235                 240

Glu Pro Val Leu Glu Glu Thr Ala Pro Glu Asp Ala Gln Lys Ser Ser
                245                 250                 255

Ser Pro Ala Pro Ala Asp Ile Ala Gln Thr Val Gln Glu Asp Leu Arg
            260                 265                 270
```

Thr Phe Ser Trp Ala Ser Val Thr Ser Lys Asn Leu Pro Pro Ser Gly
275 280 285

Ala Val Pro Val Thr Gly Ile Pro Pro His Val Val Lys Val Pro Ala
290 295 300

Ser Gln Pro Arg Pro Glu Ser Lys Pro Glu Ser Gln Ile Pro Pro Gln
305 310 315 320

Arg Pro Gln Arg Asp Gln Arg Val Arg Glu Gln Arg Ile Asn Ile Pro
325 330 335

Pro Gln Arg Gly Pro Arg Pro Ile Arg Glu Ala Gly Glu Gln Gly Asp
340 345 350

Ile Glu Pro Arg Arg Met Val Arg His Pro Asp Ser His Gln Leu Phe
355 360 365

Ile Gly Asn Leu Pro His Glu Val Asp Lys Ser Glu Leu Lys Asp Phe
370 375 380

Phe Gln Ser Tyr Gly Asn Val Val Glu Leu Arg Ile Asn Ser Gly Gly
385 390 395 400

Lys Leu Pro Asn Phe Gly Phe Val Val Phe Asp Asp Ser Glu Pro Val
405 410 415

Gln Lys Val Leu Ser Asn Arg Pro Ile Met Phe Arg Gly Glu Val Arg
420 425 430

Leu Asn Val Glu Glu Lys Lys Thr Arg Ala Ala Arg Glu Gly Asp Arg
435 440 445

Arg Asp Asn Arg Leu Arg Gly Pro Gly Gly Pro Arg Gly Gly Leu Gly
450 455 460

Gly Gly Met Arg Gly Pro Pro Arg Gly Gly Met Val Gln Lys Pro Gly
465 470 475 480

Phe Gly Val Gly Arg Gly Leu Ala Pro Arg Gln Lys Leu Ile Pro Met
485 490 495

Ala Arg Arg Ala Trp Leu Glu His Gly His Ser Cys Phe Leu Cys Glu
500 505 510

Ile Val Ile Arg Ser Gln Phe His Thr Thr Tyr Glu Pro Glu Ala
515 520 525

<210> SEQ ID NO 39
<211> LENGTH: 583
<212> TYPE: PRT
<213> ORGANISM: Artificial Sequence
<220> FEATURE:
<223> OTHER INFORMATION: Synthetic construct

<400> SEQUENCE: 39

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

-continued

```
Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Thr Ala
    290                 295                 300

Pro Glu Asp Ala Gln Lys Ser Ser Ser Pro Ala Pro Ala Asp Ile Ala
305                 310                 315                 320

Gln Thr Val Gln Glu Asp Leu Arg Thr Phe Ser Trp Ala Ser Val Thr
                325                 330                 335

Ser Lys Asn Leu Pro Pro Ser Gly Ala Val Pro Val Thr Gly Ile Pro
            340                 345                 350

Pro His Val Val Lys Val Pro Ala Ser Gln Pro Arg Pro Glu Ser Lys
        355                 360                 365

Pro Glu Ser Gln Ile Pro Pro Gln Arg Pro Gln Arg Asp Gln Arg Val
    370                 375                 380

Arg Glu Gln Arg Ile Asn Ile Pro Pro Gln Arg Gly Pro Arg Pro Ile
385                 390                 395                 400

Arg Glu Ala Gly Glu Gln Gly Asp Ile Glu Pro Arg Arg Met Val Arg
                405                 410                 415

His Pro Asp Ser His Gln Leu Phe Ile Gly Asn Leu Pro His Glu Val
            420                 425                 430

Asp Lys Ser Glu Leu Lys Asp Phe Phe Gln Ser Tyr Gly Asn Val Val
        435                 440                 445

Glu Leu Arg Ile Asn Ser Gly Gly Lys Leu Pro Asn Phe Gly Phe Val
    450                 455                 460

Val Phe Asp Asp Ser Glu Pro Val Gln Lys Val Leu Ser Asn Arg Pro
465                 470                 475                 480

Ile Met Phe Arg Gly Glu Val Arg Leu Asn Val Glu Glu Lys Lys Thr
                485                 490                 495

Arg Ala Ala Arg Glu Gly Asp Arg Arg Asp Asn Arg Leu Arg Gly Pro
            500                 505                 510

Gly Gly Pro Arg Gly Gly Leu Gly Gly Gly Met Arg Gly Pro Pro Arg
        515                 520                 525
```

Gly Gly Met Val Gln Lys Pro Gly Phe Gly Val Gly Arg Gly Leu Ala
530 535 540

Pro Arg Gln Lys Leu Ile Pro Met Ala Arg Arg Ala Trp Leu Glu His
545 550 555 560

Gly His Ser Cys Phe Leu Cys Glu Ile Val Ile Arg Ser Gln Phe His
565 570 575

Thr Thr Tyr Glu Pro Glu Ala
580

<210> SEQ ID NO 40
<211> LENGTH: 546
<212> TYPE: PRT
<213> ORGANISM: Artificial Sequence
<220> FEATURE:
<223> OTHER INFORMATION: Synthetic construct

<400> SEQUENCE: 40

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Met Val Met Glu Lys Pro Ser Pro Leu Leu Val Gly Arg
165 170 175

Glu Phe Val Arg Gln Tyr Tyr Thr Leu Leu Asn Gln Ala Pro Asp Met
180 185 190

Leu His Arg Phe Tyr Gly Lys Asn Ser Ser Tyr Val His Gly Gly Leu
195 200 205

Asp Ser Asn Gly Lys Pro Ala Asp Ala Val Tyr Gly Gln Lys Glu Ile
210 215 220

His Arg Lys Val Met Ser Gln Asn Phe Thr Asn Cys His Thr Lys Ile
225 230 235 240

Arg His Val Asp Ala His Ala Thr Leu Asn Asp Gly Val Val Val Gln
245 250 255

Val Met Gly Leu Leu Ser Asn Asn Asn Gln Ala Leu Arg Arg Phe Met
260 265 270

Gln Thr Phe Val Leu Ala Pro Glu Gly Ser Val Ala Asn Lys Phe Tyr
275 280 285

Val His Asn Asp Ile Phe Arg Tyr Gln Asp Glu Val Phe Gly Gly Phe
290 295 300

-continued

Val Thr Glu Pro Gln Glu Glu Ser Glu Glu Glu Val Glu Glu Pro Glu
305 310 315 320

Glu Arg Gln Gln Thr Pro Glu Val Val Pro Asp Asp Ser Gly Thr Phe
325 330 335

Tyr Asp Gln Ala Val Val Ser Asn Asp Met Glu Glu His Leu Glu Glu
340 345 350

Pro Val Ala Glu Pro Glu Pro Asp Pro Glu Pro Glu Pro Glu Gln Glu
355 360 365

Pro Val Ser Glu Ile Gln Glu Glu Lys Pro Glu Pro Val Leu Glu Glu
370 375 380

Gln Leu Phe Ile Gly Asn Leu Pro His Glu Val Asp Lys Ser Glu Leu
385 390 395 400

Lys Asp Phe Phe Gln Ser Tyr Gly Asn Val Val Glu Leu Arg Ile Asn
405 410 415

Ser Gly Gly Lys Leu Pro Asn Phe Gly Phe Val Val Phe Asp Asp Ser
420 425 430

Glu Pro Val Gln Lys Val Leu Ser Asn Arg Pro Ile Met Phe Arg Gly
435 440 445

Glu Val Arg Leu Asn Val Glu Glu Lys Lys Thr Arg Ala Ala Arg Glu
450 455 460

Gly Asp Arg Arg Asp Asn Arg Leu Arg Gly Pro Gly Gly Pro Arg Gly
465 470 475 480

Gly Leu Gly Gly Gly Met Arg Gly Pro Pro Arg Gly Gly Met Val Gln
485 490 495

Lys Pro Gly Phe Gly Val Gly Arg Gly Leu Ala Pro Arg Gln Lys Leu
500 505 510

Ile Pro Met Ala Arg Arg Ala Trp Leu Glu His Gly His Ser Cys Phe
515 520 525

Leu Cys Glu Ile Val Ile Arg Ser Gln Phe His Thr Thr Tyr Glu Pro
530 535 540

Glu Ala
545

<210> SEQ ID NO 41
<211> LENGTH: 594
<212> TYPE: PRT
<213> ORGANISM: Artificial Sequence
<220> FEATURE:
<223> OTHER INFORMATION: Synthetic construct

<400> SEQUENCE: 41

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

-continued

```
Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Glu Lys Lys Thr Arg Ala Ala Arg Glu
            500                 505                 510

Gly Asp Arg Arg Asp Asn Arg Leu Arg Gly Pro Gly Gly Pro Arg Gly
        515                 520                 525
```

-continued

Gly Leu Gly Gly Gly Met Arg Gly Pro Pro Arg Gly Gly Met Val Gln
530 535 540

Lys Pro Gly Phe Gly Val Gly Arg Gly Leu Ala Pro Arg Gln Lys Leu
545 550 555 560

Ile Pro Met Ala Arg Arg Ala Trp Leu Glu His Gly His Ser Cys Phe
565 570 575

Leu Cys Glu Ile Val Ile Arg Ser Gln Phe His Thr Thr Tyr Glu Pro
580 585 590

Glu Ala

<210> SEQ ID NO 42
<211> LENGTH: 574
<212> TYPE: PRT
<213> ORGANISM: Artificial Sequence
<220> FEATURE:
<223> OTHER INFORMATION: Synthetic construct

<400> SEQUENCE: 42

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Met Val Met Glu Lys Pro Ser Pro Leu Leu Val Gly Arg
165 170 175

Glu Phe Val Arg Gln Tyr Tyr Thr Leu Leu Asn Gln Ala Pro Asp Met
180 185 190

Leu His Arg Phe Tyr Gly Lys Asn Ser Ser Tyr Val His Gly Gly Leu
195 200 205

Asp Ser Asn Gly Lys Pro Ala Asp Ala Val Tyr Gly Gln Lys Glu Ile
210 215 220

His Arg Lys Val Met Ser Gln Asn Phe Thr Asn Cys His Thr Lys Ile
225 230 235 240

Arg His Val Asp Ala His Ala Thr Leu Asn Asp Gly Val Val Val Gln
245 250 255

Val Met Gly Leu Leu Ser Asn Asn Asn Gln Ala Leu Arg Arg Phe Met
260 265 270

Gln Thr Phe Val Leu Ala Pro Glu Gly Ser Val Ala Asn Lys Phe Tyr
275 280 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Gln Leu Phe Ile Gly Asn Leu Pro His
            500                 505                 510

Glu Val Asp Lys Ser Glu Leu Lys Asp Phe Phe Gln Ser Tyr Gly Asn
        515                 520                 525

Val Val Glu Leu Arg Ile Asn Ser Gly Gly Lys Leu Pro Asn Phe Gly
    530                 535                 540

Phe Val Val Phe Asp Asp Ser Glu Pro Val Gln Lys Val Leu Ser Asn
545                 550                 555                 560

Arg Pro Ile Met Phe Arg Gly Glu Val Arg Leu Asn Val Glu
                565                 570

<210> SEQ ID NO 43
<211> LENGTH: 503
<212> TYPE: PRT
<213> ORGANISM: Artificial Sequence
<220> FEATURE:
<223> OTHER INFORMATION: Synthetic construct

<400> SEQUENCE: 43

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

-continued

```
Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480
```

Pro Ile Arg Glu Ala Gly Glu Gln Gly Asp Ile Glu Pro Arg Arg Met
485 490 495

Val Arg His Pro Asp Ser His
500

<210> SEQ ID NO 44
<211> LENGTH: 665
<212> TYPE: PRT
<213> ORGANISM: Artificial Sequence
<220> FEATURE:
<223> OTHER INFORMATION: Synthetic construct

<400> SEQUENCE: 44

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Met Val Met Glu Lys Pro Ser Pro Leu Leu Val Gly Arg
165 170 175

Glu Phe Val Arg Gln Tyr Tyr Thr Leu Leu Asn Gln Ala Pro Asp Met
180 185 190

Leu His Arg Phe Tyr Gly Lys Asn Ser Ser Tyr Val His Gly Gly Leu
195 200 205

Asp Ser Asn Gly Lys Pro Ala Asp Ala Val Tyr Gly Gln Lys Glu Ile
210 215 220

His Arg Lys Val Met Ser Gln Asn Phe Thr Asn Cys His Thr Lys Ile
225 230 235 240

Arg His Val Asp Ala His Ala Thr Leu Asn Asp Gly Val Val Val Gln
245 250 255

Val Met Gly Leu Leu Ser Asn Asn Asn Gln Ala Leu Arg Arg Phe Met
260 265 270

Gln Thr Phe Val Leu Ala Pro Glu Gly Ser Val Ala Asn Lys Phe Tyr
275 280 285

Val His Asn Asp Ile Phe Arg Tyr Gln Asp Glu Val Phe Gly Gly Phe
290 295 300

Val Thr Glu Pro Gln Glu Glu Ser Glu Glu Glu Val Glu Glu Pro Glu
305 310 315 320

Glu Arg Gln Gln Thr Pro Glu Val Val Pro Asp Asp Ser Gly Thr Phe
325 330 335

-continued

```
Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Gln Leu Phe Ile Gly Asn Leu Pro His
            500                 505                 510

Glu Val Asp Lys Ser Glu Leu Lys Asp Phe Phe Gln Ser Tyr Gly Asn
        515                 520                 525

Val Val Glu Leu Arg Ile Asn Ser Gly Gly Lys Leu Pro Asn Phe Gly
    530                 535                 540

Phe Val Val Phe Asp Asp Ser Glu Pro Val Gln Lys Val Leu Ser Asn
545                 550                 555                 560

Arg Pro Ile Met Phe Arg Gly Glu Val Arg Leu Asn Val Glu Glu Lys
                565                 570                 575

Lys Thr Arg Ala Ala Arg Glu Gly Asp Arg Arg Asp Asn Arg Leu Arg
            580                 585                 590

Gly Pro Gly Gly Pro Arg Gly Gly Leu Gly Gly Gly Met Arg Gly Pro
        595                 600                 605

Pro Arg Gly Gly Met Val Gln Lys Pro Gly Phe Gly Val Gly Arg Gly
    610                 615                 620

Leu Ala Pro Arg Gln Lys Leu Ile Pro Met Ala Arg Arg Ala Trp Leu
625                 630                 635                 640

Glu His Gly His Ser Cys Phe Leu Cys Glu Ile Val Ile Arg Ser Gln
                645                 650                 655

Phe His Thr Thr Tyr Glu Pro Glu Ala
            660                 665


<210> SEQ ID NO 45
<211> LENGTH: 527
<212> TYPE: PRT
<213> ORGANISM: Artificial Sequence
<220> FEATURE:
<223> OTHER INFORMATION: Synthetic construct

<400> SEQUENCE: 45

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30
```

-continued

```
Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Gly Phe Val Thr Glu Pro Gln Glu Glu Ser Glu Glu
                165                 170                 175

Glu Val Glu Glu Pro Glu Glu Arg Gln Gln Thr Pro Glu Val Val Pro
            180                 185                 190

Asp Asp Ser Gly Thr Phe Tyr Asp Gln Ala Val Val Ser Asn Asp Met
        195                 200                 205

Glu Glu His Leu Glu Glu Pro Val Ala Glu Pro Glu Pro Asp Pro Glu
    210                 215                 220

Pro Glu Pro Glu Gln Glu Pro Val Ser Glu Ile Gln Glu Glu Lys Pro
225                 230                 235                 240

Glu Pro Val Leu Glu Glu Thr Ala Pro Glu Asp Ala Gln Lys Ser Ser
                245                 250                 255

Ser Pro Ala Pro Ala Asp Ile Ala Gln Thr Val Gln Glu Asp Leu Arg
            260                 265                 270

Thr Phe Ser Trp Ala Ser Val Thr Ser Lys Asn Leu Pro Pro Ser Gly
        275                 280                 285

Ala Val Pro Val Thr Gly Ile Pro Pro His Val Val Lys Val Pro Ala
    290                 295                 300

Ser Gln Pro Arg Pro Glu Ser Lys Pro Glu Ser Gln Ile Pro Pro Gln
305                 310                 315                 320

Arg Pro Gln Arg Asp Gln Arg Val Arg Glu Gln Arg Ile Asn Ile Pro
                325                 330                 335

Pro Gln Arg Gly Pro Arg Pro Ile Arg Glu Ala Gly Glu Gln Gly Asp
            340                 345                 350

Ile Glu Pro Arg Arg Met Val Arg His Pro Asp Ser His Gln Leu Phe
        355                 360                 365

Ile Gly Asn Leu Pro His Glu Val Asp Lys Ser Glu Leu Lys Asp Phe
    370                 375                 380

Phe Gln Ser Tyr Gly Asn Val Val Glu Leu Arg Ile Asn Ser Gly Gly
385                 390                 395                 400

Lys Leu Pro Asn Phe Gly Phe Val Val Phe Asp Asp Ser Glu Pro Val
                405                 410                 415

Gln Lys Val Leu Ser Asn Arg Pro Ile Met Phe Arg Gly Glu Val Arg
            420                 425                 430

Leu Asn Val Glu Glu Lys Lys Thr Arg Ala Ala Arg Glu Gly Asp Arg
        435                 440                 445
```

```
Arg Asp Asn Arg Leu Arg Gly Pro Gly Gly Pro Arg Gly Gly Leu Gly
    450                 455                 460

Gly Gly Met Arg Gly Pro Pro Arg Gly Gly Met Val Gln Lys Pro Gly
465                 470                 475                 480

Phe Gly Val Gly Arg Gly Leu Ala Pro Arg Gln Lys Leu Ile Pro Met
                485                 490                 495

Ala Arg Arg Ala Trp Leu Glu His Gly His Ser Cys Phe Leu Cys Glu
            500                 505                 510

Ile Val Ile Arg Ser Gln Phe His Thr Thr Tyr Glu Pro Glu Ala
        515                 520                 525


<210> SEQ ID NO 46
<211> LENGTH: 583
<212> TYPE: PRT
<213> ORGANISM: Artificial Sequence
<220> FEATURE:
<223> OTHER INFORMATION: Synthetic construct

<400> SEQUENCE: 46

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285
```

Val His Asn Asp Ile Phe Arg Tyr Gln Asp Glu Val Phe Gly Thr Ala
    290                 295                 300

Pro Glu Asp Ala Gln Lys Ser Ser Ser Pro Ala Pro Ala Asp Ile Ala
305                 310                 315                 320

Gln Thr Val Gln Glu Asp Leu Arg Thr Phe Ser Trp Ala Ser Val Thr
                325                 330                 335

Ser Lys Asn Leu Pro Pro Ser Gly Ala Val Pro Val Thr Gly Ile Pro
            340                 345                 350

Pro His Val Val Lys Val Pro Ala Ser Gln Pro Arg Pro Glu Ser Lys
        355                 360                 365

Pro Glu Ser Gln Ile Pro Pro Gln Arg Pro Gln Arg Asp Gln Arg Val
    370                 375                 380

Arg Glu Gln Arg Ile Asn Ile Pro Pro Gln Arg Gly Pro Arg Pro Ile
385                 390                 395                 400

Arg Glu Ala Gly Glu Gln Gly Asp Ile Glu Pro Arg Arg Met Val Arg
                405                 410                 415

His Pro Asp Ser His Gln Leu Phe Ile Gly Asn Leu Pro His Glu Val
            420                 425                 430

Asp Lys Ser Glu Leu Lys Asp Phe Phe Gln Ser Tyr Gly Asn Val Val
        435                 440                 445

Glu Leu Arg Ile Asn Ser Gly Gly Lys Leu Pro Asn Phe Gly Phe Val
    450                 455                 460

Val Phe Asp Asp Ser Glu Pro Val Gln Lys Val Leu Ser Asn Arg Pro
465                 470                 475                 480

Ile Met Phe Arg Gly Glu Val Arg Leu Asn Val Glu Glu Lys Lys Thr
                485                 490                 495

Arg Ala Ala Arg Glu Gly Asp Arg Arg Asp Asn Arg Leu Arg Gly Pro
            500                 505                 510

Gly Gly Pro Arg Gly Gly Leu Gly Gly Gly Met Arg Gly Pro Pro Arg
        515                 520                 525

Gly Gly Met Val Gln Lys Pro Gly Phe Gly Val Gly Arg Gly Leu Ala
    530                 535                 540

Pro Arg Gln Lys Leu Ile Pro Met Ala Arg Arg Ala Trp Leu Glu His
545                 550                 555                 560

Gly His Ser Cys Phe Leu Cys Glu Ile Val Ile Arg Ser Gln Phe His
                565                 570                 575

Thr Thr Tyr Glu Pro Glu Ala
            580

<210> SEQ ID NO 47
<211> LENGTH: 546
<212> TYPE: PRT
<213> ORGANISM: Artificial Sequence
<220> FEATURE:
<223> OTHER INFORMATION: Synthetic construct

<400> SEQUENCE: 47

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

-continued

```
Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Gln Leu Phe Ile Gly Asn Leu Pro His Glu Val Asp Lys Ser Glu Leu
385                 390                 395                 400

Lys Asp Phe Phe Gln Ser Tyr Gly Asn Val Val Glu Leu Arg Ile Asn
                405                 410                 415

Ser Gly Gly Lys Leu Pro Asn Phe Gly Phe Val Val Phe Asp Asp Ser
            420                 425                 430

Glu Pro Val Gln Lys Val Leu Ser Asn Arg Pro Ile Met Phe Arg Gly
        435                 440                 445

Glu Val Arg Leu Asn Val Glu Glu Lys Lys Thr Arg Ala Ala Arg Glu
    450                 455                 460

Gly Asp Arg Arg Asp Asn Arg Leu Arg Gly Pro Gly Gly Pro Arg Gly
465                 470                 475                 480
```

```
Gly Leu Gly Gly Gly Met Arg Gly Pro Pro Arg Gly Gly Met Val Gln
                485                 490                 495

Lys Pro Gly Phe Gly Val Gly Arg Gly Leu Ala Pro Arg Gln Lys Leu
            500                 505                 510

Ile Pro Met Ala Arg Arg Ala Trp Leu Glu His Gly His Ser Cys Phe
        515                 520                 525

Leu Cys Glu Ile Val Ile Arg Ser Gln Phe His Thr Thr Tyr Glu Pro
    530                 535                 540

Glu Ala
545


<210> SEQ ID NO 48
<211> LENGTH: 594
<212> TYPE: PRT
<213> ORGANISM: Artificial Sequence
<220> FEATURE:
<223> OTHER INFORMATION: Synthetic construct

<400> SEQUENCE: 48

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285
```

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His Glu Lys Lys Thr Arg Ala Ala Arg Glu
            500                 505                 510

Gly Asp Arg Arg Asp Asn Arg Leu Arg Gly Pro Gly Gly Pro Arg Gly
        515                 520                 525

Gly Leu Gly Gly Gly Met Arg Gly Pro Pro Arg Gly Gly Met Val Gln
    530                 535                 540

Lys Pro Gly Phe Gly Val Gly Arg Gly Leu Ala Pro Arg Gln Lys Leu
545                 550                 555                 560

Ile Pro Met Ala Arg Arg Ala Trp Leu Glu His Gly His Ser Cys Phe
                565                 570                 575

Leu Cys Glu Ile Val Ile Arg Ser Gln Phe His Thr Thr Tyr Glu Pro
            580                 585                 590

Glu Ala

<210> SEQ ID NO 49
<211> LENGTH: 574
<212> TYPE: PRT
<213> ORGANISM: Artificial Sequence
<220> FEATURE:
<223> OTHER INFORMATION: Synthetic construct

<400> SEQUENCE: 49

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

-continued

```
Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Met Val Met Glu Lys Pro Ser Pro Leu Leu Val Gly Arg
                165                 170                 175

Glu Phe Val Arg Gln Tyr Tyr Thr Leu Leu Asn Gln Ala Pro Asp Met
            180                 185                 190

Leu His Arg Phe Tyr Gly Lys Asn Ser Ser Tyr Val His Gly Gly Leu
        195                 200                 205

Asp Ser Asn Gly Lys Pro Ala Asp Ala Val Tyr Gly Gln Lys Glu Ile
    210                 215                 220

His Arg Lys Val Met Ser Gln Asn Phe Thr Asn Cys His Thr Lys Ile
225                 230                 235                 240

Arg His Val Asp Ala His Ala Thr Leu Asn Asp Gly Val Val Val Gln
                245                 250                 255

Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460
```

Arg Val Arg Glu Gln Arg Ile Asn Ile Pro Pro Gln Arg Gly Pro Arg
465 470 475 480

Pro Ile Arg Glu Ala Gly Glu Gln Gly Asp Ile Glu Pro Arg Arg Met
485 490 495

Val Arg His Pro Asp Ser His Gln Leu Phe Ile Gly Asn Leu Pro His
500 505 510

Glu Val Asp Lys Ser Glu Leu Lys Asp Phe Phe Gln Ser Tyr Gly Asn
515 520 525

Val Val Glu Leu Arg Ile Asn Ser Gly Gly Lys Leu Pro Asn Phe Gly
530 535 540

Phe Val Val Phe Asp Asp Ser Glu Pro Val Gln Lys Val Leu Ser Asn
545 550 555 560

Arg Pro Ile Met Phe Arg Gly Glu Val Arg Leu Asn Val Glu
565 570

<210> SEQ ID NO 50
<211> LENGTH: 503
<212> TYPE: PRT
<213> ORGANISM: Artificial Sequence
<220> FEATURE:
<223> OTHER INFORMATION: Synthetic construct

<400> SEQUENCE: 50

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Met Val Met Glu Lys Pro Ser Pro Leu Leu Val Gly Arg
165 170 175

Glu Phe Val Arg Gln Tyr Tyr Thr Leu Leu Asn Gln Ala Pro Asp Met
180 185 190

Leu His Arg Phe Tyr Gly Lys Asn Ser Ser Tyr Val His Gly Gly Leu
195 200 205

Asp Ser Asn Gly Lys Pro Ala Asp Ala Val Tyr Gly Gln Lys Glu Ile
210 215 220

His Arg Lys Val Met Ser Gln Asn Phe Thr Asn Cys His Thr Lys Ile
225 230 235 240

Arg His Val Asp Ala His Ala Thr Leu Asn Asp Gly Val Val Val Gln
245 250 255

-continued

```
Val Met Gly Leu Leu Ser Asn Asn Asn Gln Ala Leu Arg Arg Phe Met
            260                 265                 270

Gln Thr Phe Val Leu Ala Pro Glu Gly Ser Val Ala Asn Lys Phe Tyr
        275                 280                 285

Val His Asn Asp Ile Phe Arg Tyr Gln Asp Glu Val Phe Gly Gly Phe
    290                 295                 300

Val Thr Glu Pro Gln Glu Glu Ser Glu Glu Glu Val Glu Glu Pro Glu
305                 310                 315                 320

Glu Arg Gln Gln Thr Pro Glu Val Val Pro Asp Asp Ser Gly Thr Phe
                325                 330                 335

Tyr Asp Gln Ala Val Val Ser Asn Asp Met Glu Glu His Leu Glu Glu
            340                 345                 350

Pro Val Ala Glu Pro Glu Pro Asp Pro Glu Pro Glu Pro Glu Gln Glu
        355                 360                 365

Pro Val Ser Glu Ile Gln Glu Glu Lys Pro Glu Pro Val Leu Glu Glu
    370                 375                 380

Thr Ala Pro Glu Asp Ala Gln Lys Ser Ser Ser Pro Ala Pro Ala Asp
385                 390                 395                 400

Ile Ala Gln Thr Val Gln Glu Asp Leu Arg Thr Phe Ser Trp Ala Ser
                405                 410                 415

Val Thr Ser Lys Asn Leu Pro Pro Ser Gly Ala Val Pro Val Thr Gly
            420                 425                 430

Ile Pro Pro His Val Val Lys Val Pro Ala Ser Gln Pro Arg Pro Glu
        435                 440                 445

Ser Lys Pro Glu Ser Gln Ile Pro Pro Gln Arg Pro Gln Arg Asp Gln
    450                 455                 460

Arg Val Arg Glu Gln Arg Ile Asn Ile Pro Pro Gln Arg Gly Pro Arg
465                 470                 475                 480

Pro Ile Arg Glu Ala Gly Glu Gln Gly Asp Ile Glu Pro Arg Arg Met
                485                 490                 495

Val Arg His Pro Asp Ser His
            500


<210> SEQ ID NO 51
<211> LENGTH: 674
<212> TYPE: PRT
<213> ORGANISM: Artificial Sequence
<220> FEATURE:
<223> OTHER INFORMATION: Synthetic construct

<400> SEQUENCE: 51

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110
```

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Val Met Glu
165 170 175

Lys Pro Ser Pro Leu Leu Val Gly Arg Glu Phe Val Arg Gln Tyr Tyr
180 185 190

Thr Leu Leu Asn Gln Ala Pro Asp Met Leu His Arg Phe Tyr Gly Lys
195 200 205

Asn Ser Ser Tyr Val His Gly Gly Leu Asp Ser Asn Gly Lys Pro Ala
210 215 220

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Gly Phe Val Thr Glu Pro Gln Glu Glu
305 310 315 320

Ser Glu Glu Glu Val Glu Glu Pro Glu Glu Arg Gln Gln Thr Pro Glu
325 330 335

Val Val Pro Asp Asp Ser Gly Thr Phe Tyr Asp Gln Ala Val Val Ser
340 345 350

Asn Asp Met Glu Glu His Leu Glu Glu Pro Val Ala Glu Pro Glu Pro
355 360 365

Asp Pro Glu Pro Glu Pro Glu Gln Glu Pro Val Ser Glu Ile Gln Glu
370 375 380

Glu Lys Pro Glu Pro Val Leu Glu Glu Thr Ala Pro Glu Asp Ala Gln
385 390 395 400

Lys Ser Ser Ser Pro Ala Pro Ala Asp Ile Ala Gln Thr Val Gln Glu
405 410 415

Asp Leu Arg Thr Phe Ser Trp Ala Ser Val Thr Ser Lys Asn Leu Pro
420 425 430

Pro Ser Gly Ala Val Pro Val Thr Gly Ile Pro Pro His Val Val Lys
435 440 445

Val Pro Ala Ser Gln Pro Arg Pro Glu Ser Lys Pro Glu Ser Gln Ile
450 455 460

Pro Pro Gln Arg Pro Gln Arg Asp Gln Arg Val Arg Glu Gln Arg Ile
465 470 475 480

Asn Ile Pro Pro Gln Arg Gly Pro Arg Pro Ile Arg Glu Ala Gly Glu
485 490 495

Gln Gly Asp Ile Glu Pro Arg Arg Met Val Arg His Pro Asp Ser His
500 505 510

Gln Leu Phe Ile Gly Asn Leu Pro His Glu Val Asp Lys Ser Glu Leu
515 520 525

-continued

Lys Asp Phe Phe Gln Ser Tyr Gly Asn Val Val Glu Leu Arg Ile Asn
    530                 535                 540

Ser Gly Gly Lys Leu Pro Asn Phe Gly Phe Val Val Phe Asp Asp Ser
545                 550                 555                 560

Glu Pro Val Gln Lys Val Leu Ser Asn Arg Pro Ile Met Phe Arg Gly
                565                 570                 575

Glu Val Arg Leu Asn Val Glu Glu Lys Lys Thr Arg Ala Ala Arg Glu
            580                 585                 590

Gly Asp Arg Arg Asp Asn Arg Leu Arg Gly Pro Gly Gly Pro Arg Gly
        595                 600                 605

Gly Leu Gly Gly Gly Met Arg Gly Pro Pro Arg Gly Gly Met Val Gln
    610                 615                 620

Lys Pro Gly Phe Gly Val Gly Arg Gly Leu Ala Pro Arg Gln Lys Leu
625                 630                 635                 640

Ile Pro Met Ala Arg Arg Ala Trp Leu Glu His Gly His Ser Cys Phe
                645                 650                 655

Leu Cys Glu Ile Val Ile Arg Ser Gln Phe His Thr Thr Tyr Glu Pro
            660                 665                 670

Glu Ala

<210> SEQ ID NO 52
<211> LENGTH: 536
<212> TYPE: PRT
<213> ORGANISM: Artificial Sequence
<220> FEATURE:
<223> OTHER INFORMATION: Synthetic construct

<400> SEQUENCE: 52

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Gly Phe Val
                165                 170                 175

Thr Glu Pro Gln Glu Glu Ser Glu Glu Glu Val Glu Glu Pro Glu Glu
            180                 185                 190

Arg Gln Gln Thr Pro Glu Val Val Pro Asp Asp Ser Gly Thr Phe Tyr
        195                 200                 205

-continued

```
Asp Gln Ala Val Val Ser Asn Asp Met Glu Glu His Leu Glu Glu Pro
    210                 215                 220

Val Ala Glu Pro Glu Pro Asp Pro Glu Pro Glu Pro Glu Gln Glu Pro
225                 230                 235                 240

Val Ser Glu Ile Gln Glu Glu Lys Pro Glu Pro Val Leu Glu Glu Thr
                245                 250                 255

Ala Pro Glu Asp Ala Gln Lys Ser Ser Ser Pro Ala Pro Ala Asp Ile
            260                 265                 270

Ala Gln Thr Val Gln Glu Asp Leu Arg Thr Phe Ser Trp Ala Ser Val
        275                 280                 285

Thr Ser Lys Asn Leu Pro Pro Ser Gly Ala Val Pro Val Thr Gly Ile
    290                 295                 300

Pro Pro His Val Val Lys Val Pro Ala Ser Gln Pro Arg Pro Glu Ser
305                 310                 315                 320

Lys Pro Glu Ser Gln Ile Pro Pro Gln Arg Pro Gln Arg Asp Gln Arg
                325                 330                 335

Val Arg Glu Gln Arg Ile Asn Ile Pro Pro Gln Arg Gly Pro Arg Pro
            340                 345                 350

Ile Arg Glu Ala Gly Glu Gln Gly Asp Ile Glu Pro Arg Arg Met Val
        355                 360                 365

Arg His Pro Asp Ser His Gln Leu Phe Ile Gly Asn Leu Pro His Glu
    370                 375                 380

Val Asp Lys Ser Glu Leu Lys Asp Phe Phe Gln Ser Tyr Gly Asn Val
385                 390                 395                 400

Val Glu Leu Arg Ile Asn Ser Gly Gly Lys Leu Pro Asn Phe Gly Phe
                405                 410                 415

Val Val Phe Asp Asp Ser Glu Pro Val Gln Lys Val Leu Ser Asn Arg
            420                 425                 430

Pro Ile Met Phe Arg Gly Glu Val Arg Leu Asn Val Glu Glu Lys Lys
        435                 440                 445

Thr Arg Ala Ala Arg Glu Gly Asp Arg Arg Asp Asn Arg Leu Arg Gly
    450                 455                 460

Pro Gly Gly Pro Arg Gly Gly Leu Gly Gly Gly Met Arg Gly Pro Pro
465                 470                 475                 480

Arg Gly Gly Met Val Gln Lys Pro Gly Phe Gly Val Gly Arg Gly Leu
                485                 490                 495

Ala Pro Arg Gln Lys Leu Ile Pro Met Ala Arg Arg Ala Trp Leu Glu
            500                 505                 510

His Gly His Ser Cys Phe Leu Cys Glu Ile Val Ile Arg Ser Gln Phe
        515                 520                 525

His Thr Thr Tyr Glu Pro Glu Ala
    530                 535
```

<210> SEQ ID NO 53
<211> LENGTH: 592
<212> TYPE: PRT
<213> ORGANISM: Artificial Sequence
<220> FEATURE:
<223> OTHER INFORMATION: Synthetic construct

<400> SEQUENCE: 53

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30
```

-continued

```
Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Thr Ala Pro Glu Asp Ala Gln Lys Ser
305                 310                 315                 320

Ser Ser Pro Ala Pro Ala Asp Ile Ala Gln Thr Val Gln Glu Asp Leu
                325                 330                 335

Arg Thr Phe Ser Trp Ala Ser Val Thr Ser Lys Asn Leu Pro Pro Ser
            340                 345                 350

Gly Ala Val Pro Val Thr Gly Ile Pro Pro His Val Val Lys Val Pro
        355                 360                 365

Ala Ser Gln Pro Arg Pro Glu Ser Lys Pro Glu Ser Gln Ile Pro Pro
    370                 375                 380

Gln Arg Pro Gln Arg Asp Gln Arg Val Arg Glu Gln Arg Ile Asn Ile
385                 390                 395                 400

Pro Pro Gln Arg Gly Pro Arg Pro Ile Arg Glu Ala Gly Glu Gln Gly
                405                 410                 415

Asp Ile Glu Pro Arg Arg Met Val Arg His Pro Asp Ser His Gln Leu
            420                 425                 430

Phe Ile Gly Asn Leu Pro His Glu Val Asp Lys Ser Glu Leu Lys Asp
        435                 440                 445
```

-continued

```
Phe Phe Gln Ser Tyr Gly Asn Val Val Glu Leu Arg Ile Asn Ser Gly
    450                 455                 460

Gly Lys Leu Pro Asn Phe Gly Phe Val Val Phe Asp Asp Ser Glu Pro
465                 470                 475                 480

Val Gln Lys Val Leu Ser Asn Arg Pro Ile Met Phe Arg Gly Glu Val
                485                 490                 495

Arg Leu Asn Val Glu Glu Lys Lys Thr Arg Ala Ala Arg Glu Gly Asp
            500                 505                 510

Arg Arg Asp Asn Arg Leu Arg Gly Pro Gly Gly Pro Arg Gly Gly Leu
        515                 520                 525

Gly Gly Gly Met Arg Gly Pro Pro Arg Gly Gly Met Val Gln Lys Pro
    530                 535                 540

Gly Phe Gly Val Gly Arg Gly Leu Ala Pro Arg Gln Lys Leu Ile Pro
545                 550                 555                 560

Met Ala Arg Arg Ala Trp Leu Glu His Gly His Ser Cys Phe Leu Cys
                565                 570                 575

Glu Ile Val Ile Arg Ser Gln Phe His Thr Thr Tyr Glu Pro Glu Ala
            580                 585                 590


<210> SEQ ID NO 54
<211> LENGTH: 555
<212> TYPE: PRT
<213> ORGANISM: Artificial Sequence
<220> FEATURE:
<223> OTHER INFORMATION: Synthetic construct

<400> SEQUENCE: 54

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220
```

-continued

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Gly Phe Val Thr Glu Pro Gln Glu Glu
305 310 315 320

Ser Glu Glu Glu Val Glu Glu Pro Glu Glu Arg Gln Gln Thr Pro Glu
325 330 335

Val Val Pro Asp Asp Ser Gly Thr Phe Tyr Asp Gln Ala Val Val Ser
340 345 350

Asn Asp Met Glu Glu His Leu Glu Glu Pro Val Ala Glu Pro Glu Pro
355 360 365

Asp Pro Glu Pro Glu Pro Glu Gln Glu Pro Val Ser Glu Ile Gln Glu
370 375 380

Glu Lys Pro Glu Pro Val Leu Glu Glu Gln Leu Phe Ile Gly Asn Leu
385 390 395 400

Pro His Glu Val Asp Lys Ser Glu Leu Lys Asp Phe Phe Gln Ser Tyr
405 410 415

Gly Asn Val Val Glu Leu Arg Ile Asn Ser Gly Gly Lys Leu Pro Asn
420 425 430

Phe Gly Phe Val Val Phe Asp Asp Ser Glu Pro Val Gln Lys Val Leu
435 440 445

Ser Asn Arg Pro Ile Met Phe Arg Gly Glu Val Arg Leu Asn Val Glu
450 455 460

Glu Lys Lys Thr Arg Ala Ala Arg Glu Gly Asp Arg Arg Asp Asn Arg
465 470 475 480

Leu Arg Gly Pro Gly Gly Pro Arg Gly Gly Leu Gly Gly Gly Met Arg
485 490 495

Gly Pro Pro Arg Gly Gly Met Val Gln Lys Pro Gly Phe Gly Val Gly
500 505 510

Arg Gly Leu Ala Pro Arg Gln Lys Leu Ile Pro Met Ala Arg Arg Ala
515 520 525

Trp Leu Glu His Gly His Ser Cys Phe Leu Cys Glu Ile Val Ile Arg
530 535 540

Ser Gln Phe His Thr Thr Tyr Glu Pro Glu Ala
545 550 555

<210> SEQ ID NO 55
<211> LENGTH: 603
<212> TYPE: PRT
<213> ORGANISM: Artificial Sequence
<220> FEATURE:
<223> OTHER INFORMATION: Synthetic construct

<400> SEQUENCE: 55

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

-continued

```
Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445
```

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Glu Lys Lys Thr Arg Ala Ala Arg Glu Gly Asp Arg Arg Asp Asn Arg
        515                 520                 525

Leu Arg Gly Pro Gly Gly Pro Arg Gly Gly Leu Gly Gly Gly Met Arg
    530                 535                 540

Gly Pro Pro Arg Gly Gly Met Val Gln Lys Pro Gly Phe Gly Val Gly
545                 550                 555                 560

Arg Gly Leu Ala Pro Arg Gln Lys Leu Ile Pro Met Ala Arg Arg Ala
                565                 570                 575

Trp Leu Glu His Gly His Ser Cys Phe Leu Cys Glu Ile Val Ile Arg
            580                 585                 590

Ser Gln Phe His Thr Thr Tyr Glu Pro Glu Ala
        595                 600

<210> SEQ ID NO 56
<211> LENGTH: 583
<212> TYPE: PRT
<213> ORGANISM: Artificial Sequence
<220> FEATURE:
<223> OTHER INFORMATION: Synthetic construct

<400> SEQUENCE: 56

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

-continued

```
Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Gln Leu Phe Ile Gly Asn Leu Pro His Glu Val Asp Lys Ser Glu Leu
        515                 520                 525

Lys Asp Phe Phe Gln Ser Tyr Gly Asn Val Val Glu Leu Arg Ile Asn
    530                 535                 540

Ser Gly Gly Lys Leu Pro Asn Phe Gly Phe Val Val Phe Asp Asp Ser
545                 550                 555                 560

Glu Pro Val Gln Lys Val Leu Ser Asn Arg Pro Ile Met Phe Arg Gly
                565                 570                 575

Glu Val Arg Leu Asn Val Glu
            580
```

<210> SEQ ID NO 57
<211> LENGTH: 512
<212> TYPE: PRT
<213> ORGANISM: Artificial Sequence
<220> FEATURE:

<223> OTHER INFORMATION: Synthetic construct

<400> SEQUENCE: 57

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400
```

-continued

Lys Ser Ser Ser Pro Ala Pro Ala Asp Ile Ala Gln Thr Val Gln Glu
405 410 415

Asp Leu Arg Thr Phe Ser Trp Ala Ser Val Thr Ser Lys Asn Leu Pro
420 425 430

Pro Ser Gly Ala Val Pro Val Thr Gly Ile Pro Pro His Val Val Lys
435 440 445

Val Pro Ala Ser Gln Pro Arg Pro Glu Ser Lys Pro Glu Ser Gln Ile
450 455 460

Pro Pro Gln Arg Pro Gln Arg Asp Gln Arg Val Arg Glu Gln Arg Ile
465 470 475 480

Asn Ile Pro Pro Gln Arg Gly Pro Arg Pro Ile Arg Glu Ala Gly Glu
485 490 495

Gln Gly Asp Ile Glu Pro Arg Arg Met Val Arg His Pro Asp Ser His
500 505 510

<210> SEQ ID NO 58
<211> LENGTH: 674
<212> TYPE: PRT
<213> ORGANISM: Artificial Sequence
<220> FEATURE:
<223> OTHER INFORMATION: Synthetic construct

<400> SEQUENCE: 58

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Val Met Glu
165 170 175

Lys Pro Ser Pro Leu Leu Val Gly Arg Glu Phe Val Arg Gln Tyr Tyr
180 185 190

Thr Leu Leu Asn Gln Ala Pro Asp Met Leu His Arg Phe Tyr Gly Lys
195 200 205

Asn Ser Ser Tyr Val His Gly Gly Leu Asp Ser Asn Gly Lys Pro Ala
210 215 220

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

-continued

```
Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Gln Leu Phe Ile Gly Asn Leu Pro His Glu Val Asp Lys Ser Glu Leu
        515                 520                 525

Lys Asp Phe Phe Gln Ser Tyr Gly Asn Val Val Glu Leu Arg Ile Asn
    530                 535                 540

Ser Gly Gly Lys Leu Pro Asn Phe Gly Phe Val Val Phe Asp Asp Ser
545                 550                 555                 560

Glu Pro Val Gln Lys Val Leu Ser Asn Arg Pro Ile Met Phe Arg Gly
                565                 570                 575

Glu Val Arg Leu Asn Val Glu Glu Lys Lys Thr Arg Ala Ala Arg Glu
            580                 585                 590

Gly Asp Arg Arg Asp Asn Arg Leu Arg Gly Pro Gly Gly Pro Arg Gly
        595                 600                 605

Gly Leu Gly Gly Gly Met Arg Gly Pro Pro Arg Gly Gly Met Val Gln
    610                 615                 620

Lys Pro Gly Phe Gly Val Gly Arg Gly Leu Ala Pro Arg Gln Lys Leu
625                 630                 635                 640

Ile Pro Met Ala Arg Arg Ala Trp Leu Glu His Gly His Ser Cys Phe
                645                 650                 655

Leu Cys Glu Ile Val Ile Arg Ser Gln Phe His Thr Thr Tyr Glu Pro
            660                 665                 670

Glu Ala
```

<210> SEQ ID NO 59
<211> LENGTH: 536
<212> TYPE: PRT
<213> ORGANISM: Artificial Sequence
<220> FEATURE:
<223> OTHER INFORMATION: Synthetic construct

<400> SEQUENCE: 59

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Gly Phe Val
165 170 175

Thr Glu Pro Gln Glu Glu Ser Glu Glu Glu Val Glu Glu Pro Glu Glu
180 185 190

Arg Gln Gln Thr Pro Glu Val Val Pro Asp Asp Ser Gly Thr Phe Tyr
195 200 205

Asp Gln Ala Val Val Ser Asn Asp Met Glu Glu His Leu Glu Glu Pro
210 215 220

Val Ala Glu Pro Glu Pro Asp Pro Glu Pro Glu Pro Glu Gln Glu Pro
225 230 235 240

Val Ser Glu Ile Gln Glu Glu Lys Pro Glu Pro Val Leu Glu Glu Thr
245 250 255

Ala Pro Glu Asp Ala Gln Lys Ser Ser Ser Pro Ala Pro Ala Asp Ile
260 265 270

Ala Gln Thr Val Gln Glu Asp Leu Arg Thr Phe Ser Trp Ala Ser Val
275 280 285

Thr Ser Lys Asn Leu Pro Pro Ser Gly Ala Val Pro Val Thr Gly Ile
290 295 300

Pro Pro His Val Val Lys Val Pro Ala Ser Gln Pro Arg Pro Glu Ser
305 310 315 320

Lys Pro Glu Ser Gln Ile Pro Pro Gln Arg Pro Gln Arg Asp Gln Arg
325 330 335

Val Arg Glu Gln Arg Ile Asn Ile Pro Pro Gln Arg Gly Pro Arg Pro
340 345 350

Ile Arg Glu Ala Gly Glu Gln Gly Asp Ile Glu Pro Arg Arg Met Val
355 360 365

Arg His Pro Asp Ser His Gln Leu Phe Ile Gly Asn Leu Pro His Glu
370 375 380

Val Asp Lys Ser Glu Leu Lys Asp Phe Phe Gln Ser Tyr Gly Asn Val
385 390 395 400

Val Glu Leu Arg Ile Asn Ser Gly Gly Lys Leu Pro Asn Phe Gly Phe
405 410 415

Val Val Phe Asp Asp Ser Glu Pro Val Gln Lys Val Leu Ser Asn Arg
420 425 430

Pro Ile Met Phe Arg Gly Glu Val Arg Leu Asn Val Glu Glu Lys Lys
435 440 445

Thr Arg Ala Ala Arg Glu Gly Asp Arg Arg Asp Asn Arg Leu Arg Gly
450 455 460

Pro Gly Gly Pro Arg Gly Gly Leu Gly Gly Gly Met Arg Gly Pro Pro
465 470 475 480

Arg Gly Gly Met Val Gln Lys Pro Gly Phe Gly Val Gly Arg Gly Leu
485 490 495

Ala Pro Arg Gln Lys Leu Ile Pro Met Ala Arg Arg Ala Trp Leu Glu
500 505 510

His Gly His Ser Cys Phe Leu Cys Glu Ile Val Ile Arg Ser Gln Phe
515 520 525

His Thr Thr Tyr Glu Pro Glu Ala
530 535

<210> SEQ ID NO 60
<211> LENGTH: 592
<212> TYPE: PRT
<213> ORGANISM: Artificial Sequence
<220> FEATURE:
<223> OTHER INFORMATION: Synthetic construct

<400> SEQUENCE: 60

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Cys Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Val Met Glu
165 170 175

Lys Pro Ser Pro Leu Leu Val Gly Arg Glu Phe Val Arg Gln Tyr Tyr
180 185 190

-continued

Thr Leu Leu Asn Gln Ala Pro Asp Met Leu His Arg Phe Tyr Gly Lys
195 200 205

Asn Ser Ser Tyr Val His Gly Gly Leu Asp Ser Asn Gly Lys Pro Ala
210 215 220

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Thr Ala Pro Glu Asp Ala Gln Lys Ser
305 310 315 320

Ser Ser Pro Ala Pro Ala Asp Ile Ala Gln Thr Val Gln Glu Asp Leu
325 330 335

Arg Thr Phe Ser Trp Ala Ser Val Thr Ser Lys Asn Leu Pro Pro Ser
340 345 350

Gly Ala Val Pro Val Thr Gly Ile Pro Pro His Val Val Lys Val Pro
355 360 365

Ala Ser Gln Pro Arg Pro Glu Ser Lys Pro Glu Ser Gln Ile Pro Pro
370 375 380

Gln Arg Pro Gln Arg Asp Gln Arg Val Arg Glu Gln Arg Ile Asn Ile
385 390 395 400

Pro Pro Gln Arg Gly Pro Arg Pro Ile Arg Glu Ala Gly Glu Gln Gly
405 410 415

Asp Ile Glu Pro Arg Arg Met Val Arg His Pro Asp Ser His Gln Leu
420 425 430

Phe Ile Gly Asn Leu Pro His Glu Val Asp Lys Ser Glu Leu Lys Asp
435 440 445

Phe Phe Gln Ser Tyr Gly Asn Val Val Glu Leu Arg Ile Asn Ser Gly
450 455 460

Gly Lys Leu Pro Asn Phe Gly Phe Val Val Phe Asp Asp Ser Glu Pro
465 470 475 480

Val Gln Lys Val Leu Ser Asn Arg Pro Ile Met Phe Arg Gly Glu Val
485 490 495

Arg Leu Asn Val Glu Glu Lys Lys Thr Arg Ala Ala Arg Glu Gly Asp
500 505 510

Arg Arg Asp Asn Arg Leu Arg Gly Pro Gly Gly Pro Arg Gly Gly Leu
515 520 525

Gly Gly Gly Met Arg Gly Pro Pro Arg Gly Gly Met Val Gln Lys Pro
530 535 540

Gly Phe Gly Val Gly Arg Gly Leu Ala Pro Arg Gln Lys Leu Ile Pro
545 550 555 560

Met Ala Arg Arg Ala Trp Leu Glu His Gly His Ser Cys Phe Leu Cys
565 570 575

Glu Ile Val Ile Arg Ser Gln Phe His Thr Thr Tyr Glu Pro Glu Ala
580 585 590

<210> SEQ ID NO 61
<211> LENGTH: 555

<212> TYPE: PRT
<213> ORGANISM: Artificial Sequence
<220> FEATURE:
<223> OTHER INFORMATION: Synthetic construct

<400> SEQUENCE: 61

```
Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380
```

```
Glu Lys Pro Glu Pro Val Leu Glu Glu Gln Leu Phe Ile Gly Asn Leu
385                 390                 395                 400

Pro His Glu Val Asp Lys Ser Glu Leu Lys Asp Phe Phe Gln Ser Tyr
                405                 410                 415

Gly Asn Val Val Glu Leu Arg Ile Asn Ser Gly Gly Lys Leu Pro Asn
            420                 425                 430

Phe Gly Phe Val Val Phe Asp Asp Ser Glu Pro Val Gln Lys Val Leu
        435                 440                 445

Ser Asn Arg Pro Ile Met Phe Arg Gly Glu Val Arg Leu Asn Val Glu
    450                 455                 460

Glu Lys Lys Thr Arg Ala Ala Arg Glu Gly Asp Arg Arg Asp Asn Arg
465                 470                 475                 480

Leu Arg Gly Pro Gly Gly Pro Arg Gly Gly Leu Gly Gly Gly Met Arg
                485                 490                 495

Gly Pro Pro Arg Gly Gly Met Val Gln Lys Pro Gly Phe Gly Val Gly
            500                 505                 510

Arg Gly Leu Ala Pro Arg Gln Lys Leu Ile Pro Met Ala Arg Arg Ala
        515                 520                 525

Trp Leu Glu His Gly His Ser Cys Phe Leu Cys Glu Ile Val Ile Arg
    530                 535                 540

Ser Gln Phe His Thr Thr Tyr Glu Pro Glu Ala
545                 550                 555


<210> SEQ ID NO 62
<211> LENGTH: 603
<212> TYPE: PRT
<213> ORGANISM: Artificial Sequence
<220> FEATURE:
<223> OTHER INFORMATION: Synthetic construct

<400> SEQUENCE: 62

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190
```

-continued

```
Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Glu Lys Lys Thr Arg Ala Ala Arg Glu Gly Asp Arg Arg Asp Asn Arg
        515                 520                 525

Leu Arg Gly Pro Gly Gly Pro Arg Gly Gly Leu Gly Gly Gly Met Arg
    530                 535                 540

Gly Pro Pro Arg Gly Gly Met Val Gln Lys Pro Gly Phe Gly Val Gly
545                 550                 555                 560

Arg Gly Leu Ala Pro Arg Gln Lys Leu Ile Pro Met Ala Arg Arg Ala
                565                 570                 575

Trp Leu Glu His Gly His Ser Cys Phe Leu Cys Glu Ile Val Ile Arg
            580                 585                 590

Ser Gln Phe His Thr Thr Tyr Glu Pro Glu Ala
        595                 600
```

<210> SEQ ID NO 63
<211> LENGTH: 583
<212> TYPE: PRT
<213> ORGANISM: Artificial Sequence
<220> FEATURE:
<223> OTHER INFORMATION: Synthetic construct

<400> SEQUENCE: 63

```
Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365
```

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Gln Leu Phe Ile Gly Asn Leu Pro His Glu Val Asp Lys Ser Glu Leu
        515                 520                 525

Lys Asp Phe Phe Gln Ser Tyr Gly Asn Val Val Glu Leu Arg Ile Asn
    530                 535                 540

Ser Gly Gly Lys Leu Pro Asn Phe Gly Phe Val Val Phe Asp Asp Ser
545                 550                 555                 560

Glu Pro Val Gln Lys Val Leu Ser Asn Arg Pro Ile Met Phe Arg Gly
                565                 570                 575

Glu Val Arg Leu Asn Val Glu
            580

<210> SEQ ID NO 64
<211> LENGTH: 512
<212> TYPE: PRT
<213> ORGANISM: Artificial Sequence
<220> FEATURE:
<223> OTHER INFORMATION: Synthetic construct

<400> SEQUENCE: 64

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Cys Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

```
Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510
```

<210> SEQ ID NO 65
<211> LENGTH: 674
<212> TYPE: PRT
<213> ORGANISM: Artificial Sequence
<220> FEATURE:
<223> OTHER INFORMATION: Synthetic construct

<400> SEQUENCE: 65

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

```
Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Gln Leu Phe Ile Gly Asn Leu Pro His Glu Val Asp Lys Ser Glu Leu
        515                 520                 525

Lys Asp Phe Phe Gln Ser Tyr Gly Asn Val Val Glu Leu Arg Ile Asn
    530                 535                 540

Ser Gly Gly Lys Leu Pro Asn Phe Gly Phe Val Val Phe Asp Asp Ser
545                 550                 555                 560

Glu Pro Val Gln Lys Val Leu Ser Asn Arg Pro Ile Met Phe Arg Gly
                565                 570                 575

Glu Val Arg Leu Asn Val Glu Glu Lys Lys Thr Arg Ala Ala Arg Glu
            580                 585                 590

Gly Asp Arg Arg Asp Asn Arg Leu Arg Gly Pro Gly Gly Pro Arg Gly
        595                 600                 605

Gly Leu Gly Gly Gly Met Arg Gly Pro Pro Arg Gly Gly Met Val Gln
    610                 615                 620

Lys Pro Gly Phe Gly Val Gly Arg Gly Leu Ala Pro Arg Gln Lys Leu
625                 630                 635                 640

Ile Pro Met Ala Arg Arg Ala Trp Leu Glu His Gly His Ser Cys Phe
                645                 650                 655

Leu Cys Glu Ile Val Ile Arg Ser Gln Phe His Thr Thr Tyr Glu Pro
            660                 665                 670

Glu Ala


<210> SEQ ID NO 66
<211> LENGTH: 536
<212> TYPE: PRT
<213> ORGANISM: Artificial Sequence
<220> FEATURE:
<223> OTHER INFORMATION: Synthetic construct

<400> SEQUENCE: 66

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80
```

-continued

```
Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Gly Phe Val
                165                 170                 175

Thr Glu Pro Gln Glu Glu Ser Glu Glu Glu Val Glu Glu Pro Glu Glu
            180                 185                 190

Arg Gln Gln Thr Pro Glu Val Val Pro Asp Asp Ser Gly Thr Phe Tyr
        195                 200                 205

Asp Gln Ala Val Val Ser Asn Asp Met Glu Glu His Leu Glu Glu Pro
    210                 215                 220

Val Ala Glu Pro Glu Pro Asp Pro Glu Pro Glu Pro Glu Gln Glu Pro
225                 230                 235                 240

Val Ser Glu Ile Gln Glu Glu Lys Pro Glu Pro Val Leu Glu Glu Thr
                245                 250                 255

Ala Pro Glu Asp Ala Gln Lys Ser Ser Ser Pro Ala Pro Ala Asp Ile
            260                 265                 270

Ala Gln Thr Val Gln Glu Asp Leu Arg Thr Phe Ser Trp Ala Ser Val
        275                 280                 285

Thr Ser Lys Asn Leu Pro Pro Ser Gly Ala Val Pro Val Thr Gly Ile
    290                 295                 300

Pro Pro His Val Val Lys Val Pro Ala Ser Gln Pro Arg Pro Glu Ser
305                 310                 315                 320

Lys Pro Glu Ser Gln Ile Pro Pro Gln Arg Pro Gln Arg Asp Gln Arg
                325                 330                 335

Val Arg Glu Gln Arg Ile Asn Ile Pro Pro Gln Arg Gly Pro Arg Pro
            340                 345                 350

Ile Arg Glu Ala Gly Glu Gln Gly Asp Ile Glu Pro Arg Arg Met Val
        355                 360                 365

Arg His Pro Asp Ser His Gln Leu Phe Ile Gly Asn Leu Pro His Glu
    370                 375                 380

Val Asp Lys Ser Glu Leu Lys Asp Phe Phe Gln Ser Tyr Gly Asn Val
385                 390                 395                 400

Val Glu Leu Arg Ile Asn Ser Gly Gly Lys Leu Pro Asn Phe Gly Phe
                405                 410                 415

Val Val Phe Asp Asp Ser Glu Pro Val Gln Lys Val Leu Ser Asn Arg
            420                 425                 430

Pro Ile Met Phe Arg Gly Glu Val Arg Leu Asn Val Glu Glu Lys Lys
        435                 440                 445

Thr Arg Ala Ala Arg Glu Gly Asp Arg Arg Asp Asn Arg Leu Arg Gly
    450                 455                 460

Pro Gly Gly Pro Arg Gly Gly Leu Gly Gly Gly Met Arg Gly Pro Pro
465                 470                 475                 480

Arg Gly Gly Met Val Gln Lys Pro Gly Phe Gly Val Gly Arg Gly Leu
                485                 490                 495
```

Ala Pro Arg Gln Lys Leu Ile Pro Met Ala Arg Arg Ala Trp Leu Glu
500 505 510

His Gly His Ser Cys Phe Leu Cys Glu Ile Val Ile Arg Ser Gln Phe
515 520 525

His Thr Thr Tyr Glu Pro Glu Ala
530 535

<210> SEQ ID NO 67
<211> LENGTH: 592
<212> TYPE: PRT
<213> ORGANISM: Artificial Sequence
<220> FEATURE:
<223> OTHER INFORMATION: Synthetic construct

<400> SEQUENCE: 67

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Val Met Glu
165 170 175

Lys Pro Ser Pro Leu Leu Val Gly Arg Glu Phe Val Arg Gln Tyr Tyr
180 185 190

Thr Leu Leu Asn Gln Ala Pro Asp Met Leu His Arg Phe Tyr Gly Lys
195 200 205

Asn Ser Ser Tyr Val His Gly Gly Leu Asp Ser Asn Gly Lys Pro Ala
210 215 220

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Thr Ala Pro Glu Asp Ala Gln Lys Ser
305 310 315 320

```
Ser Ser Pro Ala Pro Ala Asp Ile Ala Gln Thr Val Gln Glu Asp Leu
                325                 330                 335

Arg Thr Phe Ser Trp Ala Ser Val Thr Ser Lys Asn Leu Pro Pro Ser
            340                 345                 350

Gly Ala Val Pro Val Thr Gly Ile Pro Pro His Val Val Lys Val Pro
        355                 360                 365

Ala Ser Gln Pro Arg Pro Glu Ser Lys Pro Glu Ser Gln Ile Pro Pro
    370                 375                 380

Gln Arg Pro Gln Arg Asp Gln Arg Val Arg Glu Gln Arg Ile Asn Ile
385                 390                 395                 400

Pro Pro Gln Arg Gly Pro Arg Pro Ile Arg Glu Ala Gly Glu Gln Gly
                405                 410                 415

Asp Ile Glu Pro Arg Arg Met Val Arg His Pro Asp Ser His Gln Leu
            420                 425                 430

Phe Ile Gly Asn Leu Pro His Glu Val Asp Lys Ser Glu Leu Lys Asp
        435                 440                 445

Phe Phe Gln Ser Tyr Gly Asn Val Val Glu Leu Arg Ile Asn Ser Gly
    450                 455                 460

Gly Lys Leu Pro Asn Phe Gly Phe Val Val Phe Asp Asp Ser Glu Pro
465                 470                 475                 480

Val Gln Lys Val Leu Ser Asn Arg Pro Ile Met Phe Arg Gly Glu Val
                485                 490                 495

Arg Leu Asn Val Glu Glu Lys Lys Thr Arg Ala Ala Arg Glu Gly Asp
            500                 505                 510

Arg Arg Asp Asn Arg Leu Arg Gly Pro Gly Gly Pro Arg Gly Gly Leu
        515                 520                 525

Gly Gly Gly Met Arg Gly Pro Pro Arg Gly Gly Met Val Gln Lys Pro
    530                 535                 540

Gly Phe Gly Val Gly Arg Gly Leu Ala Pro Arg Gln Lys Leu Ile Pro
545                 550                 555                 560

Met Ala Arg Arg Ala Trp Leu Glu His Gly His Ser Cys Phe Leu Cys
                565                 570                 575

Glu Ile Val Ile Arg Ser Gln Phe His Thr Thr Tyr Glu Pro Glu Ala
            580                 585                 590
```

<210> SEQ ID NO 68
<211> LENGTH: 555
<212> TYPE: PRT
<213> ORGANISM: Artificial Sequence
<220> FEATURE:
<223> OTHER INFORMATION: Synthetic construct

<400> SEQUENCE: 68

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95
```

-continued

```
Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Gln Leu Phe Ile Gly Asn Leu
385                 390                 395                 400

Pro His Glu Val Asp Lys Ser Glu Leu Lys Asp Phe Phe Gln Ser Tyr
                405                 410                 415

Gly Asn Val Val Glu Leu Arg Ile Asn Ser Gly Gly Lys Leu Pro Asn
            420                 425                 430

Phe Gly Phe Val Val Phe Asp Asp Ser Glu Pro Val Gln Lys Val Leu
        435                 440                 445

Ser Asn Arg Pro Ile Met Phe Arg Gly Glu Val Arg Leu Asn Val Glu
    450                 455                 460

Glu Lys Lys Thr Arg Ala Ala Arg Glu Gly Asp Arg Arg Asp Asn Arg
465                 470                 475                 480

Leu Arg Gly Pro Gly Gly Pro Arg Gly Gly Leu Gly Gly Gly Met Arg
                485                 490                 495

Gly Pro Pro Arg Gly Gly Met Val Gln Lys Pro Gly Phe Gly Val Gly
            500                 505                 510
```

```
Arg Gly Leu Ala Pro Arg Gln Lys Leu Ile Pro Met Ala Arg Arg Ala
        515                 520                 525

Trp Leu Glu His Gly His Ser Cys Phe Leu Cys Glu Ile Val Ile Arg
    530                 535                 540

Ser Gln Phe His Thr Thr Tyr Glu Pro Glu Ala
545                 550                 555


<210> SEQ ID NO 69
<211> LENGTH: 603
<212> TYPE: PRT
<213> ORGANISM: Artificial Sequence
<220> FEATURE:
<223> OTHER INFORMATION: Synthetic construct

<400> SEQUENCE: 69

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320
```

-continued

```
Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Glu Lys Lys Thr Arg Ala Ala Arg Glu Gly Asp Arg Arg Asp Asn Arg
        515                 520                 525

Leu Arg Gly Pro Gly Gly Pro Arg Gly Gly Leu Gly Gly Gly Met Arg
    530                 535                 540

Gly Pro Pro Arg Gly Gly Met Val Gln Lys Pro Gly Phe Gly Val Gly
545                 550                 555                 560

Arg Gly Leu Ala Pro Arg Gln Lys Leu Ile Pro Met Ala Arg Arg Ala
                565                 570                 575

Trp Leu Glu His Gly His Ser Cys Phe Leu Cys Glu Ile Val Ile Arg
            580                 585                 590

Ser Gln Phe His Thr Thr Tyr Glu Pro Glu Ala
        595                 600
```

<210> SEQ ID NO 70
<211> LENGTH: 583
<212> TYPE: PRT
<213> ORGANISM: Artificial Sequence
<220> FEATURE:
<223> OTHER INFORMATION: Synthetic construct

<400> SEQUENCE: 70

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80
```

```
Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495
```

Gln Gly Asp Ile Glu Pro Arg Arg Met Val Arg His Pro Asp Ser His
500 505 510

Gln Leu Phe Ile Gly Asn Leu Pro His Glu Val Asp Lys Ser Glu Leu
515 520 525

Lys Asp Phe Phe Gln Ser Tyr Gly Asn Val Val Glu Leu Arg Ile Asn
530 535 540

Ser Gly Gly Lys Leu Pro Asn Phe Gly Phe Val Val Phe Asp Asp Ser
545 550 555 560

Glu Pro Val Gln Lys Val Leu Ser Asn Arg Pro Ile Met Phe Arg Gly
565 570 575

Glu Val Arg Leu Asn Val Glu
580

<210> SEQ ID NO 71
<211> LENGTH: 512
<212> TYPE: PRT
<213> ORGANISM: Artificial Sequence
<220> FEATURE:
<223> OTHER INFORMATION: Synthetic construct

<400> SEQUENCE: 71

Met His Thr Leu Tyr Ala Pro Gly Gly Tyr Asp Ile Met Gly Trp Leu
1 5 10 15

Ile Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Val Met Glu
165 170 175

Lys Pro Ser Pro Leu Leu Val Gly Arg Glu Phe Val Arg Gln Tyr Tyr
180 185 190

Thr Leu Leu Asn Gln Ala Pro Asp Met Leu His Arg Phe Tyr Gly Lys
195 200 205

Asn Ser Ser Tyr Val His Gly Gly Leu Asp Ser Asn Gly Lys Pro Ala
210 215 220

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Gly Phe Val Thr Glu Pro Gln Glu Glu
305 310 315 320

Ser Glu Glu Glu Val Glu Glu Pro Glu Glu Arg Gln Gln Thr Pro Glu
325 330 335

Val Val Pro Asp Asp Ser Gly Thr Phe Tyr Asp Gln Ala Val Val Ser
340 345 350

Asn Asp Met Glu Glu His Leu Glu Glu Pro Val Ala Glu Pro Glu Pro
355 360 365

Asp Pro Glu Pro Glu Pro Glu Gln Glu Pro Val Ser Glu Ile Gln Glu
370 375 380

Glu Lys Pro Glu Pro Val Leu Glu Glu Thr Ala Pro Glu Asp Ala Gln
385 390 395 400

Lys Ser Ser Ser Pro Ala Pro Ala Asp Ile Ala Gln Thr Val Gln Glu
405 410 415

Asp Leu Arg Thr Phe Ser Trp Ala Ser Val Thr Ser Lys Asn Leu Pro
420 425 430

Pro Ser Gly Ala Val Pro Val Thr Gly Ile Pro Pro His Val Val Lys
435 440 445

Val Pro Ala Ser Gln Pro Arg Pro Glu Ser Lys Pro Glu Ser Gln Ile
450 455 460

Pro Pro Gln Arg Pro Gln Arg Asp Gln Arg Val Arg Glu Gln Arg Ile
465 470 475 480

Asn Ile Pro Pro Gln Arg Gly Pro Arg Pro Ile Arg Glu Ala Gly Glu
485 490 495

Gln Gly Asp Ile Glu Pro Arg Arg Met Val Arg His Pro Asp Ser His
500 505 510

<210> SEQ ID NO 72
<211> LENGTH: 674
<212> TYPE: PRT
<213> ORGANISM: Artificial Sequence
<220> FEATURE:
<223> OTHER INFORMATION: Synthetic construct

<400> SEQUENCE: 72

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

```
Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Gln Leu Phe Ile Gly Asn Leu Pro His Glu Val Asp Lys Ser Glu Leu
        515                 520                 525

Lys Asp Phe Phe Gln Ser Tyr Gly Asn Val Val Glu Leu Arg Ile Asn
    530                 535                 540
```

Ser Gly Gly Lys Leu Pro Asn Phe Gly Phe Val Val Phe Asp Asp Ser
545 550 555 560

Glu Pro Val Gln Lys Val Leu Ser Asn Arg Pro Ile Met Phe Arg Gly
565 570 575

Glu Val Arg Leu Asn Val Glu Glu Lys Lys Thr Arg Ala Ala Arg Glu
580 585 590

Gly Asp Arg Arg Asp Asn Arg Leu Arg Gly Pro Gly Gly Pro Arg Gly
595 600 605

Gly Leu Gly Gly Gly Met Arg Gly Pro Pro Arg Gly Gly Met Val Gln
610 615 620

Lys Pro Gly Phe Gly Val Gly Arg Gly Leu Ala Pro Arg Gln Lys Leu
625 630 635 640

Ile Pro Met Ala Arg Arg Ala Trp Leu Glu His Gly His Ser Cys Phe
645 650 655

Leu Cys Glu Ile Val Ile Arg Ser Gln Phe His Thr Thr Tyr Glu Pro
660 665 670

Glu Ala

<210> SEQ ID NO 73
<211> LENGTH: 536
<212> TYPE: PRT
<213> ORGANISM: Artificial Sequence
<220> FEATURE:
<223> OTHER INFORMATION: Synthetic construct

<400> SEQUENCE: 73

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

Pro Val Val Tyr Ala Ser Glu Ala Phe Leu Tyr Met Thr Gly Tyr Ser
50 55 60

Asn Ala Glu Val Leu Gly Arg Asn Cys Arg Phe Leu Gln Ser Pro Asp
65 70 75 80

Gly Met Val Lys Pro Lys Ser Thr Arg Lys Tyr Val Asp Ser Asn Thr
85 90 95

Ile Asn Thr Met Arg Lys Ala Ile Asp Arg Asn Ala Glu Val Gln Val
100 105 110

Glu Val Val Asn Phe Lys Lys Asn Gly Gln Arg Phe Val Asn Phe Leu
115 120 125

Thr Met Ile Pro Val Arg Asp Glu Thr Gly Glu Tyr Arg Tyr Ser Met
130 135 140

Gly Phe Gln Cys Glu Thr Glu Gly Ser Gly Gly Ser Gly Gly Ser Gly
145 150 155 160

Gly Ser Gly Gly Thr Gly Gly Ser Gly Gly Ser Gly Met Gly Phe Val
165 170 175

Thr Glu Pro Gln Glu Glu Ser Glu Glu Glu Val Glu Glu Pro Glu Glu
180 185 190

Arg Gln Gln Thr Pro Glu Val Val Pro Asp Asp Ser Gly Thr Phe Tyr
195 200 205

Asp Gln Ala Val Val Ser Asn Asp Met Glu Glu His Leu Glu Glu Pro
210 215 220

Val Ala Glu Pro Glu Pro Asp Pro Glu Pro Glu Pro Glu Gln Glu Pro
225 230 235 240

Val Ser Glu Ile Gln Glu Glu Lys Pro Glu Pro Val Leu Glu Glu Thr
245 250 255

Ala Pro Glu Asp Ala Gln Lys Ser Ser Ser Pro Ala Pro Ala Asp Ile
260 265 270

Ala Gln Thr Val Gln Glu Asp Leu Arg Thr Phe Ser Trp Ala Ser Val
275 280 285

Thr Ser Lys Asn Leu Pro Pro Ser Gly Ala Val Pro Val Thr Gly Ile
290 295 300

Pro Pro His Val Val Lys Val Pro Ala Ser Gln Pro Arg Pro Glu Ser
305 310 315 320

Lys Pro Glu Ser Gln Ile Pro Pro Gln Arg Pro Gln Arg Asp Gln Arg
325 330 335

Val Arg Glu Gln Arg Ile Asn Ile Pro Pro Gln Arg Gly Pro Arg Pro
340 345 350

Ile Arg Glu Ala Gly Glu Gln Gly Asp Ile Glu Pro Arg Arg Met Val
355 360 365

Arg His Pro Asp Ser His Gln Leu Phe Ile Gly Asn Leu Pro His Glu
370 375 380

Val Asp Lys Ser Glu Leu Lys Asp Phe Phe Gln Ser Tyr Gly Asn Val
385 390 395 400

Val Glu Leu Arg Ile Asn Ser Gly Gly Lys Leu Pro Asn Phe Gly Phe
405 410 415

Val Val Phe Asp Asp Ser Glu Pro Val Gln Lys Val Leu Ser Asn Arg
420 425 430

Pro Ile Met Phe Arg Gly Glu Val Arg Leu Asn Val Glu Glu Lys Lys
435 440 445

Thr Arg Ala Ala Arg Glu Gly Asp Arg Arg Asp Asn Arg Leu Arg Gly
450 455 460

Pro Gly Gly Pro Arg Gly Gly Leu Gly Gly Gly Met Arg Gly Pro Pro
465 470 475 480

Arg Gly Gly Met Val Gln Lys Pro Gly Phe Gly Val Gly Arg Gly Leu
485 490 495

Ala Pro Arg Gln Lys Leu Ile Pro Met Ala Arg Arg Ala Trp Leu Glu
500 505 510

His Gly His Ser Cys Phe Leu Cys Glu Ile Val Ile Arg Ser Gln Phe
515 520 525

His Thr Thr Tyr Glu Pro Glu Ala
530 535

<210> SEQ ID NO 74
<211> LENGTH: 592
<212> TYPE: PRT
<213> ORGANISM: Artificial Sequence
<220> FEATURE:
<223> OTHER INFORMATION: Synthetic construct

<400> SEQUENCE: 74

Met His Thr Leu Tyr Ala Pro Gly Gly Tyr Asp Ile Met Gly Trp Leu
1 5 10 15

Cys Gln Ile Met Asn Arg Pro Asn Pro Gln Val Glu Leu Gly Pro Val
20 25 30

Asp Thr Ser Val Ala Leu Val Leu Cys Asp Leu Lys Gln Lys Asp Thr
35 40 45

```
Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Thr Ala Pro Glu Asp Ala Gln Lys Ser
305                 310                 315                 320

Ser Ser Pro Ala Pro Ala Asp Ile Ala Gln Thr Val Gln Glu Asp Leu
                325                 330                 335

Arg Thr Phe Ser Trp Ala Ser Val Thr Ser Lys Asn Leu Pro Pro Ser
            340                 345                 350

Gly Ala Val Pro Val Thr Gly Ile Pro Pro His Val Val Lys Val Pro
        355                 360                 365

Ala Ser Gln Pro Arg Pro Glu Ser Lys Pro Glu Ser Gln Ile Pro Pro
    370                 375                 380

Gln Arg Pro Gln Arg Asp Gln Arg Val Arg Glu Gln Arg Ile Asn Ile
385                 390                 395                 400

Pro Pro Gln Arg Gly Pro Arg Pro Ile Arg Glu Ala Gly Glu Gln Gly
                405                 410                 415

Asp Ile Glu Pro Arg Arg Met Val Arg His Pro Asp Ser His Gln Leu
            420                 425                 430

Phe Ile Gly Asn Leu Pro His Glu Val Asp Lys Ser Glu Leu Lys Asp
        435                 440                 445

Phe Phe Gln Ser Tyr Gly Asn Val Val Glu Leu Arg Ile Asn Ser Gly
    450                 455                 460
```

```
Gly Lys Leu Pro Asn Phe Gly Phe Val Val Phe Asp Asp Ser Glu Pro
465                 470                 475                 480

Val Gln Lys Val Leu Ser Asn Arg Pro Ile Met Phe Arg Gly Glu Val
                485                 490                 495

Arg Leu Asn Val Glu Glu Lys Lys Thr Arg Ala Ala Arg Glu Gly Asp
            500                 505                 510

Arg Arg Asp Asn Arg Leu Arg Gly Pro Gly Gly Pro Arg Gly Gly Leu
        515                 520                 525

Gly Gly Gly Met Arg Gly Pro Pro Arg Gly Gly Met Val Gln Lys Pro
    530                 535                 540

Gly Phe Gly Val Gly Arg Gly Leu Ala Pro Arg Gln Lys Leu Ile Pro
545                 550                 555                 560

Met Ala Arg Arg Ala Trp Leu Glu His Gly His Ser Cys Phe Leu Cys
                565                 570                 575

Glu Ile Val Ile Arg Ser Gln Phe His Thr Thr Tyr Glu Pro Glu Ala
            580                 585                 590


<210> SEQ ID NO 75
<211> LENGTH: 555
<212> TYPE: PRT
<213> ORGANISM: Artificial Sequence
<220> FEATURE:
<223> OTHER INFORMATION: Synthetic construct

<400> SEQUENCE: 75

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240
```

```
Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Gln Leu Phe Ile Gly Asn Leu
385                 390                 395                 400

Pro His Glu Val Asp Lys Ser Glu Leu Lys Asp Phe Phe Gln Ser Tyr
                405                 410                 415

Gly Asn Val Val Glu Leu Arg Ile Asn Ser Gly Gly Lys Leu Pro Asn
            420                 425                 430

Phe Gly Phe Val Val Phe Asp Asp Ser Glu Pro Val Gln Lys Val Leu
        435                 440                 445

Ser Asn Arg Pro Ile Met Phe Arg Gly Glu Val Arg Leu Asn Val Glu
    450                 455                 460

Glu Lys Lys Thr Arg Ala Ala Arg Glu Gly Asp Arg Arg Asp Asn Arg
465                 470                 475                 480

Leu Arg Gly Pro Gly Gly Pro Arg Gly Gly Leu Gly Gly Gly Met Arg
                485                 490                 495

Gly Pro Pro Arg Gly Gly Met Val Gln Lys Pro Gly Phe Gly Val Gly
            500                 505                 510

Arg Gly Leu Ala Pro Arg Gln Lys Leu Ile Pro Met Ala Arg Arg Ala
        515                 520                 525

Trp Leu Glu His Gly His Ser Cys Phe Leu Cys Glu Ile Val Ile Arg
    530                 535                 540

Ser Gln Phe His Thr Thr Tyr Glu Pro Glu Ala
545                 550                 555


<210> SEQ ID NO 76
<211> LENGTH: 603
<212> TYPE: PRT
<213> ORGANISM: Artificial Sequence
<220> FEATURE:
<223> OTHER INFORMATION: Synthetic construct

<400> SEQUENCE: 76

Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45
```

-continued

```
Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400

Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460
```

```
Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510

Glu Lys Lys Thr Arg Ala Ala Arg Glu Gly Asp Arg Arg Asp Asn Arg
        515                 520                 525

Leu Arg Gly Pro Gly Gly Pro Arg Gly Gly Leu Gly Gly Gly Met Arg
    530                 535                 540

Gly Pro Pro Arg Gly Gly Met Val Gln Lys Pro Gly Phe Gly Val Gly
545                 550                 555                 560

Arg Gly Leu Ala Pro Arg Gln Lys Leu Ile Pro Met Ala Arg Arg Ala
                565                 570                 575

Trp Leu Glu His Gly His Ser Cys Phe Leu Cys Glu Ile Val Ile Arg
            580                 585                 590

Ser Gln Phe His Thr Thr Tyr Glu Pro Glu Ala
        595                 600
```

<210> SEQ ID NO 77
<211> LENGTH: 583
<212> TYPE: PRT
<213> ORGANISM: Artificial Sequence
<220> FEATURE:
<223> OTHER INFORMATION: Synthetic construct

<400> SEQUENCE: 77

```
Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220
```

Asp Ala Val Tyr Gly Gln Lys Glu Ile His Arg Lys Val Met Ser Gln
225 230 235 240

Asn Phe Thr Asn Cys His Thr Lys Ile Arg His Val Asp Ala His Ala
245 250 255

Thr Leu Asn Asp Gly Val Val Val Gln Val Met Gly Leu Leu Ser Asn
260 265 270

Asn Asn Gln Ala Leu Arg Arg Phe Met Gln Thr Phe Val Leu Ala Pro
275 280 285

Glu Gly Ser Val Ala Asn Lys Phe Tyr Val His Asn Asp Ile Phe Arg
290 295 300

Tyr Gln Asp Glu Val Phe Gly Gly Phe Val Thr Glu Pro Gln Glu Glu
305 310 315 320

Ser Glu Glu Glu Val Glu Glu Pro Glu Glu Arg Gln Gln Thr Pro Glu
325 330 335

Val Val Pro Asp Asp Ser Gly Thr Phe Tyr Asp Gln Ala Val Val Ser
340 345 350

Asn Asp Met Glu Glu His Leu Glu Glu Pro Val Ala Glu Pro Glu Pro
355 360 365

Asp Pro Glu Pro Glu Pro Glu Gln Glu Pro Val Ser Glu Ile Gln Glu
370 375 380

Glu Lys Pro Glu Pro Val Leu Glu Glu Thr Ala Pro Glu Asp Ala Gln
385 390 395 400

Lys Ser Ser Ser Pro Ala Pro Ala Asp Ile Ala Gln Thr Val Gln Glu
405 410 415

Asp Leu Arg Thr Phe Ser Trp Ala Ser Val Thr Ser Lys Asn Leu Pro
420 425 430

Pro Ser Gly Ala Val Pro Val Thr Gly Ile Pro Pro His Val Val Lys
435 440 445

Val Pro Ala Ser Gln Pro Arg Pro Glu Ser Lys Pro Glu Ser Gln Ile
450 455 460

Pro Pro Gln Arg Pro Gln Arg Asp Gln Arg Val Arg Glu Gln Arg Ile
465 470 475 480

Asn Ile Pro Pro Gln Arg Gly Pro Arg Pro Ile Arg Glu Ala Gly Glu
485 490 495

Gln Gly Asp Ile Glu Pro Arg Arg Met Val Arg His Pro Asp Ser His
500 505 510

Gln Leu Phe Ile Gly Asn Leu Pro His Glu Val Asp Lys Ser Glu Leu
515 520 525

Lys Asp Phe Phe Gln Ser Tyr Gly Asn Val Val Glu Leu Arg Ile Asn
530 535 540

Ser Gly Gly Lys Leu Pro Asn Phe Gly Phe Val Val Phe Asp Asp Ser
545 550 555 560

Glu Pro Val Gln Lys Val Leu Ser Asn Arg Pro Ile Met Phe Arg Gly
565 570 575

Glu Val Arg Leu Asn Val Glu
580

<210> SEQ ID NO 78
<211> LENGTH: 512
<212> TYPE: PRT
<213> ORGANISM: Artificial Sequence
<220> FEATURE:
<223> OTHER INFORMATION: Synthetic construct

<400> SEQUENCE: 78

```
Met His Thr Leu Tyr Ala Pro Gly Gly Tyr Asp Ile Met Gly Trp Leu
1               5                   10                  15

Cys Gln Ile Met Asn Arg Pro Asn Pro Gln Val Glu Leu Gly Pro Val
            20                  25                  30

Asp Thr Ser Val Ala Leu Val Leu Cys Asp Leu Lys Gln Lys Asp Thr
        35                  40                  45

Pro Val Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Gly Ser Gly Gly Ser Gly Gly Ser Gly
145                 150                 155                 160

Gly Ser Gly Gly Thr Gly Gly Ser Gly Gly Ser Gly Met Val Met Glu
                165                 170                 175

Lys Pro Ser Pro Leu Leu Val Gly Arg Glu Phe Val Arg Gln Tyr Tyr
            180                 185                 190

Thr Leu Leu Asn Gln Ala Pro Asp Met Leu His Arg Phe Tyr Gly Lys
        195                 200                 205

Asn Ser Ser Tyr Val His Gly Gly Leu Asp Ser Asn Gly Lys Pro Ala
    210                 215                 220

Asp Ala Val Tyr Gly Gln Lys Glu Ile His Arg Lys Val Met Ser Gln
225                 230                 235                 240

Asn Phe Thr Asn Cys His Thr Lys Ile Arg His Val Asp Ala His Ala
                245                 250                 255

Thr Leu Asn Asp Gly Val Val Val Gln Val Met Gly Leu Leu Ser Asn
            260                 265                 270

Asn Asn Gln Ala Leu Arg Arg Phe Met Gln Thr Phe Val Leu Ala Pro
        275                 280                 285

Glu Gly Ser Val Ala Asn Lys Phe Tyr Val His Asn Asp Ile Phe Arg
    290                 295                 300

Tyr Gln Asp Glu Val Phe Gly Gly Phe Val Thr Glu Pro Gln Glu Glu
305                 310                 315                 320

Ser Glu Glu Glu Val Glu Glu Pro Glu Glu Arg Gln Gln Thr Pro Glu
                325                 330                 335

Val Val Pro Asp Asp Ser Gly Thr Phe Tyr Asp Gln Ala Val Val Ser
            340                 345                 350

Asn Asp Met Glu Glu His Leu Glu Glu Pro Val Ala Glu Pro Glu Pro
        355                 360                 365

Asp Pro Glu Pro Glu Pro Glu Gln Glu Pro Val Ser Glu Ile Gln Glu
    370                 375                 380

Glu Lys Pro Glu Pro Val Leu Glu Glu Thr Ala Pro Glu Asp Ala Gln
385                 390                 395                 400
```

```
Lys Ser Ser Ser Pro Ala Pro Ala Asp Ile Ala Gln Thr Val Gln Glu
                405                 410                 415

Asp Leu Arg Thr Phe Ser Trp Ala Ser Val Thr Ser Lys Asn Leu Pro
            420                 425                 430

Pro Ser Gly Ala Val Pro Val Thr Gly Ile Pro Pro His Val Val Lys
        435                 440                 445

Val Pro Ala Ser Gln Pro Arg Pro Glu Ser Lys Pro Glu Ser Gln Ile
    450                 455                 460

Pro Pro Gln Arg Pro Gln Arg Asp Gln Arg Val Arg Glu Gln Arg Ile
465                 470                 475                 480

Asn Ile Pro Pro Gln Arg Gly Pro Arg Pro Ile Arg Glu Ala Gly Glu
                485                 490                 495

Gln Gly Asp Ile Glu Pro Arg Arg Met Val Arg His Pro Asp Ser His
            500                 505                 510


<210> SEQ ID NO 79
<211> LENGTH: 1000
<212> TYPE: PRT
<213> ORGANISM: Artificial Sequence
<220> FEATURE:
<223> OTHER INFORMATION: Synthetic construct

<400> SEQUENCE: 79

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255
```

-continued

```
Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670
```

```
Asp Gln Ala Val Val Ser Asn Asp Met Glu Glu His Leu Glu Glu Pro
        675                 680                 685

Val Ala Glu Pro Glu Pro Asp Pro Glu Pro Glu Pro Glu Gln Glu Pro
    690                 695                 700

Val Ser Glu Ile Gln Glu Glu Lys Pro Glu Pro Val Leu Glu Glu Thr
705                 710                 715                 720

Ala Pro Glu Asp Ala Gln Lys Ser Ser Ser Pro Ala Pro Ala Asp Ile
                725                 730                 735

Ala Gln Thr Val Gln Glu Asp Leu Arg Thr Phe Ser Trp Ala Ser Val
            740                 745                 750

Thr Ser Lys Asn Leu Pro Pro Ser Gly Ala Val Pro Val Thr Gly Ile
        755                 760                 765

Pro Pro His Val Val Lys Val Pro Ala Ser Gln Pro Arg Pro Glu Ser
    770                 775                 780

Lys Pro Glu Ser Gln Ile Pro Pro Gln Arg Pro Gln Arg Asp Gln Arg
785                 790                 795                 800

Val Arg Glu Gln Arg Ile Asn Ile Pro Pro Gln Arg Gly Pro Arg Pro
                805                 810                 815

Ile Arg Glu Ala Gly Glu Gln Gly Asp Ile Glu Pro Arg Arg Met Val
            820                 825                 830

Arg His Pro Asp Ser His Gln Leu Phe Ile Gly Asn Leu Pro His Glu
        835                 840                 845

Val Asp Lys Ser Glu Leu Lys Asp Phe Phe Gln Ser Tyr Gly Asn Val
    850                 855                 860

Val Glu Leu Arg Ile Asn Ser Gly Gly Lys Leu Pro Asn Phe Gly Phe
865                 870                 875                 880

Val Val Phe Asp Asp Ser Glu Pro Val Gln Lys Val Leu Ser Asn Arg
                885                 890                 895

Pro Ile Met Phe Arg Gly Glu Val Arg Leu Asn Val Glu Glu Lys Lys
            900                 905                 910

Thr Arg Ala Ala Arg Glu Gly Asp Arg Arg Asp Asn Arg Leu Arg Gly
        915                 920                 925

Pro Gly Gly Pro Arg Gly Gly Leu Gly Gly Gly Met Arg Gly Pro Pro
    930                 935                 940

Arg Gly Gly Met Val Gln Lys Pro Gly Phe Gly Val Gly Arg Gly Leu
945                 950                 955                 960

Ala Pro Arg Gln Lys Leu Ile Pro Met Ala Arg Arg Ala Trp Leu Glu
                965                 970                 975

His Gly His Ser Cys Phe Leu Cys Glu Ile Val Ile Arg Ser Gln Phe
            980                 985                 990

His Thr Thr Tyr Glu Pro Glu Ala
        995                 1000
```

<210> SEQ ID NO 80
<211> LENGTH: 862
<212> TYPE: PRT
<213> ORGANISM: Artificial Sequence
<220> FEATURE:
<223> OTHER INFORMATION: Synthetic construct

<400> SEQUENCE: 80

```
Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30
```

-continued

```
Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445
```

```
Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Gly Phe Val Thr Glu Pro Gln Glu Glu Ser Glu Glu Glu
            500                 505                 510

Val Glu Glu Pro Glu Glu Arg Gln Gln Thr Pro Glu Val Val Pro Asp
        515                 520                 525

Asp Ser Gly Thr Phe Tyr Asp Gln Ala Val Val Ser Asn Asp Met Glu
    530                 535                 540

Glu His Leu Glu Glu Pro Val Ala Glu Pro Glu Pro Asp Pro Glu Pro
545                 550                 555                 560

Glu Pro Glu Gln Glu Pro Val Ser Glu Ile Gln Glu Glu Lys Pro Glu
                565                 570                 575

Pro Val Leu Glu Glu Thr Ala Pro Glu Asp Ala Gln Lys Ser Ser Ser
            580                 585                 590

Pro Ala Pro Ala Asp Ile Ala Gln Thr Val Gln Glu Asp Leu Arg Thr
        595                 600                 605

Phe Ser Trp Ala Ser Val Thr Ser Lys Asn Leu Pro Pro Ser Gly Ala
    610                 615                 620

Val Pro Val Thr Gly Ile Pro Pro His Val Val Lys Val Pro Ala Ser
625                 630                 635                 640

Gln Pro Arg Pro Glu Ser Lys Pro Glu Ser Gln Ile Pro Pro Gln Arg
                645                 650                 655

Pro Gln Arg Asp Gln Arg Val Arg Glu Gln Arg Ile Asn Ile Pro Pro
            660                 665                 670

Gln Arg Gly Pro Arg Pro Ile Arg Glu Ala Gly Glu Gln Gly Asp Ile
        675                 680                 685

Glu Pro Arg Arg Met Val Arg His Pro Asp Ser His Gln Leu Phe Ile
    690                 695                 700

Gly Asn Leu Pro His Glu Val Asp Lys Ser Glu Leu Lys Asp Phe Phe
705                 710                 715                 720

Gln Ser Tyr Gly Asn Val Val Glu Leu Arg Ile Asn Ser Gly Gly Lys
                725                 730                 735

Leu Pro Asn Phe Gly Phe Val Val Phe Asp Asp Ser Glu Pro Val Gln
            740                 745                 750

Lys Val Leu Ser Asn Arg Pro Ile Met Phe Arg Gly Glu Val Arg Leu
        755                 760                 765

Asn Val Glu Glu Lys Lys Thr Arg Ala Ala Arg Glu Gly Asp Arg Arg
    770                 775                 780

Asp Asn Arg Leu Arg Gly Pro Gly Gly Pro Arg Gly Gly Leu Gly Gly
785                 790                 795                 800

Gly Met Arg Gly Pro Pro Arg Gly Gly Met Val Gln Lys Pro Gly Phe
                805                 810                 815

Gly Val Gly Arg Gly Leu Ala Pro Arg Gln Lys Leu Ile Pro Met Ala
            820                 825                 830

Arg Arg Ala Trp Leu Glu His Gly His Ser Cys Phe Leu Cys Glu Ile
        835                 840                 845

Val Ile Arg Ser Gln Phe His Thr Thr Tyr Glu Pro Glu Ala
    850                 855                 860
```

<210> SEQ ID NO 81
<211> LENGTH: 918
<212> TYPE: PRT
<213> ORGANISM: Artificial Sequence
<220> FEATURE:
<223> OTHER INFORMATION: Synthetic construct

<400> SEQUENCE: 81

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

Gly Asn Ser Thr Ser Leu Leu Ser Pro Tyr Leu His Phe Gly Glu Ile
245 250 255

Ser Val Arg His Val Phe Gln Cys Ala Arg Met Lys Gln Ile Ile Trp
260 265 270

Ala Arg Asp Lys Asn Ser Glu Gly Glu Glu Ser Ala Asp Leu Phe Leu
275 280 285

Arg Gly Ile Gly Leu Arg Glu Tyr Ser Arg Tyr Ile Cys Phe Asn Phe
290 295 300

Pro Phe Thr His Glu Gln Ser Leu Leu Ser His Leu Arg Phe Phe Pro
305 310 315 320

Trp Asp Ala Asp Val Asp Lys Phe Lys Ala Trp Arg Gln Gly Arg Thr
325 330 335

Gly Tyr Pro Leu Val Asp Ala Gly Met Arg Glu Leu Trp Ala Thr Gly
340 345 350

Trp Met His Asn Arg Ile Arg Val Ile Val Ser Ser Phe Ala Val Lys
355 360 365

-continued

```
Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Thr Ala Pro
625                 630                 635                 640

Glu Asp Ala Gln Lys Ser Ser Ser Pro Ala Pro Ala Asp Ile Ala Gln
                645                 650                 655

Thr Val Gln Glu Asp Leu Arg Thr Phe Ser Trp Ala Ser Val Thr Ser
            660                 665                 670

Lys Asn Leu Pro Pro Ser Gly Ala Val Pro Val Thr Gly Ile Pro Pro
        675                 680                 685

His Val Val Lys Val Pro Ala Ser Gln Pro Arg Pro Glu Ser Lys Pro
    690                 695                 700

Glu Ser Gln Ile Pro Pro Gln Arg Pro Gln Arg Asp Gln Arg Val Arg
705                 710                 715                 720

Glu Gln Arg Ile Asn Ile Pro Pro Gln Arg Gly Pro Arg Pro Ile Arg
                725                 730                 735

Glu Ala Gly Glu Gln Gly Asp Ile Glu Pro Arg Arg Met Val Arg His
            740                 745                 750

Pro Asp Ser His Gln Leu Phe Ile Gly Asn Leu Pro His Glu Val Asp
        755                 760                 765

Lys Ser Glu Leu Lys Asp Phe Phe Gln Ser Tyr Gly Asn Val Val Glu
    770                 775                 780
```

```
Leu Arg Ile Asn Ser Gly Gly Lys Leu Pro Asn Phe Gly Phe Val Val
785                 790                 795                 800

Phe Asp Asp Ser Glu Pro Val Gln Lys Val Leu Ser Asn Arg Pro Ile
            805                 810                 815

Met Phe Arg Gly Glu Val Arg Leu Asn Val Glu Glu Lys Lys Thr Arg
            820                 825                 830

Ala Ala Arg Glu Gly Asp Arg Arg Asp Asn Arg Leu Arg Gly Pro Gly
        835                 840                 845

Gly Pro Arg Gly Gly Leu Gly Gly Gly Met Arg Gly Pro Pro Arg Gly
    850                 855                 860

Gly Met Val Gln Lys Pro Gly Phe Gly Val Gly Arg Gly Leu Ala Pro
865                 870                 875                 880

Arg Gln Lys Leu Ile Pro Met Ala Arg Arg Ala Trp Leu Glu His Gly
                885                 890                 895

His Ser Cys Phe Leu Cys Glu Ile Val Ile Arg Ser Gln Phe His Thr
            900                 905                 910

Thr Tyr Glu Pro Glu Ala
        915


<210> SEQ ID NO 82
<211> LENGTH: 881
<212> TYPE: PRT
<213> ORGANISM: Artificial Sequence
<220> FEATURE:
<223> OTHER INFORMATION: Synthetic construct

<400> SEQUENCE: 82

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220
```

-continued

```
Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640
```

Thr Glu Pro Gln Glu Glu Ser Glu Glu Glu Val Glu Glu Pro Glu Glu
645 650 655

Arg Gln Gln Thr Pro Glu Val Val Pro Asp Asp Ser Gly Thr Phe Tyr
660 665 670

Asp Gln Ala Val Val Ser Asn Asp Met Glu Glu His Leu Glu Glu Pro
675 680 685

Val Ala Glu Pro Glu Pro Asp Pro Glu Pro Glu Pro Glu Gln Glu Pro
690 695 700

Val Ser Glu Ile Gln Glu Glu Lys Pro Glu Pro Val Leu Glu Glu Gln
705 710 715 720

Leu Phe Ile Gly Asn Leu Pro His Glu Val Asp Lys Ser Glu Leu Lys
725 730 735

Asp Phe Phe Gln Ser Tyr Gly Asn Val Val Glu Leu Arg Ile Asn Ser
740 745 750

Gly Gly Lys Leu Pro Asn Phe Gly Phe Val Val Phe Asp Asp Ser Glu
755 760 765

Pro Val Gln Lys Val Leu Ser Asn Arg Pro Ile Met Phe Arg Gly Glu
770 775 780

Val Arg Leu Asn Val Glu Glu Lys Lys Thr Arg Ala Ala Arg Glu Gly
785 790 795 800

Asp Arg Arg Asp Asn Arg Leu Arg Gly Pro Gly Gly Pro Arg Gly Gly
805 810 815

Leu Gly Gly Gly Met Arg Gly Pro Pro Arg Gly Gly Met Val Gln Lys
820 825 830

Pro Gly Phe Gly Val Gly Arg Gly Leu Ala Pro Arg Gln Lys Leu Ile
835 840 845

Pro Met Ala Arg Arg Ala Trp Leu Glu His Gly His Ser Cys Phe Leu
850 855 860

Cys Glu Ile Val Ile Arg Ser Gln Phe His Thr Thr Tyr Glu Pro Glu
865 870 875 880

Ala

<210> SEQ ID NO 83
<211> LENGTH: 929
<212> TYPE: PRT
<213> ORGANISM: Artificial Sequence
<220> FEATURE:
<223> OTHER INFORMATION: Synthetic construct

<400> SEQUENCE: 83

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

```
His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525
```

-continued

```
His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670

Asp Gln Ala Val Val Ser Asn Asp Met Glu Glu His Leu Glu Glu Pro
        675                 680                 685

Val Ala Glu Pro Glu Pro Asp Pro Glu Pro Glu Pro Glu Gln Glu Pro
    690                 695                 700

Val Ser Glu Ile Gln Glu Glu Lys Pro Glu Pro Val Leu Glu Glu Thr
705                 710                 715                 720

Ala Pro Glu Asp Ala Gln Lys Ser Ser Ser Pro Ala Pro Ala Asp Ile
                725                 730                 735

Ala Gln Thr Val Gln Glu Asp Leu Arg Thr Phe Ser Trp Ala Ser Val
            740                 745                 750

Thr Ser Lys Asn Leu Pro Pro Ser Gly Ala Val Pro Val Thr Gly Ile
        755                 760                 765

Pro Pro His Val Val Lys Val Pro Ala Ser Gln Pro Arg Pro Glu Ser
    770                 775                 780

Lys Pro Glu Ser Gln Ile Pro Pro Gln Arg Pro Gln Arg Asp Gln Arg
785                 790                 795                 800

Val Arg Glu Gln Arg Ile Asn Ile Pro Pro Gln Arg Gly Pro Arg Pro
                805                 810                 815

Ile Arg Glu Ala Gly Glu Gln Gly Asp Ile Glu Pro Arg Arg Met Val
            820                 825                 830

Arg His Pro Asp Ser His Glu Lys Lys Thr Arg Ala Ala Arg Glu Gly
        835                 840                 845

Asp Arg Arg Asp Asn Arg Leu Arg Gly Pro Gly Gly Pro Arg Gly Gly
    850                 855                 860

Leu Gly Gly Gly Met Arg Gly Pro Pro Arg Gly Gly Met Val Gln Lys
865                 870                 875                 880

Pro Gly Phe Gly Val Gly Arg Gly Leu Ala Pro Arg Gln Lys Leu Ile
                885                 890                 895

Pro Met Ala Arg Arg Ala Trp Leu Glu His Gly His Ser Cys Phe Leu
            900                 905                 910

Cys Glu Ile Val Ile Arg Ser Gln Phe His Thr Thr Tyr Glu Pro Glu
        915                 920                 925

Ala
```

<210> SEQ ID NO 84

<211> LENGTH: 909
<212> TYPE: PRT
<213> ORGANISM: Artificial Sequence
<220> FEATURE:
<223> OTHER INFORMATION: Synthetic construct

<400> SEQUENCE: 84

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

Gly Asn Ser Thr Ser Leu Leu Ser Pro Tyr Leu His Phe Gly Glu Ile
245 250 255

Ser Val Arg His Val Phe Gln Cys Ala Arg Met Lys Gln Ile Ile Trp
260 265 270

Ala Arg Asp Lys Asn Ser Glu Gly Glu Glu Ser Ala Asp Leu Phe Leu
275 280 285

Arg Gly Ile Gly Leu Arg Glu Tyr Ser Arg Tyr Ile Cys Phe Asn Phe
290 295 300

Pro Phe Thr His Glu Gln Ser Leu Leu Ser His Leu Arg Phe Phe Pro
305 310 315 320

Trp Asp Ala Asp Val Asp Lys Phe Lys Ala Trp Arg Gln Gly Arg Thr
325 330 335

Gly Tyr Pro Leu Val Asp Ala Gly Met Arg Glu Leu Trp Ala Thr Gly
340 345 350

Trp Met His Asn Arg Ile Arg Val Ile Val Ser Ser Phe Ala Val Lys
355 360 365

Phe Leu Leu Leu Pro Trp Lys Trp Gly Met Lys Tyr Phe Trp Asp Thr
370 375 380

-continued

```
Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670

Asp Gln Ala Val Val Ser Asn Asp Met Glu Glu His Leu Glu Glu Pro
        675                 680                 685

Val Ala Glu Pro Glu Pro Asp Pro Glu Pro Glu Pro Glu Gln Glu Pro
    690                 695                 700

Val Ser Glu Ile Gln Glu Glu Lys Pro Glu Pro Val Leu Glu Glu Thr
705                 710                 715                 720

Ala Pro Glu Asp Ala Gln Lys Ser Ser Ser Pro Ala Pro Ala Asp Ile
                725                 730                 735

Ala Gln Thr Val Gln Glu Asp Leu Arg Thr Phe Ser Trp Ala Ser Val
            740                 745                 750

Thr Ser Lys Asn Leu Pro Pro Ser Gly Ala Val Pro Val Thr Gly Ile
        755                 760                 765

Pro Pro His Val Val Lys Val Pro Ala Ser Gln Pro Arg Pro Glu Ser
    770                 775                 780

Lys Pro Glu Ser Gln Ile Pro Pro Gln Arg Pro Gln Arg Asp Gln Arg
785                 790                 795                 800
```

Val Arg Glu Gln Arg Ile Asn Ile Pro Pro Gln Arg Gly Pro Arg Pro
805 810 815

Ile Arg Glu Ala Gly Glu Gln Gly Asp Ile Glu Pro Arg Arg Met Val
820 825 830

Arg His Pro Asp Ser His Gln Leu Phe Ile Gly Asn Leu Pro His Glu
835 840 845

Val Asp Lys Ser Glu Leu Lys Asp Phe Phe Gln Ser Tyr Gly Asn Val
850 855 860

Val Glu Leu Arg Ile Asn Ser Gly Gly Lys Leu Pro Asn Phe Gly Phe
865 870 875 880

Val Val Phe Asp Asp Ser Glu Pro Val Gln Lys Val Leu Ser Asn Arg
885 890 895

Pro Ile Met Phe Arg Gly Glu Val Arg Leu Asn Val Glu
900 905

<210> SEQ ID NO 85
<211> LENGTH: 838
<212> TYPE: PRT
<213> ORGANISM: Artificial Sequence
<220> FEATURE:
<223> OTHER INFORMATION: Synthetic construct

<400> SEQUENCE: 85

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

Gly Asn Ser Thr Ser Leu Leu Ser Pro Tyr Leu His Phe Gly Glu Ile
245 250 255

-continued

```
Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670
```

Asp Gln Ala Val Val Ser Asn Asp Met Glu Glu His Leu Glu Glu Pro
675 680 685

Val Ala Glu Pro Glu Pro Asp Pro Glu Pro Glu Pro Glu Gln Glu Pro
690 695 700

Val Ser Glu Ile Gln Glu Glu Lys Pro Glu Pro Val Leu Glu Glu Thr
705 710 715 720

Ala Pro Glu Asp Ala Gln Lys Ser Ser Ser Pro Ala Pro Ala Asp Ile
725 730 735

Ala Gln Thr Val Gln Glu Asp Leu Arg Thr Phe Ser Trp Ala Ser Val
740 745 750

Thr Ser Lys Asn Leu Pro Pro Ser Gly Ala Val Pro Val Thr Gly Ile
755 760 765

Pro Pro His Val Val Lys Val Pro Ala Ser Gln Pro Arg Pro Glu Ser
770 775 780

Lys Pro Glu Ser Gln Ile Pro Pro Gln Arg Pro Gln Arg Asp Gln Arg
785 790 795 800

Val Arg Glu Gln Arg Ile Asn Ile Pro Pro Gln Arg Gly Pro Arg Pro
805 810 815

Ile Arg Glu Ala Gly Glu Gln Gly Asp Ile Glu Pro Arg Arg Met Val
820 825 830

Arg His Pro Asp Ser His
835

<210> SEQ ID NO 86
<211> LENGTH: 1000
<212> TYPE: PRT
<213> ORGANISM: Artificial Sequence
<220> FEATURE:
<223> OTHER INFORMATION: Synthetic construct

<400> SEQUENCE: 86

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

-continued

```
Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Arg Asp Asn Arg Leu Arg Gly Pro Gly
            420                 425                 430

Gly Pro Arg Gly Gly Leu Gly Gly Gly Met Arg Gly Pro Pro Arg Gly
        435                 440                 445

Gly Met Val Gln Lys Pro Gly Phe Gly Val Gly Arg Gly Leu Ala Pro
    450                 455                 460

Arg Gln Lys Leu Ile Pro Met Ala Arg Arg Ala Trp Leu Glu His Gly
465                 470                 475                 480

His Ser Cys Phe Leu Cys Glu Ile Val Ile Arg Ser Gln Phe His Thr
                485                 490                 495

Thr Tyr Glu Pro Glu Ala Met Lys Met Asp Lys Lys Thr Ile Val Trp
            500                 505                 510

Phe Arg Arg Asp Leu Arg Ile Glu Asp Asn Pro Ala Leu Ala Ala Ala
        515                 520                 525

Ala His Glu Gly Ser Val Phe Pro Val Phe Ile Trp Cys Pro Glu Glu
    530                 535                 540

Glu Gly Gln Phe Tyr Pro Gly Arg Ala Ser Arg Trp Trp Met Lys Gln
545                 550                 555                 560

Ser Leu Ala His Leu Ser Gln Ser Leu Lys Ala Leu Gly Ser Asp Leu
                565                 570                 575

Thr Leu Ile Lys Thr His Asn Thr Ile Ser Ala Ile Leu Asp Cys Ile
            580                 585                 590

Arg Val Thr Gly Ala Thr Lys Val Val Phe Asn His Leu Tyr Asp Pro
        595                 600                 605
```

-continued

Val Ser Leu Val Arg Asp His Thr Val Lys Glu Lys Leu Val Glu Arg
610 615 620

Gly Ile Ser Val Gln Ser Tyr Asn Gly Asp Leu Leu Tyr Glu Pro Trp
625 630 635 640

Glu Ile Tyr Cys Glu Lys Gly Lys Pro Phe Thr Ser Phe Asn Ser Tyr
645 650 655

Trp Lys Lys Cys Leu Asp Met Ser Ile Glu Ser Val Met Leu Pro Pro
660 665 670

Pro Trp Arg Leu Met Pro Ile Thr Ala Ala Ala Glu Ala Ile Trp Ala
675 680 685

Cys Ser Ile Glu Glu Leu Gly Leu Glu Asn Glu Ala Glu Lys Pro Ser
690 695 700

Asn Ala Leu Leu Thr Arg Ala Trp Ser Pro Gly Trp Ser Asn Ala Asp
705 710 715 720

Lys Leu Leu Asn Glu Phe Ile Glu Lys Gln Leu Ile Asp Tyr Ala Lys
725 730 735

Asn Ser Lys Lys Val Val Gly Asn Ser Thr Ser Leu Leu Ser Pro Tyr
740 745 750

Leu His Phe Gly Glu Ile Ser Val Arg His Val Phe Gln Cys Ala Arg
755 760 765

Met Lys Gln Ile Ile Trp Ala Arg Asp Lys Asn Ser Glu Gly Glu Glu
770 775 780

Ser Ala Asp Leu Phe Leu Arg Gly Ile Gly Leu Arg Glu Tyr Ser Arg
785 790 795 800

Tyr Ile Cys Phe Asn Phe Pro Phe Thr His Glu Gln Ser Leu Leu Ser
805 810 815

His Leu Arg Phe Phe Pro Trp Asp Ala Asp Val Asp Lys Phe Lys Ala
820 825 830

Trp Arg Gln Gly Arg Thr Gly Tyr Pro Leu Val Asp Ala Gly Met Arg
835 840 845

Glu Leu Trp Ala Thr Gly Trp Met His Asn Arg Ile Arg Val Ile Val
850 855 860

Ser Ser Phe Ala Val Lys Phe Leu Leu Leu Pro Trp Lys Trp Gly Met
865 870 875 880

Lys Tyr Phe Trp Asp Thr Leu Leu Asp Ala Asp Leu Glu Cys Asp Ile
885 890 895

Leu Gly Trp Gln Tyr Ile Ser Gly Ser Ile Pro Asp Gly His Glu Leu
900 905 910

Asp Arg Leu Asp Asn Pro Ala Leu Gln Gly Ala Lys Tyr Asp Pro Glu
915 920 925

Gly Glu Tyr Ile Arg Gln Trp Leu Pro Glu Leu Ala Arg Leu Pro Thr
930 935 940

Glu Trp Ile His His Pro Trp Asp Ala Pro Leu Thr Val Leu Lys Ala
945 950 955 960

Ser Gly Val Glu Leu Gly Thr Asn Tyr Ala Lys Pro Ile Val Asp Ile
965 970 975

Asp Thr Ala Arg Glu Leu Leu Ala Lys Ala Ile Ser Arg Thr Arg Gly
980 985 990

Ala Gln Ile Met Ile Gly Ala Ala
995 1000

<210> SEQ ID NO 87
<211> LENGTH: 862
<212> TYPE: PRT

<213> ORGANISM: Artificial Sequence
<220> FEATURE:
<223> OTHER INFORMATION: Synthetic construct

<400> SEQUENCE: 87

```
Met Gly Phe Val Thr Glu Pro Gln Glu Glu Ser Glu Glu Glu Val Glu
1               5                   10                  15

Glu Pro Glu Glu Arg Gln Gln Thr Pro Glu Val Val Pro Asp Asp Ser
            20                  25                  30

Gly Thr Phe Tyr Asp Gln Ala Val Val Ser Asn Asp Met Glu Glu His
        35                  40                  45

Leu Glu Glu Pro Val Ala Glu Pro Glu Pro Asp Pro Glu Pro Glu Pro
    50                  55                  60

Glu Gln Glu Pro Val Ser Glu Ile Gln Glu Glu Lys Pro Glu Pro Val
65                  70                  75                  80

Leu Glu Glu Thr Ala Pro Glu Asp Ala Gln Lys Ser Ser Ser Pro Ala
                85                  90                  95

Pro Ala Asp Ile Ala Gln Thr Val Gln Glu Asp Leu Arg Thr Phe Ser
            100                 105                 110

Trp Ala Ser Val Thr Ser Lys Asn Leu Pro Pro Ser Gly Ala Val Pro
        115                 120                 125

Val Thr Gly Ile Pro Pro His Val Val Lys Val Pro Ala Ser Gln Pro
    130                 135                 140

Arg Pro Glu Ser Lys Pro Glu Ser Gln Ile Pro Pro Gln Arg Pro Gln
145                 150                 155                 160

Arg Asp Gln Arg Val Arg Glu Gln Arg Ile Asn Ile Pro Pro Gln Arg
                165                 170                 175

Gly Pro Arg Pro Ile Arg Glu Ala Gly Glu Gln Gly Asp Ile Glu Pro
            180                 185                 190

Arg Arg Met Val Arg His Pro Asp Ser His Gln Leu Phe Ile Gly Asn
        195                 200                 205

Leu Pro His Glu Val Asp Lys Ser Glu Leu Lys Asp Phe Phe Gln Ser
    210                 215                 220

Tyr Gly Asn Val Val Glu Leu Arg Ile Asn Ser Gly Gly Lys Leu Pro
225                 230                 235                 240

Asn Phe Gly Phe Val Val Phe Asp Asp Ser Glu Pro Val Gln Lys Val
                245                 250                 255

Leu Ser Asn Arg Pro Ile Met Phe Arg Gly Glu Val Arg Leu Asn Val
            260                 265                 270

Glu Glu Lys Lys Thr Arg Ala Ala Arg Glu Gly Asp Arg Arg Asp Asn
        275                 280                 285

Arg Leu Arg Gly Pro Gly Gly Pro Arg Gly Gly Leu Gly Gly Gly Met
    290                 295                 300

Arg Gly Pro Pro Arg Gly Gly Met Val Gln Lys Pro Gly Phe Gly Val
305                 310                 315                 320

Gly Arg Gly Leu Ala Pro Arg Gln Lys Leu Ile Pro Met Ala Arg Arg
                325                 330                 335

Ala Trp Leu Glu His Gly His Ser Cys Phe Leu Cys Glu Ile Val Ile
            340                 345                 350

Arg Ser Gln Phe His Thr Thr Tyr Glu Pro Glu Ala Met Lys Met Asp
        355                 360                 365

Lys Lys Thr Ile Val Trp Phe Arg Arg Asp Leu Arg Ile Glu Asp Asn
    370                 375                 380
```

-continued

```
Pro Ala Leu Ala Ala Ala Ala His Glu Gly Ser Val Phe Pro Val Phe
385                 390                 395                 400

Ile Trp Cys Pro Glu Glu Glu Gly Gln Phe Tyr Pro Gly Arg Ala Ser
                405                 410                 415

Arg Trp Trp Met Lys Gln Ser Leu Ala His Leu Ser Gln Ser Leu Lys
            420                 425                 430

Ala Leu Gly Ser Asp Leu Thr Leu Ile Lys Thr His Asn Thr Ile Ser
        435                 440                 445

Ala Ile Leu Asp Cys Ile Arg Val Thr Gly Ala Thr Lys Val Val Phe
    450                 455                 460

Asn His Leu Tyr Asp Pro Val Ser Leu Val Arg Asp His Thr Val Lys
465                 470                 475                 480

Glu Lys Leu Val Glu Arg Gly Ile Ser Val Gln Ser Tyr Asn Gly Asp
                485                 490                 495

Leu Leu Tyr Glu Pro Trp Glu Ile Tyr Cys Glu Lys Gly Lys Pro Phe
            500                 505                 510

Thr Ser Phe Asn Ser Tyr Trp Lys Lys Cys Leu Asp Met Ser Ile Glu
        515                 520                 525

Ser Val Met Leu Pro Pro Pro Trp Arg Leu Met Pro Ile Thr Ala Ala
    530                 535                 540

Ala Glu Ala Ile Trp Ala Cys Ser Ile Glu Glu Leu Gly Leu Glu Asn
545                 550                 555                 560

Glu Ala Glu Lys Pro Ser Asn Ala Leu Leu Thr Arg Ala Trp Ser Pro
                565                 570                 575

Gly Trp Ser Asn Ala Asp Lys Leu Leu Asn Glu Phe Ile Glu Lys Gln
            580                 585                 590

Leu Ile Asp Tyr Ala Lys Asn Ser Lys Lys Val Val Gly Asn Ser Thr
        595                 600                 605

Ser Leu Leu Ser Pro Tyr Leu His Phe Gly Glu Ile Ser Val Arg His
    610                 615                 620

Val Phe Gln Cys Ala Arg Met Lys Gln Ile Ile Trp Ala Arg Asp Lys
625                 630                 635                 640

Asn Ser Glu Gly Glu Glu Ser Ala Asp Leu Phe Leu Arg Gly Ile Gly
                645                 650                 655

Leu Arg Glu Tyr Ser Arg Tyr Ile Cys Phe Asn Phe Pro Phe Thr His
            660                 665                 670

Glu Gln Ser Leu Leu Ser His Leu Arg Phe Phe Pro Trp Asp Ala Asp
        675                 680                 685

Val Asp Lys Phe Lys Ala Trp Arg Gln Gly Arg Thr Gly Tyr Pro Leu
    690                 695                 700

Val Asp Ala Gly Met Arg Glu Leu Trp Ala Thr Gly Trp Met His Asn
705                 710                 715                 720

Arg Ile Arg Val Ile Val Ser Ser Phe Ala Val Lys Phe Leu Leu Leu
                725                 730                 735

Pro Trp Lys Trp Gly Met Lys Tyr Phe Trp Asp Thr Leu Leu Asp Ala
            740                 745                 750

Asp Leu Glu Cys Asp Ile Leu Gly Trp Gln Tyr Ile Ser Gly Ser Ile
        755                 760                 765

Pro Asp Gly His Glu Leu Asp Arg Leu Asp Asn Pro Ala Leu Gln Gly
    770                 775                 780

Ala Lys Tyr Asp Pro Glu Gly Glu Tyr Ile Arg Gln Trp Leu Pro Glu
785                 790                 795                 800
```

Leu Ala Arg Leu Pro Thr Glu Trp Ile His His Pro Trp Asp Ala Pro
805 810 815

Leu Thr Val Leu Lys Ala Ser Gly Val Glu Leu Gly Thr Asn Tyr Ala
820 825 830

Lys Pro Ile Val Asp Ile Asp Thr Ala Arg Glu Leu Leu Ala Lys Ala
835 840 845

Ile Ser Arg Thr Arg Gly Ala Gln Ile Met Ile Gly Ala Ala
850 855 860

<210> SEQ ID NO 88
<211> LENGTH: 918
<212> TYPE: PRT
<213> ORGANISM: Artificial Sequence
<220> FEATURE:
<223> OTHER INFORMATION: Synthetic construct

<400> SEQUENCE: 88

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Thr Ala Pro Glu Asp
130 135 140

Ala Gln Lys Ser Ser Ser Pro Ala Pro Ala Asp Ile Ala Gln Thr Val
145 150 155 160

Gln Glu Asp Leu Arg Thr Phe Ser Trp Ala Ser Val Thr Ser Lys Asn
165 170 175

Leu Pro Pro Ser Gly Ala Val Pro Val Thr Gly Ile Pro Pro His Val
180 185 190

Val Lys Val Pro Ala Ser Gln Pro Arg Pro Glu Ser Lys Pro Glu Ser
195 200 205

Gln Ile Pro Pro Gln Arg Pro Gln Arg Asp Gln Arg Val Arg Glu Gln
210 215 220

Arg Ile Asn Ile Pro Pro Gln Arg Gly Pro Arg Pro Ile Arg Glu Ala
225 230 235 240

Gly Glu Gln Gly Asp Ile Glu Pro Arg Arg Met Val Arg His Pro Asp
245 250 255

Ser His Gln Leu Phe Ile Gly Asn Leu Pro His Glu Val Asp Lys Ser
260 265 270

Glu Leu Lys Asp Phe Phe Gln Ser Tyr Gly Asn Val Val Glu Leu Arg
275 280 285

Ile Asn Ser Gly Gly Lys Leu Pro Asn Phe Gly Phe Val Val Phe Asp
290 295 300

-continued

```
Asp Ser Glu Pro Val Gln Lys Val Leu Ser Asn Arg Pro Ile Met Phe
305                 310                 315                 320

Arg Gly Glu Val Arg Leu Asn Val Glu Glu Lys Lys Thr Arg Ala Ala
                325                 330                 335

Arg Glu Gly Asp Arg Arg Asp Asn Arg Leu Arg Gly Pro Gly Gly Pro
            340                 345                 350

Arg Gly Gly Leu Gly Gly Gly Met Arg Gly Pro Pro Arg Gly Gly Met
        355                 360                 365

Val Gln Lys Pro Gly Phe Gly Val Gly Arg Gly Leu Ala Pro Arg Gln
    370                 375                 380

Lys Leu Ile Pro Met Ala Arg Arg Ala Trp Leu Glu His Gly His Ser
385                 390                 395                 400

Cys Phe Leu Cys Glu Ile Val Ile Arg Ser Gln Phe His Thr Thr Tyr
                405                 410                 415

Glu Pro Glu Ala Met Lys Met Asp Lys Lys Thr Ile Val Trp Phe Arg
            420                 425                 430

Arg Asp Leu Arg Ile Glu Asp Asn Pro Ala Leu Ala Ala Ala Ala His
        435                 440                 445

Glu Gly Ser Val Phe Pro Val Phe Ile Trp Cys Pro Glu Glu Glu Gly
    450                 455                 460

Gln Phe Tyr Pro Gly Arg Ala Ser Arg Trp Trp Met Lys Gln Ser Leu
465                 470                 475                 480

Ala His Leu Ser Gln Ser Leu Lys Ala Leu Gly Ser Asp Leu Thr Leu
                485                 490                 495

Ile Lys Thr His Asn Thr Ile Ser Ala Ile Leu Asp Cys Ile Arg Val
            500                 505                 510

Thr Gly Ala Thr Lys Val Val Phe Asn His Leu Tyr Asp Pro Val Ser
        515                 520                 525

Leu Val Arg Asp His Thr Val Lys Glu Lys Leu Val Glu Arg Gly Ile
    530                 535                 540

Ser Val Gln Ser Tyr Asn Gly Asp Leu Leu Tyr Glu Pro Trp Glu Ile
545                 550                 555                 560

Tyr Cys Glu Lys Gly Lys Pro Phe Thr Ser Phe Asn Ser Tyr Trp Lys
                565                 570                 575

Lys Cys Leu Asp Met Ser Ile Glu Ser Val Met Leu Pro Pro Pro Trp
            580                 585                 590

Arg Leu Met Pro Ile Thr Ala Ala Ala Glu Ala Ile Trp Ala Cys Ser
        595                 600                 605

Ile Glu Glu Leu Gly Leu Glu Asn Glu Ala Glu Lys Pro Ser Asn Ala
    610                 615                 620

Leu Leu Thr Arg Ala Trp Ser Pro Gly Trp Ser Asn Ala Asp Lys Leu
625                 630                 635                 640

Leu Asn Glu Phe Ile Glu Lys Gln Leu Ile Asp Tyr Ala Lys Asn Ser
                645                 650                 655

Lys Lys Val Val Gly Asn Ser Thr Ser Leu Leu Ser Pro Tyr Leu His
            660                 665                 670

Phe Gly Glu Ile Ser Val Arg His Val Phe Gln Cys Ala Arg Met Lys
        675                 680                 685

Gln Ile Ile Trp Ala Arg Asp Lys Asn Ser Glu Gly Glu Glu Ser Ala
    690                 695                 700

Asp Leu Phe Leu Arg Gly Ile Gly Leu Arg Glu Tyr Ser Arg Tyr Ile
705                 710                 715                 720
```

```
Cys Phe Asn Phe Pro Phe Thr His Glu Gln Ser Leu Leu Ser His Leu
                725                 730                 735

Arg Phe Phe Pro Trp Asp Ala Asp Val Asp Lys Phe Lys Ala Trp Arg
            740                 745                 750

Gln Gly Arg Thr Gly Tyr Pro Leu Val Asp Ala Gly Met Arg Glu Leu
        755                 760                 765

Trp Ala Thr Gly Trp Met His Asn Arg Ile Arg Val Ile Val Ser Ser
    770                 775                 780

Phe Ala Val Lys Phe Leu Leu Leu Pro Trp Lys Trp Gly Met Lys Tyr
785                 790                 795                 800

Phe Trp Asp Thr Leu Leu Asp Ala Asp Leu Glu Cys Asp Ile Leu Gly
                805                 810                 815

Trp Gln Tyr Ile Ser Gly Ser Ile Pro Asp Gly His Glu Leu Asp Arg
            820                 825                 830

Leu Asp Asn Pro Ala Leu Gln Gly Ala Lys Tyr Asp Pro Glu Gly Glu
        835                 840                 845

Tyr Ile Arg Gln Trp Leu Pro Glu Leu Ala Arg Leu Pro Thr Glu Trp
    850                 855                 860

Ile His His Pro Trp Asp Ala Pro Leu Thr Val Leu Lys Ala Ser Gly
865                 870                 875                 880

Val Glu Leu Gly Thr Asn Tyr Ala Lys Pro Ile Val Asp Ile Asp Thr
                885                 890                 895

Ala Arg Glu Leu Leu Ala Lys Ala Ile Ser Arg Thr Arg Gly Ala Gln
            900                 905                 910

Ile Met Ile Gly Ala Ala
        915


<210> SEQ ID NO 89
<211> LENGTH: 881
<212> TYPE: PRT
<213> ORGANISM: Artificial Sequence
<220> FEATURE:
<223> OTHER INFORMATION: Synthetic construct

<400> SEQUENCE: 89

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160
```

-continued

```
Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Gln Leu Phe
    210                 215                 220

Ile Gly Asn Leu Pro His Glu Val Asp Lys Ser Glu Leu Lys Asp Phe
225                 230                 235                 240

Phe Gln Ser Tyr Gly Asn Val Val Glu Leu Arg Ile Asn Ser Gly Gly
                245                 250                 255

Lys Leu Pro Asn Phe Gly Phe Val Val Phe Asp Asp Ser Glu Pro Val
            260                 265                 270

Gln Lys Val Leu Ser Asn Arg Pro Ile Met Phe Arg Gly Glu Val Arg
        275                 280                 285

Leu Asn Val Glu Glu Lys Lys Thr Arg Ala Ala Arg Glu Gly Asp Arg
    290                 295                 300

Arg Asp Asn Arg Leu Arg Gly Pro Gly Gly Pro Arg Gly Gly Leu Gly
305                 310                 315                 320

Gly Gly Met Arg Gly Pro Pro Arg Gly Gly Met Val Gln Lys Pro Gly
                325                 330                 335

Phe Gly Val Gly Arg Gly Leu Ala Pro Arg Gln Lys Leu Ile Pro Met
            340                 345                 350

Ala Arg Arg Ala Trp Leu Glu His Gly His Ser Cys Phe Leu Cys Glu
        355                 360                 365

Ile Val Ile Arg Ser Gln Phe His Thr Thr Tyr Glu Pro Glu Ala Met
    370                 375                 380

Lys Met Asp Lys Lys Thr Ile Val Trp Phe Arg Arg Asp Leu Arg Ile
385                 390                 395                 400

Glu Asp Asn Pro Ala Leu Ala Ala Ala Ala His Glu Gly Ser Val Phe
                405                 410                 415

Pro Val Phe Ile Trp Cys Pro Glu Glu Glu Gly Gln Phe Tyr Pro Gly
            420                 425                 430

Arg Ala Ser Arg Trp Trp Met Lys Gln Ser Leu Ala His Leu Ser Gln
        435                 440                 445

Ser Leu Lys Ala Leu Gly Ser Asp Leu Thr Leu Ile Lys Thr His Asn
    450                 455                 460

Thr Ile Ser Ala Ile Leu Asp Cys Ile Arg Val Thr Gly Ala Thr Lys
465                 470                 475                 480

Val Val Phe Asn His Leu Tyr Asp Pro Val Ser Leu Val Arg Asp His
                485                 490                 495

Thr Val Lys Glu Lys Leu Val Glu Arg Gly Ile Ser Val Gln Ser Tyr
            500                 505                 510

Asn Gly Asp Leu Leu Tyr Glu Pro Trp Glu Ile Tyr Cys Glu Lys Gly
        515                 520                 525

Lys Pro Phe Thr Ser Phe Asn Ser Tyr Trp Lys Lys Cys Leu Asp Met
    530                 535                 540

Ser Ile Glu Ser Val Met Leu Pro Pro Pro Trp Arg Leu Met Pro Ile
545                 550                 555                 560

Thr Ala Ala Ala Glu Ala Ile Trp Ala Cys Ser Ile Glu Glu Leu Gly
                565                 570                 575
```

-continued

Leu Glu Asn Glu Ala Glu Lys Pro Ser Asn Ala Leu Leu Thr Arg Ala
580 585 590

Trp Ser Pro Gly Trp Ser Asn Ala Asp Lys Leu Leu Asn Glu Phe Ile
595 600 605

Glu Lys Gln Leu Ile Asp Tyr Ala Lys Asn Ser Lys Lys Val Val Gly
610 615 620

Asn Ser Thr Ser Leu Leu Ser Pro Tyr Leu His Phe Gly Glu Ile Ser
625 630 635 640

Val Arg His Val Phe Gln Cys Ala Arg Met Lys Gln Ile Ile Trp Ala
645 650 655

Arg Asp Lys Asn Ser Glu Gly Glu Glu Ser Ala Asp Leu Phe Leu Arg
660 665 670

Gly Ile Gly Leu Arg Glu Tyr Ser Arg Tyr Ile Cys Phe Asn Phe Pro
675 680 685

Phe Thr His Glu Gln Ser Leu Leu Ser His Leu Arg Phe Phe Pro Trp
690 695 700

Asp Ala Asp Val Asp Lys Phe Lys Ala Trp Arg Gln Gly Arg Thr Gly
705 710 715 720

Tyr Pro Leu Val Asp Ala Gly Met Arg Glu Leu Trp Ala Thr Gly Trp
725 730 735

Met His Asn Arg Ile Arg Val Ile Val Ser Ser Phe Ala Val Lys Phe
740 745 750

Leu Leu Leu Pro Trp Lys Trp Gly Met Lys Tyr Phe Trp Asp Thr Leu
755 760 765

Leu Asp Ala Asp Leu Glu Cys Asp Ile Leu Gly Trp Gln Tyr Ile Ser
770 775 780

Gly Ser Ile Pro Asp Gly His Glu Leu Asp Arg Leu Asp Asn Pro Ala
785 790 795 800

Leu Gln Gly Ala Lys Tyr Asp Pro Glu Gly Glu Tyr Ile Arg Gln Trp
805 810 815

Leu Pro Glu Leu Ala Arg Leu Pro Thr Glu Trp Ile His His Pro Trp
820 825 830

Asp Ala Pro Leu Thr Val Leu Lys Ala Ser Gly Val Glu Leu Gly Thr
835 840 845

Asn Tyr Ala Lys Pro Ile Val Asp Ile Asp Thr Ala Arg Glu Leu Leu
850 855 860

Ala Lys Ala Ile Ser Arg Thr Arg Gly Ala Gln Ile Met Ile Gly Ala
865 870 875 880

Ala

<210> SEQ ID NO 90
<211> LENGTH: 929
<212> TYPE: PRT
<213> ORGANISM: Artificial Sequence
<220> FEATURE:
<223> OTHER INFORMATION: Synthetic construct

<400> SEQUENCE: 90

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

-continued

```
Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Glu Lys Lys Thr Arg Ala Ala Arg Glu Gly Asp Arg
            340                 345                 350

Arg Asp Asn Arg Leu Arg Gly Pro Gly Gly Pro Arg Gly Gly Leu Gly
        355                 360                 365

Gly Gly Met Arg Gly Pro Pro Arg Gly Gly Met Val Gln Lys Pro Gly
    370                 375                 380

Phe Gly Val Gly Arg Gly Leu Ala Pro Arg Gln Lys Leu Ile Pro Met
385                 390                 395                 400

Ala Arg Arg Ala Trp Leu Glu His Gly His Ser Cys Phe Leu Cys Glu
                405                 410                 415

Ile Val Ile Arg Ser Gln Phe His Thr Thr Tyr Glu Pro Glu Ala Met
            420                 425                 430

Lys Met Asp Lys Lys Thr Ile Val Trp Phe Arg Arg Asp Leu Arg Ile
        435                 440                 445

Glu Asp Asn Pro Ala Leu Ala Ala Ala Ala His Glu Gly Ser Val Phe
    450                 455                 460
```

-continued

```
Pro Val Phe Ile Trp Cys Pro Glu Glu Glu Gly Gln Phe Tyr Pro Gly
465                 470                 475                 480

Arg Ala Ser Arg Trp Trp Met Lys Gln Ser Leu Ala His Leu Ser Gln
                485                 490                 495

Ser Leu Lys Ala Leu Gly Ser Asp Leu Thr Leu Ile Lys Thr His Asn
            500                 505                 510

Thr Ile Ser Ala Ile Leu Asp Cys Ile Arg Val Thr Gly Ala Thr Lys
        515                 520                 525

Val Val Phe Asn His Leu Tyr Asp Pro Val Ser Leu Val Arg Asp His
    530                 535                 540

Thr Val Lys Glu Lys Leu Val Glu Arg Gly Ile Ser Val Gln Ser Tyr
545                 550                 555                 560

Asn Gly Asp Leu Leu Tyr Glu Pro Trp Glu Ile Tyr Cys Glu Lys Gly
                565                 570                 575

Lys Pro Phe Thr Ser Phe Asn Ser Tyr Trp Lys Lys Cys Leu Asp Met
            580                 585                 590

Ser Ile Glu Ser Val Met Leu Pro Pro Pro Trp Arg Leu Met Pro Ile
        595                 600                 605

Thr Ala Ala Ala Glu Ala Ile Trp Ala Cys Ser Ile Glu Glu Leu Gly
    610                 615                 620

Leu Glu Asn Glu Ala Glu Lys Pro Ser Asn Ala Leu Leu Thr Arg Ala
625                 630                 635                 640

Trp Ser Pro Gly Trp Ser Asn Ala Asp Lys Leu Leu Asn Glu Phe Ile
                645                 650                 655

Glu Lys Gln Leu Ile Asp Tyr Ala Lys Asn Ser Lys Lys Val Val Gly
            660                 665                 670

Asn Ser Thr Ser Leu Leu Ser Pro Tyr Leu His Phe Gly Glu Ile Ser
        675                 680                 685

Val Arg His Val Phe Gln Cys Ala Arg Met Lys Gln Ile Ile Trp Ala
    690                 695                 700

Arg Asp Lys Asn Ser Glu Gly Glu Glu Ser Ala Asp Leu Phe Leu Arg
705                 710                 715                 720

Gly Ile Gly Leu Arg Glu Tyr Ser Arg Tyr Ile Cys Phe Asn Phe Pro
                725                 730                 735

Phe Thr His Glu Gln Ser Leu Leu Ser His Leu Arg Phe Phe Pro Trp
            740                 745                 750

Asp Ala Asp Val Asp Lys Phe Lys Ala Trp Arg Gln Gly Arg Thr Gly
        755                 760                 765

Tyr Pro Leu Val Asp Ala Gly Met Arg Glu Leu Trp Ala Thr Gly Trp
    770                 775                 780

Met His Asn Arg Ile Arg Val Ile Val Ser Ser Phe Ala Val Lys Phe
785                 790                 795                 800

Leu Leu Leu Pro Trp Lys Trp Gly Met Lys Tyr Phe Trp Asp Thr Leu
                805                 810                 815

Leu Asp Ala Asp Leu Glu Cys Asp Ile Leu Gly Trp Gln Tyr Ile Ser
            820                 825                 830

Gly Ser Ile Pro Asp Gly His Glu Leu Asp Arg Leu Asp Asn Pro Ala
        835                 840                 845

Leu Gln Gly Ala Lys Tyr Asp Pro Glu Gly Glu Tyr Ile Arg Gln Trp
    850                 855                 860

Leu Pro Glu Leu Ala Arg Leu Pro Thr Glu Trp Ile His His Pro Trp
865                 870                 875                 880
```

Asd Ala Pro Leu Thr Val Leu Lys Ala Ser Gly Val Glu Leu Gly Thr
885 890 895

Asn Tyr Ala Lys Pro Ile Val Asp Ile Asp Thr Ala Arg Glu Leu Leu
900 905 910

Ala Lys Ala Ile Ser Arg Thr Arg Gly Ala Gln Ile Met Ile Gly Ala
915 920 925

Ala

<210> SEQ ID NO 91
<211> LENGTH: 909
<212> TYPE: PRT
<213> ORGANISM: Artificial Sequence
<220> FEATURE:
<223> OTHER INFORMATION: Synthetic construct

<400> SEQUENCE: 91

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Thr Ala Pro
210 215 220

Glu Asp Ala Gln Lys Ser Ser Ser Pro Ala Pro Ala Asp Ile Ala Gln
225 230 235 240

Thr Val Gln Glu Asp Leu Arg Thr Phe Ser Trp Ala Ser Val Thr Ser
245 250 255

Lys Asn Leu Pro Pro Ser Gly Ala Val Pro Val Thr Gly Ile Pro Pro
260 265 270

His Val Val Lys Val Pro Ala Ser Gln Pro Arg Pro Glu Ser Lys Pro
275 280 285

Glu Ser Gln Ile Pro Pro Gln Arg Pro Gln Arg Asp Gln Arg Val Arg
290 295 300

-continued

```
Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Met Lys Met Asp Lys
                405                 410                 415

Lys Thr Ile Val Trp Phe Arg Arg Asp Leu Arg Ile Glu Asp Asn Pro
            420                 425                 430

Ala Leu Ala Ala Ala Ala His Glu Gly Ser Val Phe Pro Val Phe Ile
        435                 440                 445

Trp Cys Pro Glu Glu Glu Gly Gln Phe Tyr Pro Gly Arg Ala Ser Arg
    450                 455                 460

Trp Trp Met Lys Gln Ser Leu Ala His Leu Ser Gln Ser Leu Lys Ala
465                 470                 475                 480

Leu Gly Ser Asp Leu Thr Leu Ile Lys Thr His Asn Thr Ile Ser Ala
                485                 490                 495

Ile Leu Asp Cys Ile Arg Val Thr Gly Ala Thr Lys Val Val Phe Asn
            500                 505                 510

His Leu Tyr Asp Pro Val Ser Leu Val Arg Asp His Thr Val Lys Glu
        515                 520                 525

Lys Leu Val Glu Arg Gly Ile Ser Val Gln Ser Tyr Asn Gly Asp Leu
    530                 535                 540

Leu Tyr Glu Pro Trp Glu Ile Tyr Cys Glu Lys Gly Lys Pro Phe Thr
545                 550                 555                 560

Ser Phe Asn Ser Tyr Trp Lys Lys Cys Leu Asp Met Ser Ile Glu Ser
                565                 570                 575

Val Met Leu Pro Pro Pro Trp Arg Leu Met Pro Ile Thr Ala Ala Ala
            580                 585                 590

Glu Ala Ile Trp Ala Cys Ser Ile Glu Glu Leu Gly Leu Glu Asn Glu
        595                 600                 605

Ala Glu Lys Pro Ser Asn Ala Leu Leu Thr Arg Ala Trp Ser Pro Gly
    610                 615                 620

Trp Ser Asn Ala Asp Lys Leu Leu Asn Glu Phe Ile Glu Lys Gln Leu
625                 630                 635                 640

Ile Asp Tyr Ala Lys Asn Ser Lys Lys Val Val Gly Asn Ser Thr Ser
                645                 650                 655

Leu Leu Ser Pro Tyr Leu His Phe Gly Glu Ile Ser Val Arg His Val
            660                 665                 670

Phe Gln Cys Ala Arg Met Lys Gln Ile Ile Trp Ala Arg Asp Lys Asn
        675                 680                 685

Ser Glu Gly Glu Glu Ser Ala Asp Leu Phe Leu Arg Gly Ile Gly Leu
    690                 695                 700

Arg Glu Tyr Ser Arg Tyr Ile Cys Phe Asn Phe Pro Phe Thr His Glu
705                 710                 715                 720
```

Gln Ser Leu Leu Ser His Leu Arg Phe Phe Pro Trp Asp Ala Asp Val
725 730 735

Asp Lys Phe Lys Ala Trp Arg Gln Gly Arg Thr Gly Tyr Pro Leu Val
740 745 750

Asp Ala Gly Met Arg Glu Leu Trp Ala Thr Gly Trp Met His Asn Arg
755 760 765

Ile Arg Val Ile Val Ser Ser Phe Ala Val Lys Phe Leu Leu Leu Pro
770 775 780

Trp Lys Trp Gly Met Lys Tyr Phe Trp Asp Thr Leu Leu Asp Ala Asp
785 790 795 800

Leu Glu Cys Asp Ile Leu Gly Trp Gln Tyr Ile Ser Gly Ser Ile Pro
805 810 815

Asp Gly His Glu Leu Asp Arg Leu Asp Asn Pro Ala Leu Gln Gly Ala
820 825 830

Lys Tyr Asp Pro Glu Gly Glu Tyr Ile Arg Gln Trp Leu Pro Glu Leu
835 840 845

Ala Arg Leu Pro Thr Glu Trp Ile His His Pro Trp Asp Ala Pro Leu
850 855 860

Thr Val Leu Lys Ala Ser Gly Val Glu Leu Gly Thr Asn Tyr Ala Lys
865 870 875 880

Pro Ile Val Asp Ile Asp Thr Ala Arg Glu Leu Leu Ala Lys Ala Ile
885 890 895

Ser Arg Thr Arg Gly Ala Gln Ile Met Ile Gly Ala Ala
900 905

<210> SEQ ID NO 92
<211> LENGTH: 838
<212> TYPE: PRT
<213> ORGANISM: Artificial Sequence
<220> FEATURE:
<223> OTHER INFORMATION: Synthetic construct

<400> SEQUENCE: 92

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

-continued

```
Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Met Lys Met Asp Lys Lys Thr Ile Val Trp Phe Arg
            340                 345                 350

Arg Asp Leu Arg Ile Glu Asp Asn Pro Ala Leu Ala Ala Ala Ala His
        355                 360                 365

Glu Gly Ser Val Phe Pro Val Phe Ile Trp Cys Pro Glu Glu Glu Gly
    370                 375                 380

Gln Phe Tyr Pro Gly Arg Ala Ser Arg Trp Trp Met Lys Gln Ser Leu
385                 390                 395                 400

Ala His Leu Ser Gln Ser Leu Lys Ala Leu Gly Ser Asp Leu Thr Leu
                405                 410                 415

Ile Lys Thr His Asn Thr Ile Ser Ala Ile Leu Asp Cys Ile Arg Val
            420                 425                 430

Thr Gly Ala Thr Lys Val Val Phe Asn His Leu Tyr Asp Pro Val Ser
        435                 440                 445

Leu Val Arg Asp His Thr Val Lys Glu Lys Leu Val Glu Arg Gly Ile
    450                 455                 460

Ser Val Gln Ser Tyr Asn Gly Asp Leu Leu Tyr Glu Pro Trp Glu Ile
465                 470                 475                 480

Tyr Cys Glu Lys Gly Lys Pro Phe Thr Ser Phe Asn Ser Tyr Trp Lys
                485                 490                 495

Lys Cys Leu Asp Met Ser Ile Glu Ser Val Met Leu Pro Pro Pro Trp
            500                 505                 510

Arg Leu Met Pro Ile Thr Ala Ala Ala Glu Ala Ile Trp Ala Cys Ser
        515                 520                 525

Ile Glu Glu Leu Gly Leu Glu Asn Glu Ala Glu Lys Pro Ser Asn Ala
    530                 535                 540

Leu Leu Thr Arg Ala Trp Ser Pro Gly Trp Ser Asn Ala Asp Lys Leu
545                 550                 555                 560

Leu Asn Glu Phe Ile Glu Lys Gln Leu Ile Asp Tyr Ala Lys Asn Ser
                565                 570                 575

Lys Lys Val Val Gly Asn Ser Thr Ser Leu Leu Ser Pro Tyr Leu His
            580                 585                 590
```

-continued

Phe Gly Glu Ile Ser Val Arg His Val Phe Gln Cys Ala Arg Met Lys
595 600 605

Gln Ile Ile Trp Ala Arg Asp Lys Asn Ser Glu Gly Glu Glu Ser Ala
610 615 620

Asp Leu Phe Leu Arg Gly Ile Gly Leu Arg Glu Tyr Ser Arg Tyr Ile
625 630 635 640

Cys Phe Asn Phe Pro Phe Thr His Glu Gln Ser Leu Leu Ser His Leu
645 650 655

Arg Phe Phe Pro Trp Asp Ala Asp Val Asp Lys Phe Lys Ala Trp Arg
660 665 670

Gln Gly Arg Thr Gly Tyr Pro Leu Val Asp Ala Gly Met Arg Glu Leu
675 680 685

Trp Ala Thr Gly Trp Met His Asn Arg Ile Arg Val Ile Val Ser Ser
690 695 700

Phe Ala Val Lys Phe Leu Leu Leu Pro Trp Lys Trp Gly Met Lys Tyr
705 710 715 720

Phe Trp Asp Thr Leu Leu Asp Ala Asp Leu Glu Cys Asp Ile Leu Gly
725 730 735

Trp Gln Tyr Ile Ser Gly Ser Ile Pro Asp Gly His Glu Leu Asp Arg
740 745 750

Leu Asp Asn Pro Ala Leu Gln Gly Ala Lys Tyr Asp Pro Glu Gly Glu
755 760 765

Tyr Ile Arg Gln Trp Leu Pro Glu Leu Ala Arg Leu Pro Thr Glu Trp
770 775 780

Ile His His Pro Trp Asp Ala Pro Leu Thr Val Leu Lys Ala Ser Gly
785 790 795 800

Val Glu Leu Gly Thr Asn Tyr Ala Lys Pro Ile Val Asp Ile Asp Thr
805 810 815

Ala Arg Glu Leu Leu Ala Lys Ala Ile Ser Arg Thr Arg Gly Ala Gln
820 825 830

Ile Met Ile Gly Ala Ala
835

<210> SEQ ID NO 93
<211> LENGTH: 1000
<212> TYPE: PRT
<213> ORGANISM: Artificial Sequence
<220> FEATURE:
<223> OTHER INFORMATION: Synthetic construct

<400> SEQUENCE: 93

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

-continued

```
His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525
```

-continued

```
His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670

Asp Gln Ala Val Val Ser Asn Asp Met Glu Glu His Leu Glu Glu Pro
        675                 680                 685

Val Ala Glu Pro Glu Pro Asp Pro Glu Pro Glu Pro Glu Gln Glu Pro
    690                 695                 700

Val Ser Glu Ile Gln Glu Glu Lys Pro Glu Pro Val Leu Glu Glu Thr
705                 710                 715                 720

Ala Pro Glu Asp Ala Gln Lys Ser Ser Ser Pro Ala Pro Ala Asp Ile
                725                 730                 735

Ala Gln Thr Val Gln Glu Asp Leu Arg Thr Phe Ser Trp Ala Ser Val
            740                 745                 750

Thr Ser Lys Asn Leu Pro Pro Ser Gly Ala Val Pro Val Thr Gly Ile
        755                 760                 765

Pro Pro His Val Val Lys Val Pro Ala Ser Gln Pro Arg Pro Glu Ser
    770                 775                 780

Lys Pro Glu Ser Gln Ile Pro Pro Gln Arg Pro Gln Arg Asp Gln Arg
785                 790                 795                 800

Val Arg Glu Gln Arg Ile Asn Ile Pro Pro Gln Arg Gly Pro Arg Pro
                805                 810                 815

Ile Arg Glu Ala Gly Glu Gln Gly Asp Ile Glu Pro Arg Arg Met Val
            820                 825                 830

Arg His Pro Asp Ser His Gln Leu Phe Ile Gly Asn Leu Pro His Glu
        835                 840                 845

Val Asp Lys Ser Glu Leu Lys Asp Phe Phe Gln Ser Tyr Gly Asn Val
    850                 855                 860

Val Glu Leu Arg Ile Asn Ser Gly Gly Lys Leu Pro Asn Phe Gly Phe
865                 870                 875                 880

Val Val Phe Asp Asp Ser Glu Pro Val Gln Lys Val Leu Ser Asn Arg
                885                 890                 895

Pro Ile Met Phe Arg Gly Glu Val Arg Leu Asn Val Glu Glu Lys Lys
            900                 905                 910

Thr Arg Ala Ala Arg Glu Gly Asp Arg Arg Asp Asn Arg Leu Arg Gly
        915                 920                 925

Pro Gly Gly Pro Arg Gly Gly Leu Gly Gly Gly Met Arg Gly Pro Pro
    930                 935                 940
```

Arg Gly Gly Met Val Gln Lys Pro Gly Phe Gly Val Gly Arg Gly Leu
945 950 955 960

Ala Pro Arg Gln Lys Leu Ile Pro Met Ala Arg Arg Ala Trp Leu Glu
965 970 975

His Gly His Ser Cys Phe Leu Cys Glu Ile Val Ile Arg Ser Gln Phe
980 985 990

His Thr Thr Tyr Glu Pro Glu Ala
995 1000

<210> SEQ ID NO 94
<211> LENGTH: 862
<212> TYPE: PRT
<213> ORGANISM: Artificial Sequence
<220> FEATURE:
<223> OTHER INFORMATION: Synthetic construct

<400> SEQUENCE: 94

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

Gly Asn Ser Thr Ser Leu Leu Ser Pro Tyr Leu His Phe Gly Glu Ile
245 250 255

Ser Val Arg His Val Phe Gln Cys Ala Arg Met Lys Gln Ile Ile Trp
260 265 270

Ala Arg Asp Lys Asn Ser Glu Gly Glu Glu Ser Ala Asp Leu Phe Leu
275 280 285

Arg Gly Ile Gly Leu Arg Glu Tyr Ser Arg Tyr Ile Cys Phe Asn Phe
290 295 300

-continued

```
Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Gly Phe Val Thr Glu Pro Gln Glu Glu Ser Glu Glu Glu
            500                 505                 510

Val Glu Glu Pro Glu Glu Arg Gln Gln Thr Pro Glu Val Val Pro Asp
        515                 520                 525

Asp Ser Gly Thr Phe Tyr Asp Gln Ala Val Val Ser Asn Asp Met Glu
    530                 535                 540

Glu His Leu Glu Glu Pro Val Ala Glu Pro Glu Pro Asp Pro Glu Pro
545                 550                 555                 560

Glu Pro Glu Gln Glu Pro Val Ser Glu Ile Gln Glu Glu Lys Pro Glu
                565                 570                 575

Pro Val Leu Glu Glu Thr Ala Pro Glu Asp Ala Gln Lys Ser Ser Ser
            580                 585                 590

Pro Ala Pro Ala Asp Ile Ala Gln Thr Val Gln Glu Asp Leu Arg Thr
        595                 600                 605

Phe Ser Trp Ala Ser Val Thr Ser Lys Asn Leu Pro Pro Ser Gly Ala
    610                 615                 620

Val Pro Val Thr Gly Ile Pro Pro His Val Val Lys Val Pro Ala Ser
625                 630                 635                 640

Gln Pro Arg Pro Glu Ser Lys Pro Glu Ser Gln Ile Pro Pro Gln Arg
                645                 650                 655

Pro Gln Arg Asp Gln Arg Val Arg Glu Gln Arg Ile Asn Ile Pro Pro
            660                 665                 670

Gln Arg Gly Pro Arg Pro Ile Arg Glu Ala Gly Glu Gln Gly Asp Ile
        675                 680                 685

Glu Pro Arg Arg Met Val Arg His Pro Asp Ser His Gln Leu Phe Ile
    690                 695                 700

Gly Asn Leu Pro His Glu Val Asp Lys Ser Glu Leu Lys Asp Phe Phe
705                 710                 715                 720
```

```
Gln Ser Tyr Gly Asn Val Val Glu Leu Arg Ile Asn Ser Gly Gly Lys
                725                 730                 735

Leu Pro Asn Phe Gly Phe Val Val Phe Asp Asp Ser Glu Pro Val Gln
            740                 745                 750

Lys Val Leu Ser Asn Arg Pro Ile Met Phe Arg Gly Glu Val Arg Leu
        755                 760                 765

Asn Val Glu Glu Lys Lys Thr Arg Ala Ala Arg Glu Gly Asp Arg Arg
    770                 775                 780

Asp Asn Arg Leu Arg Gly Pro Gly Gly Pro Arg Gly Gly Leu Gly Gly
785                 790                 795                 800

Gly Met Arg Gly Pro Pro Arg Gly Gly Met Val Gln Lys Pro Gly Phe
                805                 810                 815

Gly Val Gly Arg Gly Leu Ala Pro Arg Gln Lys Leu Ile Pro Met Ala
            820                 825                 830

Arg Arg Ala Trp Leu Glu His Gly His Ser Cys Phe Leu Cys Glu Ile
        835                 840                 845

Val Ile Arg Ser Gln Phe His Thr Thr Tyr Glu Pro Glu Ala
    850                 855                 860


<210> SEQ ID NO 95
<211> LENGTH: 918
<212> TYPE: PRT
<213> ORGANISM: Artificial Sequence
<220> FEATURE:
<223> OTHER INFORMATION: Synthetic construct

<400> SEQUENCE: 95

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220
```

-continued

```
Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Thr Ala Pro
625                 630                 635                 640
```

-continued

```
Glu Asp Ala Gln Lys Ser Ser Ser Pro Ala Pro Ala Asp Ile Ala Gln
                645                 650                 655

Thr Val Gln Glu Asp Leu Arg Thr Phe Ser Trp Ala Ser Val Thr Ser
            660                 665                 670

Lys Asn Leu Pro Pro Ser Gly Ala Val Pro Val Thr Gly Ile Pro Pro
        675                 680                 685

His Val Val Lys Val Pro Ala Ser Gln Pro Arg Pro Glu Ser Lys Pro
    690                 695                 700

Glu Ser Gln Ile Pro Pro Gln Arg Pro Gln Arg Asp Gln Arg Val Arg
705                 710                 715                 720

Glu Gln Arg Ile Asn Ile Pro Pro Gln Arg Gly Pro Arg Pro Ile Arg
                725                 730                 735

Glu Ala Gly Glu Gln Gly Asp Ile Glu Pro Arg Arg Met Val Arg His
            740                 745                 750

Pro Asp Ser His Gln Leu Phe Ile Gly Asn Leu Pro His Glu Val Asp
        755                 760                 765

Lys Ser Glu Leu Lys Asp Phe Phe Gln Ser Tyr Gly Asn Val Val Glu
    770                 775                 780

Leu Arg Ile Asn Ser Gly Gly Lys Leu Pro Asn Phe Gly Phe Val Val
785                 790                 795                 800

Phe Asp Asp Ser Glu Pro Val Gln Lys Val Leu Ser Asn Arg Pro Ile
                805                 810                 815

Met Phe Arg Gly Glu Val Arg Leu Asn Val Glu Glu Lys Lys Thr Arg
            820                 825                 830

Ala Ala Arg Glu Gly Asp Arg Arg Asp Asn Arg Leu Arg Gly Pro Gly
        835                 840                 845

Gly Pro Arg Gly Gly Leu Gly Gly Gly Met Arg Gly Pro Pro Arg Gly
    850                 855                 860

Gly Met Val Gln Lys Pro Gly Phe Gly Val Gly Arg Gly Leu Ala Pro
865                 870                 875                 880

Arg Gln Lys Leu Ile Pro Met Ala Arg Arg Ala Trp Leu Glu His Gly
                885                 890                 895

His Ser Cys Phe Leu Cys Glu Ile Val Ile Arg Ser Gln Phe His Thr
            900                 905                 910

Thr Tyr Glu Pro Glu Ala
        915


<210> SEQ ID NO 96
<211> LENGTH: 881
<212> TYPE: PRT
<213> ORGANISM: Artificial Sequence
<220> FEATURE:
<223> OTHER INFORMATION: Synthetic construct

<400> SEQUENCE: 96

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80
```

-continued

```
Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495
```

Ala Ala Met Val Met Glu Lys Pro Ser Pro Leu Leu Val Gly Arg Glu
500 505 510

Phe Val Arg Gln Tyr Tyr Thr Leu Leu Asn Gln Ala Pro Asp Met Leu
515 520 525

His Arg Phe Tyr Gly Lys Asn Ser Ser Tyr Val His Gly Gly Leu Asp
530 535 540

Ser Asn Gly Lys Pro Ala Asp Ala Val Tyr Gly Gln Lys Glu Ile His
545 550 555 560

Arg Lys Val Met Ser Gln Asn Phe Thr Asn Cys His Thr Lys Ile Arg
565 570 575

His Val Asp Ala His Ala Thr Leu Asn Asp Gly Val Val Val Gln Val
580 585 590

Met Gly Leu Leu Ser Asn Asn Asn Gln Ala Leu Arg Arg Phe Met Gln
595 600 605

Thr Phe Val Leu Ala Pro Glu Gly Ser Val Ala Asn Lys Phe Tyr Val
610 615 620

His Asn Asp Ile Phe Arg Tyr Gln Asp Glu Val Phe Gly Gly Phe Val
625 630 635 640

Thr Glu Pro Gln Glu Glu Ser Glu Glu Glu Val Glu Glu Pro Glu Glu
645 650 655

Arg Gln Gln Thr Pro Glu Val Val Pro Asp Asp Ser Gly Thr Phe Tyr
660 665 670

Asp Gln Ala Val Val Ser Asn Asp Met Glu Glu His Leu Glu Glu Pro
675 680 685

Val Ala Glu Pro Glu Pro Asp Pro Glu Pro Glu Pro Glu Gln Glu Pro
690 695 700

Val Ser Glu Ile Gln Glu Glu Lys Pro Glu Pro Val Leu Glu Glu Gln
705 710 715 720

Leu Phe Ile Gly Asn Leu Pro His Glu Val Asp Lys Ser Glu Leu Lys
725 730 735

Asp Phe Phe Gln Ser Tyr Gly Asn Val Val Glu Leu Arg Ile Asn Ser
740 745 750

Gly Gly Lys Leu Pro Asn Phe Gly Phe Val Val Phe Asp Asp Ser Glu
755 760 765

Pro Val Gln Lys Val Leu Ser Asn Arg Pro Ile Met Phe Arg Gly Glu
770 775 780

Val Arg Leu Asn Val Glu Glu Lys Lys Thr Arg Ala Ala Arg Glu Gly
785 790 795 800

Asp Arg Arg Asp Asn Arg Leu Arg Gly Pro Gly Gly Pro Arg Gly Gly
805 810 815

Leu Gly Gly Gly Met Arg Gly Pro Pro Arg Gly Gly Met Val Gln Lys
820 825 830

Pro Gly Phe Gly Val Gly Arg Gly Leu Ala Pro Arg Gln Lys Leu Ile
835 840 845

Pro Met Ala Arg Arg Ala Trp Leu Glu His Gly His Ser Cys Phe Leu
850 855 860

Cys Glu Ile Val Ile Arg Ser Gln Phe His Thr Thr Tyr Glu Pro Glu
865 870 875 880

Ala

<210> SEQ ID NO 97
<211> LENGTH: 929
<212> TYPE: PRT

-continued

<213> ORGANISM: Artificial Sequence
<220> FEATURE:
<223> OTHER INFORMATION: Synthetic construct

<400> SEQUENCE: 97

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

Ile Glu Lys Gln Leu Ile Asp Tyr Ala Lys Asn Ser Lys Lys Val Val
225 230 235 240

Gly Asn Ser Thr Ser Leu Leu Ser Pro Tyr Leu His Phe Gly Glu Ile
245 250 255

Ser Val Arg His Val Phe Gln Cys Ala Arg Met Lys Gln Ile Ile Trp
260 265 270

Ala Arg Asp Lys Asn Ser Glu Gly Glu Glu Ser Ala Asp Leu Phe Leu
275 280 285

Arg Gly Ile Gly Leu Arg Glu Tyr Ser Arg Tyr Ile Cys Phe Asn Phe
290 295 300

Pro Phe Thr His Glu Gln Ser Leu Leu Ser His Leu Arg Phe Phe Pro
305 310 315 320

Trp Asp Ala Asp Val Asp Lys Phe Lys Ala Trp Arg Gln Gly Arg Thr
325 330 335

Gly Tyr Pro Leu Val Asp Ala Gly Met Arg Glu Leu Trp Ala Thr Gly
340 345 350

Trp Met His Asn Arg Ile Arg Val Ile Val Ser Ser Phe Ala Val Lys
355 360 365

Phe Leu Leu Leu Pro Trp Lys Trp Gly Met Lys Tyr Phe Trp Asp Thr
370 375 380

-continued

```
Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640

Thr Glu Pro Gln Glu Glu Ser Glu Glu Glu Val Glu Glu Pro Glu Glu
                645                 650                 655

Arg Gln Gln Thr Pro Glu Val Val Pro Asp Asp Ser Gly Thr Phe Tyr
            660                 665                 670

Asp Gln Ala Val Val Ser Asn Asp Met Glu Glu His Leu Glu Glu Pro
        675                 680                 685

Val Ala Glu Pro Glu Pro Asp Pro Glu Pro Glu Pro Glu Gln Glu Pro
    690                 695                 700

Val Ser Glu Ile Gln Glu Glu Lys Pro Glu Pro Val Leu Glu Glu Thr
705                 710                 715                 720

Ala Pro Glu Asp Ala Gln Lys Ser Ser Ser Pro Ala Pro Ala Asp Ile
                725                 730                 735

Ala Gln Thr Val Gln Glu Asp Leu Arg Thr Phe Ser Trp Ala Ser Val
            740                 745                 750

Thr Ser Lys Asn Leu Pro Pro Ser Gly Ala Val Pro Val Thr Gly Ile
        755                 760                 765

Pro Pro His Val Val Lys Val Pro Ala Ser Gln Pro Arg Pro Glu Ser
    770                 775                 780

Lys Pro Glu Ser Gln Ile Pro Pro Gln Arg Pro Gln Arg Asp Gln Arg
785                 790                 795                 800
```

Val Arg Glu Gln Arg Ile Asn Ile Pro Pro Gln Arg Gly Pro Arg Pro
805 810 815

Ile Arg Glu Ala Gly Glu Gln Gly Asp Ile Glu Pro Arg Arg Met Val
820 825 830

Arg His Pro Asp Ser His Glu Lys Lys Thr Arg Ala Ala Arg Glu Gly
835 840 845

Asp Arg Arg Asp Asn Arg Leu Arg Gly Pro Gly Gly Pro Arg Gly Gly
850 855 860

Leu Gly Gly Gly Met Arg Gly Pro Pro Arg Gly Gly Met Val Gln Lys
865 870 875 880

Pro Gly Phe Gly Val Gly Arg Gly Leu Ala Pro Arg Gln Lys Leu Ile
885 890 895

Pro Met Ala Arg Arg Ala Trp Leu Glu His Gly His Ser Cys Phe Leu
900 905 910

Cys Glu Ile Val Ile Arg Ser Gln Phe His Thr Thr Tyr Glu Pro Glu
915 920 925

Ala

<210> SEQ ID NO 98
<211> LENGTH: 909
<212> TYPE: PRT
<213> ORGANISM: Artificial Sequence
<220> FEATURE:
<223> OTHER INFORMATION: Synthetic construct

<400> SEQUENCE: 98

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

Lys Val Val Phe Asn His Leu Tyr Asp Pro Val Ser Leu Val Arg Asp
100 105 110

His Thr Val Lys Glu Lys Leu Val Glu Arg Gly Ile Ser Val Gln Ser
115 120 125

Tyr Asn Gly Asp Leu Leu Tyr Glu Pro Trp Glu Ile Tyr Cys Glu Lys
130 135 140

Gly Lys Pro Phe Thr Ser Phe Asn Ser Tyr Trp Lys Lys Cys Leu Asp
145 150 155 160

Met Ser Ile Glu Ser Val Met Leu Pro Pro Pro Trp Arg Leu Met Pro
165 170 175

Ile Thr Ala Ala Ala Glu Ala Ile Trp Ala Cys Ser Ile Glu Glu Leu
180 185 190

Gly Leu Glu Asn Glu Ala Glu Lys Pro Ser Asn Ala Leu Leu Thr Arg
195 200 205

Ala Trp Ser Pro Gly Trp Ser Asn Ala Asp Lys Leu Leu Asn Glu Phe
210 215 220

```
Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Val Met Glu Lys Pro Ser Pro Leu Leu Val Gly Arg Glu
            500                 505                 510

Phe Val Arg Gln Tyr Tyr Thr Leu Leu Asn Gln Ala Pro Asp Met Leu
        515                 520                 525

His Arg Phe Tyr Gly Lys Asn Ser Ser Tyr Val His Gly Gly Leu Asp
    530                 535                 540

Ser Asn Gly Lys Pro Ala Asp Ala Val Tyr Gly Gln Lys Glu Ile His
545                 550                 555                 560

Arg Lys Val Met Ser Gln Asn Phe Thr Asn Cys His Thr Lys Ile Arg
                565                 570                 575

His Val Asp Ala His Ala Thr Leu Asn Asp Gly Val Val Val Gln Val
            580                 585                 590

Met Gly Leu Leu Ser Asn Asn Asn Gln Ala Leu Arg Arg Phe Met Gln
        595                 600                 605

Thr Phe Val Leu Ala Pro Glu Gly Ser Val Ala Asn Lys Phe Tyr Val
    610                 615                 620

His Asn Asp Ile Phe Arg Tyr Gln Asp Glu Val Phe Gly Gly Phe Val
625                 630                 635                 640
```

-continued

Thr Glu Pro Gln Glu Glu Ser Glu Glu Glu Val Glu Glu Pro Glu Glu
645 650 655

Arg Gln Gln Thr Pro Glu Val Val Pro Asp Asp Ser Gly Thr Phe Tyr
660 665 670

Asp Gln Ala Val Val Ser Asn Asp Met Glu Glu His Leu Glu Glu Pro
675 680 685

Val Ala Glu Pro Glu Pro Asp Pro Glu Pro Glu Pro Glu Gln Glu Pro
690 695 700

Val Ser Glu Ile Gln Glu Glu Lys Pro Glu Pro Val Leu Glu Glu Thr
705 710 715 720

Ala Pro Glu Asp Ala Gln Lys Ser Ser Ser Pro Ala Pro Ala Asp Ile
725 730 735

Ala Gln Thr Val Gln Glu Asp Leu Arg Thr Phe Ser Trp Ala Ser Val
740 745 750

Thr Ser Lys Asn Leu Pro Pro Ser Gly Ala Val Pro Val Thr Gly Ile
755 760 765

Pro Pro His Val Val Lys Val Pro Ala Ser Gln Pro Arg Pro Glu Ser
770 775 780

Lys Pro Glu Ser Gln Ile Pro Pro Gln Arg Pro Gln Arg Asp Gln Arg
785 790 795 800

Val Arg Glu Gln Arg Ile Asn Ile Pro Pro Gln Arg Gly Pro Arg Pro
805 810 815

Ile Arg Glu Ala Gly Glu Gln Gly Asp Ile Glu Pro Arg Arg Met Val
820 825 830

Arg His Pro Asp Ser His Gln Leu Phe Ile Gly Asn Leu Pro His Glu
835 840 845

Val Asp Lys Ser Glu Leu Lys Asp Phe Phe Gln Ser Tyr Gly Asn Val
850 855 860

Val Glu Leu Arg Ile Asn Ser Gly Gly Lys Leu Pro Asn Phe Gly Phe
865 870 875 880

Val Val Phe Asp Asp Ser Glu Pro Val Gln Lys Val Leu Ser Asn Arg
885 890 895

Pro Ile Met Phe Arg Gly Glu Val Arg Leu Asn Val Glu
900 905

<210> SEQ ID NO 99
<211> LENGTH: 838
<212> TYPE: PRT
<213> ORGANISM: Artificial Sequence
<220> FEATURE:
<223> OTHER INFORMATION: Synthetic construct

<400> SEQUENCE: 99

Met Lys Met Asp Lys Lys Thr Ile Val Trp Phe Arg Arg Asp Leu Arg
1 5 10 15

Ile Glu Asp Asn Pro Ala Leu Ala Ala Ala Ala His Glu Gly Ser Val
20 25 30

Phe Pro Val Phe Ile Trp Cys Pro Glu Glu Glu Gly Gln Phe Tyr Pro
35 40 45

Gly Arg Ala Ser Arg Trp Trp Met Lys Gln Ser Leu Ala His Leu Ser
50 55 60

Gln Ser Leu Lys Ala Leu Gly Ser Asp Leu Thr Leu Ile Lys Thr His
65 70 75 80

Asn Thr Ile Ser Ala Ile Leu Asp Cys Ile Arg Val Thr Gly Ala Thr
85 90 95

```
Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Met Val Met Glu Lys Pro Ser Pro Leu Leu Val Gly Arg Glu
            500                 505                 510
```

Phe Val Arg Gln Tyr Tyr Thr Leu Leu Asn Gln Ala Pro Asp Met Leu
515 520 525

His Arg Phe Tyr Gly Lys Asn Ser Ser Tyr Val His Gly Gly Leu Asp
530 535 540

Ser Asn Gly Lys Pro Ala Asp Ala Val Tyr Gly Gln Lys Glu Ile His
545 550 555 560

Arg Lys Val Met Ser Gln Asn Phe Thr Asn Cys His Thr Lys Ile Arg
565 570 575

His Val Asp Ala His Ala Thr Leu Asn Asp Gly Val Val Val Gln Val
580 585 590

Met Gly Leu Leu Ser Asn Asn Asn Gln Ala Leu Arg Arg Phe Met Gln
595 600 605

Thr Phe Val Leu Ala Pro Glu Gly Ser Val Ala Asn Lys Phe Tyr Val
610 615 620

His Asn Asp Ile Phe Arg Tyr Gln Asp Glu Val Phe Gly Gly Phe Val
625 630 635 640

Thr Glu Pro Gln Glu Glu Ser Glu Glu Glu Val Glu Glu Pro Glu Glu
645 650 655

Arg Gln Gln Thr Pro Glu Val Val Pro Asp Asp Ser Gly Thr Phe Tyr
660 665 670

Asp Gln Ala Val Val Ser Asn Asp Met Glu Glu His Leu Glu Glu Pro
675 680 685

Val Ala Glu Pro Glu Pro Asp Pro Glu Pro Glu Pro Glu Gln Glu Pro
690 695 700

Val Ser Glu Ile Gln Glu Glu Lys Pro Glu Pro Val Leu Glu Glu Thr
705 710 715 720

Ala Pro Glu Asp Ala Gln Lys Ser Ser Ser Pro Ala Pro Ala Asp Ile
725 730 735

Ala Gln Thr Val Gln Glu Asp Leu Arg Thr Phe Ser Trp Ala Ser Val
740 745 750

Thr Ser Lys Asn Leu Pro Pro Ser Gly Ala Val Pro Val Thr Gly Ile
755 760 765

Pro Pro His Val Val Lys Val Pro Ala Ser Gln Pro Arg Pro Glu Ser
770 775 780

Lys Pro Glu Ser Gln Ile Pro Pro Gln Arg Pro Gln Arg Asp Gln Arg
785 790 795 800

Val Arg Glu Gln Arg Ile Asn Ile Pro Pro Gln Arg Gly Pro Arg Pro
805 810 815

Ile Arg Glu Ala Gly Glu Gln Gly Asp Ile Glu Pro Arg Arg Met Val
820 825 830

Arg His Pro Asp Ser His
835

<210> SEQ ID NO 100
<211> LENGTH: 1000
<212> TYPE: PRT
<213> ORGANISM: Artificial Sequence
<220> FEATURE:
<223> OTHER INFORMATION: Synthetic construct

<400> SEQUENCE: 100

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

```
Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Arg Asp Asn Arg Leu Arg Gly Pro Gly
            420                 425                 430

Gly Pro Arg Gly Gly Leu Gly Gly Gly Met Arg Gly Pro Pro Arg Gly
        435                 440                 445
```

-continued

```
Gly Met Val Gln Lys Pro Gly Phe Gly Val Gly Arg Gly Leu Ala Pro
    450                 455                 460

Arg Gln Lys Leu Ile Pro Met Ala Arg Arg Ala Trp Leu Glu His Gly
465                 470                 475                 480

His Ser Cys Phe Leu Cys Glu Ile Val Ile Arg Ser Gln Phe His Thr
                485                 490                 495

Thr Tyr Glu Pro Glu Ala Met Lys Met Asp Lys Lys Thr Ile Val Trp
            500                 505                 510

Phe Arg Arg Asp Leu Arg Ile Glu Asp Asn Pro Ala Leu Ala Ala Ala
        515                 520                 525

Ala His Glu Gly Ser Val Phe Pro Val Phe Ile Trp Cys Pro Glu Glu
    530                 535                 540

Glu Gly Gln Phe Tyr Pro Gly Arg Ala Ser Arg Trp Trp Met Lys Gln
545                 550                 555                 560

Ser Leu Ala His Leu Ser Gln Ser Leu Lys Ala Leu Gly Ser Asp Leu
                565                 570                 575

Thr Leu Ile Lys Thr His Asn Thr Ile Ser Ala Ile Leu Asp Cys Ile
            580                 585                 590

Arg Val Thr Gly Ala Thr Lys Val Val Phe Asn His Leu Tyr Asp Pro
        595                 600                 605

Val Ser Leu Val Arg Asp His Thr Val Lys Glu Lys Leu Val Glu Arg
    610                 615                 620

Gly Ile Ser Val Gln Ser Tyr Asn Gly Asp Leu Leu Tyr Glu Pro Trp
625                 630                 635                 640

Glu Ile Tyr Cys Glu Lys Gly Lys Pro Phe Thr Ser Phe Asn Ser Tyr
                645                 650                 655

Trp Lys Lys Cys Leu Asp Met Ser Ile Glu Ser Val Met Leu Pro Pro
            660                 665                 670

Pro Trp Arg Leu Met Pro Ile Thr Ala Ala Ala Glu Ala Ile Trp Ala
        675                 680                 685

Cys Ser Ile Glu Glu Leu Gly Leu Glu Asn Glu Ala Glu Lys Pro Ser
    690                 695                 700

Asn Ala Leu Leu Thr Arg Ala Trp Ser Pro Gly Trp Ser Asn Ala Asp
705                 710                 715                 720

Lys Leu Leu Asn Glu Phe Ile Glu Lys Gln Leu Ile Asp Tyr Ala Lys
                725                 730                 735

Asn Ser Lys Lys Val Val Gly Asn Ser Thr Ser Leu Leu Ser Pro Tyr
            740                 745                 750

Leu His Phe Gly Glu Ile Ser Val Arg His Val Phe Gln Cys Ala Arg
        755                 760                 765

Met Lys Gln Ile Ile Trp Ala Arg Asp Lys Asn Ser Glu Gly Glu Glu
    770                 775                 780

Ser Ala Asp Leu Phe Leu Arg Gly Ile Gly Leu Arg Glu Tyr Ser Arg
785                 790                 795                 800

Tyr Ile Cys Phe Asn Phe Pro Phe Thr His Glu Gln Ser Leu Leu Ser
                805                 810                 815

His Leu Arg Phe Phe Pro Trp Asp Ala Asp Val Asp Lys Phe Lys Ala
            820                 825                 830

Trp Arg Gln Gly Arg Thr Gly Tyr Pro Leu Val Asp Ala Gly Met Arg
        835                 840                 845

Glu Leu Trp Ala Thr Gly Trp Met His Asn Arg Ile Arg Val Ile Val
    850                 855                 860
```

Ser Ser Phe Ala Val Lys Phe Leu Leu Leu Pro Trp Lys Trp Gly Met
865 870 875 880

Lys Tyr Phe Trp Asp Thr Leu Leu Asp Ala Asp Leu Glu Cys Asp Ile
885 890 895

Leu Gly Trp Gln Tyr Ile Ser Gly Ser Ile Pro Asp Gly His Glu Leu
900 905 910

Asp Arg Leu Asp Asn Pro Ala Leu Gln Gly Ala Lys Tyr Asp Pro Glu
915 920 925

Gly Glu Tyr Ile Arg Gln Trp Leu Pro Glu Leu Ala Arg Leu Pro Thr
930 935 940

Glu Trp Ile His His Pro Trp Asp Ala Pro Leu Thr Val Leu Lys Ala
945 950 955 960

Ser Gly Val Glu Leu Gly Thr Asn Tyr Ala Lys Pro Ile Val Asp Ile
965 970 975

Asp Thr Ala Arg Glu Leu Leu Ala Lys Ala Ile Ser Arg Thr Arg Glu
980 985 990

Ala Gln Ile Met Ile Gly Ala Ala
995 1000

<210> SEQ ID NO 101
<211> LENGTH: 862
<212> TYPE: PRT
<213> ORGANISM: Artificial Sequence
<220> FEATURE:
<223> OTHER INFORMATION: Synthetic construct

<400> SEQUENCE: 101

Met Gly Phe Val Thr Glu Pro Gln Glu Glu Ser Glu Glu Glu Val Glu
1 5 10 15

Glu Pro Glu Glu Arg Gln Gln Thr Pro Glu Val Val Pro Asp Asp Ser
20 25 30

Gly Thr Phe Tyr Asp Gln Ala Val Val Ser Asn Asp Met Glu Glu His
35 40 45

Leu Glu Glu Pro Val Ala Glu Pro Glu Pro Asp Pro Glu Pro Glu Pro
50 55 60

Glu Gln Glu Pro Val Ser Glu Ile Gln Glu Glu Lys Pro Glu Pro Val
65 70 75 80

Leu Glu Glu Thr Ala Pro Glu Asp Ala Gln Lys Ser Ser Ser Pro Ala
85 90 95

Pro Ala Asp Ile Ala Gln Thr Val Gln Glu Asp Leu Arg Thr Phe Ser
100 105 110

Trp Ala Ser Val Thr Ser Lys Asn Leu Pro Pro Ser Gly Ala Val Pro
115 120 125

Val Thr Gly Ile Pro Pro His Val Val Lys Val Pro Ala Ser Gln Pro
130 135 140

Arg Pro Glu Ser Lys Pro Glu Ser Gln Ile Pro Pro Gln Arg Pro Gln
145 150 155 160

Arg Asp Gln Arg Val Arg Glu Gln Arg Ile Asn Ile Pro Pro Gln Arg
165 170 175

Gly Pro Arg Pro Ile Arg Glu Ala Gly Glu Gln Gly Asp Ile Glu Pro
180 185 190

Arg Arg Met Val Arg His Pro Asp Ser His Gln Leu Phe Ile Gly Asn
195 200 205

Leu Pro His Glu Val Asp Lys Ser Glu Leu Lys Asp Phe Phe Gln Ser
210 215 220

Tyr Gly Asn Val Val Glu Leu Arg Ile Asn Ser Gly Gly Lys Leu Pro
225 230 235 240

Asn Phe Gly Phe Val Val Phe Asp Asp Ser Glu Pro Val Gln Lys Val
245 250 255

Leu Ser Asn Arg Pro Ile Met Phe Arg Gly Glu Val Arg Leu Asn Val
260 265 270

Glu Glu Lys Lys Thr Arg Ala Ala Arg Glu Gly Asp Arg Arg Asp Asn
275 280 285

Arg Leu Arg Gly Pro Gly Gly Pro Arg Gly Gly Leu Gly Gly Gly Met
290 295 300

Arg Gly Pro Pro Arg Gly Gly Met Val Gln Lys Pro Gly Phe Gly Val
305 310 315 320

Gly Arg Gly Leu Ala Pro Arg Gln Lys Leu Ile Pro Met Ala Arg Arg
325 330 335

Ala Trp Leu Glu His Gly His Ser Cys Phe Leu Cys Glu Ile Val Ile
340 345 350

Arg Ser Gln Phe His Thr Thr Tyr Glu Pro Glu Ala Met Lys Met Asp
355 360 365

Lys Lys Thr Ile Val Trp Phe Arg Arg Asp Leu Arg Ile Glu Asp Asn
370 375 380

Pro Ala Leu Ala Ala Ala Ala His Glu Gly Ser Val Phe Pro Val Phe
385 390 395 400

Ile Trp Cys Pro Glu Glu Glu Gly Gln Phe Tyr Pro Gly Arg Ala Ser
405 410 415

Arg Trp Trp Met Lys Gln Ser Leu Ala His Leu Ser Gln Ser Leu Lys
420 425 430

Ala Leu Gly Ser Asp Leu Thr Leu Ile Lys Thr His Asn Thr Ile Ser
435 440 445

Ala Ile Leu Asp Cys Ile Arg Val Thr Gly Ala Thr Lys Val Val Phe
450 455 460

Asn His Leu Tyr Asp Pro Val Ser Leu Val Arg Asp His Thr Val Lys
465 470 475 480

Glu Lys Leu Val Glu Arg Gly Ile Ser Val Gln Ser Tyr Asn Gly Asp
485 490 495

Leu Leu Tyr Glu Pro Trp Glu Ile Tyr Cys Glu Lys Gly Lys Pro Phe
500 505 510

Thr Ser Phe Asn Ser Tyr Trp Lys Lys Cys Leu Asp Met Ser Ile Glu
515 520 525

Ser Val Met Leu Pro Pro Pro Trp Arg Leu Met Pro Ile Thr Ala Ala
530 535 540

Ala Glu Ala Ile Trp Ala Cys Ser Ile Glu Glu Leu Gly Leu Glu Asn
545 550 555 560

Glu Ala Glu Lys Pro Ser Asn Ala Leu Leu Thr Arg Ala Trp Ser Pro
565 570 575

Gly Trp Ser Asn Ala Asp Lys Leu Leu Asn Glu Phe Ile Glu Lys Gln
580 585 590

Leu Ile Asp Tyr Ala Lys Asn Ser Lys Lys Val Val Gly Asn Ser Thr
595 600 605

Ser Leu Leu Ser Pro Tyr Leu His Phe Gly Glu Ile Ser Val Arg His
610 615 620

Val Phe Gln Cys Ala Arg Met Lys Gln Ile Ile Trp Ala Arg Asp Lys
625 630 635 640

```
Asn Ser Glu Gly Glu Glu Ser Ala Asp Leu Phe Leu Arg Gly Ile Gly
                645                 650                 655

Leu Arg Glu Tyr Ser Arg Tyr Ile Cys Phe Asn Phe Pro Phe Thr His
            660                 665                 670

Glu Gln Ser Leu Leu Ser His Leu Arg Phe Phe Pro Trp Asp Ala Asp
        675                 680                 685

Val Asp Lys Phe Lys Ala Trp Arg Gln Gly Arg Thr Gly Tyr Pro Leu
    690                 695                 700

Val Asp Ala Gly Met Arg Glu Leu Trp Ala Thr Gly Trp Met His Asn
705                 710                 715                 720

Arg Ile Arg Val Ile Val Ser Ser Phe Ala Val Lys Phe Leu Leu Leu
                725                 730                 735

Pro Trp Lys Trp Gly Met Lys Tyr Phe Trp Asp Thr Leu Leu Asp Ala
            740                 745                 750

Asp Leu Glu Cys Asp Ile Leu Gly Trp Gln Tyr Ile Ser Gly Ser Ile
        755                 760                 765

Pro Asp Gly His Glu Leu Asp Arg Leu Asp Asn Pro Ala Leu Gln Gly
    770                 775                 780

Ala Lys Tyr Asp Pro Glu Gly Glu Tyr Ile Arg Gln Trp Leu Pro Glu
785                 790                 795                 800

Leu Ala Arg Leu Pro Thr Glu Trp Ile His His Pro Trp Asp Ala Pro
                805                 810                 815

Leu Thr Val Leu Lys Ala Ser Gly Val Glu Leu Gly Thr Asn Tyr Ala
            820                 825                 830

Lys Pro Ile Val Asp Ile Asp Thr Ala Arg Glu Leu Leu Ala Lys Ala
        835                 840                 845

Ile Ser Arg Thr Arg Glu Ala Gln Ile Met Ile Gly Ala Ala
    850                 855                 860
```

<210> SEQ ID NO 102
<211> LENGTH: 918
<212> TYPE: PRT
<213> ORGANISM: Artificial Sequence
<220> FEATURE:
<223> OTHER INFORMATION: Synthetic construct

<400> SEQUENCE: 102

```
Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Thr Ala Pro Glu Asp
    130                 135                 140
```

-continued

```
Ala Gln Lys Ser Ser Ser Pro Ala Pro Ala Asp Ile Ala Gln Thr Val
145                 150                 155                 160

Gln Glu Asp Leu Arg Thr Phe Ser Trp Ala Ser Val Thr Ser Lys Asn
                165                 170                 175

Leu Pro Pro Ser Gly Ala Val Pro Val Thr Gly Ile Pro Pro His Val
            180                 185                 190

Val Lys Val Pro Ala Ser Gln Pro Arg Pro Glu Ser Lys Pro Glu Ser
        195                 200                 205

Gln Ile Pro Pro Gln Arg Pro Gln Arg Asp Gln Arg Val Arg Glu Gln
    210                 215                 220

Arg Ile Asn Ile Pro Pro Gln Arg Gly Pro Arg Pro Ile Arg Glu Ala
225                 230                 235                 240

Gly Glu Gln Gly Asp Ile Glu Pro Arg Arg Met Val Arg His Pro Asp
                245                 250                 255

Ser His Gln Leu Phe Ile Gly Asn Leu Pro His Glu Val Asp Lys Ser
            260                 265                 270

Glu Leu Lys Asp Phe Phe Gln Ser Tyr Gly Asn Val Val Glu Leu Arg
        275                 280                 285

Ile Asn Ser Gly Gly Lys Leu Pro Asn Phe Gly Phe Val Val Phe Asp
    290                 295                 300

Asp Ser Glu Pro Val Gln Lys Val Leu Ser Asn Arg Pro Ile Met Phe
305                 310                 315                 320

Arg Gly Glu Val Arg Leu Asn Val Glu Glu Lys Lys Thr Arg Ala Ala
                325                 330                 335

Arg Glu Gly Asp Arg Arg Asp Asn Arg Leu Arg Gly Pro Gly Gly Pro
            340                 345                 350

Arg Gly Gly Leu Gly Gly Gly Met Arg Gly Pro Pro Arg Gly Gly Met
        355                 360                 365

Val Gln Lys Pro Gly Phe Gly Val Gly Arg Gly Leu Ala Pro Arg Gln
    370                 375                 380

Lys Leu Ile Pro Met Ala Arg Arg Ala Trp Leu Glu His Gly His Ser
385                 390                 395                 400

Cys Phe Leu Cys Glu Ile Val Ile Arg Ser Gln Phe His Thr Thr Tyr
                405                 410                 415

Glu Pro Glu Ala Met Lys Met Asp Lys Lys Thr Ile Val Trp Phe Arg
            420                 425                 430

Arg Asp Leu Arg Ile Glu Asp Asn Pro Ala Leu Ala Ala Ala Ala His
        435                 440                 445

Glu Gly Ser Val Phe Pro Val Phe Ile Trp Cys Pro Glu Glu Glu Gly
    450                 455                 460

Gln Phe Tyr Pro Gly Arg Ala Ser Arg Trp Trp Met Lys Gln Ser Leu
465                 470                 475                 480

Ala His Leu Ser Gln Ser Leu Lys Ala Leu Gly Ser Asp Leu Thr Leu
                485                 490                 495

Ile Lys Thr His Asn Thr Ile Ser Ala Ile Leu Asp Cys Ile Arg Val
            500                 505                 510

Thr Gly Ala Thr Lys Val Val Phe Asn His Leu Tyr Asp Pro Val Ser
        515                 520                 525

Leu Val Arg Asp His Thr Val Lys Glu Lys Leu Val Glu Arg Gly Ile
    530                 535                 540

Ser Val Gln Ser Tyr Asn Gly Asp Leu Leu Tyr Glu Pro Trp Glu Ile
545                 550                 555                 560
```

```
Tyr Cys Glu Lys Gly Lys Pro Phe Thr Ser Phe Asn Ser Tyr Trp Lys
                565                 570                 575

Lys Cys Leu Asp Met Ser Ile Glu Ser Val Met Leu Pro Pro Pro Trp
            580                 585                 590

Arg Leu Met Pro Ile Thr Ala Ala Ala Glu Ala Ile Trp Ala Cys Ser
        595                 600                 605

Ile Glu Glu Leu Gly Leu Glu Asn Glu Ala Glu Lys Pro Ser Asn Ala
    610                 615                 620

Leu Leu Thr Arg Ala Trp Ser Pro Gly Trp Ser Asn Ala Asp Lys Leu
625                 630                 635                 640

Leu Asn Glu Phe Ile Glu Lys Gln Leu Ile Asp Tyr Ala Lys Asn Ser
                645                 650                 655

Lys Lys Val Val Gly Asn Ser Thr Ser Leu Leu Ser Pro Tyr Leu His
            660                 665                 670

Phe Gly Glu Ile Ser Val Arg His Val Phe Gln Cys Ala Arg Met Lys
        675                 680                 685

Gln Ile Ile Trp Ala Arg Asp Lys Asn Ser Glu Gly Glu Glu Ser Ala
    690                 695                 700

Asp Leu Phe Leu Arg Gly Ile Gly Leu Arg Glu Tyr Ser Arg Tyr Ile
705                 710                 715                 720

Cys Phe Asn Phe Pro Phe Thr His Glu Gln Ser Leu Leu Ser His Leu
                725                 730                 735

Arg Phe Phe Pro Trp Asp Ala Asp Val Asp Lys Phe Lys Ala Trp Arg
            740                 745                 750

Gln Gly Arg Thr Gly Tyr Pro Leu Val Asp Ala Gly Met Arg Glu Leu
        755                 760                 765

Trp Ala Thr Gly Trp Met His Asn Arg Ile Arg Val Ile Val Ser Ser
    770                 775                 780

Phe Ala Val Lys Phe Leu Leu Leu Pro Trp Lys Trp Gly Met Lys Tyr
785                 790                 795                 800

Phe Trp Asp Thr Leu Leu Asp Ala Asp Leu Glu Cys Asp Ile Leu Gly
                805                 810                 815

Trp Gln Tyr Ile Ser Gly Ser Ile Pro Asp Gly His Glu Leu Asp Arg
            820                 825                 830

Leu Asp Asn Pro Ala Leu Gln Gly Ala Lys Tyr Asp Pro Glu Gly Glu
        835                 840                 845

Tyr Ile Arg Gln Trp Leu Pro Glu Leu Ala Arg Leu Pro Thr Glu Trp
    850                 855                 860

Ile His His Pro Trp Asp Ala Pro Leu Thr Val Leu Lys Ala Ser Gly
865                 870                 875                 880

Val Glu Leu Gly Thr Asn Tyr Ala Lys Pro Ile Val Asp Ile Asp Thr
                885                 890                 895

Ala Arg Glu Leu Leu Ala Lys Ala Ile Ser Arg Thr Arg Glu Ala Gln
            900                 905                 910

Ile Met Ile Gly Ala Ala
        915
```

<210> SEQ ID NO 103
<211> LENGTH: 881
<212> TYPE: PRT
<213> ORGANISM: Artificial Sequence
<220> FEATURE:
<223> OTHER INFORMATION: Synthetic construct

<400> SEQUENCE: 103

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Gln Leu Phe
210 215 220

Ile Gly Asn Leu Pro His Glu Val Asp Lys Ser Glu Leu Lys Asp Phe
225 230 235 240

Phe Gln Ser Tyr Gly Asn Val Val Glu Leu Arg Ile Asn Ser Gly Gly
245 250 255

Lys Leu Pro Asn Phe Gly Phe Val Val Phe Asp Asp Ser Glu Pro Val
260 265 270

Gln Lys Val Leu Ser Asn Arg Pro Ile Met Phe Arg Gly Glu Val Arg
275 280 285

Leu Asn Val Glu Glu Lys Lys Thr Arg Ala Ala Arg Glu Gly Asp Arg
290 295 300

Arg Asp Asn Arg Leu Arg Gly Pro Gly Gly Pro Arg Gly Gly Leu Gly
305 310 315 320

Gly Gly Met Arg Gly Pro Pro Arg Gly Gly Met Val Gln Lys Pro Gly
325 330 335

Phe Gly Val Gly Arg Gly Leu Ala Pro Arg Gln Lys Leu Ile Pro Met
340 345 350

Ala Arg Arg Ala Trp Leu Glu His Gly His Ser Cys Phe Leu Cys Glu
355 360 365

Ile Val Ile Arg Ser Gln Phe His Thr Thr Tyr Glu Pro Glu Ala Met
370 375 380

Lys Met Asp Lys Lys Thr Ile Val Trp Phe Arg Arg Asp Leu Arg Ile
385 390 395 400

```
Glu Asp Asn Pro Ala Leu Ala Ala Ala Ala His Glu Gly Ser Val Phe
                405                 410                 415

Pro Val Phe Ile Trp Cys Pro Glu Glu Glu Gly Gln Phe Tyr Pro Gly
            420                 425                 430

Arg Ala Ser Arg Trp Trp Met Lys Gln Ser Leu Ala His Leu Ser Gln
        435                 440                 445

Ser Leu Lys Ala Leu Gly Ser Asp Leu Thr Leu Ile Lys Thr His Asn
    450                 455                 460

Thr Ile Ser Ala Ile Leu Asp Cys Ile Arg Val Thr Gly Ala Thr Lys
465                 470                 475                 480

Val Val Phe Asn His Leu Tyr Asp Pro Val Ser Leu Val Arg Asp His
                485                 490                 495

Thr Val Lys Glu Lys Leu Val Glu Arg Gly Ile Ser Val Gln Ser Tyr
            500                 505                 510

Asn Gly Asp Leu Leu Tyr Glu Pro Trp Glu Ile Tyr Cys Glu Lys Gly
        515                 520                 525

Lys Pro Phe Thr Ser Phe Asn Ser Tyr Trp Lys Lys Cys Leu Asp Met
    530                 535                 540

Ser Ile Glu Ser Val Met Leu Pro Pro Pro Trp Arg Leu Met Pro Ile
545                 550                 555                 560

Thr Ala Ala Ala Glu Ala Ile Trp Ala Cys Ser Ile Glu Glu Leu Gly
                565                 570                 575

Leu Glu Asn Glu Ala Glu Lys Pro Ser Asn Ala Leu Leu Thr Arg Ala
            580                 585                 590

Trp Ser Pro Gly Trp Ser Asn Ala Asp Lys Leu Leu Asn Glu Phe Ile
        595                 600                 605

Glu Lys Gln Leu Ile Asp Tyr Ala Lys Asn Ser Lys Lys Val Val Gly
    610                 615                 620

Asn Ser Thr Ser Leu Leu Ser Pro Tyr Leu His Phe Gly Glu Ile Ser
625                 630                 635                 640

Val Arg His Val Phe Gln Cys Ala Arg Met Lys Gln Ile Ile Trp Ala
                645                 650                 655

Arg Asp Lys Asn Ser Glu Gly Glu Glu Ser Ala Asp Leu Phe Leu Arg
            660                 665                 670

Gly Ile Gly Leu Arg Glu Tyr Ser Arg Tyr Ile Cys Phe Asn Phe Pro
        675                 680                 685

Phe Thr His Glu Gln Ser Leu Leu Ser His Leu Arg Phe Phe Pro Trp
    690                 695                 700

Asp Ala Asp Val Asp Lys Phe Lys Ala Trp Arg Gln Gly Arg Thr Gly
705                 710                 715                 720

Tyr Pro Leu Val Asp Ala Gly Met Arg Glu Leu Trp Ala Thr Gly Trp
                725                 730                 735

Met His Asn Arg Ile Arg Val Ile Val Ser Ser Phe Ala Val Lys Phe
            740                 745                 750

Leu Leu Leu Pro Trp Lys Trp Gly Met Lys Tyr Phe Trp Asp Thr Leu
        755                 760                 765

Leu Asp Ala Asp Leu Glu Cys Asp Ile Leu Gly Trp Gln Tyr Ile Ser
    770                 775                 780

Gly Ser Ile Pro Asp Gly His Glu Leu Asp Arg Leu Asp Asn Pro Ala
785                 790                 795                 800

Leu Gln Gly Ala Lys Tyr Asp Pro Glu Gly Glu Tyr Ile Arg Gln Trp
                805                 810                 815
```

Leu Pro Glu Leu Ala Arg Leu Pro Thr Glu Trp Ile His His Pro Trp
820 825 830

Asp Ala Pro Leu Thr Val Leu Lys Ala Ser Gly Val Glu Leu Gly Thr
835 840 845

Asn Tyr Ala Lys Pro Ile Val Asp Ile Asp Thr Ala Arg Glu Leu Leu
850 855 860

Ala Lys Ala Ile Ser Arg Thr Arg Glu Ala Gln Ile Met Ile Gly Ala
865 870 875 880

Ala

<210> SEQ ID NO 104
<211> LENGTH: 929
<212> TYPE: PRT
<213> ORGANISM: Artificial Sequence
<220> FEATURE:
<223> OTHER INFORMATION: Synthetic construct

<400> SEQUENCE: 104

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Thr Ala Pro
210 215 220

Glu Asp Ala Gln Lys Ser Ser Ser Pro Ala Pro Ala Asp Ile Ala Gln
225 230 235 240

Thr Val Gln Glu Asp Leu Arg Thr Phe Ser Trp Ala Ser Val Thr Ser
245 250 255

Lys Asn Leu Pro Pro Ser Gly Ala Val Pro Val Thr Gly Ile Pro Pro
260 265 270

His Val Val Lys Val Pro Ala Ser Gln Pro Arg Pro Glu Ser Lys Pro
275 280 285

```
Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Glu Lys Lys Thr Arg Ala Ala Arg Glu Gly Asp Arg
            340                 345                 350

Arg Asp Asn Arg Leu Arg Gly Pro Gly Gly Pro Arg Gly Gly Leu Gly
        355                 360                 365

Gly Gly Met Arg Gly Pro Pro Arg Gly Gly Met Val Gln Lys Pro Gly
    370                 375                 380

Phe Gly Val Gly Arg Gly Leu Ala Pro Arg Gln Lys Leu Ile Pro Met
385                 390                 395                 400

Ala Arg Arg Ala Trp Leu Glu His Gly His Ser Cys Phe Leu Cys Glu
                405                 410                 415

Ile Val Ile Arg Ser Gln Phe His Thr Thr Tyr Glu Pro Glu Ala Met
            420                 425                 430

Lys Met Asp Lys Lys Thr Ile Val Trp Phe Arg Arg Asp Leu Arg Ile
        435                 440                 445

Glu Asp Asn Pro Ala Leu Ala Ala Ala Ala His Glu Gly Ser Val Phe
    450                 455                 460

Pro Val Phe Ile Trp Cys Pro Glu Glu Glu Gly Gln Phe Tyr Pro Gly
465                 470                 475                 480

Arg Ala Ser Arg Trp Trp Met Lys Gln Ser Leu Ala His Leu Ser Gln
                485                 490                 495

Ser Leu Lys Ala Leu Gly Ser Asp Leu Thr Leu Ile Lys Thr His Asn
            500                 505                 510

Thr Ile Ser Ala Ile Leu Asp Cys Ile Arg Val Thr Gly Ala Thr Lys
        515                 520                 525

Val Val Phe Asn His Leu Tyr Asp Pro Val Ser Leu Val Arg Asp His
    530                 535                 540

Thr Val Lys Glu Lys Leu Val Glu Arg Gly Ile Ser Val Gln Ser Tyr
545                 550                 555                 560

Asn Gly Asp Leu Leu Tyr Glu Pro Trp Glu Ile Tyr Cys Glu Lys Gly
                565                 570                 575

Lys Pro Phe Thr Ser Phe Asn Ser Tyr Trp Lys Lys Cys Leu Asp Met
            580                 585                 590

Ser Ile Glu Ser Val Met Leu Pro Pro Pro Trp Arg Leu Met Pro Ile
        595                 600                 605

Thr Ala Ala Ala Glu Ala Ile Trp Ala Cys Ser Ile Glu Glu Leu Gly
    610                 615                 620

Leu Glu Asn Glu Ala Glu Lys Pro Ser Asn Ala Leu Leu Thr Arg Ala
625                 630                 635                 640

Trp Ser Pro Gly Trp Ser Asn Ala Asp Lys Leu Leu Asn Glu Phe Ile
                645                 650                 655

Glu Lys Gln Leu Ile Asp Tyr Ala Lys Asn Ser Lys Lys Val Val Gly
            660                 665                 670

Asn Ser Thr Ser Leu Leu Ser Pro Tyr Leu His Phe Gly Glu Ile Ser
        675                 680                 685

Val Arg His Val Phe Gln Cys Ala Arg Met Lys Gln Ile Ile Trp Ala
    690                 695                 700
```

Arg Asp Lys Asn Ser Glu Gly Glu Glu Ser Ala Asp Leu Phe Leu Arg
705 710 715 720

Gly Ile Gly Leu Arg Glu Tyr Ser Arg Tyr Ile Cys Phe Asn Phe Pro
725 730 735

Phe Thr His Glu Gln Ser Leu Leu Ser His Leu Arg Phe Phe Pro Trp
740 745 750

Asp Ala Asp Val Asp Lys Phe Lys Ala Trp Arg Gln Gly Arg Thr Gly
755 760 765

Tyr Pro Leu Val Asp Ala Gly Met Arg Glu Leu Trp Ala Thr Gly Trp
770 775 780

Met His Asn Arg Ile Arg Val Ile Val Ser Ser Phe Ala Val Lys Phe
785 790 795 800

Leu Leu Leu Pro Trp Lys Trp Gly Met Lys Tyr Phe Trp Asp Thr Leu
805 810 815

Leu Asp Ala Asp Leu Glu Cys Asp Ile Leu Gly Trp Gln Tyr Ile Ser
820 825 830

Gly Ser Ile Pro Asp Gly His Glu Leu Asp Arg Leu Asp Asn Pro Ala
835 840 845

Leu Gln Gly Ala Lys Tyr Asp Pro Glu Gly Glu Tyr Ile Arg Gln Trp
850 855 860

Leu Pro Glu Leu Ala Arg Leu Pro Thr Glu Trp Ile His His Pro Trp
865 870 875 880

Asp Ala Pro Leu Thr Val Leu Lys Ala Ser Gly Val Glu Leu Gly Thr
885 890 895

Asn Tyr Ala Lys Pro Ile Val Asp Ile Asp Thr Ala Arg Glu Leu Leu
900 905 910

Ala Lys Ala Ile Ser Arg Thr Arg Glu Ala Gln Ile Met Ile Gly Ala
915 920 925

Ala

<210> SEQ ID NO 105
<211> LENGTH: 909
<212> TYPE: PRT
<213> ORGANISM: Artificial Sequence
<220> FEATURE:
<223> OTHER INFORMATION: Synthetic construct

<400> SEQUENCE: 105

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

```
Asp Ile Phe Arg Tyr Gln Asp Glu Val Phe Gly Gly Phe Val Thr Glu
    130                 135                 140

Pro Gln Glu Glu Ser Glu Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
        275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
            340                 345                 350

Lys Ser Glu Leu Lys Asp Phe Phe Gln Ser Tyr Gly Asn Val Val Glu
        355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Met Lys Met Asp Lys
                405                 410                 415

Lys Thr Ile Val Trp Phe Arg Arg Asp Leu Arg Ile Glu Asp Asn Pro
            420                 425                 430

Ala Leu Ala Ala Ala Ala His Glu Gly Ser Val Phe Pro Val Phe Ile
        435                 440                 445

Trp Cys Pro Glu Glu Glu Gly Gln Phe Tyr Pro Gly Arg Ala Ser Arg
    450                 455                 460

Trp Trp Met Lys Gln Ser Leu Ala His Leu Ser Gln Ser Leu Lys Ala
465                 470                 475                 480

Leu Gly Ser Asp Leu Thr Leu Ile Lys Thr His Asn Thr Ile Ser Ala
                485                 490                 495

Ile Leu Asp Cys Ile Arg Val Thr Gly Ala Thr Lys Val Val Phe Asn
            500                 505                 510

His Leu Tyr Asp Pro Val Ser Leu Val Arg Asp His Thr Val Lys Glu
        515                 520                 525

Lys Leu Val Glu Arg Gly Ile Ser Val Gln Ser Tyr Asn Gly Asp Leu
    530                 535                 540
```

```
Leu Tyr Glu Pro Trp Glu Ile Tyr Cys Glu Lys Gly Lys Pro Phe Thr
545                 550                 555                 560

Ser Phe Asn Ser Tyr Trp Lys Lys Cys Leu Asp Met Ser Ile Glu Ser
                565                 570                 575

Val Met Leu Pro Pro Pro Trp Arg Leu Met Pro Ile Thr Ala Ala Ala
            580                 585                 590

Glu Ala Ile Trp Ala Cys Ser Ile Glu Glu Leu Gly Leu Glu Asn Glu
        595                 600                 605

Ala Glu Lys Pro Ser Asn Ala Leu Leu Thr Arg Ala Trp Ser Pro Gly
    610                 615                 620

Trp Ser Asn Ala Asp Lys Leu Leu Asn Glu Phe Ile Glu Lys Gln Leu
625                 630                 635                 640

Ile Asp Tyr Ala Lys Asn Ser Lys Lys Val Val Gly Asn Ser Thr Ser
                645                 650                 655

Leu Leu Ser Pro Tyr Leu His Phe Gly Glu Ile Ser Val Arg His Val
            660                 665                 670

Phe Gln Cys Ala Arg Met Lys Gln Ile Ile Trp Ala Arg Asp Lys Asn
        675                 680                 685

Ser Glu Gly Glu Glu Ser Ala Asp Leu Phe Leu Arg Gly Ile Gly Leu
    690                 695                 700

Arg Glu Tyr Ser Arg Tyr Ile Cys Phe Asn Phe Pro Phe Thr His Glu
705                 710                 715                 720

Gln Ser Leu Leu Ser His Leu Arg Phe Phe Pro Trp Asp Ala Asp Val
                725                 730                 735

Asp Lys Phe Lys Ala Trp Arg Gln Gly Arg Thr Gly Tyr Pro Leu Val
            740                 745                 750

Asp Ala Gly Met Arg Glu Leu Trp Ala Thr Gly Trp Met His Asn Arg
        755                 760                 765

Ile Arg Val Ile Val Ser Ser Phe Ala Val Lys Phe Leu Leu Leu Pro
    770                 775                 780

Trp Lys Trp Gly Met Lys Tyr Phe Trp Asp Thr Leu Leu Asp Ala Asp
785                 790                 795                 800

Leu Glu Cys Asp Ile Leu Gly Trp Gln Tyr Ile Ser Gly Ser Ile Pro
                805                 810                 815

Asp Gly His Glu Leu Asp Arg Leu Asp Asn Pro Ala Leu Gln Gly Ala
            820                 825                 830

Lys Tyr Asp Pro Glu Gly Glu Tyr Ile Arg Gln Trp Leu Pro Glu Leu
        835                 840                 845

Ala Arg Leu Pro Thr Glu Trp Ile His His Pro Trp Asp Ala Pro Leu
    850                 855                 860

Thr Val Leu Lys Ala Ser Gly Val Glu Leu Gly Thr Asn Tyr Ala Lys
865                 870                 875                 880

Pro Ile Val Asp Ile Asp Thr Ala Arg Glu Leu Leu Ala Lys Ala Ile
                885                 890                 895

Ser Arg Thr Arg Glu Ala Gln Ile Met Ile Gly Ala Ala
            900                 905
```

<210> SEQ ID NO 106
<211> LENGTH: 838
<212> TYPE: PRT
<213> ORGANISM: Artificial Sequence
<220> FEATURE:
<223> OTHER INFORMATION: Synthetic construct

<400> SEQUENCE: 106

Met Val Met Glu Lys Pro Ser Pro Leu Leu Val Gly Arg Glu Phe Val
1 5 10 15

Arg Gln Tyr Tyr Thr Leu Leu Asn Gln Ala Pro Asp Met Leu His Arg
20 25 30

Phe Tyr Gly Lys Asn Ser Ser Tyr Val His Gly Gly Leu Asp Ser Asn
35 40 45

Gly Lys Pro Ala Asp Ala Val Tyr Gly Gln Lys Glu Ile His Arg Lys
50 55 60

Val Met Ser Gln Asn Phe Thr Asn Cys His Thr Lys Ile Arg His Val
65 70 75 80

Asp Ala His Ala Thr Leu Asn Asp Gly Val Val Val Gln Val Met Gly
85 90 95

Leu Leu Ser Asn Asn Asn Gln Ala Leu Arg Arg Phe Met Gln Thr Phe
100 105 110

Val Leu Ala Pro Glu Gly Ser Val Ala Asn Lys Phe Tyr Val His Asn
115 120 125

Asp Ile Phe Arg Tyr Gln Asp Glu Val Phe Gly Gly Phe Val Thr Glu
130 135 140

Pro Gln Glu Glu Ser Glu Glu Glu Val Glu Glu Pro Glu Glu Arg Gln
145 150 155 160

Gln Thr Pro Glu Val Val Pro Asp Asp Ser Gly Thr Phe Tyr Asp Gln
165 170 175

Ala Val Val Ser Asn Asp Met Glu Glu His Leu Glu Glu Pro Val Ala
180 185 190

Glu Pro Glu Pro Asp Pro Glu Pro Glu Pro Glu Gln Glu Pro Val Ser
195 200 205

Glu Ile Gln Glu Glu Lys Pro Glu Pro Val Leu Glu Glu Thr Ala Pro
210 215 220

Glu Asp Ala Gln Lys Ser Ser Ser Pro Ala Pro Ala Asp Ile Ala Gln
225 230 235 240

Thr Val Gln Glu Asp Leu Arg Thr Phe Ser Trp Ala Ser Val Thr Ser
245 250 255

Lys Asn Leu Pro Pro Ser Gly Ala Val Pro Val Thr Gly Ile Pro Pro
260 265 270

His Val Val Lys Val Pro Ala Ser Gln Pro Arg Pro Glu Ser Lys Pro
275 280 285

Glu Ser Gln Ile Pro Pro Gln Arg Pro Gln Arg Asp Gln Arg Val Arg
290 295 300

Glu Gln Arg Ile Asn Ile Pro Pro Gln Arg Gly Pro Arg Pro Ile Arg
305 310 315 320

Glu Ala Gly Glu Gln Gly Asp Ile Glu Pro Arg Arg Met Val Arg His
325 330 335

Pro Asp Ser His Met Lys Met Asp Lys Lys Thr Ile Val Trp Phe Arg
340 345 350

Arg Asp Leu Arg Ile Glu Asp Asn Pro Ala Leu Ala Ala Ala Ala His
355 360 365

Glu Gly Ser Val Phe Pro Val Phe Ile Trp Cys Pro Glu Glu Glu Gly
370 375 380

Gln Phe Tyr Pro Gly Arg Ala Ser Arg Trp Trp Met Lys Gln Ser Leu
385 390 395 400

```
Ala His Leu Ser Gln Ser Leu Lys Ala Leu Gly Ser Asp Leu Thr Leu
                405                 410                 415

Ile Lys Thr His Asn Thr Ile Ser Ala Ile Leu Asp Cys Ile Arg Val
            420                 425                 430

Thr Gly Ala Thr Lys Val Val Phe Asn His Leu Tyr Asp Pro Val Ser
        435                 440                 445

Leu Val Arg Asp His Thr Val Lys Glu Lys Leu Val Glu Arg Gly Ile
    450                 455                 460

Ser Val Gln Ser Tyr Asn Gly Asp Leu Leu Tyr Glu Pro Trp Glu Ile
465                 470                 475                 480

Tyr Cys Glu Lys Gly Lys Pro Phe Thr Ser Phe Asn Ser Tyr Trp Lys
                485                 490                 495

Lys Cys Leu Asp Met Ser Ile Glu Ser Val Met Leu Pro Pro Pro Trp
            500                 505                 510

Arg Leu Met Pro Ile Thr Ala Ala Ala Glu Ala Ile Trp Ala Cys Ser
        515                 520                 525

Ile Glu Glu Leu Gly Leu Glu Asn Glu Ala Glu Lys Pro Ser Asn Ala
    530                 535                 540

Leu Leu Thr Arg Ala Trp Ser Pro Gly Trp Ser Asn Ala Asp Lys Leu
545                 550                 555                 560

Leu Asn Glu Phe Ile Glu Lys Gln Leu Ile Asp Tyr Ala Lys Asn Ser
                565                 570                 575

Lys Lys Val Val Gly Asn Ser Thr Ser Leu Leu Ser Pro Tyr Leu His
            580                 585                 590

Phe Gly Glu Ile Ser Val Arg His Val Phe Gln Cys Ala Arg Met Lys
        595                 600                 605

Gln Ile Ile Trp Ala Arg Asp Lys Asn Ser Glu Gly Glu Glu Ser Ala
    610                 615                 620

Asp Leu Phe Leu Arg Gly Ile Gly Leu Arg Glu Tyr Ser Arg Tyr Ile
625                 630                 635                 640

Cys Phe Asn Phe Pro Phe Thr His Glu Gln Ser Leu Leu Ser His Leu
                645                 650                 655

Arg Phe Phe Pro Trp Asp Ala Asp Val Asp Lys Phe Lys Ala Trp Arg
            660                 665                 670

Gln Gly Arg Thr Gly Tyr Pro Leu Val Asp Ala Gly Met Arg Glu Leu
        675                 680                 685

Trp Ala Thr Gly Trp Met His Asn Arg Ile Arg Val Ile Val Ser Ser
    690                 695                 700

Phe Ala Val Lys Phe Leu Leu Leu Pro Trp Lys Trp Gly Met Lys Tyr
705                 710                 715                 720

Phe Trp Asp Thr Leu Leu Asp Ala Asp Leu Glu Cys Asp Ile Leu Gly
                725                 730                 735

Trp Gln Tyr Ile Ser Gly Ser Ile Pro Asp Gly His Glu Leu Asp Arg
            740                 745                 750

Leu Asp Asn Pro Ala Leu Gln Gly Ala Lys Tyr Asp Pro Glu Gly Glu
        755                 760                 765

Tyr Ile Arg Gln Trp Leu Pro Glu Leu Ala Arg Leu Pro Thr Glu Trp
    770                 775                 780

Ile His His Pro Trp Asp Ala Pro Leu Thr Val Leu Lys Ala Ser Gly
785                 790                 795                 800

Val Glu Leu Gly Thr Asn Tyr Ala Lys Pro Ile Val Asp Ile Asp Thr
                805                 810                 815
```

```
Ala Arg Glu Leu Leu Ala Lys Ala Ile Ser Arg Thr Arg Glu Ala Gln
            820                 825                 830

Ile Met Ile Gly Ala Ala
        835


<210> SEQ ID NO 107
<211> LENGTH: 161
<212> TYPE: PRT
<213> ORGANISM: Avena sativa

<400> SEQUENCE: 107

Gly Glu Phe Leu Ala Thr Thr Leu Glu Arg Ile Glu Lys Asn Phe Val
1               5                   10                  15

Ile Thr Asp Pro Arg Leu Pro Asp Asn Pro Ile Ile Phe Ala Ser Asp
            20                  25                  30

Ser Phe Leu Gln Leu Thr Glu Tyr Ser Arg Glu Glu Ile Leu Gly Arg
        35                  40                  45

Asn Cys Arg Phe Leu Gln Gly Pro Glu Thr Asp Arg Ala Thr Val Arg
    50                  55                  60

Lys Ile Arg Asp Ala Ile Asp Asn Gln Thr Glu Val Thr Val Gln Leu
65                  70                  75                  80

Ile Asn Tyr Thr Lys Ser Gly Lys Lys Phe Trp Asn Leu Phe His Leu
                85                  90                  95

Gln Pro Met Arg Asp Gln Lys Gly Asp Val Gln Tyr Phe Ile Gly Val
            100                 105                 110

Gln Leu Asp Gly Thr Glu His Val Arg Asp Ala Ala Glu Arg Glu Gly
        115                 120                 125

Val Met Leu Ile Lys Lys Thr Ala Glu Asn Ile Asp Glu Ala Ala Lys
    130                 135                 140

Glu Leu Pro Asp Ala Asn Leu Arg Pro Glu Asp Leu Trp Ala Asn His
145                 150                 155                 160

Gly


<210> SEQ ID NO 108
<211> LENGTH: 225
<212> TYPE: PRT
<213> ORGANISM: Erythrobacter litoralis

<400> SEQUENCE: 108

Met Leu Asp Met Gly Gln Asp Arg Pro Ile Asp Gly Ser Gly Ala Pro
1               5                   10                  15

Gly Ala Asp Asp Thr Arg Val Glu Val Gln Pro Pro Ala Gln Trp Val
            20                  25                  30

Leu Asp Leu Ile Glu Ala Ser Pro Ile Ala Ser Val Val Ser Asp Pro
        35                  40                  45

Arg Leu Ala Asp Asn Pro Leu Ile Ala Ile Asn Gln Ala Phe Thr Asp
    50                  55                  60

Leu Thr Gly Tyr Ser Glu Glu Glu Cys Val Gly Arg Asn Cys Arg Phe
65                  70                  75                  80

Leu Ala Gly Ser Gly Thr Glu Pro Trp Leu Thr Asp Lys Ile Arg Gln
                85                  90                  95

Gly Val Arg Glu His Lys Pro Val Leu Val Glu Ile Leu Asn Tyr Lys
            100                 105                 110

Lys Asp Gly Thr Pro Phe Arg Asn Ala Val Leu Val Ala Pro Ile Tyr
        115                 120                 125
```

```
Asp Asp Asp Asp Glu Leu Leu Tyr Phe Leu Gly Ser Gln Val Glu Val
    130                 135                 140

Asp Asp Asp Gln Pro Asn Met Gly Met Ala Arg Arg Glu Arg Ala Ala
145                 150                 155                 160

Glu Met Leu Lys Thr Leu Ser Pro Arg Gln Leu Glu Val Thr Thr Leu
                165                 170                 175

Val Ala Ser Gly Leu Arg Asn Lys Glu Val Ala Ala Arg Leu Gly Leu
            180                 185                 190

Ser Glu Lys Thr Val Lys Met His Arg Gly Leu Val Met Glu Lys Leu
        195                 200                 205

Asn Leu Lys Thr Ser Ala Asp Leu Val Arg Ile Ala Val Glu Ala Gly
    210                 215                 220

Ile
225


<210> SEQ ID NO 109
<211> LENGTH: 261
<212> TYPE: PRT
<213> ORGANISM: Bacillus subtillis

<400> SEQUENCE: 109

Met Ala Ser Phe Gln Ser Phe Gly Ile Pro Gly Gln Leu Glu Val Ile
1               5                   10                  15

Lys Lys Ala Leu Asp His Val Arg Val Gly Val Val Ile Thr Asp Pro
            20                  25                  30

Ala Leu Glu Asp Asn Pro Ile Val Tyr Val Asn Gln Gly Phe Val Gln
        35                  40                  45

Met Thr Gly Tyr Glu Thr Glu Glu Ile Leu Gly Lys Asn Cys Arg Phe
    50                  55                  60

Leu Gln Gly Lys His Thr Asp Pro Ala Glu Val Asp Asn Ile Arg Thr
65                  70                  75                  80

Ala Leu Gln Asn Lys Glu Pro Val Thr Val Gln Ile Gln Asn Tyr Lys
                85                  90                  95

Lys Asp Gly Thr Met Phe Trp Asn Glu Leu Asn Ile Asp Pro Met Glu
            100                 105                 110

Ile Glu Asp Lys Thr Tyr Phe Val Gly Ile Gln Asn Asp Ile Thr Lys
        115                 120                 125

Gln Lys Glu Tyr Glu Lys Leu Leu Glu Asp Ser Leu Thr Glu Ile Thr
    130                 135                 140

Ala Leu Ser Thr Pro Ile Val Pro Ile Arg Asn Gly Ile Ser Ala Leu
145                 150                 155                 160

Pro Leu Val Gly Asn Leu Thr Glu Glu Arg Phe Asn Ser Ile Val Cys
                165                 170                 175

Thr Leu Thr Asn Ile Leu Ser Thr Ser Lys Asp Asp Tyr Leu Ile Ile
            180                 185                 190

Asp Leu Ser Gly Leu Ala Gln Val Asn Glu Gln Thr Ala Asp Gln Ile
        195                 200                 205

Phe Lys Leu Ser His Leu Leu Lys Leu Thr Gly Thr Glu Leu Ile Ile
    210                 215                 220

Thr Gly Ile Lys Pro Glu Leu Ala Met Lys Met Asn Lys Leu Asp Ala
225                 230                 235                 240

Asn Phe Ser Ser Leu Lys Thr Tyr Ser Asn Val Lys Asp Ala Val Lys
                245                 250                 255
```

-continued

```
Val Leu Pro Ile Met
            260


<210> SEQ ID NO 110
<211> LENGTH: 176
<212> TYPE: PRT
<213> ORGANISM: Rhodobacter sphaeroides

<400> SEQUENCE: 110

Met Asp Gln Lys Gln Phe Glu Lys Ile Arg Ala Val Phe Asp Arg Ser
1               5                   10                  15

Gly Val Ala Leu Thr Leu Val Asp Met Ser Leu Pro Glu Gln Pro Val
            20                  25                  30

Val Leu Ala Asn Pro Pro Phe Leu Arg Met Thr Gly Tyr Thr Glu Gly
        35                  40                  45

Gln Ile Leu Gly Phe Asn Cys Arg Phe Leu Gln Arg Gly Asp Glu Asn
    50                  55                  60

Ala Gln Ala Arg Ala Asp Ile Arg Asp Ala Leu Lys Leu Gly Arg Glu
65                  70                  75                  80

Leu Gln Val Val Leu Arg Asn Tyr Arg Ala Asn Asp Glu Pro Phe Asp
                85                  90                  95

Asn Leu Leu Phe Leu His Pro Val Gly Gly Arg Pro Asp Ala Pro Asp
            100                 105                 110

Tyr Phe Leu Gly Ser Gln Phe Glu Leu Gly Arg Ser Gly Asn Ser Glu
        115                 120                 125

Glu Ala Ala Ala Ala Gly His Ala Gly Ala Leu Thr Gly Glu Leu Ala
    130                 135                 140

Arg Ile Gly Thr Val Ala Ala Arg Leu Glu Met Asp Ser Arg Arg His
145                 150                 155                 160

Leu Ala Gln Ala Ala Ala Ala Leu Val Arg Ala Trp Glu Arg Arg Gly
                165                 170                 175
```